United States Patent
James et al.

(10) Patent No.: US 9,944,659 B2
(45) Date of Patent: *Apr. 17, 2018

(54) BORON-CONTAINING DIACYLHYDRAZINE COMPOUNDS

(71) Applicant: Intrexon Corporation, Blacksburg, VA (US)

(72) Inventors: Ray A. James, Montgomery Village, MD (US); Sheela K. Chellappan, Clarksburg, MD (US); Robert E. Hormann, Melrose Park, PA (US)

(73) Assignee: INTREXON CORPORATION, Blacksburg, VA (US)

( * ) Notice: Subject to any disclaimer, the term of this patent is extended or adjusted under 35 U.S.C. 154(b) by 72 days.

This patent is subject to a terminal disclaimer.

(21) Appl. No.: 14/855,646

(22) Filed: Sep. 16, 2015

(65) Prior Publication Data

US 2016/0083403 A1    Mar. 24, 2016

Related U.S. Application Data

(60) Provisional application No. 62/051,649, filed on Sep. 17, 2014.

(51) Int. Cl.
| | |
|---|---|
| *C07F 5/02* | (2006.01) |
| *C07D 263/06* | (2006.01) |
| *A01N 37/28* | (2006.01) |
| *A01N 55/08* | (2006.01) |
| *A61K 31/69* | (2006.01) |
| *A61K 45/06* | (2006.01) |

(52) U.S. Cl.
CPC .............. *C07F 5/025* (2013.01); *A01N 37/28* (2013.01); *A01N 55/08* (2013.01); *A61K 31/69* (2013.01); *A61K 45/06* (2013.01); *C07D 263/06* (2013.01)

(58) Field of Classification Search
CPC ..................................................... C07F 5/025
See application file for complete search history.

(56) References Cited

U.S. PATENT DOCUMENTS

| | | |
|---|---|---|
| 4,631,211 A | 12/1986 | Houghten |
| 4,814,349 A | 3/1989 | Addor et al. |
| 4,859,609 A | 8/1989 | Dull et al. |
| 4,906,280 A | 3/1990 | Sandler et al. |
| 4,950,666 A | 8/1990 | Peake et al. |
| 4,954,655 A | 9/1990 | Kelly |
| 4,981,784 A | 1/1991 | Evans et al. |
| 4,985,461 A | 1/1991 | Hsu et al. |
| 5,010,175 A | 4/1991 | Rutter et al. |
| 5,071,773 A | 12/1991 | Evans et al. |
| 5,075,471 A | 12/1991 | Michelotti et al. |
| 5,117,057 A | 5/1992 | Hsu et al. |
| 5,171,671 A | 12/1992 | Evans et al. |
| 5,225,443 A | 7/1993 | Murphy et al. |
| 5,283,173 A | 2/1994 | Fields et al. |
| 5,344,958 A | 9/1994 | Lidert et al. |
| 5,354,762 A | 10/1994 | Hsu et al. |
| 5,358,966 A | 10/1994 | James, Jr. et al. |
| 5,378,726 A | 1/1995 | Yanagi et al. |
| 5,424,333 A | 6/1995 | Wing |
| 5,429,952 A | 7/1995 | Garner et al. |
| 5,459,127 A | 10/1995 | Feigner et al. |
| 5,482,962 A | 1/1996 | Hormann |
| 5,514,578 A | 5/1996 | Hogness |
| 5,530,021 A | 6/1996 | Yanagi et al. |
| 5,530,028 A | 6/1996 | Lidert et al. |

(Continued)

FOREIGN PATENT DOCUMENTS

| | | |
|---|---|---|
| CA | 2 103 110 C | 5/1994 |
| CN | 1245638 A | 3/2000 |

(Continued)

OTHER PUBLICATIONS

Antoniewski, C. et al., "The Ecdysone Response Enhancer of the Fbp1 Gene of *Drosophila melanogaster* Is a Direct Target for the Ecr/USP Nuclear Receptor," *Mol. Cell. Biol.* 14:4465-4474, American Society for Microbiology (1994).

Ashburner, M. et al., "Temporal Control of Puffing Activity in Polytene Chromosomes," *Cold Spring Harb. Symp. Quant. Biol.* 38:655-662, Cold Spring Harbor Laboratory Press (1974).

Belshaw, P.J. et al., "Rational Design of Orthogonal Receptor—Ligand Combinations," *Angew. Chem. Int. Ed. Engl.* 34:2129-2132, VCH Verlagsgesellschaft mbH, Weinheim (1995).

Cao, S. et al., "N'-tert-Butyl-N'-aroyl-N-(alkoxycarbonylmethyl)-N-aroylhydrazines, a novel nonsteroidal ecdysone agonist: syntheses, insecticidal activity, conformational, and crystal structure analysis," *Can. J. Chem.* 79:272-278, NRC Canada (2001).

Cao, S. et al., "Synthesis of N-Tert-butyl-N,N'-aroyl(aryloxyacetyl)hydrazine," *Huadong Ligong Daxue Xuebao* 27:316-319, Huodeng Shifan Daxue Chubanshe, China (2001).

(Continued)

*Primary Examiner* — Joseph R Kosack
(74) *Attorney, Agent, or Firm* — Sterne, Kessler, Goldstein & Fox P.L.L.C.

(57) ABSTRACT

The present disclosure provides boron-containing diacylhydrazines having Formula I:

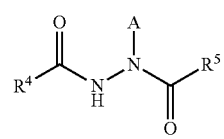

and the pharmaceutically acceptable salts and solvates thereof, wherein A, $R^4$, and $R^5$ are defined as set forth in the specification. The present disclosure also provides the use of boron-containing diacylhydrazines is ecdysone receptor-based inducible gene expression systems. Thus, the present disclosure is useful for applications such as gene therapy, treatment of disease, large scale production of proteins and antibodies, cell-based screening assays, functional genomics, proteomics, metabolomics, and regulation of traits in transgenic organisms, where control of gene expression levels is desirable.

19 Claims, 6 Drawing Sheets

(56) References Cited

U.S. PATENT DOCUMENTS

| | | |
|---|---|---|
| 5,599,904 A | 2/1997 | Evans et al. |
| 5,641,652 A | 6/1997 | Oro et al. |
| 5,668,175 A | 9/1997 | Evans et al. |
| 5,710,004 A | 1/1998 | Evans et al. |
| 5,723,329 A | 3/1998 | Mangelsdorf et al. |
| 5,880,333 A | 3/1999 | Goff et al. |
| 5,919,667 A | 7/1999 | Gage et al. |
| 5,945,400 A | 8/1999 | Scherman et al. |
| 5,948,406 A | 9/1999 | Stavinski et al. |
| 5,981,196 A | 11/1999 | Stavinski et al. |
| 5,989,863 A | 11/1999 | Tang et al. |
| 6,013,836 A | 1/2000 | Hsu et al. |
| 6,025,483 A | 2/2000 | Yanofsky |
| 6,096,787 A | 8/2000 | Evans et al. |
| 6,107,286 A | 8/2000 | Byk et al. |
| 6,117,639 A | 9/2000 | Germann et al. |
| 6,147,282 A | 11/2000 | Goff et al. |
| 6,245,531 B1 | 6/2001 | Hogness et al. |
| 6,258,603 B1 | 7/2001 | Carlson et al. |
| 6,265,173 B1 | 7/2001 | Evans et al. |
| 6,281,330 B1 | 8/2001 | Evans et al. |
| 6,300,488 B1 | 10/2001 | Gage et al. |
| 6,326,403 B1 | 12/2001 | Hölzemann et al. |
| 6,333,318 B1 | 12/2001 | Evans et al. |
| 6,379,945 B1 | 4/2002 | Jepson et al. |
| 6,458,926 B1 | 10/2002 | Evans et al. |
| 6,723,531 B2 | 4/2004 | Evans et al. |
| 6,756,491 B2 | 6/2004 | Evans et al. |
| 6,875,569 B2 | 4/2005 | Gage et al. |
| 6,939,711 B2 | 9/2005 | Goff et al. |
| 7,038,022 B1 | 5/2006 | Evans et al. |
| 7,045,315 B2 | 5/2006 | Evans et al. |
| 7,057,015 B1 | 6/2006 | Gage et al. |
| 7,091,038 B2 | 8/2006 | Palli et al. |
| 7,119,077 B1 | 10/2006 | Evans et al. |
| 7,304,161 B2 | 12/2007 | Hormann et al. |
| 7,456,315 B2 | 11/2008 | Hormann et al. |
| 7,563,928 B2 | 7/2009 | Hormann et al. |
| 7,851,220 B2 | 12/2010 | Hormann et al. |
| 8,076,517 B2 | 12/2011 | Hormann et al. |
| 8,524,948 B2 | 9/2013 | Hormann et al. |
| 9,127,024 B2 | 9/2015 | Chellappan et al. |
| 9,272,986 B2 | 3/2016 | Hormann et al. |
| 9,512,148 B2 * | 12/2016 | Chellappan .............. C07F 7/082 |
| 2002/0110861 A1 | 8/2002 | Dhadialla et al. |
| 2002/0119521 A1 | 8/2002 | Palli et al. |
| 2002/0177564 A1 | 11/2002 | Evans et al. |
| 2003/0010253 A1 | 1/2003 | Oki et al. |
| 2003/0203360 A1 | 10/2003 | Weinstein et al. |
| 2004/0033600 A1 | 2/2004 | Palli et al. |
| 2004/0096942 A1 | 5/2004 | Kapitskaya et al. |
| 2004/0197861 A1 | 10/2004 | Palli, Sr. |
| 2004/0235097 A1 | 11/2004 | Zhang et al. |
| 2005/0209283 A1 | 9/2005 | Hormann et al. |
| 2005/0266457 A1 | 12/2005 | Palli et al. |
| 2006/0100416 A1 | 5/2006 | Palli et al. |
| 2007/0093529 A1 | 4/2007 | Finsinger et al. |
| 2007/0161086 A1 | 7/2007 | Palli et al. |
| 2008/0064741 A1 | 3/2008 | Hormann et al. |
| 2008/0103113 A1 | 5/2008 | Hormann et al. |
| 2008/0194521 A1 | 8/2008 | Hormann et al. |
| 2008/0214627 A1 | 9/2008 | Hormann et al. |
| 2012/0116090 A1 | 5/2012 | Hormann et al. |
| 2012/0316066 A1 | 12/2012 | Hormann et al. |
| 2013/0035487 A1 | 2/2013 | Hormann et al. |
| 2014/0045903 A1 | 2/2014 | Hormann et al. |

FOREIGN PATENT DOCUMENTS

| | | |
|---|---|---|
| CN | 1161325 C | 8/2004 |
| DE | 198 37 620 A1 | 2/1999 |
| EP | 0 228 564 B1 | 7/1987 |
| EP | 0 232 075 A1 | 8/1987 |
| EP | 0 234 944 A1 | 9/1987 |
| EP | 0 236 618 A2 | 9/1987 |
| EP | 0 245 950 A2 | 11/1987 |
| EP | 0 253 468 A2 | 1/1988 |
| EP | 0 339 854 B1 | 11/1989 |
| EP | 0 347 216 A2 | 12/1989 |
| EP | 0 361 645 A2 | 4/1990 |
| EP | 0 395 581 A1 | 10/1990 |
| EP | 0 286 746 B1 | 2/1991 |
| EP | 0 461 809 A1 | 12/1991 |
| EP | 0 496 342 B1 | 7/1992 |
| EP | 0 639 559 A1 | 2/1995 |
| EP | 0 798 378 A2 | 10/1997 |
| EP | 0 965 644 A2 | 12/1999 |
| EP | 0 984 009 A1 | 3/2000 |
| EP | 1 266 015 B1 | 12/2002 |
| GB | 2 231 268 A | 11/1990 |
| JP | 62-209053 A | 9/1987 |
| JP | 62-263150 A | 11/1987 |
| JP | 2-207066 A | 8/1990 |
| JP | 3-141245 A | 6/1991 |
| JP | 3-145447 A | 6/1991 |
| JP | 4-089471 A | 3/1992 |
| JP | 4-178380 A | 6/1992 |
| JP | 4-235177 A | 8/1992 |
| JP | 5-39252 A | 2/1993 |
| JP | 6-172342 A | 6/1994 |
| JP | 6-184076 A | 7/1994 |
| JP | 8-231528 A | 9/1996 |
| JP | 8-231529 A | 9/1996 |
| JP | 9-100262 A | 4/1997 |
| JP | 2000-26423 A | 1/2000 |
| WO | WO 89/12690 A1 | 12/1989 |
| WO | WO 94/28028 A1 | 12/1994 |
| WO | WO 95/18863 A1 | 7/1995 |
| WO | WO 95/21931 A1 | 8/1995 |
| WO | WO 96/17823 A1 | 6/1996 |
| WO | WO 96/25508 A1 | 8/1996 |
| WO | WO 96/27673 A1 | 9/1996 |
| WO | WO 96/37609 A1 | 11/1996 |
| WO | WO 97/38117 A1 | 10/1997 |
| WO | WO 99/02683 A1 | 1/1999 |
| WO | WO 99/10510 A2 | 3/1999 |
| WO | WO 99/36520 A1 | 7/1999 |
| WO | WO 99/58155 A1 | 11/1999 |
| WO | WO 01/36447 A2 | 5/2001 |
| WO | WO 01/62780 A1 | 8/2001 |
| WO | WO 01/70816 A2 | 9/2001 |
| WO | WO 02/29075 A2 | 4/2002 |
| WO | WO 02/066612 A2 | 8/2002 |
| WO | WO 02/066613 A2 | 8/2002 |
| WO | WO 02/066614 A2 | 8/2002 |
| WO | WO 02/066615 A2 | 8/2002 |
| WO | WO 03/105849 A1 | 12/2003 |
| WO | WO 2004/005478 A2 | 1/2004 |
| WO | WO 2004/072254 A2 | 8/2004 |
| WO | WO 2004/078924 A2 | 9/2004 |
| WO | WO 2005/017126 A2 | 2/2005 |
| WO | WO 2005/108617 A2 | 11/2005 |
| WO | WO 2006/083253 A1 | 8/2006 |

OTHER PUBLICATIONS

Carlson, G.R. et al., "The chemical and biological properties of methoxyfenozide, a new insecticidal ecdysteroid agonist," *Pest Manag. Sci.* 57:115-119, Society of Chemical Industry (2001).

Cherbas, L. et al., "Identification of Ecdysone response elements by analysis of the *Drosophila* Eip28/29 gene," *Genes & Develop.* 5:120-131, Cold Spring Harbor Laboratory Press (1991).

Cho, W.-L. et al., "Mosquito Ecdysteroid Receptor: Analysis of the cDNA and Expression During Vitellogenesis," *Insect Biochem. Molec. Biol.* 25:19-27, Elsevier Science Ltd. (1995).

Christopherson, K.S. et al., "Ecdysteroid-dependent regulation of genes in mammalian cells by a *Drosophila* ecdysone receptor and chimeric transactivators," *PNAS* 89:6314-6318, National Academy of Sciences (1992).

Chung, A.C.-K. et al., "Cloning of crustacean ecdysteroid receptor and retinoid-X receptor gene homologs and elevation of retinoid-X receptor mRNA by retinoic acid," *Mol. Cell. Endocrinol.* 139:209-227, Elsevier Science Ireland Ltd. (1998).

(56) References Cited

OTHER PUBLICATIONS

D'Avino, P.P. et al., "The moulting hormone ecdysone is able to recognize target elements composed of direct repeats," *Mol. Cell. Endocrinol.* 113:1-9, Elsevier Science Ireland Ltd. (1995).
Dhadialla, T.S. et al., "New Insecticides With Ecdysteroidal and Juvenile Hormone Activity," *Annu. Rev. Entomol.* 43:545-569, Annual Reviews Inc. (1998).
Evans, R.M., "The Steroid and Thyroid Hormone Receptor Superfamily," *Science* 240:889-895, American Association for the Advancement of Science (1988).
Fujiwara, H. et al., "Cloning of an Ecdysone Receptor Homolog from *Manduca sexta* and the Developmental Profile of Its mRNA in Wings," *Insect Biochem. Molec. Biol.* 25:845-856, Elsevier Science Ltd. (1995).
Godowski, P.J. et al., "Signal Transduction and Transcriptional Regulation by Glucocorticoid Receptor—LexA Fusion Proteins," *Science* 241:812-816, American Association for the Advancement of Science (1988).
Guo, X. et al., "Isolation of a Functional Ecdysteroid Receptor Homologue from the Ixodid Tick *Amblyomma americanum* (L.)," *Insect Biochem. Molec. Biol.* 27:945-962, Elsevier Science Ltd. (1998).
Hannan, G.N. and Hill, R.J., "Cloning and Characterization of LcEdR: A Functional Ecdysone Receptor from the Sheep Blowfly *Lucilia cuprina,*" *Insect Biochem. Molec. Biol.* 27:479-488, Elsevier Science Ltd. (1997).
Hayward, D.C. et al, "The structure of the USP/RXR of *Xenos pecki* indicates that Strepsiptera are not closely related to Diptera," *Dev. Genes Evol.* 215:213-219, Springer-Verlag (2005).
Heberlein, U. et al., "Characterization of *Drosophila* Transcription Factors That Activate the Tandem Promoters of the Alcohol Dehydrogenase Gene," *Cell* 41:965-977, MIT (1985).
Holt, J.R. et al., "Functional Expression of Exogenous Proteins in Mammalian Sensory Hair Cells Infected With Adenoviral Vectors," *J. Neurophysiol.* 81:1881-1888, American Physiological Society (1999).
Hoppe, U.C. et al., "Adenovirus-Mediated Inducible Gene Expression in Vivo by a Hybrid Ecdysone Receptor," *Mol. Ther.* 1:159-164, The American Society of Gene Therapy (2000).
Imhof, M.O. et al., "Cloning of a *Chironomus tentans* cDNA Encoding a Protein (cEcRH) Homologous to the *Drosophila melanogaster* Ecdysteroid Receptor (dEcR)," *Insect Biochem. Molec. Biol.* 23:115-124, Pergamon Press Ltd. (1993).
International Search Report and the Witten Opinion of the International Searching Authority for International Appl. No. PCT/US2014/028768, dated Jul. 8, 2014, United States Patent and Trademark Office, Alexandria, VA.
Kakizawa, T. et al., "Ligand-dependent Heterodimerization of Thyroid Hormone Receptor and Retinoid X Receptor," *J. Biol. Chem.* 272:23799-23804, The American Society for Biochemistry and Molecular Biology, Inc. (1997).
Koelle, M.R. et al., "The *Drosophila* EcR Gene Encodes an Ecdysone Receptor, a New Member of the Steroid Receptor Superfamily," *Cell* 67:59-77, Cell Press (1991).
Kothapalli, R. et al., "Cloning and Developmental Expression of the Ecdysone Receptor Gene From the Spruce Budworm, *Choristoneura fumiferana,*" *Dev. Genet.* 17:319-330, Wiley-Liss, Inc. (1995).
Kumar, M.B. et al., "A single point mutation in ecdysone receptor leads to increased ligand specificity: Implications for gene switch applications," *PNAS* 99:14710-14715, National Academy of Sciences (2002).
Le, D.P. et al., "RH-2485: A New Selective Insecticide for Caterpillar Control," *Brighton Crop Protection Conference—Pests and Diseases* 2:481-486, British Crop Protection Council (1996).
Leid, M. et al., "Purification, Cloning, and RXR Identity of the HeLa Cell Factor with Which RAR or TR Heterodimerizes to Bind Target. Sequences Efficiently," *Cell* 68:377-395, Cell Press (1992).
Leonhardt, S.A. et al., "Agonist and Antagonists Induce Homodimerization and Mixed Ligand Heterodimerization of Human Progesterone Receptors in Vivo by a Mammalian Two-Hybrid Assay," *Mol. Endocrinol.* 12:1914-1930, The Endocrine Society (1998).
Licitra, E.J. and Liu, J.O., "A three-hybrid system for detecting small ligand—protein receptor interactions," *PNAS* 93:12817-12821, National Academy of Sciences (1996).
Martinez, A. et al., "Creation of ecdysone receptor chimeras in plants for controlled regulation of gene expression," *Mol. Gen. Genet.* 261:546-552, Springer-Verlag, Germany (1999).
Metzger, D. et al., "The human oestrogen receptor functions in yeast," *Nature* 334:31-36, Nature Publishing Group (1988).
Morrison, D.A. et al., "Isolation of Transformation-Deficient *Streptococcus pneumoniae* Mutants Defective in Control of Competence, Using Insertion-Duplication Mutagenesis with the Erythromycin Resistance Determinant of pAMβ1," *J. Bacteriol.* 159:870-876, American Society for Microbiology (1984).
Mouillet J.-F. et al., "Cloning of two putative ecdysteroid receptor isoforms from *Tenebrio molitor* and their developmental expression in the epidermis during metamorphosis," *Eur. J. Biochem.* 248:856-863, FEBS (1997).
Nakagawa, Y. et al., "Quantitative Structure—Activity Relationships and Designed Synthesis of Larvicidal N,N'-Dibenzoyl-N-tert-butylhydrazines against *Chilo suppressalis,*" *Pestic. Sci.* 44:102-105, SCI (1995).
Nakagawa, Y. et al., "Quantitative Structure—Activity Studies of Insect Growth Regulators. XI. Stimulation and Inhibition of N-Acetylglucosamine Incorporation in a Cultured Integument System by Substituted N-tert-Butyl-N,N'-dibenzoylhydrazines," *Pestic. Sci.* 43:339-345, SCI (1995).
Nakagawa, Y. et al., "Quantitative structure—activity studies of insect growth regulators: XIX. Effects of substituents on the aromatic moiety of dibenzoylhydrazines on larvicidal activity against the beet armyworm *Spodoptera exigua,*" *Pest Manag. Sci.* 58:131-138, published online by EarlyView in Wiley InterScience (2001).
Nakagawa, Y. et al., "Quantitative structure—activity studies of insect growth regulators: XVI. Substituent effects of dibenzoylhydrazines on the insecticidal activity to Colorado potato beetle *Leptinotarsa decemlineata,*" *Pestic. Sci.* 55:909-918, Society of Chemical Industry (1999).
Nakagawa, Y. et al., "Quantitative structure—activity studies of insect growth regulators: XVIII. Effects of substituents on the aromatic moiety of dibenzoylhydrazines on larvicidal activity against the Colorado potato beetle *Leptinotarsa decemlineata,*" *Pest Manag. Sci.* 57:858-865, SCI (2001).
Neuberger, M.S. et al., "Recombinant antibodies possessing novel effector functions," *Nature* 312:604-608, Nature Publishing Group (1984).
Nie, K.-S. et al., "New Insect Growth Regulators—Central Tebufenozide," *Nongyaoxue Xuebao* 40:42-43, Gai Kan Bianjibu, Beijing (2001).
No, D. et al., "Ecdysone-inducible gene expression in mammalian cells and transgenic mice," *PNAS* 93:3346-3351, National Academy of Sciences (1996).
Oikawa, N. et al., "Quantitative Structure—Activity Analysis of Larvicidal 1-(Substituted benzoyl)-2-benzoyl-1-tert-butylhydrazines against *Chilo suppressalis,*" *Pestic. Sci.* 41:139-147, SCI (1994).
Peet, D.J. et al., "Engineering novel specificities for ligand-activated transcription in the nuclear hormone receptor RXR," *Chem. & Biol.* 5:13-21, Current Biology Ltd. (1998).
Perera, S.C. et al., "An Analysis of Ecdysone Receptor Domains Required for Heterodimerization With Ultraspiracle," *Arch. Insect Biochem. Physiol.* 41:61-70, Wiley-Liss, Inc. (1999).
Perera, S.C. et al., "Studies on two ecdysone receptor isoforms of the spruce budworm, *Choristoneura fumiferana,*" *Mol. Cell. Endocrinol.* 152:73-84, Elsevier Science Ireland Ltd. (1999).
Pierce, A.C. and Jorgensen, W.L., "Computational Binding Studies of Orthogonal Cyclosporin-Cyclophilin Pairs," *Angew. Chem. Int. Ed. Engl.* 36:1466-1469, VCH Verlagsgesellschaft mbH, Weinheim (1997).
Riddiford, L.M. et al., "Ecdysone Receptors and Their Biological Actions," *Vitamins and Hormones* 60:1-73, Academic Press (2001).

(56) References Cited

OTHER PUBLICATIONS

Saleh, D.S. et al., "Cloning and characterization of an ecdysone receptor cDNA from *Locusta migratoria*," *Mol. Cell. Endocrinol.* *143*:91-99, Elsevier Science Ireland Ltd. (1998).

Sawada, Y. et al., "Synthesis and Insecticidal Activity of 3,5-Dimethylbenzoyl Moiety Modified Analogues of N-tert-Butyl-N'-(4-ethylbenzoyl)-3,5-dimethylbenzohydrazide," *J. Pesticide Sci.* *27*:365-373, Pesticide Science Society of Japan, Tokyo (2002).

Sawada, Y. et al., "Synthesis and insecticidal activity of benzoheterocyclic analogues of N'-benzoyl-N-(tert-butyl)benzohydrazide: Part 2. Introdution of substituents on the benzene rings of the benzoheteroycle moiety," *Pest Manag. Sci.* *59*:36-48, published online by EarlyView in Wiley InterScience (2002).

Sawada, Y. et al., "Synthesis and insecticidal activity of benzoheterocyclic analogues of N'-benzoyl-N-(tert-butyl)benzohydrazide: Part 3. Modification of N-tert-butylhydrazine moiety," *Pest Manag. Sci.* *59*:49-57, published online by EarlyView in Wiley InterScience (2002).

Sawada, Y. et al., "Synthesis and insecticidal activity of benzoheterocyclic analogues of N'-benzoyl-N-tert-butyl)benzohydrazide: Part 1. Design of benzoheterocyclic analogues," *Pest Manag. Sci.* *59*:25-35, published online by EarlyView in Wiley InterScience (2003).

Suhr, S.T. et al., "High level transactivation by a modified Bombyx ecdysone receptor in mammalian cells without exogenous retinoid X receptor," *PNAS 95*:7999-8004, National Academy of Sciences (1998).

Swevers, L. et al., "The Silkmoth Homolog of the *Drosophila* Ecdysone Receptor (B1 Isoform): Cloning and Analysis of Expression During Follicular Cell Differentiation," *Insect Biochem. Molec. Biol. 25*:857-866, Elsevier Science Ltd. (1995).

Tice, C.M. et al., Optimization of α-Acylaminoketone Ecdysone Agonists for Control of Gene Expression, *Biorg. Med. Chem. Letts. 13*:1883-1886, Elsevier Science Ltd. (2003).

Verras, M. et al., "Cloning and characterization of CcEcR, An ecdysone receptor homolog from the Mediterranean fruit fly *Ceratitis capitata*," *Eur. J. Biochem. 265*:798-808, FEBS (1999).

Wheelock, C.E. et al., "High-throughput screening of ecdysone agonists using a reporter gene assay followed by 3-D QSAR analysis of the molting hormonal activity," *Bioorg. Med. Chem. 14*:1143-1159, Elsevier Ltd. (2006).

Wilson, J.M. et al., "Hepatocyte-directed Gene Transfer in Vivo Leads to Transient Improvement of Hypercholesterolernia in Low Density Lipoprotein Receptor-deficient Rabbits," *J. Biol. Chem. 267*:963-967, The American Society for Biochemistry and Molecular Biology, Inc. (1992).

Wing, K.D., "RH 5849, a Nonsteroidal Ecdysone Agonist: Effects on a *Drosophila* Cell Line," *Science 241*:467-469, The American Association for the Advancement of Science ( 1988).

Yao, T.-P. et al., "*Drosophila* ultraspiracle Modulates Ecdysone Receptor Function via Heterodimer Formation," *Cell 71*:63-72, Cell Press (1992).

Yao, T.-P. et al., "Functional ecdysone receptor is the product of EcR and Ultraspirack genes," *Nature 366*:476-479, Nature Publishing Group (1993).

Zhang, X.-N. et al., "Innovation Hydrazines insect growth regulator JS118 the synthesis and biological activity. Synthesis and Study of Ait of New Diacylhydrazines IGRs JS118," *Pesticides 42*:18-20 (2003).

Zou X.-J. et al., "Synthesis and Crystal Structure of N-tert-butyl-N'-(2,4-dichlorobenzoyl)-N-[1-(4-chlorophenyl)-1,4-dihydro-6-methylpyridazine-4-oxo-3-carbonyl] hydrazine," *Jiegou Huaxue 20*:344-348, Zhingguo ke xue Yuan, Fujian wu zhi jie gou yan jiusuo, China (2001).

Zou, X.-J. and Jin G.-Y., "Synthesis of N-tert-butyl-N'(N)-(1-aryl-1,4-dihydro-6-methylpyridazine-4-oxo-3-carbonyl)-N (N')-(substituted) benzoylhydrazine," *Indian J. Chem. 42B*:2608-2611, Council of Scientific & Industrial Research, New Delhi (2003).

Chan, T. et al., Gene Therapy of Cancer: Translational Approaches from Preclinical Studies to Clinical Implementation 363-376 (Edmund C. Lattime & Stanton L. Gerson eds., 3$^{rd}$ ed. 2014) Elsevier Inc.

Del Vecchio, M. et al., "Interleukin-12: Biological Properties and Clinical Application," *Clin. Cancer Res. 13*:4677-4685, American Association for Cancer Research (2007).

Baker, S.J. e al., "Boron-containing inhibitors of synthetases," *Chem. Soc. Rev. 40*:4279-4285, The Royal Society of Chemistry, United Kingdom (Feb. 7, 2011).

International Search Report for International Patent Appl. No. PCT/US2015/050375, U.S. Patent and Trademark Office, Alexandria, Virginia, dated Jan. 19, 2016.

Written Opinion of the International Search Authority for International Patent Appl. No. PCT/US2015/050375, U.S. Patent and Trademark Office, Alexandria, Virginia, dated Jan. 19, 2016.

* cited by examiner

Fig. 2A

```
GCTGAGCTATGCCTAATCAAGTCACGGTAACTATGACTCTCTTAAGGTAGCCAAATGGCG
CCACGAAAGGAGGTCGTGAAATGGATAAAAAAATACAGCGTTTTTCATGTACAACTATAC
TAGTTGTAGTGCCTAAATAATGCTTTTAAAACTTAAAAATATCAGATAACAGCTTGGTGG
CACCCATTGTGTTCACAGGAGATACAGCTTTATCTGTACTGATATTAATGACATGCTGCA
CTCGGTGTGAAAGGGCATCTAGTAGGCTATGGCAGGGCCTGCCGCCCCGACGTTGGCTGC
GAGCCCTGGGCCTTCACCCGAACTTGGGGGGTGGGGTGGGGAAAAGGAAGAAACGCGGGC
GTATTGGCCCCAATGGGGTCTCGGTGGGGTATCGACAGAGTGCCAGCCCTGGGACCGAAC
CCCGCGTTTATGAACAAACGACCCAACACCGTGCGTTTTATTCTGTCTTTTTATTGCCGT
CATAGCGCGGGTTCCTTCCGGTATTGTCTCCTTCCGTGTTTCATCAGAAAAACTCGTCCA
GCAGGCGGTAGAAAGCGATGCGCTGAGAATCTGGTGCAGCGATGCCGTACAGAACCAGGA
AGCGGTCAGCCCATTCGCCGCCCAGTTCTTCAGCGATGTCGCGGGTAGCCAGAGCGATGT
CCTGGTAGCGGTCAGCAACGCCCAGACGACCACAGTCGATGAAGCCAGAGAAGCGGCCGT
TTTCAACCATGATGTTCGGCAGGCAAGCGTCGCCGTGGGTAACAACCAGGTCTTCGCCGT
CTGGCATACGAGCTTTCAGGCGAGCGAACAGTTCAGCCGGAGCCAGGCCCTGGTGTTCTT
CGTCCAGGTCGTCCTGGTCAACCAGGCCAGCTTCCATGCGGGTGCGAGCGCGTTCGATGC
GGTGTTTAGCCTGGTGGTCGAACGGACAAGTAGCCGGGTCCAGGGTGTGCAGGCGGCGCA
TAGCGTCAGCCATGATAGAAACTTTTTCAGCCGGAGCCAGGTGAGAAGACAGCAGATCCT
GGCCCGGAACTTCGCCCAGCAGCAGCCAGTCGCGGCCAGCTTCGGTAACAACGTCCAGAA
CAGCAGCGCACGGAACGCCGGTGGTAGCCAGCCAAGACAGGCGAGCAGCTTCGTCTTGCA
GTTCGTTCAGAGCGCCAGACAGGTCGGTTTTAACGAACAGAACCGGGCGGCCCTGAGCAG
ACAGGCGGAAAACAGCAGCGTCAGAGCAGCCGATGGTTTGTTGTGCCCAGTCGTAACCAA
ACAGACGTTCAACCCAAGCAGCCGGAGAGCCAGCGTGCAGGCCGTCCTGTTCGATCATGG
TGGCCCCCCCCCCCCGGAATAGCTCTGAGGCCGAGGCAGCTTCGGCCTCTGCATAAAT
AAAAAAAATTAGTCAGCCATGGGGCGGAGAATGGGCGGAACTGGGCGGAGTTAGGGGCGG
GATGGGCGGAGTTAGGGGCGGGACTATGGTTGCTGACTAATTGAGATGCTTGCTTTGCAT
ACTTCTGCCTGCTGGGGAGCCTGGGGACTTTCCACACCTGGTTGCTGACTAATTGAGATG
CTTGCTTTGCATACTTCTGCCTGCTGGGGAGCCTGGGGACTTTCCACACCCTAACCATGC
ATTCAACTATCCCAACGAGGGATTCGAAGGACGATACCTACGTTAGACTTAACTATAACG
GTCCTAAGGTAGCGACCACTTAGACGTGTTGAAACCCTAGGGCCGCACAGGCCCGCCGAC
GATCCGAGCGTGGCCATCGTGGCCCACCTAAGTGGTCCAGGAACGGCGTGGGCTCGTTTA
AACCGTACCATTAGGGAAAGTACCCACTTATGTGGGCGATCGCTTAATTAAGGCCGGCCG
CCGCAATAAAATATCTTTATTTTCATTACATCTGTGTGTTGGTTTTTGTGTGAATCCAT
AGTACTAACATACGCTCTCCATCAAAACAAAACGAAACAAAACAAACTAGCAAAATAGGC
TGTCCCCAGTGCAAGTCCAGGTGCCAGAACATTTCTCTATCCATAATGCAGGGGTACCGG
GTGATGACGGTGAAAACCTCCAATTG[CGGAGTACTGTCCTCCGAGCGGAGTACTGTCCT
CCGAGCGGAGTACTGTCCTCCGAGCGGAGTACTGTCCTCCGAGCGGAGTACTGTCCTCCG
AGCGGAGTACTGTCCTCCGAGCGGAGAGTC]¹CCCGGGGACCTAGAGGGTATATAATGGG
TGCCTTAGCTGGTGTGTGACCTCATCTTCCTGTACGCCCTGCAGGGGCGCGCCACGCGT
CCGCGGGCTAGCGCCACC[ATGGAAGATGCCAAAAACATTAAGAAGGGCCCAGCGCCATT
CTACCCACTCGAAGACGGGACCGCTGGCGAGCAGCTGCACAAAGCCATGAAGCGCTACGC
CCTGGTGCCCGGCACCATCGCCTTTACCGACGCACATATCGAGGTGGACATTACCTACGC
CGAGTACTTCGAGATGAGCGTTCGGCTGGCAGAAGCTATGAAGCGCTATGGGCTGAATAC
```

[6x GalRE]¹

Fig. 2B

AAACCATCGGATCGTGGTGTGCAGCGAGAATAGCTTGCAGTTCTTCATGCCCGTGTTGGG
TGCCCTGTTCATCGGTGTGGCTGTGGCCCCAGCTAACGACATCTACAACGAGCGCGAGCT
GCTGAACAGCATGGGCATCAGCCAGCCCACCGTCGTATTCGTGAGCAAGAAAGGGCTGCA
AAAGATCCTCAACGTGCAAAAGAAGCTACCGATCATACAAAGATCATCATCATGGATAG
CAAGACCGACTACCAGGGCTTCCAAAGCATGTACACCTTCGTGACTTCCCATTTGCCACC
CGGCTTCAACGAGTACGACTTCGTGCCCGAGAGCTTCGACCGGGACAAAACCATCGCCCT
GATCATGAACAGTAGTGGCAGTACCGGATTGCCCAAGGGCGTAGCCCTACCGCACCGCAC
CGCTTGTGTCCGATTCAGTCATGCCCGCGACCCCATCTTCGGCAACCAGATCATCCCCGA
CACCGCTATTCTCAGCGTGGTGCCATTTCACCACGGCTTCGGCATGTTCACCACGCTGGG
CTACTTGATCTGCGGCTTTCGGGTCGTGCTCATGTACCGCTTCGAGGAGGAGCTATTCTT
GCGCAGCTTGCAAGACTATAAGATTCAATCTGCCCTGCTGGTGCCCACACTATTTAGCTT
CTTCGCTAAGAGCACTCTCATCGACAAGTACGACCTAAGCAACTTGCACGAGATCGCCAG
CGGCGGAGCGCCTCTCAGCAAGGAGGTAGGTGAGGCCGTGGCCAAACGCTTCCACCTACC
AGGCATCCGCCAGGGCTACGGCCTGACAGAAACAACCAGCGCCATTCTGATCACCCCCGA
AGGGGACGACAAGCCTGGCGCAGTAGGCAAGGTGGTGCCCTTCTTCGAGGCTAAGGTGGT
GGACTTGGACACAGGTAAGACCCTGGGTGTGAACCAGCGCGGCGAGCTGTGCGTCCGTGG
CCCCATGATCATGAGCGGCTACGTGAACAACCCCGAGGCTACAAACGCTCTCATCGACAA
GGACGGCTGGCTGCACAGCGGCGACATCGCCTACTGGGACGAGGACGAGCACTTCTTCAT
CGTGGACCGGCTCAAGAGCCTGATCAAATACAAGGGCTACCAGGTAGCCCCAGCCGAACT
GGAGAGCATCCTGCTGCAACACCCCAACATCTTCGACGCCGGGTCGCTGGCCTGCCCGA
CGACGATGCTGGCGAGCTGCCCGCCGCAGTCGTCGTGCTGGAACACGGTAAAACCATGAC
CGAGAAGGAGATCGTGGACTATGTGGCCAGCCAGGTTACAACCGCCAAGAAGCTGCGCGG
TGGTGTTGTGTTCGTGGACGAGGTGCCTAAAGGACTGACCGGCAAGTTGGACGCCCGCAA
GATCCGCGAGATTCTCATTAAGGCCAAGAAGGGCGGCAAGATCGCCGTGTAA]²ATCGAT
TGCGCAAAGCTTTCGCGATAGGCGAGACCAATGGGTGTGTACGTAGCGGCCGCGTCGACT
GATGGGTGGCATCCCTGTGACCCCTCCCCAGTGCCTCTCCTGGCCCTGGAAGTTGCCACT
CCAGTGCCCACCAGCCTTGTCCTAATAAAATTAAGTTGCATCATTTTGTCTGACTAGGTG
TCCTTCTATAATATTATGGGGTGGAGGGGGGTGGTATGGAGCAAGGGGCAAGTTGGGAAG
ACAACCTGTAGGGCCTGCGGGGTCTATTGGGAACCAAGCTGGAGTGCAGTGGCACAATCT
TGGCTCACTGCAATCTCCGCCTCCTGGGTTCAAGCGATTCTCCTGCCTCAGCCTCCCGAG
TTGTTGGGATTCCAGGCATGCATGACCAGGCTCAGCTAATTTTGTTTTTTTGGTAGAGA
CGGGGTTTCACCATATTGGCCAGGCTGGTCTCCAACTCCTAATCTCAGGTGATCTACCCA
CCTTGGCCTCCCAAATTGCTGGGATTACAGGCGTGAACCACTGCTCCCTTCCCTGTCCTT
CTGATTTTAAAATAACTATACCAGCAGGAGGACGTCCAGACACAGCATAGGCTACCTGGC
CATGCCCAACCGGTGGGACATTTGAGTTGCTTGCTTGGCACTGTCCTCTCATGCGTTGGG
TCCACTCAGTAGATGCCTGTTGAATTATTTAAATCGGTCCGCGTACGGCTCTTCTCCCCC
TCGAGGGCCTCCGCGCCGGGTTTTGGCGCCTCCCGCGGGCGCCCCCTCCTCACGGCGAG
CGCTGCCACGTCAGACGAAGGCGCAGCGAGCGTCCTGATCCTTCCGCCGGACGCTCAG
GACAGCGGCCGCTGCTCATAAGACTCGGCCTTAGAACCCAGTATCAGCAGAAGGACAT
TTTAGGACGGGACTTGGGTGACTCTAGGGCACTGGTTTTCTTTCCAGAGAGCGGAACAGG
CGAGGAAAAGTAGTCCCTTCTCGGCGATTCTGCGGAGGGATCTCCGTGGGCGGTGAACG
CCGATGATTATATAAGGACGCGCCGGGTGTGGCACAGCTAGTTCCGTCGCAGCCGGGATT

[fLuc]²

Fig. 2C

TGGGTCGCGGTTCTTGTTTGTGGATCGCTGTGATCGTCACTTGGTGAGTAGCGGGCTGCT
GGGCTGGGTACGTGCGCTCGGGGTTGGCGAGTGTGTTTTGTGAAGTTTTTTAGGCACCTT
TTGAAATGTAATCATTTGGGTCAATATGTAATTTTCAGTGTTAGACTAGTAAATTGTCCG
CTAAATTCTGGCCGTTTTTGGCTTTTTTGTTAGACGCCGCGGGGGGGGGGGGGGGCTAG
CGCCACC[ATGGGCCCCAAGAAGAAAGGAAGGTGGCCCCCCCCACCGACGTGAGCCTGG
GCGACGAGCTGCACCTGGACGGCGAGGACGTGGCCATGGCCCACGCCGACGCCCTGGACG
ACTTCGACCTGGACATGCTGGGCGACGGCGACAGCCCCGGCCCCGGCTTCACCCCCACG
ACAGCGCCCCTACGGCGCCCTGGACATGGCCGACTTCGAGTTCGAGCAGATGTTCACCG
ACGCCCTGGGCATCGACGAGTACGGCGGC]³GAATTC[GAGATGCCCGTGGACAGGATTC
TGGAGGCCGAACTCGCCGTGGAGCAGAAAAGCGACCAGGGCGTGGAGGGCCCCGGCGGAA
CCGGCGGCAGCGGCAGCAGCCCCAACGACCCCGTGACCAACATCTGCCAGGCCGCCGACA
AGCAGCTGTTCACCCTGGTGGAGTGGGCCAAGAGGATTCCCCACTTCAGCAGCCTGCCCC
TGGACGACCAGGTGATCCTGCTGAGGGCCGGATGGAACGAGCTGCTGATCGCCAGCTTCA
GCCACAGGAGCATCGACGTGAGGGACGGCATCCTGCTGGCCACCGGCCTGCACGTCCATA
GGAACAGCGCCCACAGCGCCGGAGTGGGCGCCATCTTCGACAGGGTGCTGACCGAGCTGG
TGAGCAAGATGAGGGACATGAGGATGGACAAGACCGAGCTGGGCTGCCTGAGGGCCATCA
TCCTGTTCAACCCCGAGGTGAGGGGCCTGAAAAGCGCCCAGGAGGTGGAGCTGCTGAGGG
AGAAGGTGTACGCCGCCCTGGAGGAGTACACCAGGACCACCCACCCCGACGAGCCCGGCA
GATTCGCCAAGCTGCTGCTGAGGCTGCCCAGCCTGAGGAGCATCGGCCTGAAGTGCCTGG
AGCACCTGTTCTTCTTCAGGCTGATCGGCGACGTGCCCATCGACACCTTCCTGATGGAGA
TGCTGGAGAGCCCCAGCGACAGCTGA]⁴ GCATGCCCCCTCTCCCTCCCCCCCCCTAAC
GTTACTGGCCGAAGCCGCTTGGAATAAGGCCGGTGTGCGTTTGTCTATATGTTATTTTCC
ACCATATTGCCGTCTTTTGGCAATGTGAGGGCCCGGAAACCTGGCCCTGTCTTCTTGACG
AGCATTCCTAGGGGTCTTTCCCCTCTCGCCAAAGGAATGCAAGGTCTGTTGAATGTCGTG
AAGGAAGCAGTTCCTCTGGAAGCTTCTTGAAGACAAACAACGTCTGTAGCGACCCTTTGC
AGGCAGCGGAACCCCCCACCTGGCGACAGGTGCCTCTGCGGCCAAAAGCCACGTGTATAA
GATACACCTGCAAAGGCGGCACAACCCCAGTGCCACGTTGTGAGTTGGATAGTTGTGGAA
AGAGTCAAATGGCTCTCCTCAAGCGTATTCAACAAGGGGCTGAAGGATGCCCAGAAGGTA
CCCCATTGTATGGGATCTGATCTGGGGCCTCGGTGCACATGCTTTACATGTGTTTAGTCG
AGGTTAAAAAACGTCTAGGCCCCCCGAACCACGGGGACGTGGTTTTCCTTTGAAAAACAC
GATCCATATGGCCACC[ATGAAGCTGCTGAGCAGCATCGAGCAGGCTTGCGACATCTGCA
GGCTGAAGAAGCTGAAGTGCAGCAAGGAGAAGCCCAAGTGCGCCAAGTGCCTGAAGAACA
ACTGGGAGTGCAGATACAGCCCCAAGACCAAGAGGAGCCCCCTGACCAGGGCCCACCTGA
CCGAGGTGGAGAGCAGGCTGGAGAGGCTGGAGCAGCTGTTCCTGCTGATCTTCCCCAGGG
AGGACCTGGACATGATCCTGAAGATGGACAGCCTGCAAGACATCAAGGCCCTGCTGACCG
GCCTGTTCGTGCAGGACAACGTGAACAAGGACGCCGTGACCGACAGGCTGGCCAGCGTGG
AGACCGACATGCCCCTGACCCTGAGGCAGCACAGGATCAGCGCCACCAGCAGCAGCGAGG
AGAGCAGCAACAAGGGCCAGAGGCAGCTGACCGTGAGCCCCGAGTTT]⁵ CCCGGG[ATCA
GGCCCGAGTGCGTGGTGCCCGAGACCCAGTGCGCCATGAAAAGGAAGGAGAAGAAGGCCC
AGAAGGAGAAGGACAAGCTGCCCGTGAGCACCACCACCGTCGATGACCACATGCCCCCCA

---

[VP16]³

[RXR]⁴

[Gal4DBD]⁵

Fig. 2D

**TCATGCAGTGCGAGCCCCCCCCCCCGAGGCCGCCAGGATTCACGAGGTCGTGCCCAGGT
TCCTGAGCGACAAGCTGCTGGTGACCAACAGGCAGAAGAACATCCCCCAGCTGACCGCCA
ACCAGCAGTTCCTGATCGCCAGGCTGATCTGGTATCAGGACGGCTACGAGCAGCCCAGCG
ACGAGGACCTGAAAAGGATCACCCAGACCTGGCAGCAGGCCGACGACGAGAACGAGGAGA
GCGACACCCCTTCAGGCAGATCACCGAGATGACCATCCTGACCGTGCAGCTGATCGTGG
AGTTCGCCAAGGGCCTGCCCGGATTCGCCAAGATCAGCCAGCCCGACCAGATCACCCTGC
TGAAGGCTTGCAGCAGCGAGGTGATGATGCTGAGGGTGGCCAGGAGGTACGACGCCGCCA
GCGACAGCATCCTGTTCGCCAACAACCAGGCTTACACCAGGGACAACTACAGGAAGGCTG
GCATGGCCGAGGTGATCGAGGACCTCCTGCACTTCTGCAGATGTATGTACAGCATGGCCC
TGGACAACATCCACTACGCCCTGCTGACCGCCGTGGTGATCTTCAGCGACAGGCCCGGCC
TGGAGCAGCCCCAGCTGGTGGAGGAGATCCAGAGGTACTACCTGAACACCCTGAGGATCT
ACATCCTGAACCAGCTGAGCGGCAGCGCCAGGAGCAGCGTGATCTACGGCAAGATCCTGA
GCATCCTGAGCGAGCTGAGGACCCTGGGAATGCAGAACAGCAATATGTGTATCAGCCTGA
AGCTGAAGAACAGGAAGCTGCCCCCCTTCCTGGAGGAGATTTGGGACGTGGCCGACATGA
GCCACACCCAGCCCCCCCCATCCTGGAGAGCCCCACCAACCTGTGA]** [6] ATCGATTAGAC
ATGATAAGATACATTGATGAGTTTGGACAAACCACAACTAGAATGCAGTGAAAAAAATGC
TTAATTTGTGAAATTTGTGATGCTATTGCTTAATTTGTAACCATTATAAGCTGCAATAAA
CAAGTTAATAAAACATTTGCATTCATTTTATGTTTCAGGTCAGGGGAGATGTGGGAGG
TTTTTTAAAGCAAGTAAAACCTCTACAAATGTGGTATCTAGAGCTCTTCCAAAATTAATA
CGCATTCGCGTGCGAAATCATTACCCTGTTATCCCTACGCCTAGCCTTAGGGTTCACATC
TATGTCGGGTGCGGAGAAAGAGGTAATGAAATGGCAATAACAGGCTAGAACCAGCTAACG
TTAGGAGCATAGATTGGGGCATTCCGGAACTATAAATTGCGTTGCGCTCACTGCCCGCTT
TCCAGTCGGGAAACCTGTCGTGCCAGCTGCATAAATGAATCGGCCAACGCGCGGGGAGAG
GCGGTTTGCGTATTGGGCGCGCTTCCGCTTCCTCGCTCACTGACTCGCTGCGCTCGGTCG
TTCGGCTGCGGCGAGCGGTATCAGCTCACTCAAAGGCGGTAATACGGTTATCCACAGAAT
CAGGGGATAACGCAGGAAAGAACATGTGAGCAAAAGGCCAGCAAAAGGCCAGGAACCGTA
AAAAGGCCGCGTTGCTGGCGTTTTTCCATAGGCTCCGCCCCCTGACGAGCATCACAAAA
ATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGT
CCGCCTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGACACGACTTAT
CGCCACTGGCAGCAGCCACTGGTAACAGGATTAGCAGAGCGAGGTATGTAGGCGGTGCTA
CAGAGTTCTTGAAGTGGTGGCCTAACTACGGCTACACTAGAAGAACAGTATTTGGTATCT
GCGCTCTGCTGAAGCCAGTTACCTTCGGAAAAAGAGTTGGTAGCTCTTGATCCGGCAAAC
AAACCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTGACA
TGCGCAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAG

---

[EcR VY][6]

Fig. 2E

```
CAATAAACCAGCCAGCCGGAAGCGCCGAGCGCAGAAGTGGTCCTGCAACTTTATCCGCCT
CCATCCAGTCTATTAACTGTTGCCGGGAAGCTAGAGTAAGTAGTTCGCCAGTTAATAGTT
TGCGGAGCGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCATGTTGTGCA
AAAAAGCGGTTAGCTCCTTCGGTCCTCCGATGGTTGTCAGAAGTAAGTTGGCCGCAGTGT
TATCACTCATGGTTATGGCAGCACTGCATAATTCTCTTACTGTCATGCCATCCGTAAGAT
GCTTTTCTGTGACTGGTGAGTATTCAACCAAGTCATTCTGAGAATAGTGTATGCGGCGAC
CGAGTTGCTCTTGCCCGGCGTCAATACGGGATAATACCGCGCCACATAGCAGAACTTTAA
AAGTGCTCATCATTGGGAAGCGTTCTTCGGGGCGAAAACTCTCAAGGATCTTACCGCTGT
TGAGATCCAGTTCGATGTAACCCACACGAGCACCCAACTGATCTTCAGCATCTTTTACTT
TCACCAGCGTTTCTGGGTGAGCAAAAACAGGAAGGCAAAATGCCGCAAAAAAGGGAATAA
GGGCGACACGGAAATGTTGAATACTCATACTCTTCCTTTTTCAATATTATTGAAGCATTT
ATCAGGGTTATTGTCTCATGAGCGGATACATATTTGAATGTATTTAGAAAAATAAACAAA
TAGGGGTTCCGCGCACATTTCCCCGAAAAGTGCCACCTGAGGTCTAAGAAACCATTATTA
TCATGACATTAACCTATAAAAATAGGCGTATCACGAGGCCCTTTCTTCTCGCGCGTTTCG
GTGATGACGGTGAAAACCTCTGACACATGCAGCTCCCGGATACGGTCACAGCTTGTCTGT
AAGCGGATGCCGGGAGCAGACAAGCCCGTCAGGGCGCGTCAGCGGGTGTTGGCGGGTGTC
GGGGCTGGCTTAA     (SEQ ID NO: 1)
```

BORON-CONTAINING DIACYLHYDRAZINE COMPOUNDS

BACKGROUND OF THE INVENTION

Field of the Invention

This invention is in the fields of biotechnology, genetic engineering, gene expression, and medicinal chemistry. The invention provides novel boron-containing diacylhydrazines and the use of these compounds in nuclear receptor-based inducible gene expression systems.

Background

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., *Proc. Natl. Acad. Sci. USA* 83:5414-5418 (1986); Arnheiter et al., *Cell* 62:51-61 (1990); Filmus et al., *Nucleic Acids Research* 20:27550-27560 (1992)). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., *Science* 262:1019-24 (1993); Belshaw et al., *Proc Natl Acad Sci USA* 93:4604-7 (1996)). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla et al., *Annu. Rev. Entomol.* 43: 545-569 (1998)). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al., *Cell*, 67:59-77 (1991)). EcR receptors are responsive to a number of steroidal compounds such as ponasterone A and muristerone A. Non-steroidal compounds with ecdysteroid agonist activity have been described, including the commercially available insecticides tebufenozide and methoxyfenozide (see WO 96/27673 and U.S. Pat. No. 5,530,028). Both analogs have exceptional safety profiles in other organisms.

The insect ecdysone receptor (EcR) heterodimerizes with Ultraspiracle (USP), the insect homologue of the mammalian retinoid X receptor (RXR), and binds ecdysteroids and ecdysone receptor response elements to activate transcription of ecdysone responsive genes. The EcR/USP/ligand complexes play important roles during insect development and reproduction. The EcR has five modular domains, A/B (transactivation), C (DNA binding, heterodimerization), D (Hinge, heterodimerization), E (ligand binding, heterodimerization and transactivation) and F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals.

The first version of an EcR-based gene switch used *Drosophila melanogaster* EcR (DmEcR) and *Mus musculus* RXR (MmRXR) and showed that these receptors in the presence of steroid, ponasterone A, transactivate reporter genes in mammalian cell lines and transgenic mice (Christopherson et al., *Proc. Natl. Acad. Sci. U.S.A.* 89:6314-6318 (1992); No et al., *Proc. Natl. Acad. Sci. U.S.A.* 93:3346-3351 (1996)). Later, Suhr et al., *Proc. Natl. Acad. Sci.* 95:7999-8004 (1998) showed that non-steroidal ecdysone agonist, tebufenozide, induced high level of transactivation of reporter genes in mammalian cells through *Bombyx mori* EcR (BmEcR) in the absence of exogenous heterodimer partner.

WO 97/38117 and WO99/58155 disclose methods for modulating the expression of an exogenous gene in which a DNA construct comprising the exogenous gene and an ecdysone response element is activated by a second DNA construct comprising an ecdysone receptor that, in the presence of a ligand therefore, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. WO 99/02683 discloses that the ecdysone receptor isolated from the silk moth *Bombyx mori* is functional in mammalian systems without the need for an exogenous dimer partner.

U.S. Pat. No. 6,265,173 B1 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression.

In each of these cases, the transactivation domain and the DNA binding domain (either as native EcR as in WO 99/02683 or as modified EcR as in WO 97/38117) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880,333). Therefore, a need exists in the art for improved EcR-based systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. For certain applications such as gene therapy, it may be desirable to have an inducible gene expression system that responds well to synthetic non-steroid ligands and, at the same time, is insensitive to the natural steroids. Thus, improved systems that are simple, compact, and dependent on ligands that are relatively inexpensive, readily available, and of low toxicity to the host would prove useful for regulating biological systems.

It has been shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (see WO 01/70816 A1). This two-hybrid system is a significantly improved inducible gene expression modulation system compared to the two systems disclosed in applications WO 97/38117 and WO 99/02683. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. Furthermore, the two-hybrid system avoids some side effects due to overexpression of RXR that often occur when unmodified RXR is used as a heterodimer receptor partner. In one two-hybrid system, native DNA binding and transactivation domains of EcR or RXR are eliminated and as a result, these hybrid molecules have less chance of interacting with other steroid hormone receptors present in the cell resulting in reduced side effects. Additional gene switch systems include those described in the following patents and patent applications: U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S. Pat. No. 6,258,603; US20050209283; US20050228016; US20060020146; EP0965644; U.S. Pat. No. 7,304,162; and U.S. Pat. No. 7,304,161.

With the improvement in ecdysone receptor-based gene regulation systems, there has been an increase in their use for various applications. Diacylhydrazine ("DAH") compounds, and their application as ligands in ecdysone receptor-based gene regulation systems are disclosed U.S. Pat. Nos. 8,076,517; 7,456,315; 7,304,161; and 6,258,603, and patents cited therein. However, a need exists for DAHs with improved physiochemical and/or pharmacological properties.

BRIEF SUMMARY OF THE FIGURES

FIGS. 2A-2E set forth the nucleic acid sequence (SEQ ID NO: 1) for the vector map of FIG. 1. The nucleic acid sequence set forth in brackets represent the following vector sequence components: [6×GalRE]¹, [fLuc]², [VP16]³, [RXR]⁴, [Gal4DBD]⁵ and [EcR VY]⁶.

BRIEF SUMMARY OF THE INVENTION

Figure 1:
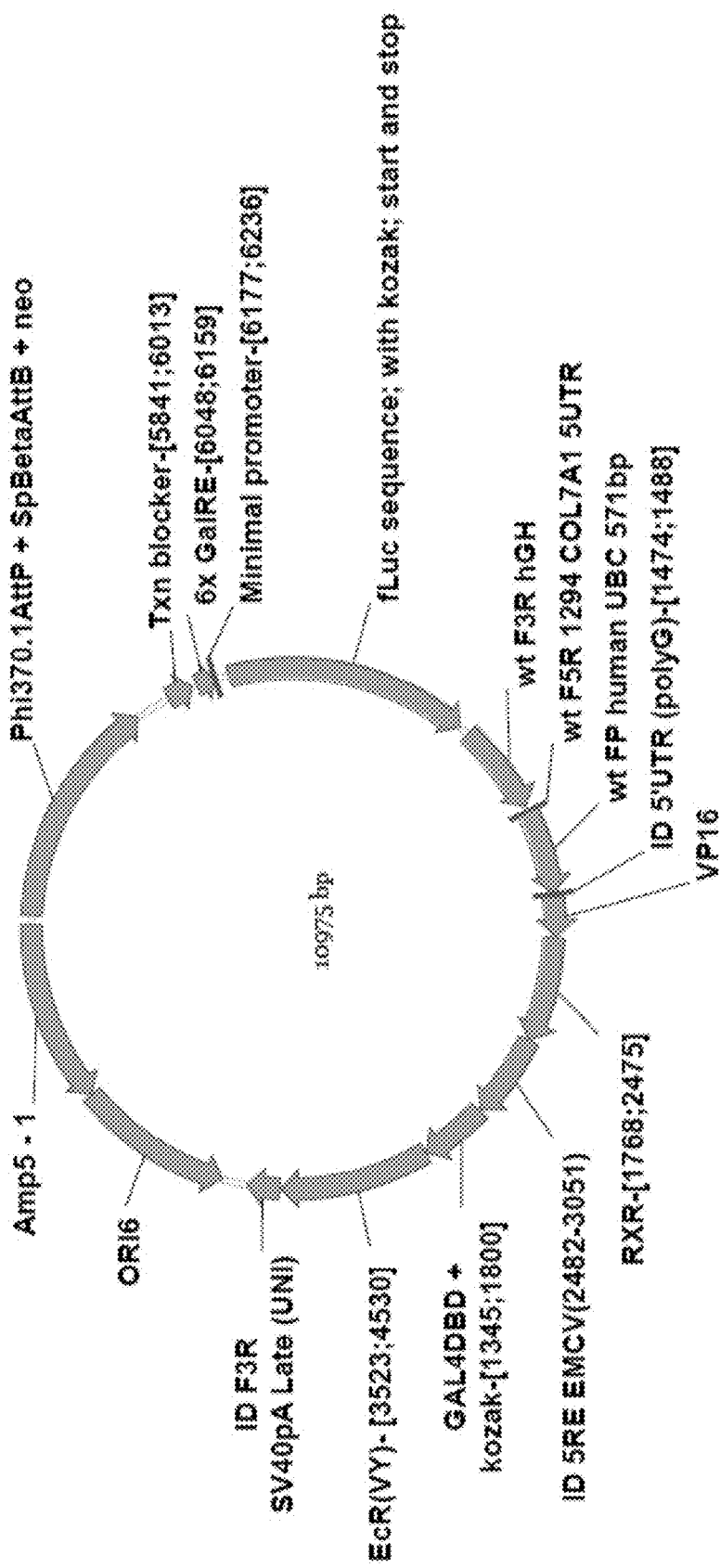
FIG. 1 is a vector map for the RheoSwitch® Vector (RS-1).

In one aspect, the present disclosure provides boron-containing diacylhydrazine compounds represented by Formulae I-XXI below, and the pharmaceutically acceptable salts and solvates, e.g., hydrates thereof, collectively referred to herein as "Compounds of the Disclosure." Compounds of the Disclosure contain at least one boron atom in their structure.

In another aspect, the present disclosure provides compositions comprising a Compound of the Disclosure and one or more excipients. In a further aspect, the composition is a pharmaceutically acceptable composition.

In another aspect, the present disclosure provides Compounds of the Disclosure for use as ligands in ecdysone receptor-based inducible gene expression systems. An advantage of the present disclosure is that it provides a means to regulate gene expression and to tailor expression levels to suit the user's requirements.

In another aspect, the present disclosure provides methods of regulating gene expression of a gene of interest in an isolated host cell or a non-human organism, comprising contacting the host cell or a non-human organism with a Compound of the Disclosure, or composition thereof.

In another aspect, the present disclosure provides methods of treating a disease, disorder, injury, or condition in a subject, comprising administering to the subject a Compound of the Disclosure, or composition thereof.

In another aspect, the present disclosure provides a Compound of the Disclosure, or composition thereof, for use in treating a disease, disorder, injury, or condition.

In another aspect, the present disclosure provides a Compound of the Disclosure, or composition thereof, for use in the manufacture of a medicament for treating a disease, disorder, injury, or condition.

In another aspect, the present disclosure provides a method of controlling insects, comprising contacting said insects or their habitat with an insecticidally effective amount of a Compound of the Disclosure, or composition thereof.

DETAILED DESCRIPTION OF THE INVENTION

In one embodiment, Compounds of the Disclosure are compounds having Formula I:

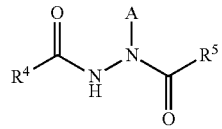

I and the pharmaceutically acceptable salts, solvates, e.g., hydrates, multimeric forms, and/or open- and closed-ring forms thereof, wherein:

A is selected from the group consisting of hydrogen and —C($R^1$)($R^2$)($R^3$);

$R^1$, $R^2$, and $R^3$ are each independently selected from the group consisting of hydrogen and optionally substituted alkyl;

$R^4$ is selected from the group consisting of:

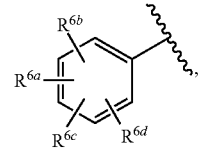

$R^4$-1

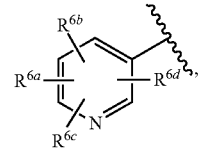

$R^4$-2

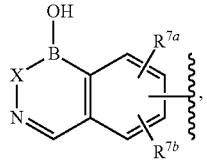

$R^4$-3

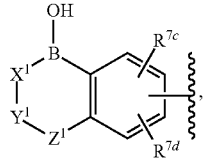

$R^4$-4

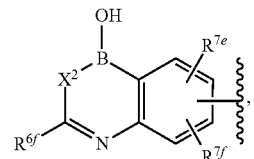

$R^4$-5

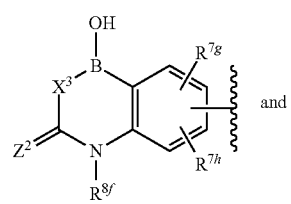

$R^4$-6 and

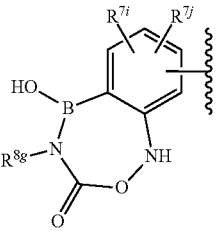

$R^4$-7

X is selected from the group consisting of —O— and —N($R^{8a}$)—;

$X^1$ is selected from the group consisting of —O— and —N($R^{8b}$)—;

$X^2$ is selected from the group consisting of —O— and —N($R^{8c}$)—;

$X^3$ is selected from the group consisting of —O— and —N($R^{8d}$)—;

$Y^1$ is —($CR^{9a}R^{9b}$)$_m$—;

m is 0, 1, 2, or 3;

$Z^1$ is selected from the group consisting of —O— and —N($R^{8e}$)—, or $Z^1$ is absent;

$Z^2$ is selected from the group consisting of O, S, and NH;

$R^{6a}$ is selected from the group consisting of hydrogen, —B(OH)$_2$, and pinacolborane;

$R^{6b}$, $R^{6c}$, and $R^{6d}$ are each independently selected from the group consisting of hydrogen, halo, nitro, cyano, hydroxy, amino, —N(H)CHO, —N(H)CN, —N(H)(cyano)alkyl, —CHO, optionally substituted alkyl, haloalkyl, alkoxyalkyl, hydroxyalkyl, arylalkyl, (amino)alkyl, (alkylamino)alkyl, (dialkylamino)alkyl, (cyano)alkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{10}$, —SO$_2$R$^{11}$, —N(R$^{12}$)COR$^{13}$, —N(R$^{12}$)SO$_2$R$^{14}$ or N(R$^{12}$)C=N(R$^{15}$)-amino; or $R^{6b}$ is selected from the group consisting of hydrogen, halo, nitro, cyano, hydroxy, —N(H)CHO, —N(H)CN, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{10}$, —SO$_2$R$^{11}$, —N(R$^{12}$)COR$^{13}$, —N(R$^{12}$)SO$_2$R$^{14}$ or N(R$^{12}$)C=N(R$^{15}$)-amino; and/or $R^{6c}$ and $R^{6d}$ taken together with two adjacent carbon atoms form a fused optionally substituted cycloalkyl, optionally substituted heterocyclo, or optionally substituted heteroaryl group;

$R^{6f}$ is selected from the group consisting of hydrogen, alkyl, amino, alkylamino, dialkylamino, and hydroxy;

$R^{7a}$, $R^{7b}$, $R^{7a}$, $R^{7d}$, $R^{7e}$, $R^{7f}$, $R^{7g}$, $R^{7h}$, $R^{7i}$, and $R^{7j}$ are each independently selected from the group consisting of hydrogen, halo, nitro, cyano, hydroxy, amino, optionally substituted alkyl, haloalkyl, hydroxyalkyl, alkoxy, and alkylthio;

$R^{8a}$, $R^{8b}$, $R^{8c}$, $R^{8d}$, $R^{8e}$, $R^{8f}$, and $R^{8g}$ are each independently selected from the group consisting of hydrogen, alkyl, optionally substituted aryl, optionally substituted heteroaryl, alkylsulfonyl, arylsulfonyl, alkylcarbonyl, and arylcarbonyl;

$R^{9a}$ and $R^{9b}$ are each independently selected from the group consisting of hydrogen, alkyl, and cyano;

$R^5$ is selected from the group consisting of:

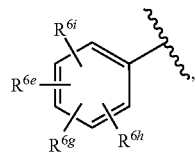

R$^5$-1

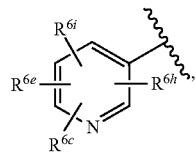

R$^5$-2

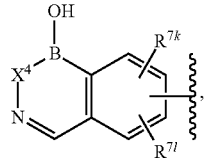

R$^5$-3

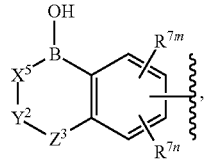

R$^5$-4

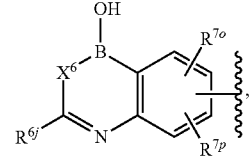

R$^5$-5

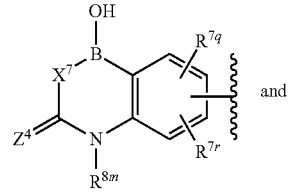

R$^5$-6 and

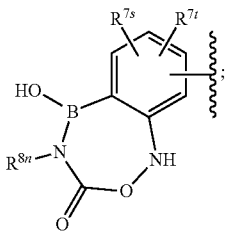

R$^5$-7;

$X^4$ is selected from the group consisting of —O— and —N($R^{8h}$)—;

$X^5$ is selected from the group consisting of —O— and —N($R^{8i}$)—;

$X^6$ is selected from the group consisting of —O— and —N($R^{8j}$)—;

$X^7$ is selected from the group consisting of —O— and —N($R^{8k}$)—;

$Y^2$ is —($CR^{9c}R^{9d}$)$_n$—;

n is 0, 1 2, or 3;

$Z^3$ is selected from the group consisting of —O— and —N($R^{8l}$)—, or $Z^3$ is absent;

$Z^4$ is selected from the group consisting of O, S, and NH;

$R^{6e}$ is selected from the group consisting of hydrogen, —B(OH)$_2$, and pinacolborane;

$R^{6g}$, $R^{6h}$, and $R^{6i}$ are each independently selected from the group consisting of hydrogen, halo, nitro, cyano, hydroxy, amino, —N(H)CHO, —N(H)CN, —N(H)(cyano)alkyl, —CHO, optionally substituted alkyl, haloalkyl, alkoxyalkyl, hydroxyalkyl, arylalkyl, (amino)alkyl, (alkylamino)alkyl, (dialkylamino)alkyl, (cyano)alkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{10}$, —SO$_2$R$^{11}$, —N(R$^{12}$)COR$^{13}$, —N(R$^{12}$)SO$_2$R$^{14}$ or N(R$^{12}$)C=N(R$^{15}$)-amino; or R$^{6g}$ is selected from the group consisting of hydrogen, halo, nitro, cyano, hydroxy, —N(H)CHO, —N(H)CN, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{10}$, —SO$_2$R$^{11}$, —N(R$^{12}$)COR$^{13}$, —N(R$^{12}$)SO$_2$R$^{14}$ or N(R$^{12}$)C=N(R$^{15}$)-amino; and/or R$^{6h}$ and R$^{6i}$ taken together with two adjacent carbon atoms form a fused optionally substituted cycloalkyl, optionally substituted heterocyclo, or optionally substituted heteroaryl group;

R$^{6j}$ is selected from the group consisting of hydrogen, alkyl, amino, and hydroxy;

R$^{7k}$, R$^{7l}$, R$^{7m}$, R$^{7n}$, R$^{7o}$, R$^{7p}$, R$^{7q}$, R$^{7r}$, R$^{7s}$, and R$^{7t}$ are each independently selected from the group consisting of hydrogen, halo, nitro, cyano, hydroxy, amino, optionally substituted alkyl, haloalkyl, hydroxyalkyl, alkoxy, and alkylthio;

R$^{8h}$, R$^{8i}$, R$^{8j}$, R$^{8k}$, R$^{8l}$, R$^{8m}$, and R$^{8n}$ are each independently selected from the group consisting of hydrogen, alkyl, optionally substituted aryl, optionally substituted heteroaryl, alkylsulfonyl, arylsulfonyl, alkylcarbonyl, and arylcarbonyl;

R$^{9c}$ and R$^{9d}$ are each independently selected from the group consisting of hydrogen, alkyl, and cyano;

R$^{10}$ is selected from the group consisting of hydrogen, hydroxy, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy, and arylalkyloxy;

R$^{11}$ is selected from the group consisting of haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, and optionally substituted heteroaryl;

R$^{12}$ is selected from the group consisting of hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, and optionally substituted heteroaryl;

R$^{13}$ is selected from the group consisting of hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy, arylalkyloxy, and amino;

R$^{14}$ is selected from the group consisting of haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, and amino; and R$^{15}$ is selected from the group consisting of hydrogen, alkyl, aryl, cyano, and nitro.

In another embodiment, Compounds of the Disclosure are compounds having Formula I, and the pharmaceutically acceptable salts, solvates, e.g., hydrates, multimeric forms, and/or open- and closed-ring forms, thereof, with the proviso that when R$^4$ is R$^4$-1 or R$^4$-2 and R$^5$ is R$^5$-1 or R$^5$-2, then one of R$^{6a}$ or R$^{6e}$ is —B(OH)$_2$ or pinacolborane.

In another embodiment, Compounds of the Disclosure are compounds having Formula I, and the pharmaceutically acceptable salts, solvates, e.g., hydrates, multimeric forms, and/or open- and closed-ring forms, thereof, wherein R$^4$ is selected from the group consisting of R$^4$-3, R$^4$-4, R$^4$-5, R$^4$-6, and R$^4$-7; R$^5$ is selected from the group consisting of R$^5$-1 and R$^5$-2; and R$^{6e}$ is hydrogen.

In another embodiment, Compounds of the Disclosure are compounds having Formula I, and the pharmaceutically acceptable salts, solvates, e.g., hydrates, multimeric forms, and/or open- and closed-ring forms thereof, wherein R$^5$ is selected from the group consisting of R$^5$-3, R$^5$-4, R$^5$-5, R$^5$-6, and R$^5$-7; R$^4$ is selected from the group consisting of R$^4$-1 and R$^4$-2; and R$^{6a}$ is hydrogen.

In another embodiment, Compounds of the Disclosure are compounds having Formula II:

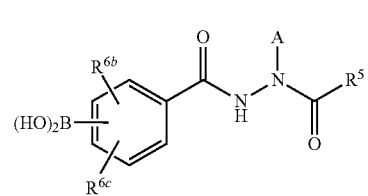

and the pharmaceutically acceptable salts, solvates, e.g., hydrates, multimeric forms, and/or open- and closed-ring forms thereof, wherein R$^5$ is selected from the group consisting of R$^5$-1 and R$^5$-2; R$^{6e}$ is hydrogen; and A, R$^{6b}$, and R$^{6c}$ are as defined above in connection with Formula I. In another embodiment, R$^{6b}$ is selected from the group consisting of —CHO, —N(R$^{12}$)SO$_2$R$^{14}$, hydroxyalkyl, (amino)alkyl, (alkylamino)alkyl, (dialkylamino)alkyl, and —N(H)(cyano)alkyl. In another embodiment, R$^{6c}$ is hydrogen.

In another embodiment, Compounds of the Disclosure are compounds having Formula III:

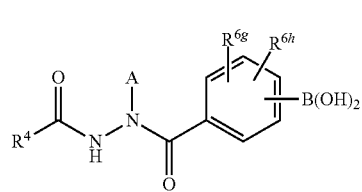

and the pharmaceutically acceptable salts, solvates, e.g., hydrates, multimeric forms, and/or open- and closed-ring forms thereof, wherein R$^4$ is selected from the group consisting of R$^4$-1 and R$^4$-2; R$^{6a}$ is hydrogen; and A, R$^{6g}$, and R$^{6h}$ are as defined above in connection with Formula I. In another embodiment, R$^{6g}$ is selected from the group consisting of —CHO, —N(R$^{12}$)SO$_2$R$^{14}$, halo, hydroxyalkyl, (amino)alkyl, (alkylamino)alkyl, and (dialkylamino)alkyl. In another embodiment, R$^{6h}$ is hydrogen.

In another embodiment, Compounds of the Disclosure are compounds having Formula IV:

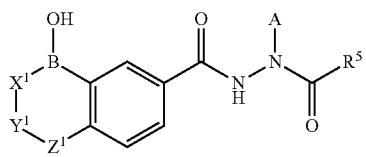

IV and the pharmaceutically acceptable salts, solvates, e.g., hydrates, multimeric forms, and/or open- and closed-ring forms thereof, wherein $R^5$ is selected from the group consisting of $R^5$-1 and $R^5$-2; $R^{6e}$ is hydrogen; and A, $X^1$, $Y^1$ and $Z^1$ are as defined above in connection with Formula I. In another embodiment, $Z^1$ is absent; $Y^1$ is selected from the group consisting of —CH$_2$— and —CH$_2$CH$_2$—; and $X^1$ is selected from the group consisting of —O— and —N(H)—. In another embodiment, $Z^1$ is —N(H)—; $Y^1$ is —CH$_2$CH$_2$—; and $X^1$ is —O—.

In another embodiment, Compounds of the Disclosure are compounds having Formula V:

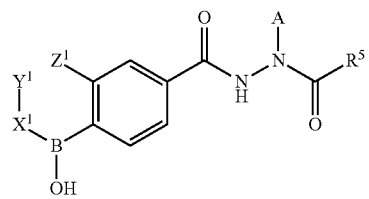

V and the pharmaceutically acceptable salts, solvates, e.g., hydrates, multimeric forms, and/or open- and closed-ring forms thereof, wherein $R^5$ is selected from the group consisting of $R^5$-1 and $R^5$-2; $R^{6e}$ is hydrogen; and A, $X^1$, $Y^1$ and $Z^1$ are as defined above in connection with Formula I. In another embodiment, $Z^1$ is absent; $Y^1$ is selected from the group consisting of —CH$_2$— and —CH$_2$CH$_2$—; and $X^1$ is selected from the group consisting of —O— and —N(H)—. In another embodiment, $Z^1$ is —N(H)—; $Y^1$ is —CH$_2$CH$_2$—; and $X^1$ is —O—.

In another embodiment, Compounds of the Disclosure are compounds having Formula VI:

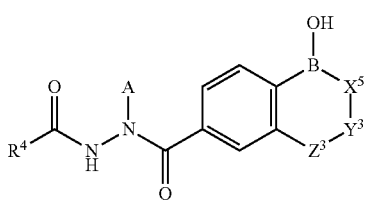

VI and the pharmaceutically acceptable salts, solvates, e.g., hydrates, multimeric forms, and/or open- and closed-ring forms thereof, wherein $R^4$ is selected from the group consisting of $R^4$-1 and $R^4$-2; $R^{6a}$ is hydrogen; and A, $X^5$, $Y^3$ and $Z^3$ are as defined above in connection with Formula I. In another embodiment, $Z^3$ is absent; $Y^2$ is selected from the group consisting of —CH$_2$— and —CH$_2$CH$_2$—; and $X^5$ is selected from the group consisting of —O— and —N(H)—. In another embodiment, $Z^3$ is —N(H)—; $Y^2$ is —CH$_2$CH$_2$—; and $X^5$ is —O—.

In another embodiment, Compounds of the Disclosure are compounds having Formula VII:

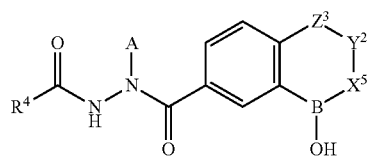

VII and the pharmaceutically acceptable salts, solvates, e.g., hydrates, multimeric forms, and/or open- and closed-ring forms thereof, wherein $R^4$ is selected from the group consisting of $R^4$-1 and $R^4$-2; $R^{6a}$ is hydrogen; and A, $X^5$, $Y^3$ and $Z^3$ are as defined above in connection with Formula I. In another embodiment, $Z^3$ is absent; $Y^2$ is selected from the group consisting of —CH$_2$— and —CH$_2$CH$_2$—; and $X^5$ is selected from the group consisting of —O— and —N(H)—. In another embodiment, $Z^3$ is —N(H)—; $Y^2$ is —CH$_2$CH$_2$—; and $X^5$ is —O—.

In another embodiment, Compounds of the Disclosure are compounds having Formula VIII:

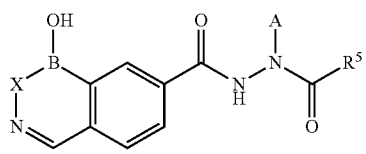

VIII and the pharmaceutically acceptable salts, solvates, e.g., hydrates, multimeric forms, and/or open- and closed-ring forms thereof, wherein $R^5$ is selected from the group consisting of $R^5$-1 and $R^5$-2; $R^{6e}$ is hydrogen; and A and X are as defined above in connection with Formula I. In another embodiment, X is —O—. In another embodiment, X is —N($R^{8a}$)—; and $R^{8a}$ is selected from the group consisting of hydrogen, alkyl, optionally substituted aryl, optionally substituted heteroaryl, alkylsulfonyl, arylsulfonyl, and alkylcarbonyl.

In another embodiment, Compounds of the Disclosure are compounds having Formula IX:

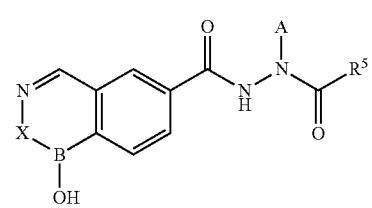

IX and the pharmaceutically acceptable salts, solvates, e.g., hydrates, multimeric forms, and/or open- and closed-ring forms thereof, wherein $R^5$ is selected from the group consisting of $R^5$-1 and $R^5$-2; $R^{6e}$ is hydrogen; and A and X are as defined above in connection with Formula I. In another embodiment, X is —O—. In another embodiment, X is —N($R^{8a}$)—; and $R^{8a}$ is selected from the group consisting of hydrogen, alkyl, optionally substituted aryl, optionally substituted heteroaryl, alkylsulfonyl, arylsulfonyl, and alkylcarbonyl.

In another embodiment, Compounds of the Disclosure are compounds having Formula X:

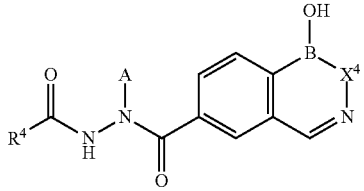

X and the pharmaceutically acceptable salts, solvates, e.g., hydrates, multimeric forms, and/or open- and closed-ring forms thereof, wherein $R^4$ is selected from the group consisting of $R^4$-1 and $R^4$-2; $R^{6a}$ is hydrogen; and A and $X^4$ are as defined above in connection with Formula I. In another embodiment, $X^4$ is —O—. In another embodiment, $X^4$ is —N($R^{8h}$)—; and $R^{8h}$ is selected from the group consisting of hydrogen, alkyl, optionally substituted aryl, alkylsulfonyl, arylsulfonyl, and alkylcarbonyl.

In another embodiment, Compounds of the Disclosure are compounds having Formula XI:

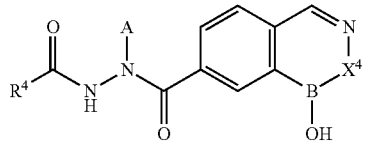

XI and the pharmaceutically acceptable salts, solvates, e.g., hydrates, multimeric forms, and/or open- and closed-ring forms thereof, wherein $R^4$ is selected from the group consisting of $R^4$-1 and $R^4$-2; and $R^{ha}$ is hydrogen; and A and $X^4$ are as defined above in connection with Formula I. In another embodiment, $X^4$ is —O—. In another embodiment, $X^4$ is —N($R^{8h}$)—; and $R^{8h}$ is selected from the group consisting of hydrogen, alkyl, optionally substituted aryl, alkylsulfonyl, arylsulfonyl, and alkylcarbonyl.

In another embodiment, Compounds of the Disclosure are compounds having Formula XII:

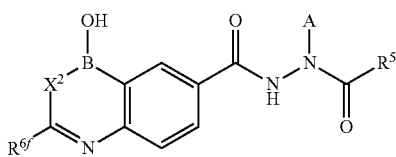

XII and the pharmaceutically acceptable salts, solvates, e.g., hydrates, multimeric forms, and/or open- and closed-ring forms thereof, wherein $R^5$ is selected from the group consisting of $R^5$-1 and $R^5$-2; $R^{6e}$ is hydrogen; and A, $X^2$, and $R^{6f}$ are as defined above in connection with Formula I. In another embodiment, $X^2$ is —O—. In another embodiment, $X^2$ is N($R^{8b}$)—; and $R^{8b}$ is selected from the group consisting of hydrogen and alkyl.

In another embodiment, Compounds of the Disclosure are compounds having Formula XIII:

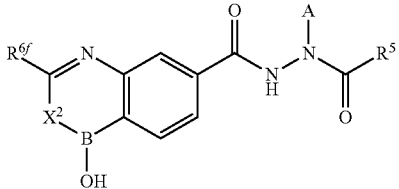

XIII and the pharmaceutically acceptable salts, solvates, e.g., hydrates, multimeric forms, and/or open- and closed-ring forms thereof, wherein $R^5$ is selected from the group consisting of $R^5$-1 and $R^5$-2; $R^{6e}$ is hydrogen; and A, $X^2$, and $R^{6f}$ are as defined above in connection with Formula I. In another embodiment, $X^2$ is —O—. In another embodiment, $X^2$ is N($R^{8b}$)—; and $R^{8b}$ is selected from the group consisting of hydrogen and alkyl.

In another embodiment, Compounds of the Disclosure are compounds having Formula XIV:

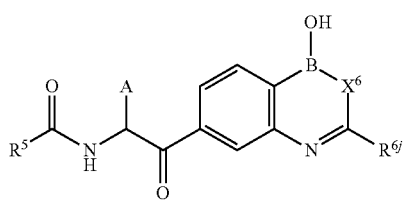

XIV and the pharmaceutically acceptable salts, solvates, e.g., hydrates, multimeric forms, and/or open- and closed-ring forms thereof, wherein $R^4$ is selected from the group consisting of $R^4$-1 and $R^4$-2; $R^{6a}$ is hydrogen; and A, $X^6$, and $R^{6j}$ are as defined above in connection with Formula I. In another embodiment, $X^6$ is —O—. In another embodiment, $X^6$ is —N($R^{8j}$)—; and $R^{8j}$ is selected from the group consisting of hydrogen and alkyl.

In another embodiment, Compounds of the Disclosure are compounds having Formula XV:

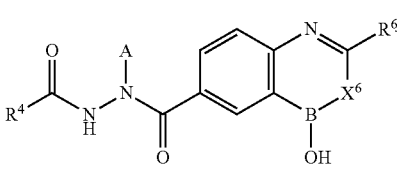

XV and the pharmaceutically acceptable salts, solvates, e.g., hydrates, multimeric forms, and/or open- and closed-ring forms thereof, wherein $R^4$ is selected from the group consisting of $R^4$-1 and $R^4$-2; $R^{6a}$ is hydrogen; and A, $X^6$, and $R^{6j}$ are as defined above in connection with Formula I. In another embodiment, $X^6$ is —O—. In another embodiment, $X^6$ is —N($R^{8j}$)—; and $R^{8j}$ is selected from the group consisting of hydrogen and alkyl.

In another embodiment, Compounds of the Disclosure are compounds having Formula XVI:

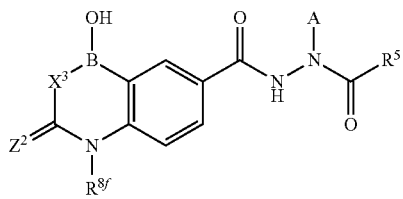

XVI and the pharmaceutically acceptable salts, solvates, e.g., hydrates, multimeric forms, and/or open- and closed-ring forms thereof, wherein $R^5$ is selected from the group consisting of $R^5$-1 and $R^5$-2; $R^{6e}$ is hydrogen; and A, $X^3$, $Z^2$, and $R^{8f}$ are as defined above in connection with Formula I. In another embodiment, $Z^2$ is O. In another embodiment, $X^3$ is —N($R^{8d}$)—; and $R^{8d}$ is selected from the group consisting of hydrogen, alkyl, and optionally substituted aryl.

In another embodiment, Compounds of the Disclosure are compounds having Formula XVII:

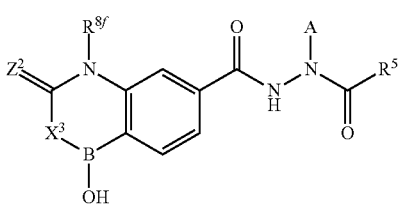

XVII and the pharmaceutically acceptable salts, solvates, e.g., hydrates, multimeric forms, and/or open- and closed-ring forms thereof, wherein $R^5$ is selected from the group consisting of $R^5$-1 and $R^5$-2; $R^{6e}$ is hydrogen; and A, $X^3$, $Z^2$, and $R^{8f}$ are as defined above in connection with Formula I. In another embodiment, $Z^2$ is O. In another embodiment, $X^3$ is —N($R^{8d}$)—; and $R^{8d}$ is selected from the group consisting of hydrogen, alkyl, and optionally substituted aryl.

In another embodiment, Compounds of the Disclosure are compounds having Formula XVIII:

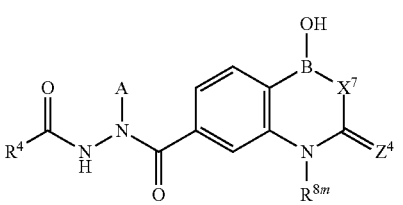

XVIII and the pharmaceutically acceptable salts, solvates, e.g., hydrates, multimeric forms, and/or open- and closed-ring forms thereof, wherein $R^4$ is selected from the group consisting of $R^4$-1 and $R^4$-2; $R^{6a}$ is hydrogen; and A, $X^7$, $Z^4$, and $R^{8m}$ are as defined above in connection with Formula I. In another embodiment, $Z^4$ is O. In another embodiment, $X^7$ is —N($R^{8k}$)—; and $R^{8k}$ is selected from the group consisting of hydrogen, alkyl, and optionally substituted aryl.

In another embodiment, Compounds of the Disclosure are compounds having Formula XIX:

XIX and the pharmaceutically acceptable salts, solvates, e.g., hydrates, multimeric forms, and/or open- and closed-ring forms thereof, wherein $R^4$ is selected from the group consisting of $R^4$-1 and $R^4$-2; $R^{6a}$ is hydrogen; and A, $X^7$, $Z^4$, and $R^{8m}$ are as defined above in connection with Formula I. In another embodiment, $Z^4$ is O. In another embodiment, $X^7$ is —N($R^{8k}$)—; and $R^{8k}$ is selected from the group consisting of hydrogen, alkyl, and optionally substituted aryl.

In another embodiment, Compounds of the Disclosure are compounds having any one of Formulae I-XIX, and the pharmaceutically acceptable salts, solvates, e.g., hydrates, multimeric forms, and/or open- and closed-ring forms thereof, wherein A is hydrogen.

In another embodiment, Compounds of the Disclosure are compounds having any one of Formulae I-XIX, and the pharmaceutically acceptable salts, solvates, e.g., hydrates, multimeric forms, and/or open- and closed-ring forms thereof, wherein A is —C($R^1$)($R^2$)($R^3$), e.g., a compound having:

Formula II-A:

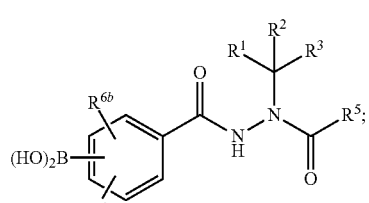

II-A

Formula III-A:

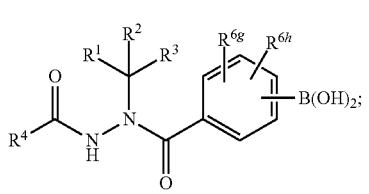

III-A

Formula IV-A:

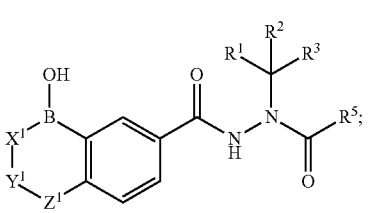

IV-A

Formula V-A:
V-A
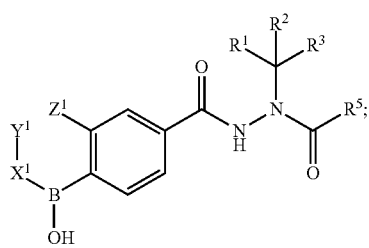
Formula VI-A:
VI-A
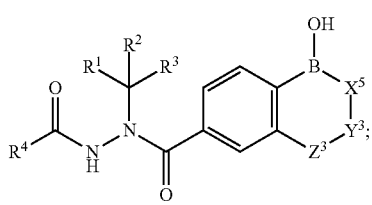
Formula VII-A:
VII-A
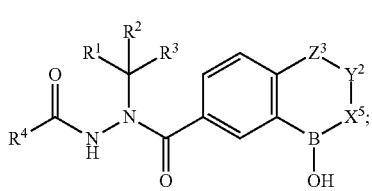
Formula VIII-A:
VIII-A
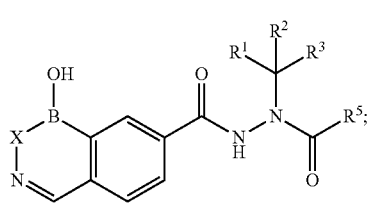
Formula IX-A:
IX-A
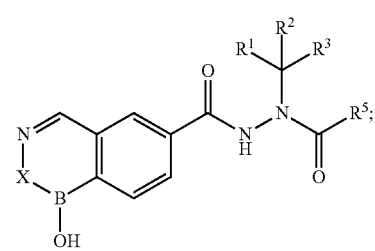
Formula VIII-A:
VIII-A
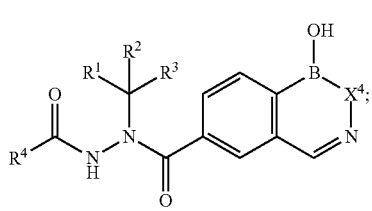
Formula IX-A:
IX-A
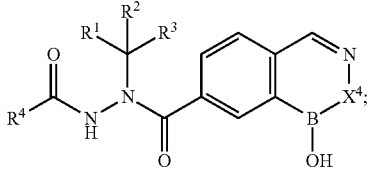
Formula X-A:
X-A
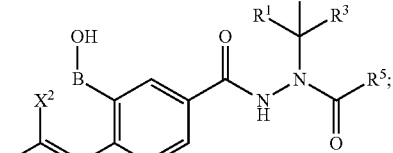
Formula XI-A:
XI-A
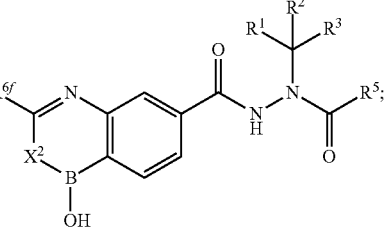
Formula XII-A:
XII-A
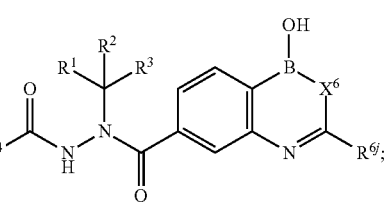
Formula XIII-A:
XIII-A
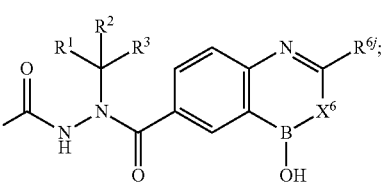
Formula XIV-A:
XIV-A
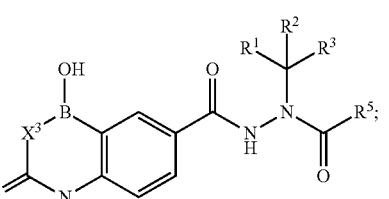

Formula XV-A:

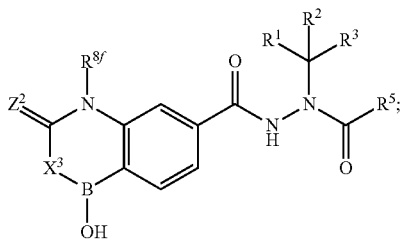

Formula XVI-A:

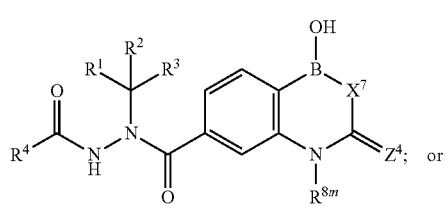

Formula XVII-A:

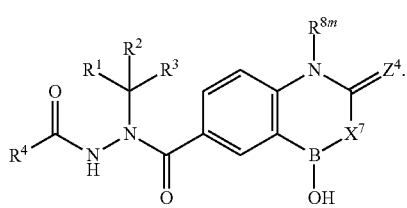

In another embodiment, Compounds of the Disclosure are compounds having any one of Formulae I-XIX, and the pharmaceutically acceptable salts, solvates, e.g., hydrates, multimeric forms, and/or open- and closed-ring forms thereof, wherein A is —C($R^1$)($R^2$)($R^3$) and $R^1$, $R^2$, and $R^3$ are each methyl, or a pharmaceutically acceptable salt or solvate thereof. In another embodiment, $R^1$ is selected from the group consisting of methyl, ethyl, n-propyl, and n-butyl; and $R^2$ is selected from the group consisting of hydrogen and methyl. In another embodiment, $R^3$ is selected from the group consisting of methyl and tert-butyl. In another embodiment, $R^2$ is hydrogen and $R^3$ is tert-butyl.

In another embodiment, Compounds of the Disclosure are compounds having any one of Formulae I-XIX, and the pharmaceutically acceptable salts, solvates, e.g., hydrates, multimeric forms, and/or open- and closed-ring forms thereof, wherein the compound does not exhibit optical activity.

In another embodiment, Compounds of the Disclosure are compounds having any one of Formulae I-XIX, and the pharmaceutically acceptable salts, solvates, e.g., hydrates, multimeric forms, and/or open- and closed-ring forms thereof, wherein the carbon atom bearing $R^1$, $R^2$, and $R^3$ is an asymmetric carbon atom and the absolute configuration of said asymmetric carbon atom is R, i.e., the compound is enantiomerically enriched in the R isomer, and the pharmaceutically acceptable salts and solvates thereof. In a further embodiment, Compounds of the Disclosure are compounds having any one of Formulae I-XIX, and the pharmaceutically acceptable salts, solvates, e.g., hydrates, multimeric forms, and/or open- and closed-ring forms thereof, wherein the enantiomeric excess of the R isomer is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of the R isomer is at least about 90%. In a further embodiment, the enantiomeric excess of the R isomer is at least about 95%. In a further embodiment, the enantiomeric excess of the R isomer is at least about 98%. In a further embodiment, the enantiomeric excess of the R isomer is at least about 98%.

In another embodiment, Compounds of the Disclosure are compounds having any one of Formulae I-XIX, and the pharmaceutically acceptable salts, solvates, e.g., hydrates, multimeric forms, and/or open- and closed-ring forms thereof, wherein the carbon atom bearing $R^1$, $R^2$, and $R^3$ is an asymmetric carbon atom and the absolute configuration of said asymmetric carbon atom is S, i.e., the compound is enantiomerically enriched in the S isomer, and the pharmaceutically acceptable salts and solvates thereof. In a further embodiment, Compounds of the Disclosure are compounds having any one of Formulae I-XIX, and the pharmaceutically acceptable salts, solvates, e.g., hydrates, multimeric forms, and/or open- and closed-ring forms thereof, wherein the enantiomeric excess of the S isomer is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of the S isomer is at least about 90%. In a further embodiment, the enantiomeric excess of the S isomer is at least about 95%. In a further embodiment, the enantiomeric excess of the S isomer is at least about 98%. In a further embodiment, the enantiomeric excess of the S isomer is at least about 99%.

In another embodiment, Compounds of the Disclosure are compounds having Formula XX:

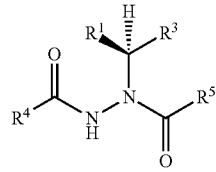

wherein $R^1$ does not equal $R^3$, and $R^1$, $R^3$, $R^4$, and $R^5$ are as defined in connection with Formula I, and the pharmaceutically acceptable salts and solvates thereof. In a further embodiment, the enantiomeric excess of a compound having Formula X, in a mixture of compounds having Formulae XX and XXI, is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of a compound having Formula XX is at least about 90%. In a further embodiment, the enantiomeric excess of a compound having Formula XX is at least about 95%. In a further embodiment, the enantiomeric excess of a compound having Formula XX is at least about 98%. In a further embodiment, the enantiomeric excess of a compound having Formula XX is at least about 99%.

In another embodiment, Compounds of the Disclosure are compounds having Formula XXI:

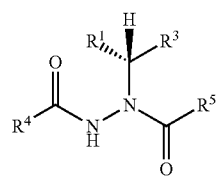

XXI wherein $R^1$ does not equal $R^3$, and $R^1$, $R^3$, $R^4$, and $R^5$ are as defined in connection with Formula I, and the pharmaceutically acceptable salts and solvates thereof. In a further embodiment, the enantiomeric excess of a compound having Formula XXI, in a mixture of compounds having Formulae XX and XXI, is at least about 60%, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In a further embodiment, the enantiomeric excess of a compound having Formula XXI is at least about 90%. In a further embodiment, the enantiomeric excess of a compound having Formula XXI is at least about 95%. In a further embodiment, the enantiomeric excess of a compound having Formula XXI is at least about 98%. In a further embodiment, the enantiomeric excess of a compound having Formula XI is at least about 99%.

In another embodiment, Compounds of the Disclosure are compounds of Table 1, and the pharmaceutically acceptable salts, solvates, e.g., hydrates, multimeric forms, and/or open- and closed-ring forms thereof. It should be appreciated that the Compounds of the Disclosure in certain embodiments exist as di- or trimeric forms, and/or open- and closed-ring forms, and are not limited to the particular form listed in Table 1.

TABLE 1

| Cpd. No. | Structure | Chemical Name |
|---|---|---|
| 1 | 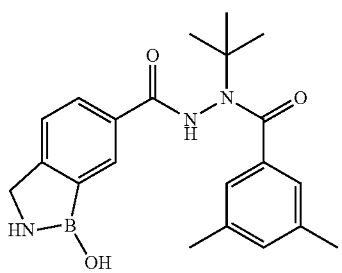 [SMILES: Cc1cc(C)cc(C(=O)N(NC(=O)c2ccc3c(c2)B(O)NC3)C(C)(C)C)c1] | N'-(tert-butyl)-N'-(3,5-dimethylbenzoyl)-1-hydroxy-2,3-dihydro-1H-benzo[c][1,2]azaborole-6-carbohydrazide |
| 2 | 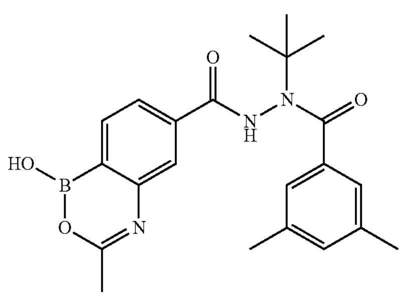 [SMILES: CC1=Nc2cc(C(=O)NN(C(=O)c3cc(C)cc(C)c3)C(C)(C)C)ccc2B(O)O1] | N'-(tert-butyl)-N'-(3,5-dimethylbenzoyl)-1-hydroxy-3-methyl-1H-benzo[c][1,5,2]oxazaborinine-6-carbohydrazide |
| 3 | 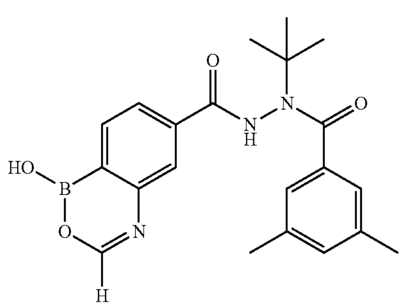 [SMILES: Cc1cc(C)cc(C(=O)N(NC(=O)c2ccc3c(c2)N=COB3O)C(C)(C)C)c1] | N'-(tert-butyl)-N'-(3,5-dimethylbenzoyl)-1-hydroxy-1H-benzo[c][1,5,2]oxazaborinine-6-carbohydrazide |

TABLE 1-continued

| Cpd. No. | Structure | Chemical Name |
|---|---|---|
| 4 | 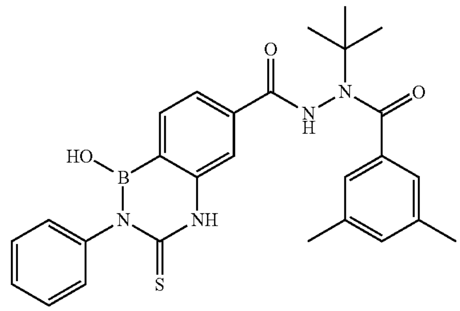 [SMILES: Cc1cc(C)cc(C(=O)N(NC(=O)c2ccc3c(c2)NC(=S)N(c2ccccc2)B3O)C(C)(C)C)c1] | N'-(tert-butyl)-N'-(3,5-dimethylbenzoyl)-1-hydroxy-2-phenyl-3-thioxo-1,2,3,4-tetrahydrobenzo[c][1,5,2]diazaborinine-6-carbohydrazide |
| 5 | 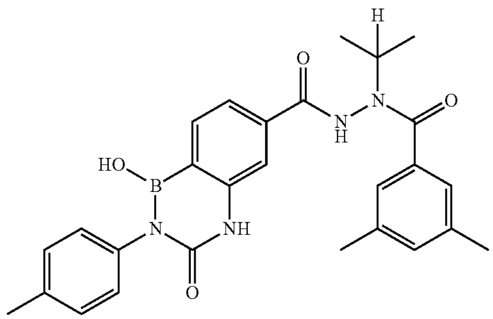 | N'-(tert-butyl)-N'-(3,5-dimethylbenzoyl)-1-hydroxy-3-oxo-2-(p-tolyl)-1,2,3,4-tetrahydrobenzo[c][1,5,2]diazaborinine-6-carbohydrazide |
| 6 | 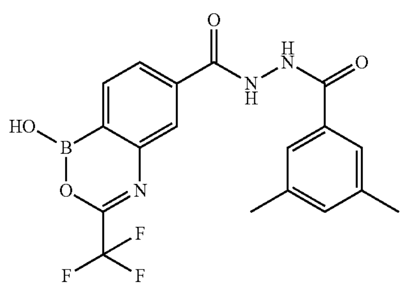 [SMILES: Cc1cc(C)cc(C(=O)NNC(=O)c2ccc3c(c2)N=C(C(F)(F)F)OB3O)c1] | N'-(3,5-dimethylbenzoyl)-1-hydroxy-3-(trifluoromethyl)-1H-benzo[c][1,5,2]oxazaborinine-6-carbohydrazide |
| 7 | 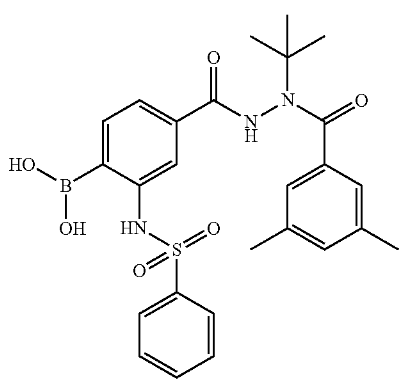 [SMILES: Cc1cc(C)cc(C(=O)N(NC(=O)c2ccc(B(O)O)c(NS(=O)(=O)c3ccccc3)c2)C(C)(C)C)c1] | (4-(2-(tert-butyl)-2-(3,5-dimethylbenzoyl)hydrazine-1-carbonyl)-2-(phenylsulfonamido)phenyl)boronic acid |
| 8 | 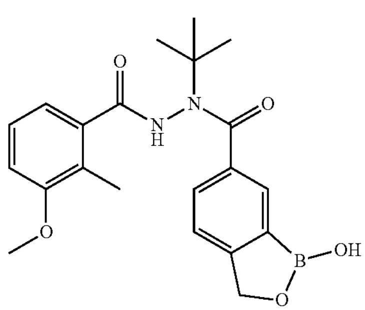 [SMILES: COc1cccc(C(=O)NN(C(=O)c2ccc3c(c2)B(O)OC3)C(C)(C)C)c1C] | N-(tert-butyl)-1-hydroxy-N'-(3-methoxy-2-methylbenzoyl)-1,3-dihydrobenzo[c][1,2]oxaborole-6-carbohydrazide |

| Cpd. No. | Structure | Chemical Name |
|---|---|---|
| 9 | 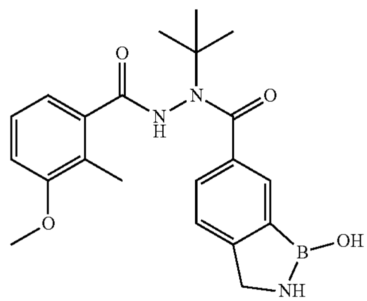 [SMILES: COc1cccc(C(=O)NN(C(=O)c2ccc3c(c2)B(O)NC3)C(C)(C)C)c1C] | N-(tert-butyl)-1-hydroxy-N'-(3-methoxy-2-methylbenzoyl)-2,3-dihydro-1H-benzo[c][1,2]azaborole-6-carbohydrazide |
| 10 | 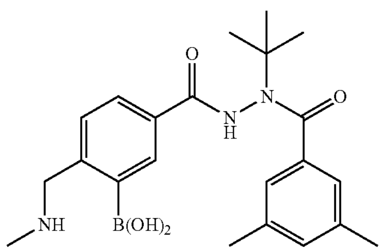 | (5-(2-(tert-butyl)-2-(3,5-dimethylbenzoyl)hydrazine-1-carbonyl)-2-((methylamino)methyl)phenyl)boronic acid |
| 11 | 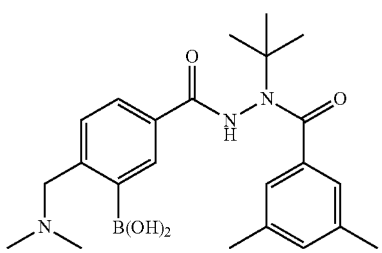 | (5-(2-(tert-butyl)-2-(3,5-dimethylbenzoyl)hydrazine-1-carbonyl)-2-((dimethylamino)methyl)phenyl)boronic acid |
| 12 | 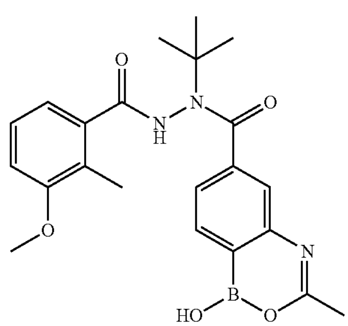 [SMILES: COc1cccc(C(=O)NN(C(=O)c2ccc3c(c2)N=C(C)OB3O)C(C)(C)C)c1C] | N-(tert-butyl)-1-hydroxy-N'-(3-methoxy-2-methylbenzoyl)-3-methyl-1H-benzo[c][1,5,2]oxazaborinine-6-carbohydrazide |
| 13 | 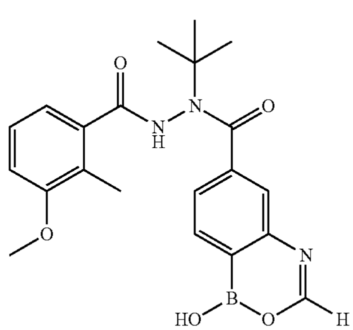 [SMILES: COc1cccc(C(=O)NN(C(=O)c2ccc3c(c2)N=COB3O)C(C)(C)C)c1C] | N-(tert-butyl)-1-hydroxy-N'-(3-methoxy-2-methylbenzoyl)-1H-benzo[c][1,5,2]oxazaborinine-6-carbohydrazide |

TABLE 1-continued

| Cpd. No. | Structure | Chemical Name |
|---|---|---|
| 14 | 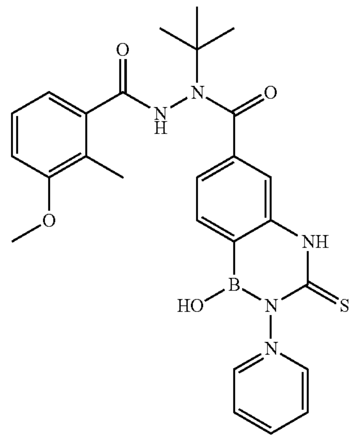 | N-(tert-butyl)-1-hydroxy-N'-(3-methoxy-2-methylbenzoyl)-2-phenyl-3-thioxo-1,2,3,4-tetrahydrobenzo[c][1,5,2]diazaborinine-6-carbohydrazide |
| 15 | 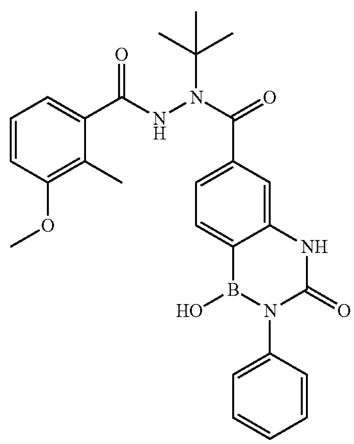 [SMILES: COc1cccc(C(=O)NN(C(=O)c2ccc3c(c2)NC(=O)N(c2ccccc2)B3O)C(C)(C)C)c1C] | N-(tert-butyl)-1-hydroxy-N'-(3-methoxy-2-methylbenzoyl)-3-oxo-2-phenyl-1,2,3,4-tetrahydrobenzo[c][1,5,2]diazaborinine-6-carbohydrazide |
| 16 | 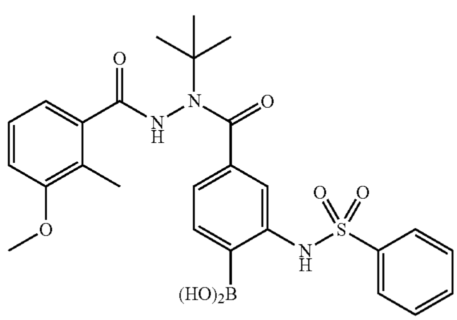 [SMILES: COc1cccc(C(=O)NN(C(=O)c2ccc(B(O)O)c(NS(=O)(=O)c3ccccc3)c2)C(C)(C)C)c1C] | (4-(1-(tert-butyl)-2-(3-methoxy-2-methylbenzoyl)hydrazine-1-carbonyl)-2-(phenylsulfonamido)phenyl)boronic acid |
| 17 | 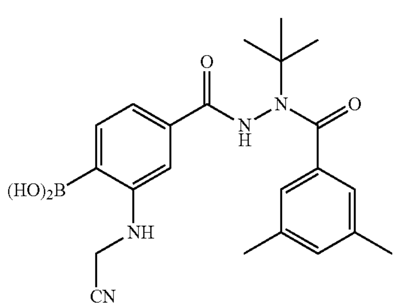 [SMILES: Cc1cc(C)cc(C(=O)N(NC(=O)c2ccc(B(O)O)c(NCC#N)c2)C(C)(C)C)c1] | (4-(2-(tert-butyl)-2-(3,5-dimethylbenzoyl)hydrazine-1-carbonyl)-2-((cyanomethyl)amino)phenyl)boronic acid |

TABLE 1-continued

| Cpd. No. | Structure | Chemical Name |
|---|---|---|
| 18 | 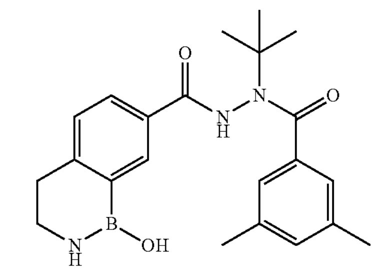 [SMILES: Cc1cc(C)cc(C(=O)N(NC(=O)c2ccc3c(c2)B(O)NCC3)C(C)(C)C)c1] | N'-(tert-butyl)-N'-(3,5-dimethylbenzoyl)-1-hydroxy-1,2,3,4-tetrahydrobenzo[c][1,2]azaborinine-7-carbohydrazide |
| 19 | 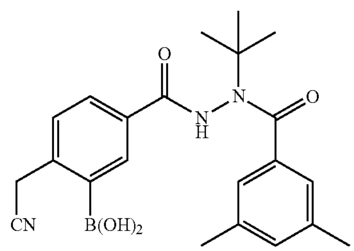 [SMILES: Cc1cc(C)cc(C(=O)N(NC(=O)c2ccc(CC#N)c(B(O)O)c2)C(C)(C)C)c1] | (5-(2-(tert-butyl)-2-(3,5-dimethylbenzoyl)hydrazine-1-carbonyl)-2-(cyanomethyl)phenyl)boronic acid |
| 20 | 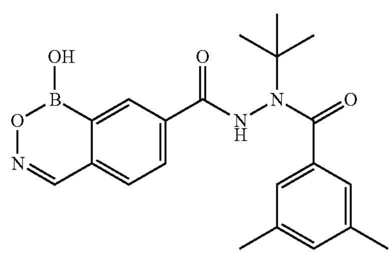 [SMILES: Cc1cc(C)cc(C(=O)N(NC(=O)c2ccc3c(c2)B(O)ON=C3)C(C)(C)C)c1] | N'-(tert-butyl)-N'-(3,5-dimethylbenzoyl)-1-hydroxy-1H-benzo[d][1,2,6]oxazaborinine-7-carbohydrazide |
| 21 | 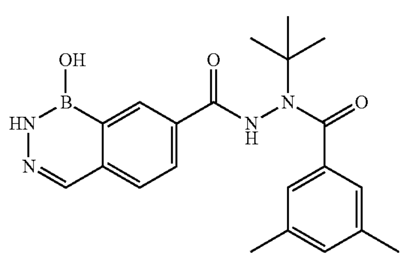 [SMILES: Cc1cc(C)cc(C(=O)N(NC(=O)c2ccc3c(c2)B(O)NN=C3)C(C)(C)C)c1] | N'-(tert-butyl)-N'-(3,5-dimethylbenzoyl)-1-hydroxy-1,2-dihydrobenzo[d][1,2,3]diazaborinine-7-carbohydrazide |
| 22 | 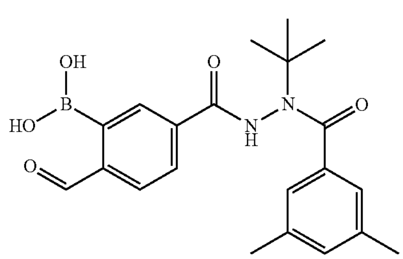 | (5-(2-(tert-butyl)-2-(3,5-dimethylbenzoyl)hydrazine-1-carbonyl)-2-formylphenyl)boronic acid |

TABLE 1-continued

| Cpd. No. | Structure | Chemical Name |
|---|---|---|
| 23 | 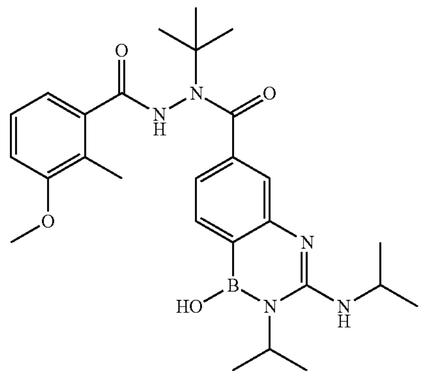 [SMILES: COc1cccc(C(=O)NN(C(=O)c2ccc3c(c2)N=C(NC(C)C)N(C(C)C)B3O)C(C)(C)C)c1C] | N-(tert-butyl)-1-hydroxy-2-isopropyl-3-(isopropylamino)-N'-(3-methoxy-2-methylbenzoyl)-1,2-dihydrobenzo[c][1,5,2]diazaborinine-6-carbohydrazide |
| 24 | 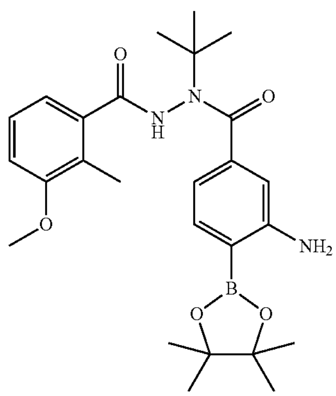 [SMILES: COc1cccc(C(=O)NN(C(=O)c2ccc(B3OC(C)(C)C(C)(C)O3)c(N)c2)C(C)(C)C)c1C] | N'-(3-amino-4-(4,4,5,5-tetramethyl-1,3,2-dioxaborolan-2-yl)benzoyl)-N'-(tert-butyl)-3-methoxy-2-methylbenzohydrazide |
| 25 | 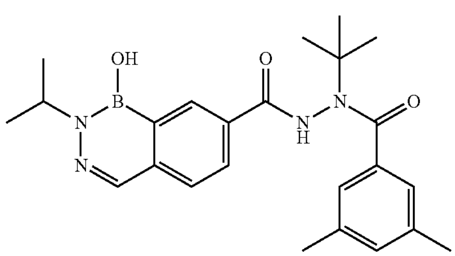 [SMILES: Cc1cc(C)cc(C(=O)N(NC(=O)c2ccc3c(c2)B(O)N(C(C)C)N=C3)C(C)(C)C)c1] | N'-(tert-butyl)-N'-(3,5-dimethylbenzoyl)-1-hydroxy-2-isopropyl-1,2-dihydrobenzo[d][1,2,3]diazaborinine-7-carbohydrazide |
| 26 | 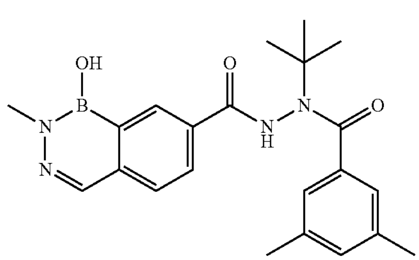 | N'-(tert-butyl)-N'-(3,5-dimethylbenzoyl)-1-hydroxy-2-methyl-1,2-dihydrobenzo[d][1,2,3]diazaborinine-7-carbohydrazide |

TABLE 1-continued

| Cpd. No. | Structure | Chemical Name |
|---|---|---|
| 27 | 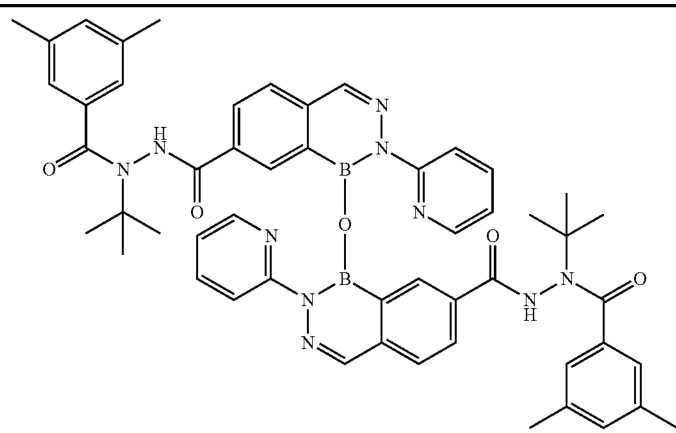 | 1,1'-oxybis(N'-(tert-butyl)-N'-(3,5-dimethylbenzoyl)-2-(pyridin-2-yl)-1,2-dihydrobenzo[d][1,2,3]diazaborinine-7-carbohydrazide) |
| 28 | 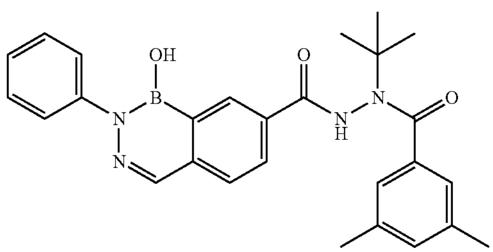 [SMILES: Cc1cc(C)cc(C(=O)N(NC(=O)c2ccc3c(c2)B(O)N(c2ccccc2)N=C3)C(C)(C)C)c1] | N'-(tert-butyl)-N'-(3,5-dimethylbenzoyl)-1-hydroxy-2-phenyl-1,2-dihydrobenzo[d][1,2,3]diazaborinine-7-carbohydrazide |
| 29 | 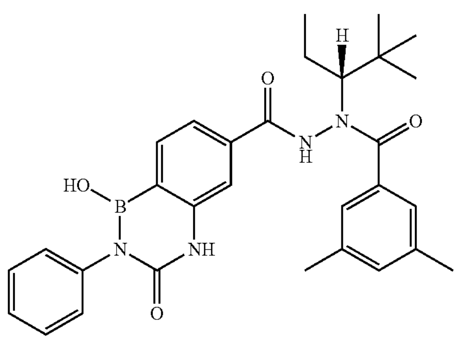 [SMILES: CC[C@@H](N(NC(=O)c1ccc2c(c1)NC(=O)N(c1ccccc1)B2O)C(=O)c1cc(C)cc(C)c1)C(C)(C)C] | (R)-N'-(3,5-dimethylbenzoyl)-N'-(2,2-dimethylpentan-3-yl)-1-hydroxy-3-oxo-2-phenyl-1,2,3,4-tetrahydrobenzo[c][1,5,2]diazaborinine-6-carbohydrazide |
| 30 | 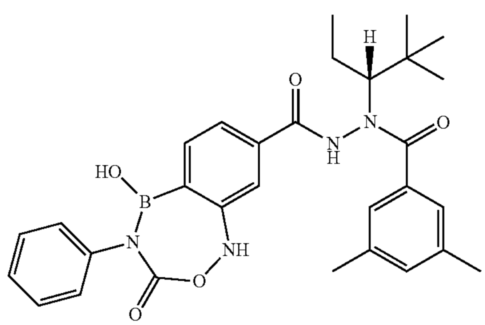 [SMILES: CC[C@@H](N(NC(=O)c1ccc2c(c1)NOC(=O)N(c1ccccc1)B2O)C(=O)c1cc(C)cc(C)c1)C(C)(C)C] | (R)-N'-(3,5-dimethylbenzoyl)-N'-(2,2-dimethylpentan-3-yl)-5-hydroxy-3-oxo-4-phenyl-1,3,4,5-tetrahydrobenzo[c][1,2,6,5]oxadiazaborepine-8-carbohydrazide |
| 31 | 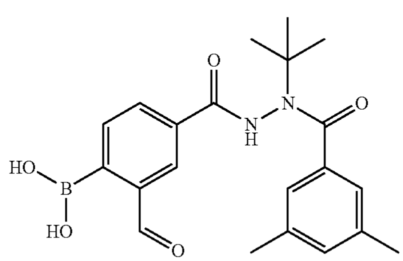 [SMILES: Cc1cc(C)cc(C(=O)N(NC(=O)c2ccc(B(O)O)c(C=O)c2)C(C)(C)C)c1] | (4-(2-(tert-butyl)-2-(3,5-dimethylbenzoyl)hydrazine-1-carbonyl)-2-formylphenyl)boronic acid |

TABLE 1-continued

| Cpd. No. | Structure | Chemical Name |
|---|---|---|
| 32 | 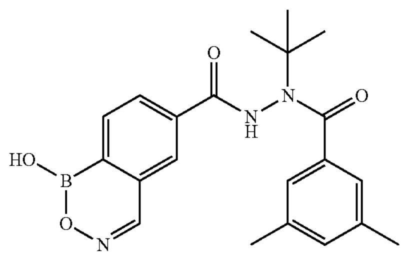 [SMILES: Cc1cc(C)cc(C(=O)N(NC(=O)c2ccc3c(c2)C=NOB3O)C(C)(C)C)c1] | N'-(tert-butyl)-N'-(3,5-dimethylbenzoyl)-1-hydroxy-1H-benzo[d][1,2,6]oxazaborinine-6-carbohydrazide |
| 33 | 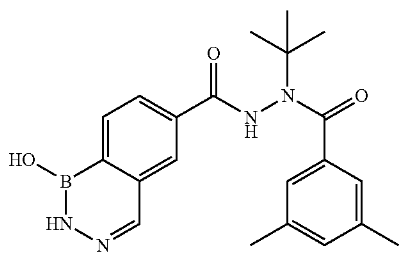 [SMILES: Cc1cc(C)cc(C(=O)N(NC(=O)c2ccc3c(c2)C=NNB3O)C(C)(C)C)c1] | N'-(tert-butyl)-N'-(3,5-dimethylbenzoyl)-1-hydroxy-1,2-dihydrobenzo[d][1,2,3]diazaborinine-6-carbohydrazide |
| 34 | 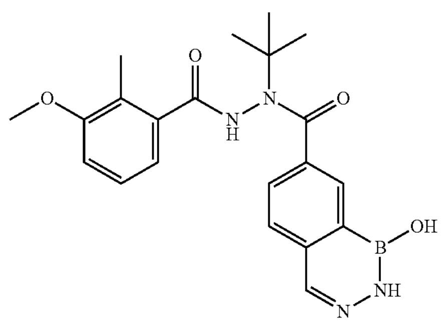 [SMILES: COc1cccc(C(=O)NN(C(=O)c2ccc3c(c2)B(O)NN=C3)C(C)(C)C)c1C] | N-(tert-butyl)-1-hydroxy-N'-(3-methoxy-2-methylbenzoyl)-1,2-dihydrobenzo[d][1,2,3]diazaborinine-7-carbohydrazide |
| 35 | 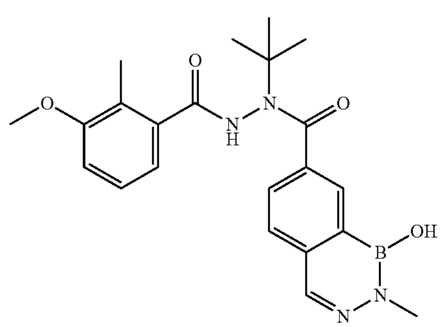 | N-(tert-butyl)-1-hydroxy-N'-(3-methoxy-2-methylbenzoyl)-2-methyl-1,2-dihydrobenzo[d][1,2,3]diazaborinine-7-carbohydrazide |
| 36 | 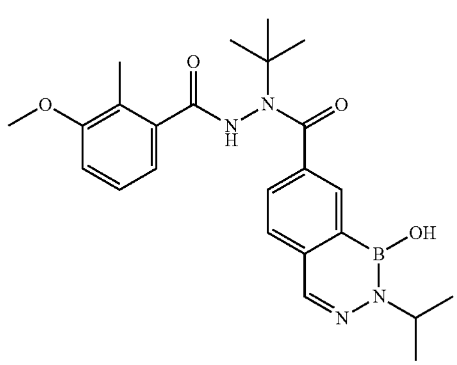 [SMILES: COc1cccc(C(=O)NN(C(=O)c2ccc3c(c2)B(O)N(C(C)C)N=C3)C(C)(C)C)c1C] | N-(tert-butyl)-1-hydroxy-2-isopropyl-N'-(3-methoxy-2-methylbenzoyl)-1,2-dihydrobenzo[d][1,2,3]diazaborinine-7-carbohydrazide |

TABLE 1-continued

| Cpd. No. | Structure | Chemical Name |
|---|---|---|
| 37 | 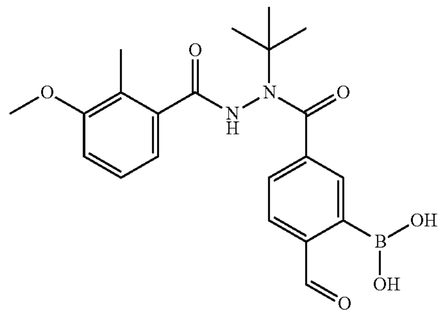 [SMILES: COc1cccc(C(=O)NN(C(=O)c2ccc(C=O)c(B(O)O)c2)C(C)(C)C)c1C] | (5-(1-(tert-butyl)-2-(3-methoxy-2-methylbenzoyl)hydrazine-1-carbonyl)-2-formylphenyl)boronic acid |
| 38 | 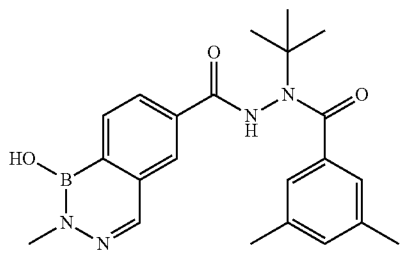 | N'-(tert-butyl)-N'-(3,5-dimethylbenzoyl)-1-hydroxy-2-methyl-1,2-dihydrobenzo[d][1,2,3]diazaborinine-6-carbohydrazide |
| 39 | 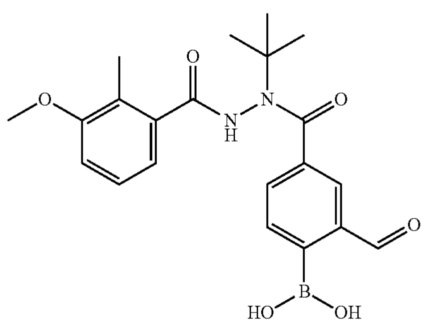 [SMILES: COc1cccc(C(=O)NN(C(=O)c2ccc(B(O)O)c(C=O)c2)C(C)(C)C)c1C] | (4-(1-(tert-butyl)-2-(3-methoxy-2-methylbenzoyl)hydrazine-1-carbonyl)-2-formylphenyl)boronic acid |
| 40 | 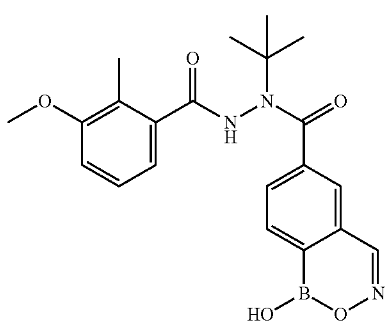 [SMILES: COc1cccc(C(=O)NN(C(=O)c2ccc3c(c2)C=NOB3O)C(C)(C)C)c1C] | N-(tert-butyl)-1-hydroxy-N'-(3-methoxy-2-methylbenzoyl)-1H-benzo[d][1,2,6]oxazaborinine-6-carbohydrazide |
| 41 | 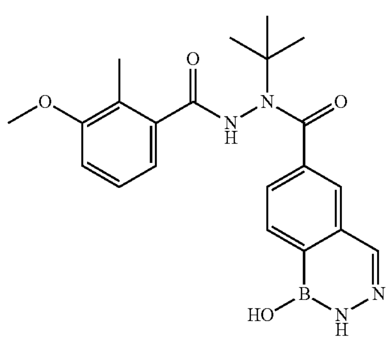 [SMILES: COc1cccc(C(=O)NN(C(=O)c2ccc3c(c2)C=NNB3O)C(C)(C)C)c1C] | N-(tert-butyl)-1-hydroxy-N'-(3-methoxy-2-methylbenzoyl)-1,2-dihydrobenzo[d][1,2,3]diazaborinine-6-carbohydrazide |

TABLE 1-continued

| Cpd. No. | Structure | Chemical Name |
| --- | --- | --- |
| 42 | 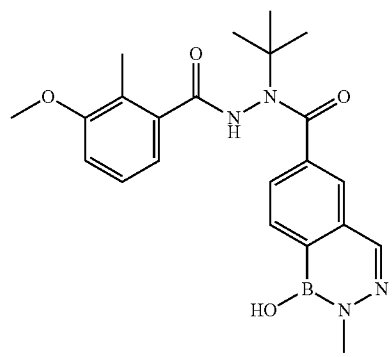 [SMILES: COc1cccc(C(=O)NN(C(=O)c2ccc3c(c2)C=NN(C)B3O)C(C)(C)C)c1C] | N-(tert-butyl)-1-hydroxy-N'-(3-methoxy-2-methylbenzoyl)-2-methyl-1,2-dihydrobenzo[d][1,2,3]diazaborinine-6-carbohydrazide |
| 43 | 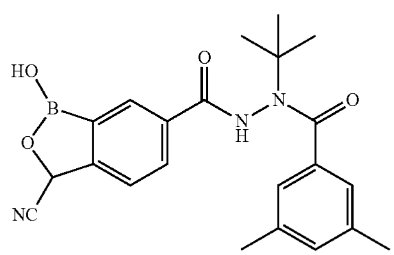 [SMILES: Cc1cc(C)cc(C(=O)N(NC(=O)c2ccc3c(c2)B(O)OC3C#N)C(C)(C)C)c1] | N'-(tert-butyl)-3-cyano-N'-(3,5-dimethylbenzoyl)-1-hydroxy-1,3-dihydrobenzo[c][1,2]oxaborole-6-carbohydrazide |
| 44 | 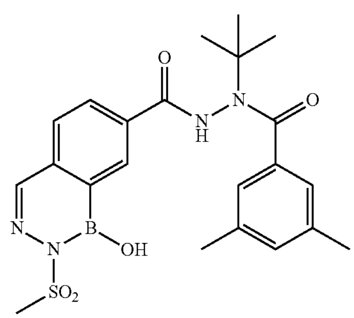 [SMILES: Cc1cc(C)cc(C(=O)N(NC(=O)c2ccc3c(c2)B(O)N(S(C)(=O)=O)N=C3)C(C)(C)C)c1] | N'-(tert-butyl)-N'-(3,5-dimethylbenzoyl)-1-hydroxy-2-(methylsulfonyl)-1,2-dihydrobenzo[d][1,2,3]diazaborinine-7-carbohydrazide |
| 45 | 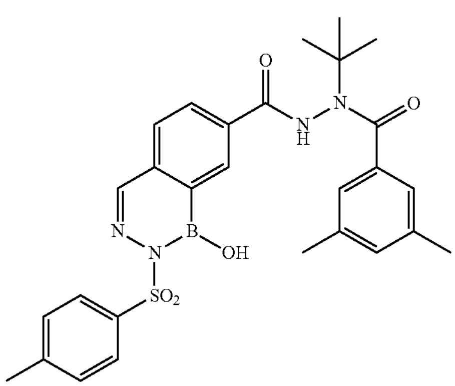 | N'-(tert-butyl)-N'-(3,5-dimethylbenzoyl)-1-hydroxy-2-tosyl-1,2-dihydrobenzo[d][1,2,3]diazaborinine-7-carbohydrazide |

TABLE 1-continued

| Cpd. No. | Structure | Chemical Name |
| --- | --- | --- |
| 46 | 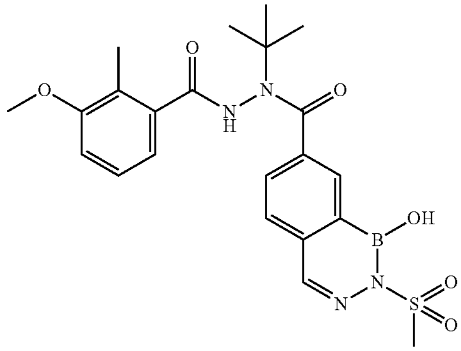 [SMILES: COc1cccc(C(=O)NN(C(=O)c2ccc3c(c2)B(O)N(S(C)(=O)=O)N=C3)C(C)(C)C)c1C] | N-(tert-butyl)-1-hydroxy-N'-(3-methoxy-2-methylbenzoyl)-2-(methylsulfonyl)-1,2-dihydrobenzo[d][1,2,3]diazaborinine-7-carbohydrazide |
| 47 | 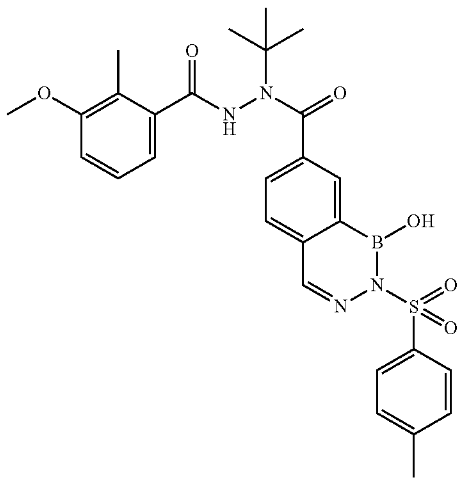 [SMILES: COc1cccc(C(=O)NN(C(=O)c2ccc3c(c2)B(O)N(S(=O)(=O)c2ccc(C)cc2)N=C3)C(C)(C)C)c1C] | N-(tert-butyl)-1-hydroxy-N'-(3-methoxy-2-methylbenzoyl)-2-tosyl-1,2-dihydrobenzo[d][1,2,3]diazaborinine-7-carbohydrazide |
| 48 | 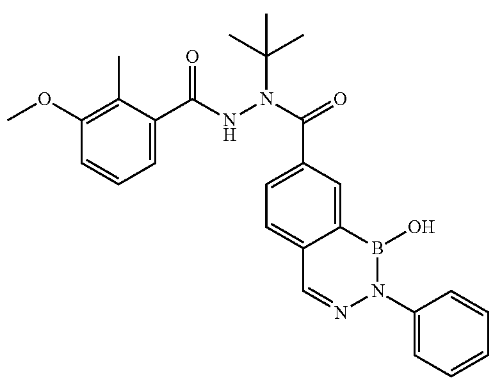 [SMILES: COc1cccc(C(=O)NN(C(=O)c2ccc3c(c2)B(O)N(c2ccccc2)N=C3)C(C)(C)C)c1C] | N-(tert-butyl)-1-hydroxy-N'-(3-methoxy-2-methylbenzoyl)-2-phenyl-1,2-dihydrobenzo[d][1,2,3]diazaborinine-7-carbohydrazide |
| 49 | 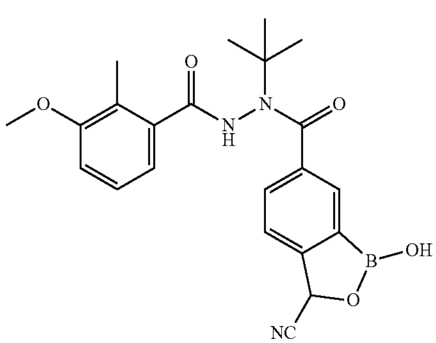 [SMILES: COc1cccc(C(=O)NN(C(=O)c2ccc3c(c2)B(O)OC3C#N)C(C)(C)C)c1C] | N-(tert-butyl)-3-cyano-1-hydroxy-N'-(3-methoxy-2-methylbenzoyl)-1,3-dihydrobenzo[c][1,2]oxaborole-6-carbohydrazide |

TABLE 1-continued

| Cpd. No. | Structure | Chemical Name |
|---|---|---|
| 50 | 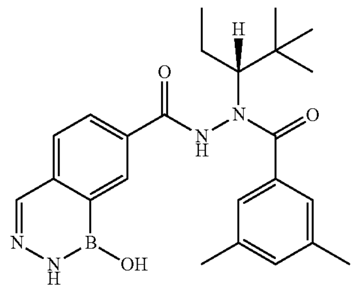 [SMILES: CC[C@@H](N(NC(=O)c1ccc2c(c1)B(O)NN=C2)C(=O)c1cc(C)cc(C)c1)C(C)(C)C] | (R)-N'-(3,5-dimethylbenzoyl)-N'-(2,2-dimethylpentan-3-yl)-1-hydroxy-1,2-dihydrobenzo[d][1,2,3]diazaborinine-7-carbohydrazide |
| 51 | 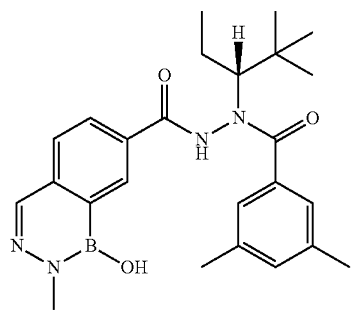 [SMILES: CC[C@@H](N(NC(=O)c1ccc2c(c1)B(O)N(C)N=C2)C(=O)c1cc(C)cc(C)c1)C(C)(C)C] | (R)-N'-(3,5-dimethylbenzoyl)-N'-(2,2-dimethylpentan-3-yl)-1-hydroxy-2-methyl-1,2-dihydrobenzo[d][1,2,3]diazaborinine-7-carbohydrazide |
| 52 | 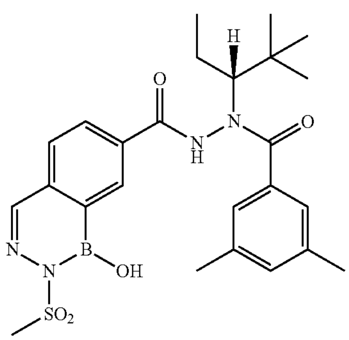 [SMILES: CC[C@@H](N(NC(=O)c1ccc2c(c1)B(O)N(S(C)(=O)=O)N=C2)C(=O)c1cc(C)cc(C)c1)C(C)(C)C] | (R)-N'-(3,5-dimethylbenzoyl)-N'-(2,2-dimethylpentan-3-yl)-1-hydroxy-2-(methylsulfonyl)-1,2-dihydrobenzo[d][1,2,3]diazaborinine-7-carbohydrazide |
| 53 | 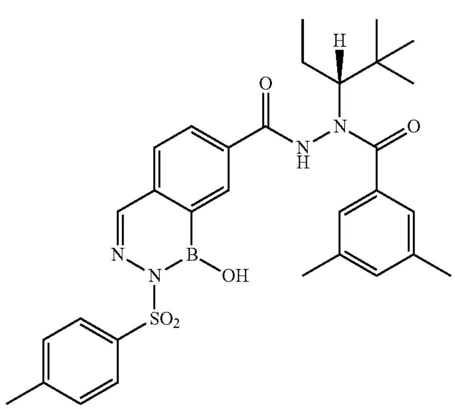 | (R)-N'-(3,5-dimethylbenzoyl)-N'-(2,2-dimethylpentan-3-yl)-1-hydroxy-2-tosyl-1,2-dihydrobenzo[d][1,2,3]diazaborinine-7-carbohydrazide |

TABLE 1-continued

| Cpd. No. | Structure | Chemical Name |
|---|---|---|
| 54 | 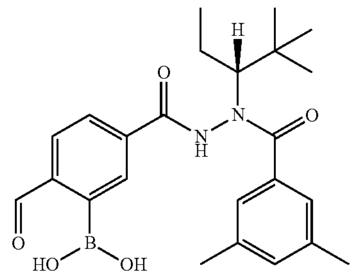 [SMILES: CC[C@@H](N(NC(=O)c1ccc(C=O)c(B(O)O)c1)C(=O)c1cc(C)cc(C)c1)C(C)(C)C] | (R)-(5-(2-(3,5-dimethylbenzoyl)-2-(2,2-dimethylpentan-3-yl)hydrazine-1-carbonyl)-2-formylphenyl)boronic acid |
| 55 | 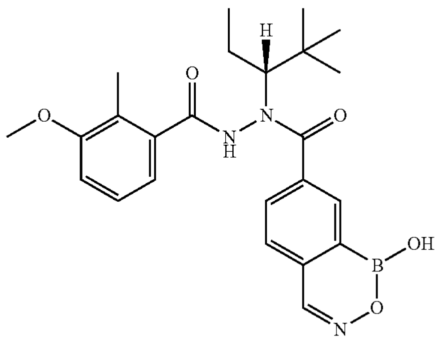 [SMILES: CC[C@@H](N(NC(=O)c1cccc(OC)c1C)C(=O)c1ccc2c(c1)B(O)ON=C2)C(C)(C)C] | (R)-N-(2,2-dimethylpentan-3-yl)-1-hydroxy-N'-(3-methoxy-2-methylbenzoyl)-1H-benzo[d][1,2,6]oxazaborinine-7-carbohydrazide |
| 56 | 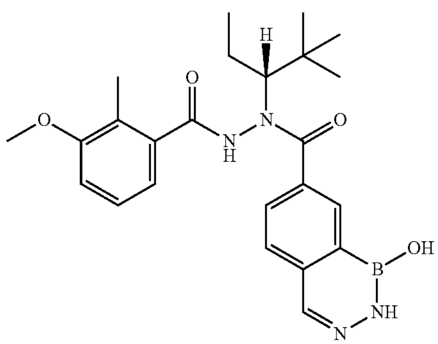 | (R)-N-(2,2-dimethylpentan-3-yl)-1-hydroxy-N'-(3-methoxy-2-methylbenzoyl)-1,2-dihydrobenzo[d][1,2,3]diazaborinine-7-carbohydrazide |
| 57 | 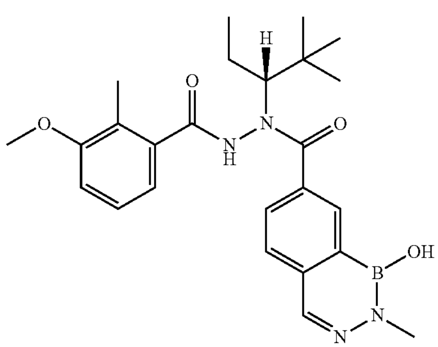 | (R)-N-(2,2-dimethylpentan-3-yl)-1-hydroxy-N'-(3-methoxy-2-methylbenzoyl)-2-methyl-1,2-dihydrobenzo[d][1,2,3]diazaborinine-7-carbohydrazide |

TABLE 1-continued

| Cpd. No. | Structure | Chemical Name |
|---|---|---|
| 58 | 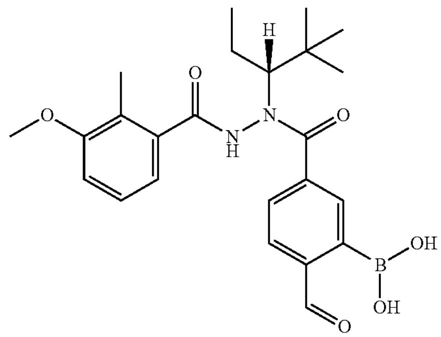 [SMILES: CC[C@@H](N(NC(=O)c1cccc(OC)c1C)C(=O)c1ccc(C=O)c(B(O)O)c1)C(C)(C)C] | (R)-(5-(1-(2,2-dimethylpentan-3-yl)-2-(3-methoxy-2-methylbenzoyl)hydrazine-1-carbonyl)-2-formylphenyl)boronic acid |
| 59 | 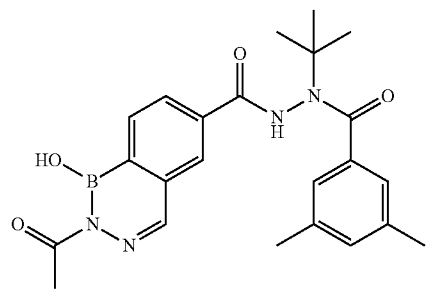 [SMILES: CC(=O)N1N=Cc2cc(C(=O)NN(C(=O)c3cc(C)cc(C)c3)C(C)(C)C)ccc2B1O] | 2-acetyl-N'-(tert-butyl)-N'-(3,5-dimethylbenzoyl)-1-hydroxy-1,2-dihydrobenzo[d][1,2,3]diazaborinine-6-carbohydrazide |
| 60 | 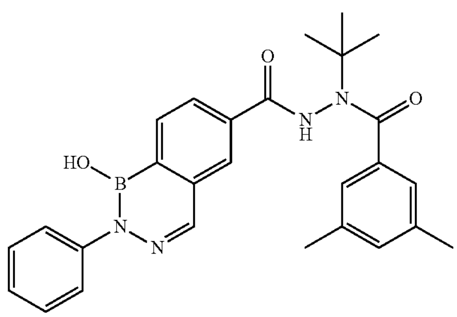 [SMILES: Cc1cc(C)cc(C(=O)N(NC(=O)c2ccc3c(c2)C=NN(c2ccccc2)B3O)C(C)(C)C)c1] | N'-(tert-butyl)-N'-(3,5-dimethylbenzoyl)-1-hydroxy-2-phenyl-1,2-dihydrobenzo[d][1,2,3]diazaborinine-6-carbohydrazide |
| 61 | 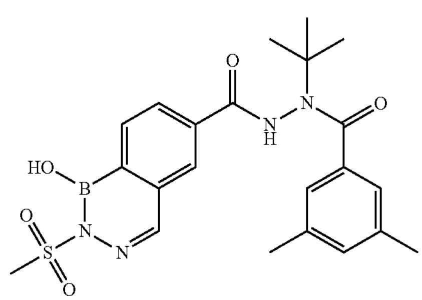 | N'-(tert-butyl)-N'-(3,5-dimethylbenzoyl)-1-hydroxy-2-(methylsulfonyl)-1,2-dihydrobenzo[d][1,2,3]diazaborinine-6-carbohydrazide |
| 62 | 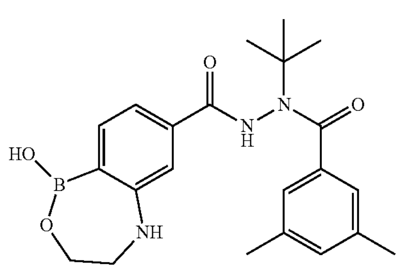 [SMILES: Cc1cc(C)cc(C(=O)N(NC(=O)c2ccc3c(c2)NCCOB3O)C(C)(C)C)c1] | (R)-N'-(3,5-dimethylbenzoyl)-N'-(2,2-dimethylpentan-3-yl)-1-hydroxy-1,3,4,5-tetrahydrobenzo[c][1,5,2]oxazaborepine-7-carbohydrazide |

TABLE 1-continued

| Cpd. No. | Structure | Chemical Name |
| --- | --- | --- |
| 63 | 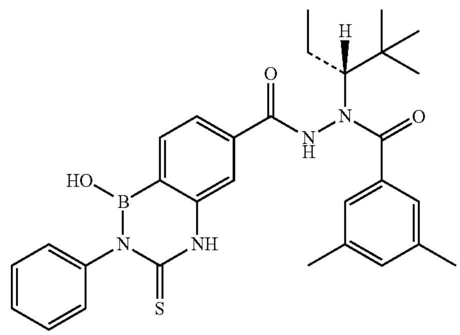 [SMILES: CC[C@@H](N(NC(=O)c1ccc2c(c1)NC(=S)N(c1ccccc1)B2O)C(=O)c1cc(C)cc(C)c1)C(C)(C)C] | (R)-N'-(3,5-dimethylbenzoyl)-N'-(2,2-dimethylpentan-3-yl)-1-hydroxy-2-phenyl-3-thioxo-1,2,3,4-tetrahydrobenzo[c][1,5,2]diazaborinine-6-carbohydrazide |
| 64 | 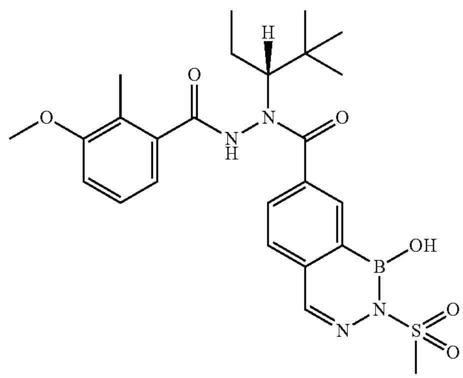 [SMILES: CC[C@@H](N(NC(=O)c1cccc(OC)c1C)C(=O)c1ccc2c(c1)B(O)N(S(C)(=O)=O)N=C2)C(C)(C)C] | (R)-N-(2,2-dimethylpentan-3-yl)-1-hydroxy-N'-(3-methoxy-2-methylbenzoyl)-2-(methylsulfonyl)-1,2-dihydrobenzo[d][1,2,3]diazaborinine-7-carbohydrazide |
| 65 | 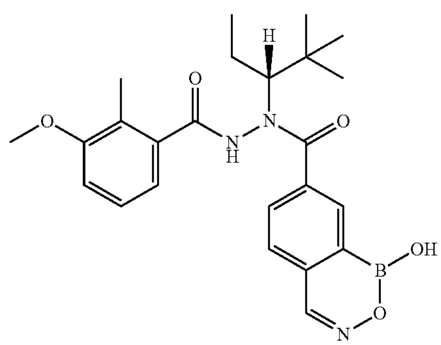 [SMILES: CC[C@@H](N(NC(=O)c1cccc(OC)c1C)C(=O)c1ccc2c(c1)B(O)ON=C2)C(C)(C)C] | (R)-N-(2,2-dimethylpentan-3-yl)-1-hydroxy-N'-(3-methoxy-2-methylbenzoyl)-1H-benzo[d][1,2,6]oxazaborinine-7-carbohydrazide |
| 66 | 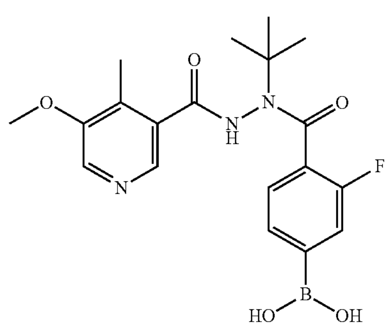 [SMILES: COc1cncc(C(=O)NN(C(=O)c2ccc(B(O)O)cc2F)C(C)(C)C)c1C] | (4-(1-(tert-butyl)-2-(5-methoxy-4-methylnicotinoyl)hydrazine-1-carbonyl)-3-fluorophenyl)boronic acid |

TABLE 1-continued

| Cpd. No. | Structure | Chemical Name |
|---|---|---|
| 67 | 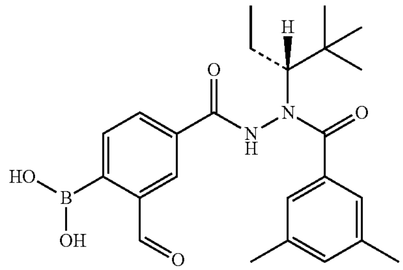 [SMILES: CC[C@@H](N(NC(=O)c1ccc(B(O)O)c(C=O)c1)C(=O)c1cc(C)cc(C)c1)C(C)(C)C] | (R)-(4-(2-(3,5-dimethylbenzoyl)-2-(2,2-dimethylpentan-3-yl)hydrazine-1-carbonyl)-2-formylphenyl)boronic acid |
| 68 | 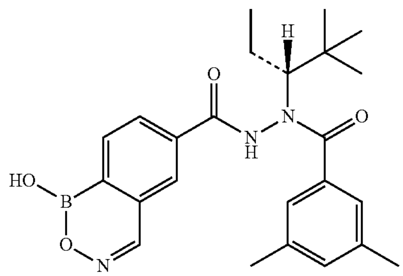 [SMILES: CC[C@@H](N(NC(=O)c1ccc2c(c1)C=NOB2O)C(=O)c1cc(C)cc(C)c1)C(C)(C)C] | (R)-N'-(3,5-dimethylbenzoyl)-N'-(2,2-dimethylpentan-3-yl)-1-hydroxy-1H-benzo[d][1,2,6]oxazaborinine-6-carbohydrazide |
| 69 | 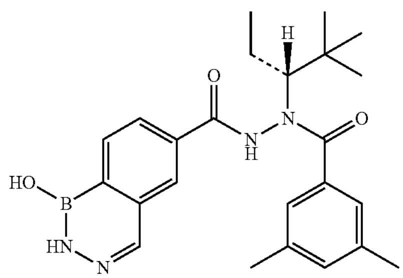 [SMILES: CC[C@@H](N(NC(=O)c1ccc2c(c1)C=NNB2O)C(=O)c1cc(C)cc(C)c1)C(C)(C)C] | (R)-N'-(3,5-dimethylbenzoyl)-N'-(2,2-dimethylpentan-3-yl)-1-hydroxy-1,2-dihydrobenzo[d][1,2,3]diazaborinine-6-carbohydrazide |
| 70 | 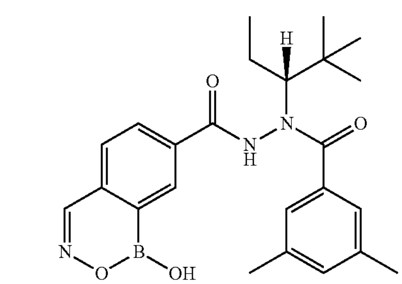 [SMILES: CC[C@@H](N(NC(=O)c1ccc2c(c1)B(O)ON=C2)C(=O)c1cc(C)cc(C)c1)C(C)(C)C] | (R)-N'-(3,5-dimethylbenzoyl)-N'-(2,2-dimethylpentan-3-yl)-1-hydroxy-1H-benzo[d][1,2,6]oxazaborinine-7-carbohydrazide |
| 71 | 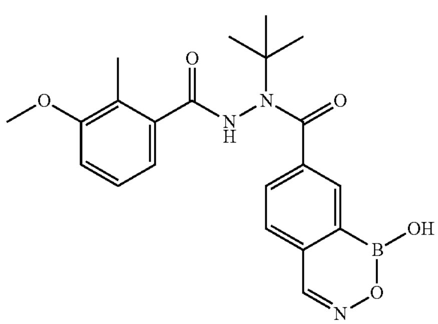 [SMILES: COc1cccc(C(=O)NN(C(=O)c2ccc3c(c2)B(O)ON=C3)C(C)(C)C)c1C] | N-(tert-butyl)-1-hydroxy-N'-(3-methoxy-2-methylbenzoyl)-1H-benzo[d][1,2,6]oxazaborinine-7-carbohydrazide |

TABLE 1-continued

| Cpd. No. | Structure | Chemical Name |
|---|---|---|
| 72 | 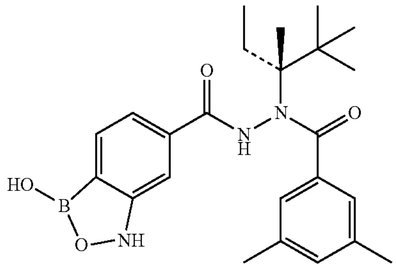 [SMILES: CC[C@@](C)(N(NC(=O)c1ccc2c(c1)NOB2O)C(=O)c1cc(C)cc(C)c1)C(C)(C)C] | R)-N'-(3,5-dimethylbenzoyl)-3-hydroxy-N'-(2,2,3-trimethylpentan-3-yl)-1,3-dihydrobenzo[c][1,2,5]oxazaborole-6-carbohydrazide |

In another embodiment, a Compound of the Disclosure is a compound having Formulae I-XXI, provided the compound is not a compound of Table 2, or a pharmaceutically acceptable salt or solvate thereof.

TABLE 2

| Structure | Name |
|---|---|
| 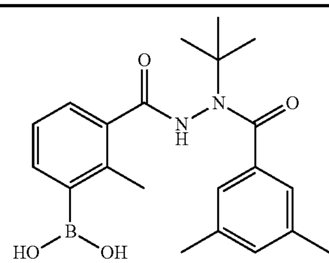 | (3-(2-(tert-butyl)-2-(3,5-dimethylbenzoyl)hydrazine-1-carbonyl)-2-methylphenyl)boronic acid |
| 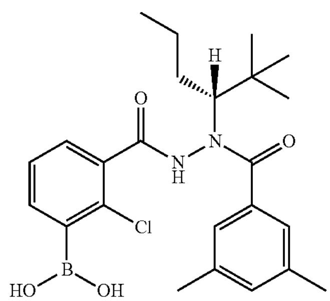 [SMILES: CCC[C@@H](N(NC(=O)c1cccc(B(O)O)c1Cl)C(=O)c1cc(C)cc(C)c1)C(C)(C)C] | (R)-(2-chloro-3-(2-(3,5-dimethylbenzoyl)-2-(2,2-dimethylhexan-3-yl)hydrazine-1-carbonyl)phenyl)boronic acid |
| 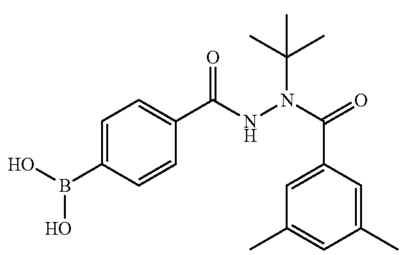 [SMILES: Cc1cc(C)cc(C(=O)N(NC(=O)c2ccc(B(O)O)cc2)C(C)(C)C)c1] | (4-(2-(tert-butyl)-2-(3,5-dimethylbenzoyl)hydrazine-1-carbonyl)phenyl)boronic acid |
| 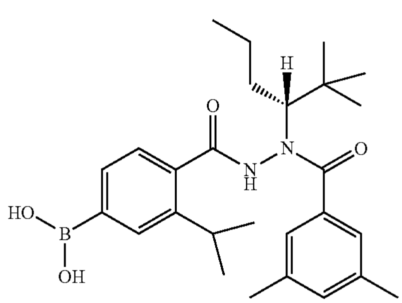 [SMILES: CCC[C@@H](N(NC(=O)c1ccc(B(O)O)cc1C(C)C)C(=O)c1cc(C)cc(C)c1)C(C)(C)C] | (R)-(4-(2-(3,5-dimethylbenzoyl)-2-(2,2-dimethylhexan-3-yl)hydrazine-1-carbonyl)-3-isopropylphenyl)boronic acid |

TABLE 2-continued

| Structure | Name |
|---|---|
| 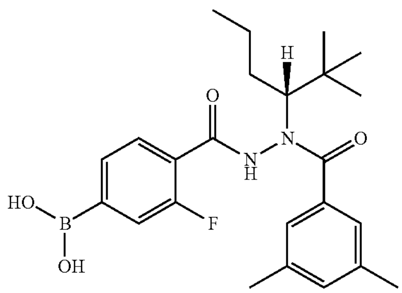 [SMILES: CCC[C@@H](N(NC(=O)c1ccc(B(O)O)cc1F)C(=O)c1cc(C)cc(C)c1)C(C)(C)C] | (R)-(4-(2-(3,5-dimethylbenzoyl)-2-(2,2-dimethylhexan-3-yl)hydrazine-1-carbonyl)-3-fluorophenyl)boronic acid |
| 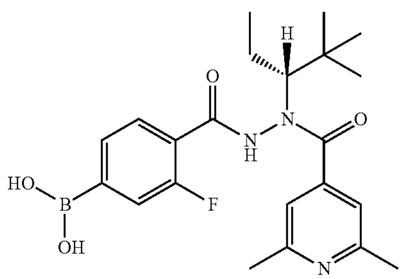 [SMILES: CC[C@@H](N(NC(=O)c1ccc(B(O)O)cc1F)C(=O)c1cc(C)nc(C)c1)C(C)(C)C] | (R)-(4-(2-(2,6-dimethylisonicotinoyl)-2-(2,2-dimethylpentan-3-yl)hydrazine-1-carbonyl)-3-fluorophenyl)boronic acid |
| 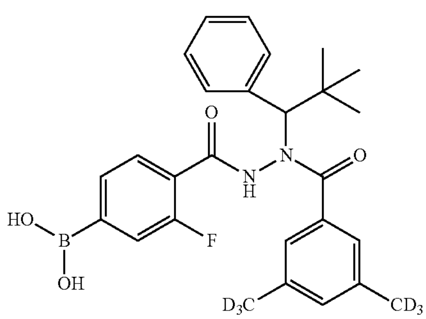 [SMILES: [2H]C([2H])([2H])c1cc(C(=O)N(NC(=O)c2ccc(B(O)O)cc2F)C(c2ccccc2)C(C)(C)C)cc(C([2H])([2H])[2H])c1] | (4-(2-(3,5-bis(methyl-d3)benzoyl)-2-(2,2-dimethyl-1-phenylpropyl)hydrazine-1-carbonyl)-3-fluorophenyl)boronic acid |
| 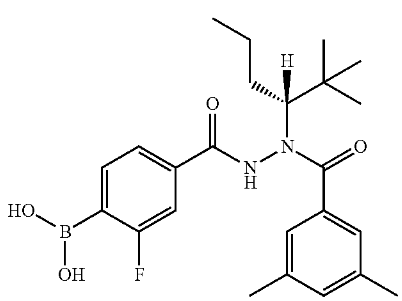 [SMILES: CCC[C@@H](N(NC(=O)c1ccc(B(O)O)c(F)c1)C(=O)c1cc(C)cc(C)c1)C(C)(C)C] | (R)-(4-(2-(3,5-dimethylbenzoyl)-2-(2,2-dimethylhexan-3-yl)hydrazine-1-carbonyl)-2-fluorophenyl)boronic acid |
| 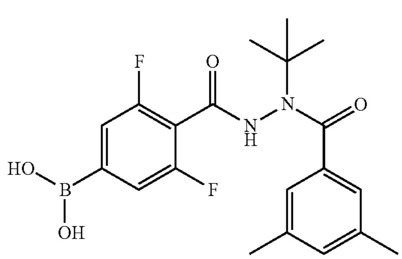 [SMILES: Cc1cc(C)cc(C(=O)N(NC(=O)c2c(F)cc(B(O)O)cc2F)C(C)(C)C)c1] | (4-(2-(tert-butyl)-2-(3,5-dimethylbenzoyl)hydrazine-1-carbonyl)-3,5-difluorophenyl)boronic acid |

TABLE 2-continued

| Structure | Name |
|---|---|
| 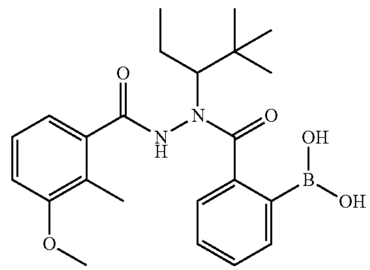 [SMILES: CCC(N(NC(=O)c1cccc(OC)c1C)C(=O)c1ccccc1B(O)O)C(C)(C)C] | (2-(1-(2,2-dimethylpentan-3-yl)-2-(3-methoxy-2-methylbenzoyl)hydrazine-1-carbonyl)phenyl)boronic acid |
| 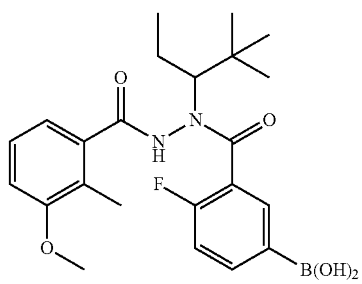 [SMILES: CCC(N(NC(=O)c1cccc(OC)c1C)C(=O)c1cc(B(O)O)ccc1F)C(C)(C)C] | (3-(1-(2,2-dimethylpentan-3-yl)-2-(3-methoxy-2-methylbenzoyl)hydrazine-1-carbonyl)-4-fluorophenyl)boronic acid |
| 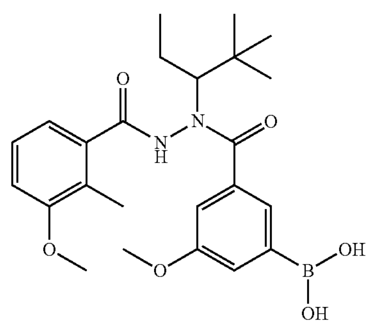 [SMILES: CCC(N(NC(=O)c1cccc(OC)c1C)C(=O)c1cc(OC)cc(B(O)O)c1)C(C)(C)C] | (3-(1-(2,2-dimethylpentan-3-yl)-2-(3-methoxy-2-methylbenzoyl)hydrazine-1-carbonyl)-5-methoxyphenyl)boronic acid |
| 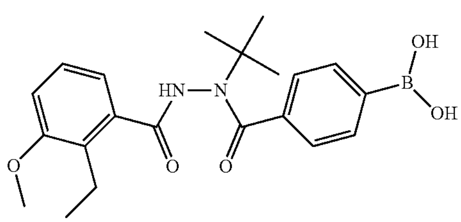 [SMILES: CCc1c(OC)cccc1C(=O)NN(C(=O)c1ccc(B(O)O)cc1)C(C)(C)C] | (4-(1-(tert-butyl)-2-(2-ethyl-3-methoxybenzoyl)hydrazine-1-carbonyl)phenyl)boronic acid |
| 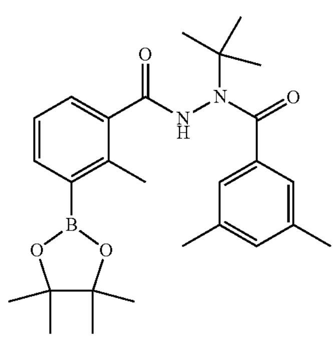 | N'-(tert-butyl)-N'-(3,5-dimethylbenzoyl)-2-methyl-3-(4,4,5,5-tetramethyl-1,3,2-dioxaborolan-2-yl)benzohydrazide |

TABLE 2-continued

| Structure | Name |
|---|---|
| 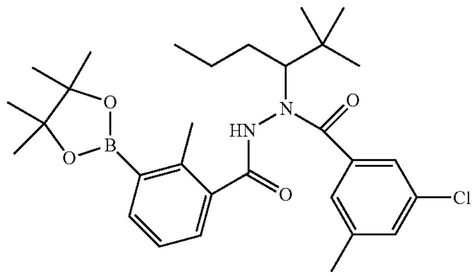 [SMILES: CCCC(N(NC(=O)c1cccc(B2OC(C)(C)C(C)(C)O2)c1C)C(=O)c1cc(C)cc(Cl)c1)C(C)(C)C] | N'-(3-chloro-5-methylbenzoyl)-N'-(2,2-dimethylhexan-3-yl)-2-methyl-3-(4,4,5,5-tetramethyl-1,3,2-dioxaborolan-2-yl)benzohydrazide |
| 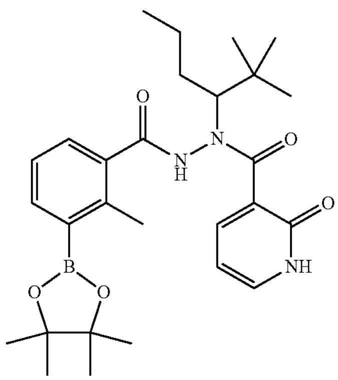 [SMILES: CCCC(N(NC(=O)c1cccc(B2OC(C)(C)C(C)(C)O2)c1C)C(=O)c1ccc[nH]c1=O)C(C)(C)C] | N-(2,2-dimethylhexan-3-yl)-N'-(2-methyl-3-(4,4,5,5-tetramethyl-1,3,2-dioxaborolan-2-yl)benzoyl)-2-oxo-1,2-dihydropyridine-3-carbohydrazide |
| 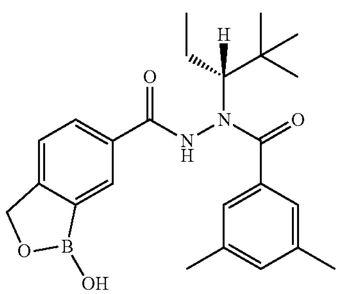 [SMILES: CC[C@@H](N(NC(=O)c1ccc2c(c1)B(O)OC2)C(=O)c1cc(C)cc(C)c1)C(C)(C)C] | (R)-N'-(3,5-dimethylbenzoyl)-N'-(2,2-dimethylpentan-3-yl)-1-hydroxy-1,3-dihydrobenzo[c][1,2]oxaborole-6-carbohydrazide |
| 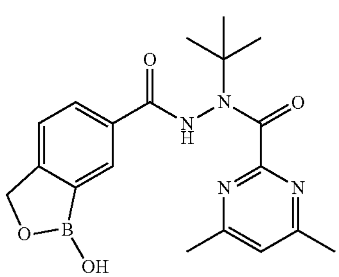 [SMILES: Cc1cc(C)nc(C(=O)N(NC(=O)c2ccc3c(c2)B(O)OC3)C(C)(C)C)n1] | N-(tert-butyl)-N'-(1-hydroxy-1,3-dihydrobenzo[c][1,2]oxaborole-6-carbonyl)-4,6-dimethylpyrimidine-2-carbohydrazide |
| 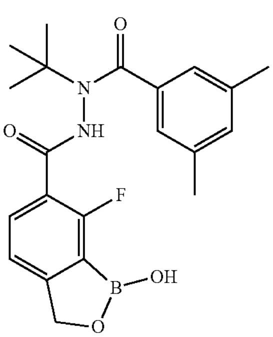 [SMILES: Cc1cc(C)cc(C(=O)N(NC(=O)c2ccc3c(c2F)B(O)OC3)C(C)(C)C)c1] | N'-(tert-butyl)-N'-(3,5-dimethylbenzoyl)-7-fluoro-1-hydroxy-1,3-dihydrobenzo[c][1,2]oxaborole-6-carbohydrazide |

TABLE 2-continued

| Structure | Name |
|---|---|
| 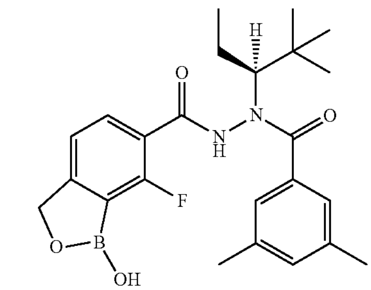 [SMILES: CC[C@H](N(NC(=O)c1ccc2c(c1F)B(O)OC2)C(=O)c1cc(C)cc(C)c1)C(C)(C)C] | (S)-N'-(3,5-dimethylbenzoyl)-N'-(2,2-dimethylpentan-3-yl)-7-fluoro-1-hydroxy-1,3-dihydrobenzo[c][1,2]oxaborole-6-carbohydrazide |
| 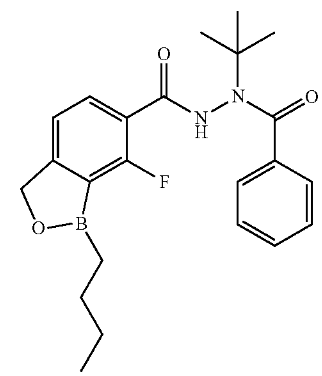 [SMILES: CCCCB1OCc2ccc(C(=O)NN(C(=O)c3ccccc3)C(C)(C)C)c(F)c21] | N'-benzoyl-N'-(tert-butyl)-1-butyl-7-fluoro-1,3-dihydrobenzo[c][1,2]oxaborole-6-carbohydrazide |
| 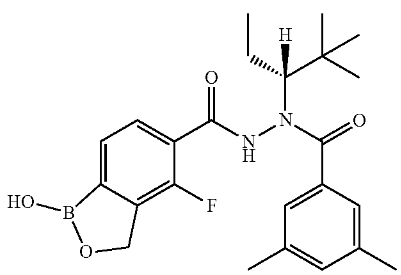 [SMILES: CC[C@@H](N(NC(=O)c1ccc2c(c1F)COB2O)C(=O)c1cc(C)cc(C)c1)C(C)(C)C] | (R)-N'-(3,5-dimethylbenzoyl)-N'-(2,2-dimethylpentan-3-yl)-4-fluoro-1-hydroxy-1,3-dihydrobenzo[c][1,2]oxaborole-5-carbohydrazide |
| 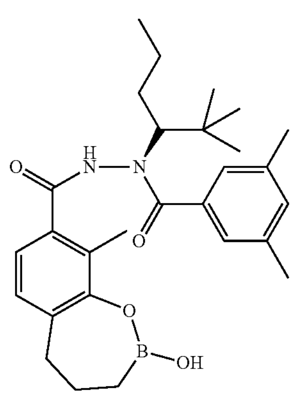 | (R)-N'-(3,5-dimethylbenzoyl)-N'-(2,2-dimethylhexan-3-yl)-2-hydroxy-9-methyl-2,3,4,5-tetrahydrobenzo[1,2]oxaborepine-8-carbohydrazide |
| 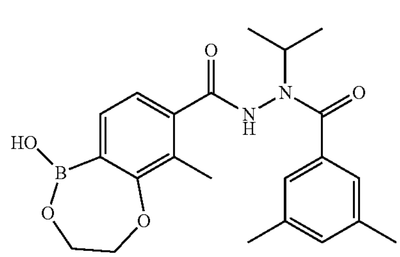 [SMILES: Cc1cc(C)cc(C(=O)N(NC(=O)c2ccc3c(c2C)OCCOB3O)C(C)C)c1] | N'-(3,5-dimethylbenzoyl)-1-hydroxy-N'-isopropyl-6-methyl-3,4-dihydro-1H-benzo[c][1,5,2]dioxaborepine-7-carbohydrazide |

TABLE 2-continued

| Structure | Name |
|---|---|
| 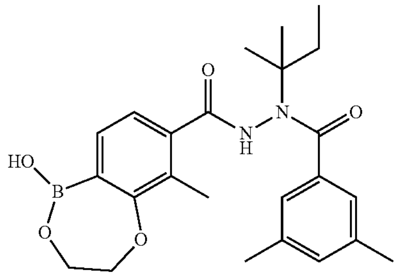 [SMILES: CCC(C)(C)N(NC(=O)c1ccc2c(c1C)OCCOB2O)C(=O)c1cc(C)cc(C)c1] | N'-(3,5-dimethylbenzoyl)-1-hydroxy-6-methyl-N'-(tert-pentyl)-3,4-dihydro-1H-benzo[c][1,5,2]dioxaborepine-7-carbohydrazide |
| 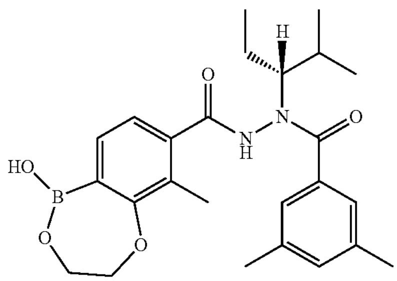 [SMILES: CC[C@H](C(C)C)N(NC(=O)c1ccc2c(c1C)OCCOB2O)C(=O)c1cc(C)cc(C)c1] | (R)-N'-(3,5-dimethylbenzoyl)-N'-(2,2-dimethylpentan-3-yl)-1-hydroxy-6-methyl-3,4-dihydro-1H-benzo[c][1,5,2]dioxaborepine-7-carbohydrazide |
| 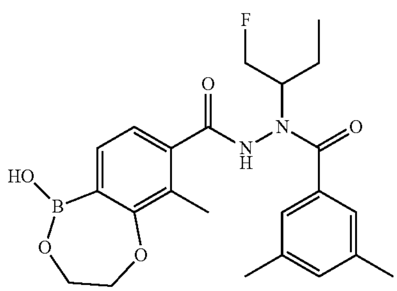 [SMILES: CCC(CF)N(NC(=O)c1ccc2c(c1C)OCCOB2O)C(=O)c1cc(C)cc(C)c1] | N'-(3,5-dimethylbenzoyl)-N'-(1-fluorobutan-2-yl)-1-hydroxy-6-methyl-3,4-dihydro-1H-benzo[c][1,5,2]dioxaborepine-7-carbohydrazide |
| 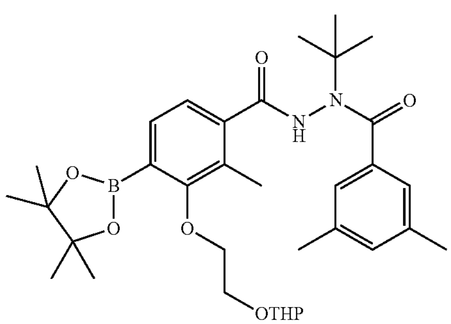 | N'-(tert-butyl)-N'-(3,5-dimethylbenzoyl)-2-methyl-3-(2-((tetrahydro-2H-pyran-2-yl)oxy)ethoxy)-4-(4,4,5,5-tetramethyl-1,3,2-dioxaborolan-2-yl)benzohydrazide |
| 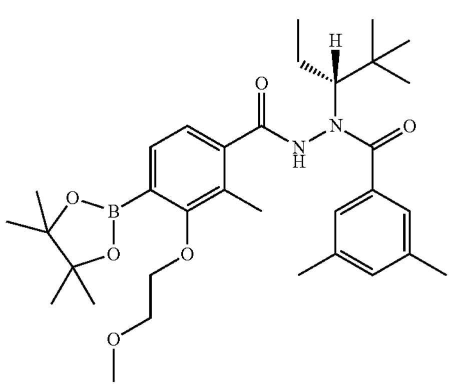 | (R)-N'-(3,5-dimethylbenzoyl)-N'-(2,2-dimethylpentan-3-yl)-3-(2-methoxyethoxy)-2-methyl-4-(4,4,5,5-tetramethyl-1,3,2-dioxaborolan-2-yl)benzohydrazide |

TABLE 2-continued

| Structure | Name |
|---|---|
| 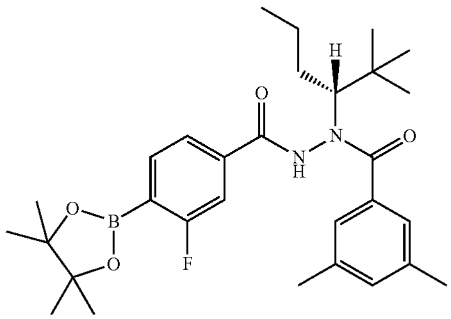 | (R)-N'-(3,5-dimethylbenzoyl)-N'-(2,2-dimethylhexan-3-yl)-3-fluoro-4-(4,4,5,5-tetramethyl-1,3,2-dioxaborolan-2-yl)benzohydrazide |
| 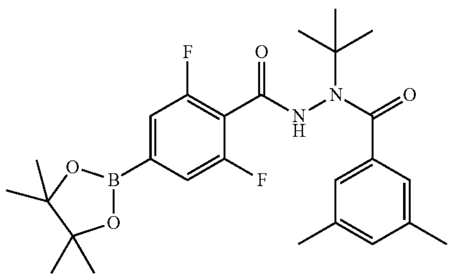 | N'-(tert-butyl)-N'-(3,5-dimethylbenzoyl)-2,6-difluoro-4-(4,4,5,5-tetramethyl-1,3,2-dioxaborolan-2-yl)benzohydrazide |
| 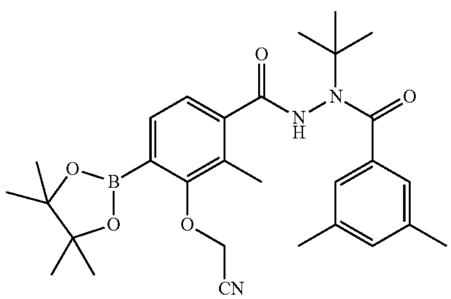 | N'-(tert-butyl)-3-(cyanomethoxy)-N'-(3,5-dimethylbenzoyl)-2-methyl-4-(4,4,5,5-tetramethyl-1,3,2-dioxaborolan-2-yl)benzohydrazide |
| 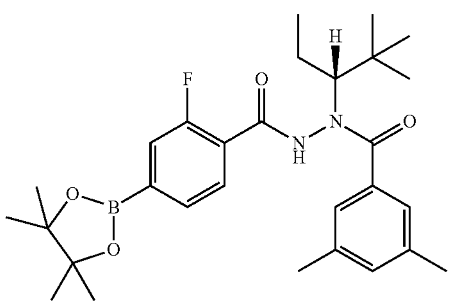 | (R)-N'-(3,5-dimethylbenzoyl)-N'-(2,2-dimethylpentan-3-yl)-2-fluoro-4-(4,4,5,5-tetramethyl-1,3,2-dioxaborolan-2-yl)benzohydrazide |
| 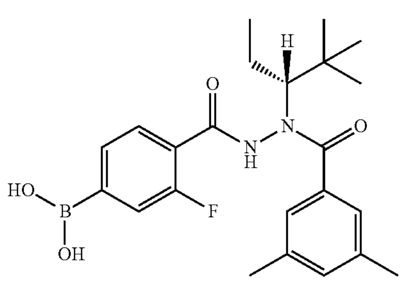 [SMILES: CC[C@@H](N(NC(=O)c1ccc(B(O)O)cc1F)C(=O)c1cc(C)cc(C)c1)C(C)(C)C] | (R)-(4-(2-(3,5-dimethylbenzoyl)-2-(2,2-dimethylpentan-3-yl)hydrazine-1-carbonyl)-3-fluorophenyl)boronic acid |

TABLE 2-continued

| Structure | Name |
|---|---|
| 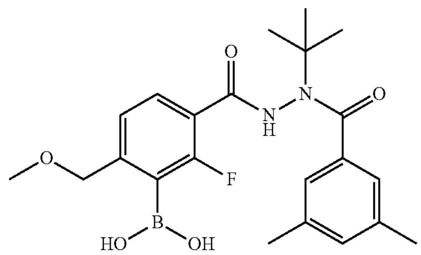 | (3-(2-(tert-butyl)-2-(3,5-dimethylbenzoyl)hydrazine-1-carbonyl)-2-fluoro-6-(methoxymethyl)phenyl)boronic acid |
| 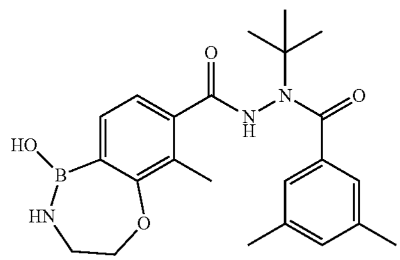 [SMILES: Cc1cc(C)cc(C(=O)N(NC(=O)c2ccc3c(c2C)OCCNB3O)C(C)(C)C)c1] | N'-(tert-butyl)-N'-(3,5-dimethylbenzoyl)-1-hydroxy-6-methyl-1,2,3,4-tetrahydrobenzo[f][1,4,5]oxazaborepine-7-carbohydrazide |
| 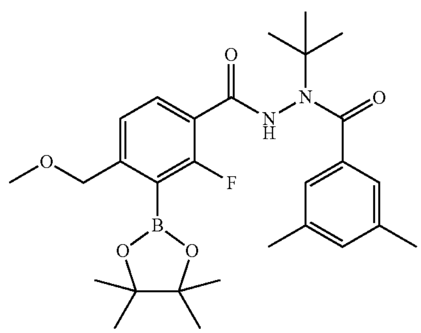 | N'-(tert-butyl)-N'-(3,5-dimethylbenzoyl)-2-fluoro-4-(methoxymethyl)-3-(4,4,5,5-tetramethyl-1,3,2-dioxaborolan-2-yl)benzohydrazide |
| 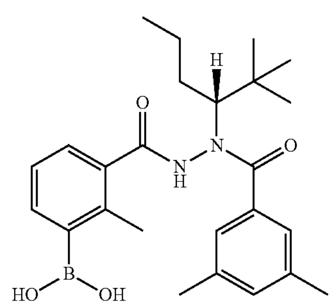 [SMILES: CCC[C@@H](N(NC(=O)c1cccc(B(O)O)c1C)C(=O)c1cc(C)cc(C)c1)C(C)(C)C] | (R)-(3-(2-(3,5-dimethylbenzoyl)-2-(2,2-dimethylhexan-3-yl)hydrazine-1-carbonyl)-2-methylphenyl)boronic acid |
| 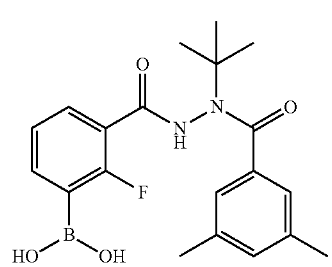 [SMILES: Cc1cc(C)cc(C(=O)N(NC(=O)c2cccc(B(O)O)c2F)C(C)(C)C)c1] | (3-(2-(tert-butyl)-2-(3,5-dimethylbenzoyl)hydrazine-1-carbonyl)-2-fluorophenyl)boronic acid |

TABLE 2-continued

| Structure | Name |
|---|---|
| 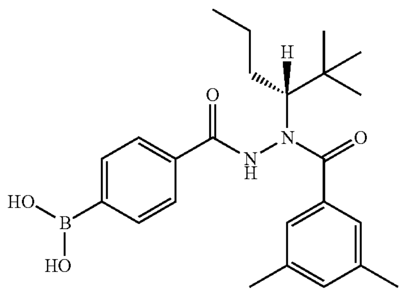 [SMILES: CCC[C@@H](N(NC(=O)c1ccc(B(O)O)cc1)C(=O)c1cc(C)cc(C)c1)C(C)(C)C] | (R)-(4-(2-(3,5-dimethylbenzoyl)-2-(2,2-dimethylhexan-3-yl)hydrazine-1-carbonyl)phenyl)boronic acid |
| 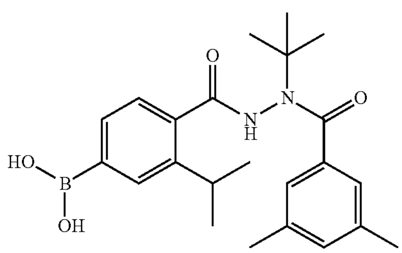 [SMILES: Cc1cc(C)cc(C(=O)N(NC(=O)c2ccc(B(O)O)cc2C(C)C)C(C)(C)C)c1] | (4-(2-(tert-butyl)-2-(3,5-dimethylbenzoyl)hydrazine-1-carbonyl)-3-isopropylphenyl)boronic acid |
| 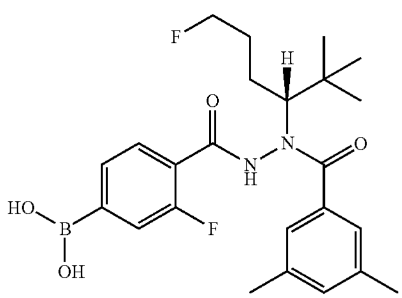 [SMILES: Cc1cc(C)cc(C(=O)N(NC(=O)c2ccc(B(O)O)cc2F)[C@H](CCCF)C(C)(C)C)c1] | (R)-(4-(2-(3,5-dimethylbenzoyl)-2-(6-fluoro-2,2-dimethylhexan-3-yl)hydrazine-1-carbonyl)-3-fluorophenyl)boronic acid |
| 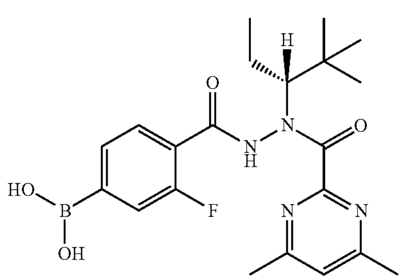 [SMILES: CC[C@@H](N(NC(=O)c1ccc(B(O)O)cc1F)C(=O)c1nc(C)cc(C)n1)C(C)(C)C] | (R)-(4-(2-(2,2-dimethylpentan-3-yl)-2-(4,6-dimethylpyrimidine-2-carbonyl)hydrazine-1-carbonyl)-3-fluorophenyl)boronic acid |
| 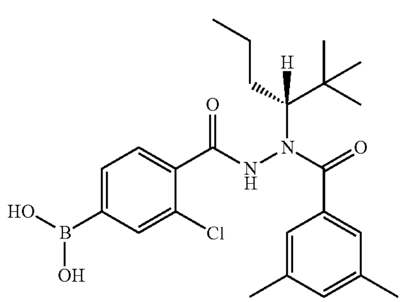 [SMILES: CCC[C@@H](N(NC(=O)c1ccc(B(O)O)cc1Cl)C(=O)c1cc(C)cc(C)c1)C(C)(C)C] | (R)-(3-chloro-4-(2-(3,5-dimethylbenzoyl)-2-(2,2-dimethylhexan-3-yl)hydrazine-1-carbonyl)phenyl)boronic acid |

TABLE 2-continued

| Structure | Name |
|---|---|
| 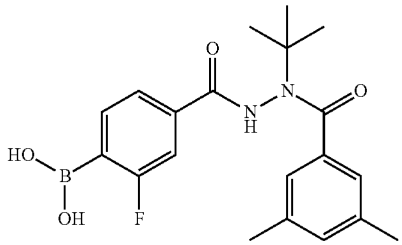 [SMILES: Cc1cc(C)cc(C(=O)N(NC(=O)c2ccc(B(O)O)c(F)c2)C(C)(C)C)c1] | (4-(2-(tert-butyl)-2-(3,5-dimethylbenzoyl)hydrazine-1-carbonyl)-2-fluorophenyl)boronic acid |
| 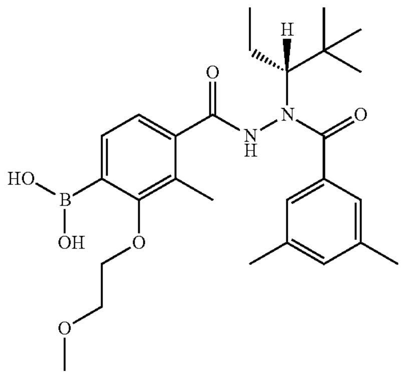 [SMILES: CC[C@@H](N(NC(=O)c1ccc(B(O)O)c(OCCOC)c1C)C(=O)c1cc(C)cc(C)c1)C(C)(C)C] | (R)-(4-(2-(3,5-dimethylbenzoyl)-2-(2,2-dimethylpentan-3-yl)hydrazine-1-carbonyl)-2-(2-methoxyethoxy)-3-methylphenyl)boronic acid |
| 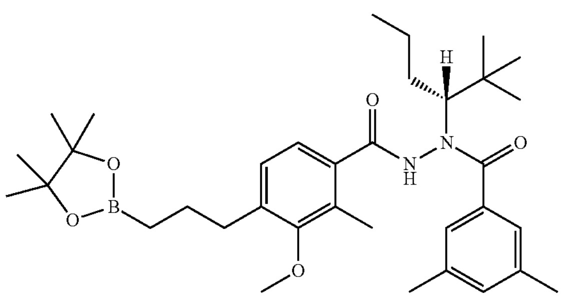 | (R)-N'-(3,5-dimethylbenzoyl)-N'-(2,2-dimethylhexan-3-yl)-3-methoxy-2-methyl-4-(3-(4,4,5,5-tetramethyl-1,3,2-dioxaborolan-2-yl)propyl)benzohydrazide |
| 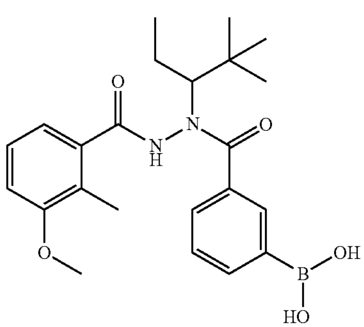 [SMILES: CCC(N(NC(=O)c1cccc(OC)c1C)C(=O)c1cccc(B(O)O)c1)C(C)(C)C] | (3-(1-(2,2-dimethylpentan-3-yl)-2-(3-methoxy-2-methylbenzoyl)hydrazine-1-carbonyl)phenyl)boronic acid |
| 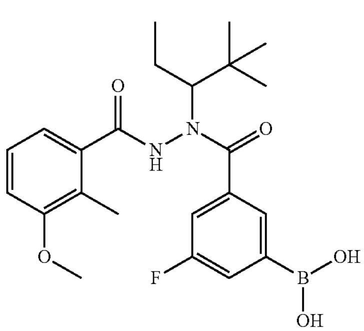 [SMILES: CCC(N(NC(=O)c1cccc(OC)c1C)C(=O)c1cc(F)cc(B(O)O)c1)C(C)(C)C] | (3-(1-(2,2-dimethylpentan-3-yl)-2-(3-methoxy-2-methylbenzoyl)hydrazine-1-carbonyl)-5-fluorophenyl)boronic acid |

TABLE 2-continued

| Structure | Name |
|---|---|
| 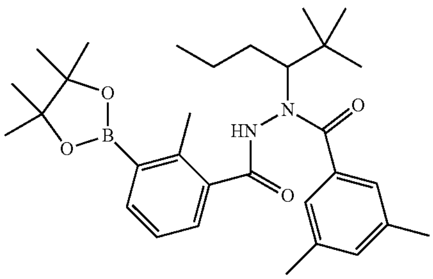 | N'-(3,5-dimethylbenzoyl)-N'-(2,2-dimethylhexan-3-yl)-2-methyl-3-(4,4,5,5-tetramethyl-1,3,2-dioxaborolan-2-yl)benzohydrazide |
| 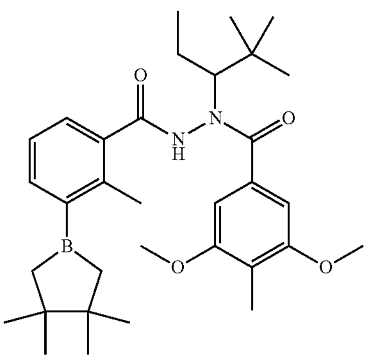 | N-(2,2-dimethylpentan-3-yl)-3,5-dimethoxy-4-methyl-N'-(2-methyl-3-(4,4,5,5-tetramethyl-1,3,2-dioxaborolan-2-yl)benzoyl)benzohydrazide |
| 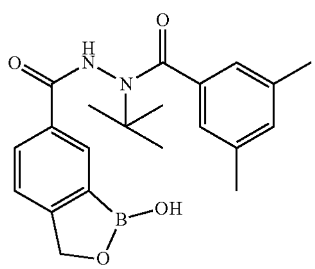 [SMILES: Cc1cc(C)cc(C(=O)N(NC(=O)c2ccc3c(c2)B(O)OC3)C(C)(C)C)c1] | N'-(tert-butyl)-N'-(3,5-dimethylbenzoyl)-1-hydroxy-1,3-dihydrobenzo[c][1,2]oxaborole-6-carbohydrazide |
| 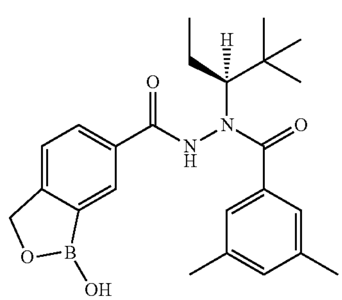 [SMILES: CC[C@H](N(NC(=O)c1ccc2c(c1)B(O)OC2)C(=O)c1cc(C)cc(C)c1)C(C)(C)C] | (S)-N'-(3,5-dimethylbenzoyl)-N'-(2,2-dimethylpentan-3-yl)-1-hydroxy-1,3-dihydrobenzo[c][1,2]oxaborole-6-carbohydrazide |
| 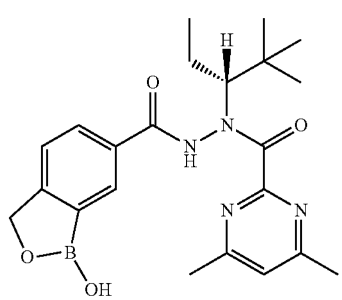 [SMILES: CC[C@@H](N(NC(=O)c1ccc2c(c1)B(O)OC2)C(=O)c1nc(C)cc(C)n1)C(C)(C)C] | (R)-N-(2,2-dimethylpentan-3-yl)-N'-(1-hydroxy-1,3-dihydrobenzo[c][1,2]oxaborole-6-carbonyl)-4,6-dimethylpyrimidine-2-carbohydrazide |

TABLE 2-continued

| Structure | Name |
|---|---|
| 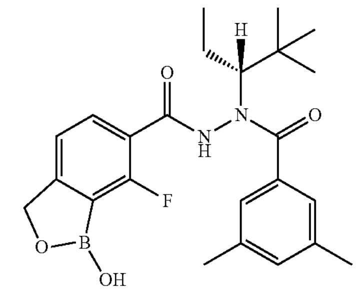 [SMILES: CC[C@@H](N(NC(=O)c1ccc2c(c1F)B(O)OC2)C(=O)c1cc(C)cc(C)c1)C(C)(C)C] | (R)-N'-(3,5-dimethylbenzoyl)-N'-(2,2-dimethylpentan-3-yl)-7-fluoro-1-hydroxy-1,3-dihydrobenzo[c][1,2]oxaborole-6-carbohydrazide |
| 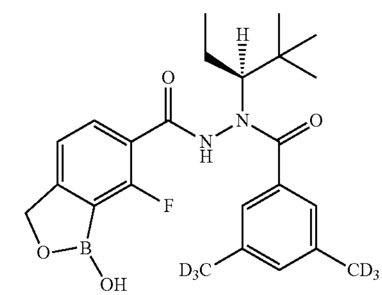 [SMILES: [2H]C([2H])([2H])c1cc(C(=O)N(NC(=O)c2ccc3c(c2F)B(O)OC3)[C@@H](CC)C(C)(C)C)cc(C([2H])([2H])[2H])c1] | (S)-N'-(3,5-bis(methyl-d3)benzoyl)-N'-(2,2-dimethylpentan-3-yl)-7-fluoro-1-hydroxy-1,3-dihydrobenzo[c][1,2]oxaborole-6-carbohydrazide |
| 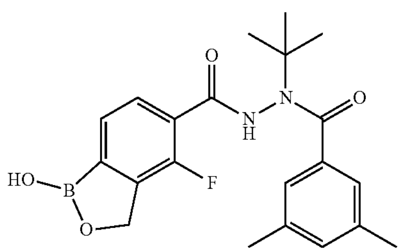 [SMILES: Cc1cc(C)cc(C(=O)N(NC(=O)c2ccc3c(c2F)COB3O)C(C)(C)C)c1] | N'-(tert-butyl)-N'-(3,5-dimethylbenzoyl)-4-fluoro-1-hydroxy-1,3-dihydrobenzo[c][1,2]oxaborole-5-carbohydrazide |
| 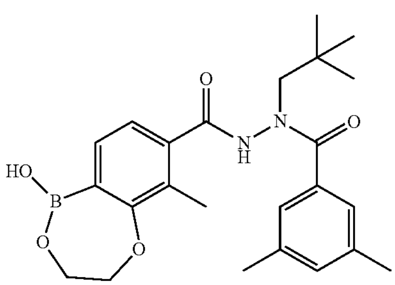 [SMILES: Cc1cc(C)cc(C(=O)N(CC(C)(C)C)NC(=O)c2ccc3c(c2C)OCCOB3O)c1] | N'-(3,5-dimethylbenzoyl)-1-hydroxy-6-methyl-N'-neopentyl-3,4-dihydro-1H-benzo[c][1,5,2]dioxaborepine-7-carbohydrazide |
| 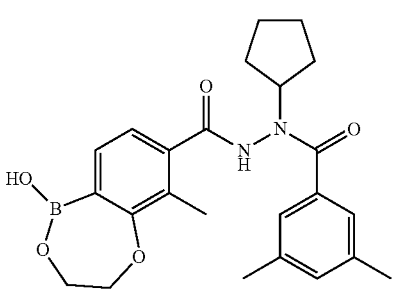 [SMILES: Cc1cc(C)cc(C(=O)N(NC(=O)c2ccc3c(c2C)OCCOB3O)C2CCCC2)c1] | N'-cyclopentyl-N'-(3,5-dimethylbenzoyl)-1-hydroxy-6-methyl-3,4-dihydro-1H-benzo[c][1,5,2]dioxaborepine-7-carbohydrazide |

TABLE 2-continued

| Structure | Name |
|---|---|
| 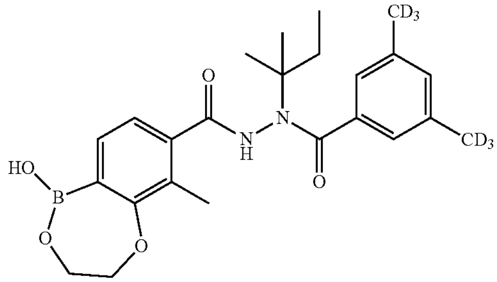 [SMILES: [2H]C([2H])([2H])c1cc(C(=O)N(NC(=O)c2ccc3c(c2C)OCCOB3O)C(C)(C)CC)cc(C([2H])([2H])[2H])c1] | N'-(3,5-bis(methyl-d3)benzoyl)-1-hydroxy-6-methyl-N'-(tert-pentyl)-3,4-dihydro-1H-benzo[c][1,5,2]dioxaborepine-7-carbohydrazide |
| 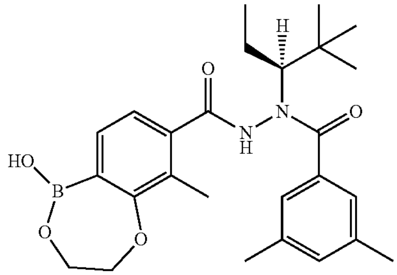 [SMILES: CC[C@H](N(NC(=O)c1ccc2c(c1C)OCCOB2O)C(=O)c1cc(C)cc(C)c1)C(C)(C)C] | (S)-N'-(3,5-dimethylbenzoyl)-N'-(2,2-dimethylpentan-3-yl)-1-hydroxy-6-methyl-3,4-dihydro-1H-benzo[c][1,5,2]dioxaborepine-7-carbohydrazide |
| 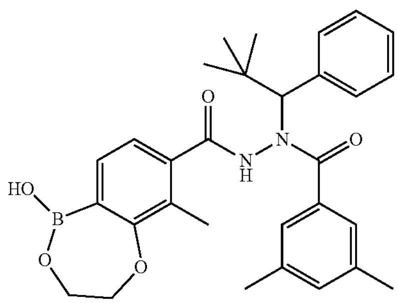 [SMILES: Cc1cc(C)cc(C(=O)N(NC(=O)c2ccc3c(c2C)OCCOB3O)C(c2ccccc2)C(C)(C)C)c1] | N'-(2,2-dimethyl-1-phenylpropyl)-N'-(3,5-dimethylbenzoyl)-1-hydroxy-6-methyl-3,4-dihydro-1H-benzo[c][1,5,2]dioxaborepine-7-carbohydrazide |
| 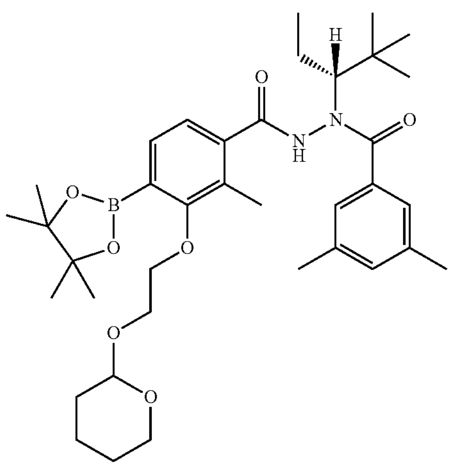 | N'-(3,5-dimethylbenzoyl)-N'-((R)-2,2-dimethylpentan-3-yl)-2-methyl-3-(2-((tetrahydro-2H-pyran-2-yl)oxy)ethoxy)-4-(4,4,5,5-tetramethyl-1,3,2-dioxaborolan-2-yl)benzohydrazide |
| 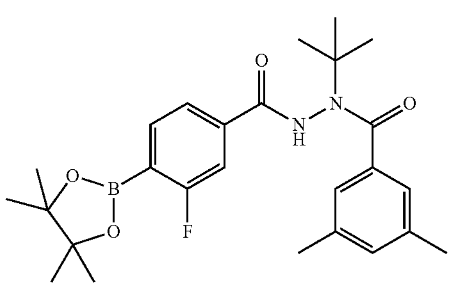 | N'-(tert-butyl)-N'-(3,5-dimethylbenzoyl)-3-fluoro-4-(4,4,5,5-tetramethyl-1,3,2-dioxaborolan-2-yl)benzohydrazide |

TABLE 2-continued

| Structure | Name |
|---|---|
| 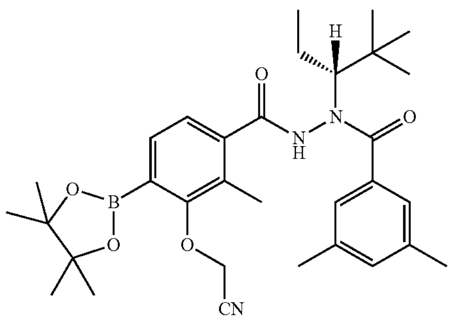 | (R)-3-(cyanomethoxy)-N'-(3,5-dimethylbenzoyl)-N'-(2,2-dimethylpentan-3-yl)-2-methyl-4-(4,4,5,5-tetramethyl-1,3,2-dioxaborolan-2-yl)benzohydrazide |
| 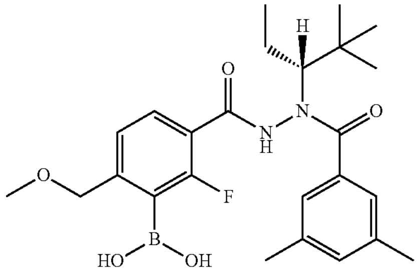 | (R)-(3-(2-(3,5-dimethylbenzoyl)-2-(2,2-dimethylpentan-3-yl)hydrazine-1-carbonyl)-2-fluoro-6-(methoxymethyl)phenyl)boronic acid |
| 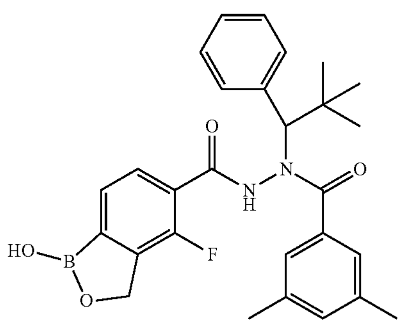 [SMILES: Cc1cc(C)cc(C(=O)N(NC(=O)c2ccc3c(c2F)COB3O)C(c2ccccc2)C(C)(C)C)c1] | N'-(2,2-dimethyl-1-phenylpropyl)-N'-(3,5-dimethylbenzoyl)-4-fluoro-1-hydroxy-1,3-dihydrobenzo[c][1,2]oxaborole-5-carbohydrazide |
| 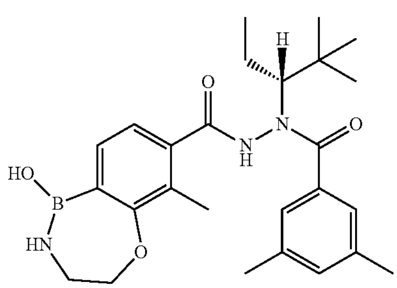 [SMILES: CC[C@@H](N(NC(=O)c1ccc2c(c1C)OCCNB2O)C(=O)c1cc(C)cc(C)c1)C(C)(C)C] | (R)-N'-(3,5-dimethylbenzoyl)-N'-(2,2-dimethylpentan-3-yl)-1-hydroxy-6-methyl-1,2,3,4-tetrahydrobenzo[f][1,4,5]oxazaborepine-7-carbohydrazide |
| | N'-(3,5-dimethylbenzoyl)-N'-((R)-2,2-dimethylpentan-3-yl)-7-fluoro-5'-oxo-3H-1λ4-spiro[benzo[c][1,2]oxaborole-1,2'-[1,3,2]oxazaborolidine]-6-carbohydrazide |

TABLE 2-continued

| Structure | Name |
|---|---|
| 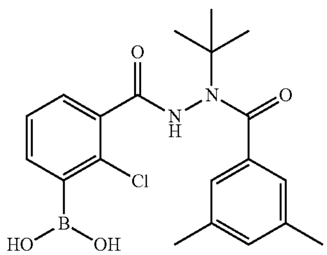 | (3-(2-(tert-butyl)-2-(3,5-dimethylbenzoyl)hydrazine-1-carbonyl)-2-chlorophenyl)boronic acid |
| 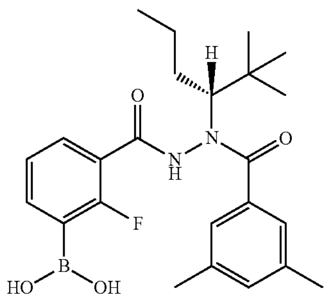 | (R)-(3-(2-(3,5-dimethylbenzoyl)-2-(2,2-dimethylhexan-3-yl)hydrazine-1-carbonyl)-2-fluorophenyl)boronic acid |
| 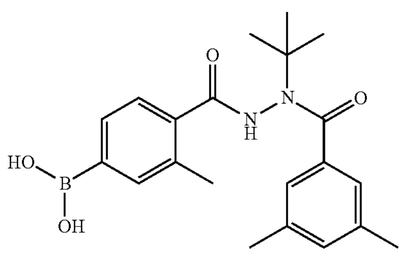 [SMILES: Cc1cc(C)cc(C(=O)N(NC(=O)c2ccc(B(O)O)cc2C)C(C)(C)C)c1] | (4-(2-(tert-butyl)-2-(3,5-dimethylbenzoyl)hydrazine-1-carbonyl)-3-methylphenyl)boronic acid |
| 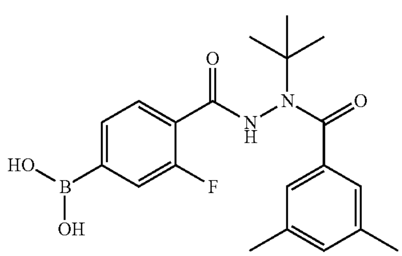 [SMILES: Cc1cc(C)cc(C(=O)N(NC(=O)c2ccc(B(O)O)cc2F)C(C)(C)C)c1] | (4-(2-(tert-butyl)-2-(3,5-dimethylbenzoyl)hydrazine-1-carbonyl)-3-fluorophenyl)boronic acid |
| 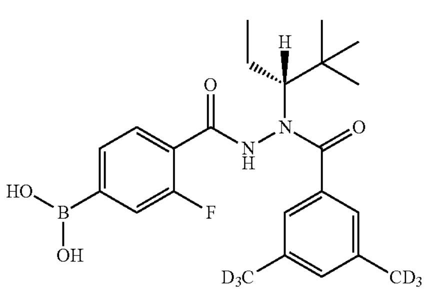 [SMILES: [2H]C([2H])([2H])c1cc(C(=O)N(NC(=O)c2ccc(B(O)O)cc2F)[C@H](CC)C(C)(C)C)cc(C([2H])([2H])[2H])c1] | (R)-(4-(2-(3,5-bis(methyl-d3)benzoyl)-2-(2,2-dimethylpentan-3-yl)hydrazine-1-carbonyl)-3-fluorophenyl)boronic acid |

TABLE 2-continued

| Structure | Name |
|---|---|
| 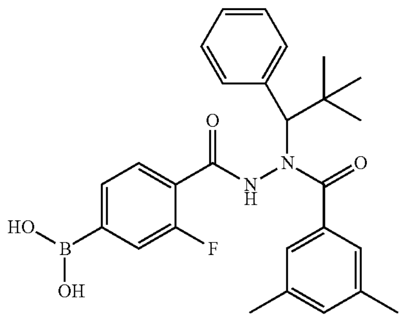 [SMILES: Cc1cc(C)cc(C(=O)N(NC(=O)c2ccc(B(O)O)cc2F)C(c2ccccc2)C(C)(C)C)c1] | (4-(2-(2,2-dimethyl-1-phenylpropyl)-2-(3,5-dimethylbenzoyl)hydrazine-1-carbonyl)-3-fluorophenyl)boronic acid |
| 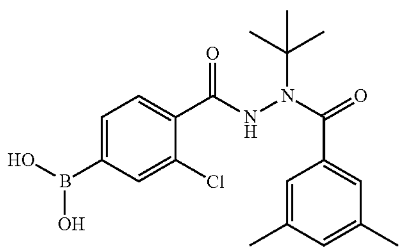 [SMILES: Cc1cc(C)cc(C(=O)N(NC(=O)c2ccc(B(O)O)cc2Cl)C(C)(C)C)c1] | (4-(2-(tert-butyl)-2-(3,5-dimethylbenzoyl)hydrazine-1-carbonyl)-3-chlorophenyl)boronic acid |
| 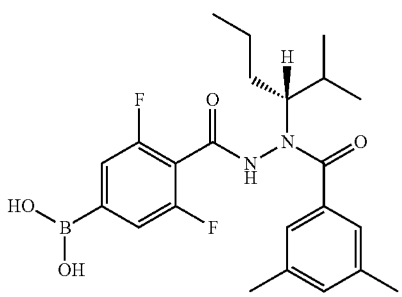 [SMILES: CCC[C@H](C(C)C)N(NC(=O)c1c(F)cc(B(O)O)cc1F)C(=O)c1cc(C)cc(C)c1] | (R)-(4-(2-(3,5-dimethylbenzoyl)-2-(2,2-dimethylhexan-3-yl)hydrazine-1-carbonyl)-3,5-difluorophenyl)boronic acid |
| 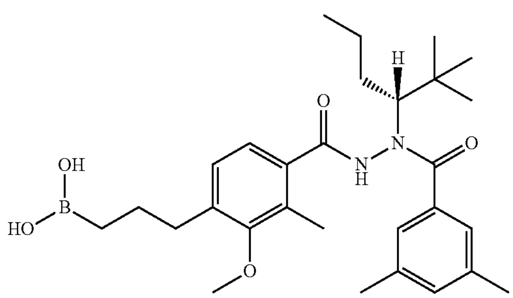 [SMILES: CCC[C@@H](N(NC(=O)c1ccc(CCCB(O)O)c(OC)c1C)C(=O)c1cc(C)cc(C)c1)C(C)(C)C] | (R)-(3-(4-(2-(3,5-dimethylbenzoyl)-2-(2,2-dimethylhexan-3-yl)hydrazine-1-carbonyl)-2-methoxy-3-methylphenyl)propyl)boronic acid |
| 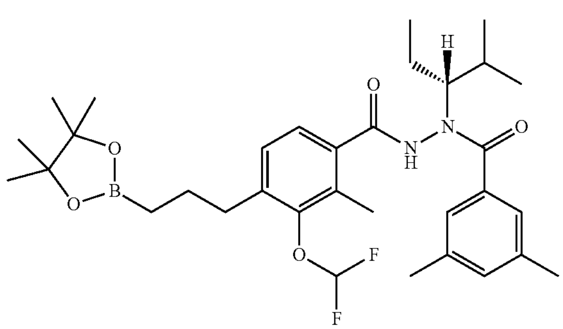 | (R)-3-(difluoromethoxy)-N'-(3,5-dimethylbenzoyl)-N'-(2,2-dimethylhexan-3-yl)-2-methyl-4-(3-(4,4,5,5-tetramethyl-1,3,2-dioxaborolan-2-yl)propyl)benzohydrazide |

TABLE 2-continued

| Structure | Name |
|---|---|
| 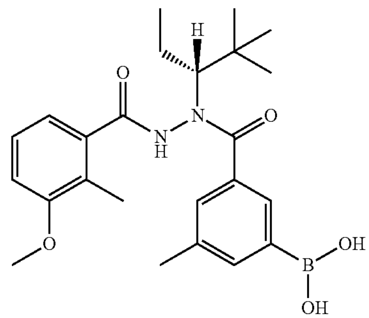 [SMILES: CC[C@@H](N(NC(=O)c1cccc(OC)c1C)C(=O)c1cc(C)cc(B(O)O)c1)C(C)(C)C] | (R)-(3-(1-(2,2-dimethylpentan-3-yl)-2-(3-methoxy-2-methylbenzoyl)hydrazine-1-carbonyl)-5-methylphenyl)boronic acid |
| 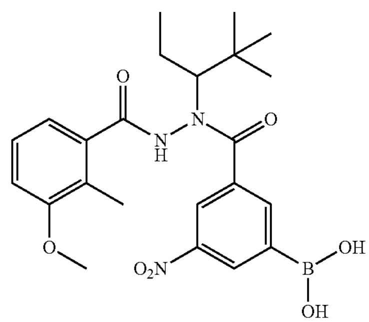 | (3-(1-(2,2-dimethylpentan-3-yl)-2-(3-methoxy-2-methylbenzoyl)hydrazine-1-carbonyl)-5-nitrophenyl)boronic acid |
| 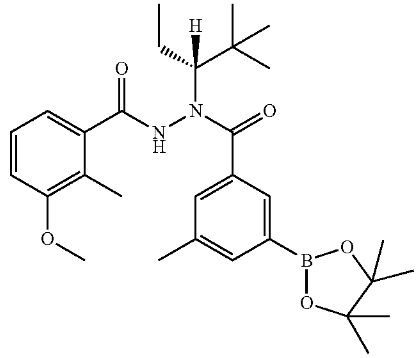 [SMILES: CC[C@@H](N(NC(=O)c1cccc(OC)c1C)C(=O)c1cc(C)cc(B2OC(C)(C)C(C)(C)O2)c1)C(C)(C)C] | (R)-N'-(2,2-dimethylpentan-3-yl)-3-methoxy-2-methyl-N'-(3-methyl-5-(4,4,5,5-tetramethyl-1,3,2-dioxaborolan-2-yl)benzoyl)benzohydrazide |
| 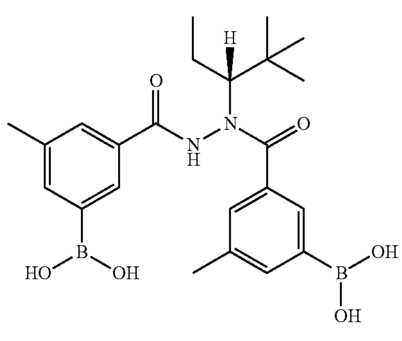 [SMILES: CC[C@@H](N(NC(=O)c1cc(C)cc(B(O)O)c1)C(=O)c1cc(C)cc(B(O)O)c1)C(C)(C)C] | (R)-(3-(2-(3-borono-5-methylbenzoyl)-1-(2,2-dimethylpentan-3-yl)hydrazine-1-carbonyl)-5-methylphenyl)boronic acid |

TABLE 2-continued

| Structure | Name |
|---|---|
| 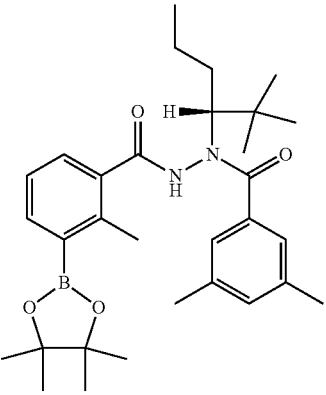 | (R)-N'-(3,5-dimethylbenzoyl)-N'-(2,2-dimethylhexan-3-yl)-2-methyl-3-(4,4,5,5-tetramethyl-1,3,2-dioxaborolan-2-yl)benzohydrazide |
| 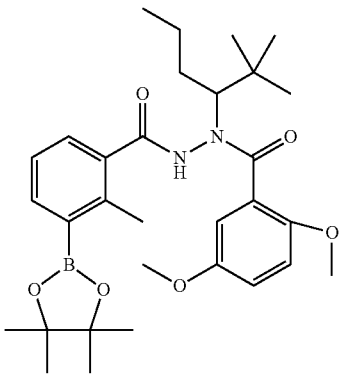 | N'-(2,5-dimethoxybenzoyl)-N'-(2,2-dimethylhexan-3-yl)-2-methyl-3-(4,4,5,5-tetramethyl-1,3,2-dioxaborolan-2-yl)benzohydrazide |
| 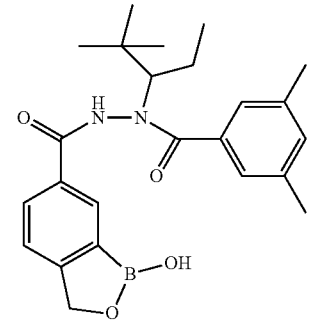 [SMILES: CCC(N(NC(=O)c1ccc2c(c1)B(O)OC2)C(=O)c1cc(C)cc(C)c1)C(C)(C)C] | N'-(3,5-dimethylbenzoyl)-N'-(2,2-dimethylpentan-3-yl)-1-hydroxy-1,3-dihydrobenzo[c][1,2]oxaborole-6-carbohydrazide |
| 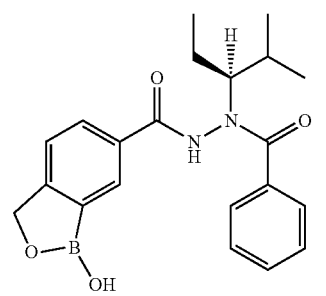 [SMILES: CC[C@@H](C(C)C)N(NC(=O)c1ccc2c(c1)B(O)OC2)C(=O)c1ccccc1] | (S)-N'-benzoyl-N'-(2,2-dimethylpentan-3-yl)-1-hydroxy-1,3-dihydrobenzo[c][1,2]oxaborole-6-carbohydrazide |

TABLE 2-continued

| Structure | Name |
|---|---|
| 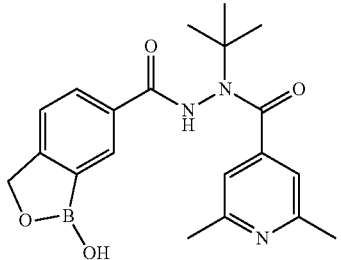 [SMILES: Cc1cc(C(=O)N(NC(=O)c2ccc3c(c2)B(O)OC3)C(C)(C)C)cc(C)n1] | N-(tert-butyl)-N'-(1-hydroxy-1,3-dihydrobenzo[c][1,2]oxaborole-6-carbonyl)-2,6-dimethylisonicotinohydrazide |
| 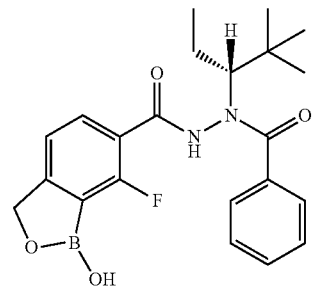 [SMILES: CC[C@@H](N(NC(=O)c1ccc2c(c1F)B(O)OC2)C(=O)c1ccccc1)C(C)(C)C] | (R)-N'-benzoyl-N'-(2,2-dimethylpentan-3-yl)-7-fluoro-1-hydroxy-1,3-dihydrobenzo[c][1,2]oxaborole-6-carbohydrazide |
| 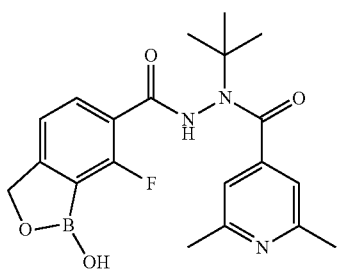 [SMILES: Cc1cc(C(=O)N(NC(=O)c2ccc3c(c2F)B(O)OC3)C(C)(C)C)cc(C)n1] | N-(tert-butyl)-N'-(7-fluoro-1-hydroxy-1,3-dihydrobenzo[c][1,2]oxaborole-6-carbonyl)-2,6-dimethylisonicotinohydrazide |
| 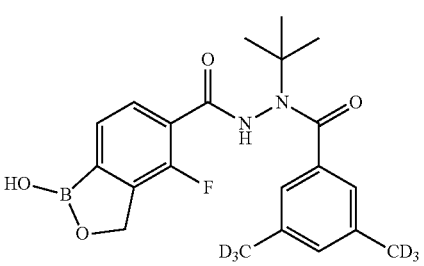 [SMILES: [2H]C([2H])([2H])c1cc(C(=O)N(NC(=O)c2ccc3c(c2F)COB3O)C(C)(C)C)cc(C([2H])([2H])[2H])c1] | N'-(3,5-bis(methyl-d3)benzoyl)-N'-(tert-butyl)-4-fluoro-1-hydroxy-1,3-dihydrobenzo[c][1,2]oxaborole-5-carbohydrazide |
| 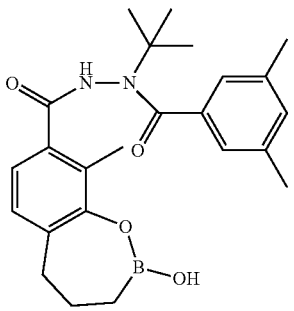 [SMILES: Cc1cc(C)cc(C(=O)N(NC(=O)c2ccc3c(c2C)OB(O)CCC3)C(C)(C)C)c1] | N'-(tert-butyl)-N'-(3,5-dimethylbenzoyl)-2-hydroxy-9-methyl-2,3,4,5-tetrahydrobenzo[f][1,2]oxaborepine-8-carbohydrazide |

TABLE 2-continued

| Structure | Name |
|---|---|
| 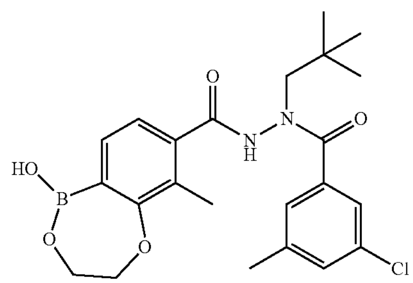 [SMILES: Cc1cc(Cl)cc(C(=O)N(CC(C)(C)C)NC(=O)c2ccc3c(c2C)OCCOB3O)c1] | N'-(3-chloro-5-methylbenzoyl)-1-hydroxy-6-methyl-N'-neopentyl-3,4-dihydro-1H-benzo[c][1,5,2]dioxaborepine-7-carbohydrazide |
| 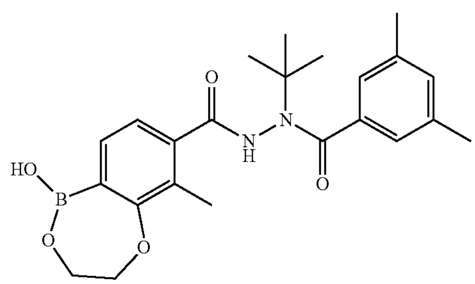 [SMILES: Cc1cc(C)cc(C(=O)N(NC(=O)c2ccc3c(c2C)OCCOB3O)C(C)(C)C)c1] | N'-(tert-butyl)-N'-(3,5-dimethylbenzoyl)-1-hydroxy-6-methyl-3,4-dihydro-1H-benzo[c][1,5,2]dioxaborepine-7-carbohydrazide |
| 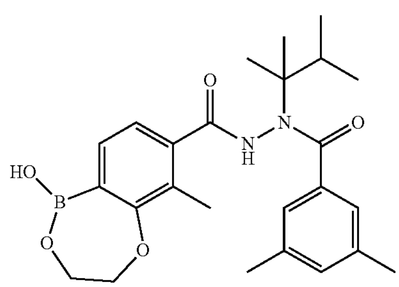 [SMILES: Cc1cc(C)cc(C(=O)N(NC(=O)c2ccc3c(c2C)OCCOB3O)C(C)(C)C(C)C)c1] | N'-(3,5-dimethylbenzoyl)-N'-(2,3-dimethylbutan-2-yl)-1-hydroxy-6-methyl-3,4-dihydro-1H-benzo[c][1,5,2]dioxaborepine-7-carbohydrazide |
| 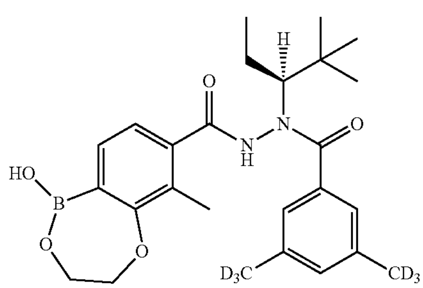 [SMILES: [2H]C([2H])([2H])c1cc(C(=O)N(NC(=O)c2ccc3c(c2C)OCCOB3O)[C@@H](CC)C(C)(C)C)cc(C([2H])([2H])[2H])c1] | (S)-N'-(3,5-bis(methyl-d3)benzoyl)-N'-(2,2-dimethylpentan-3-yl)-1-hydroxy-6-methyl-3,4-dihydro-1H-benzo[c][1,5,2]dioxaborepine-7-carbohydrazide |
| 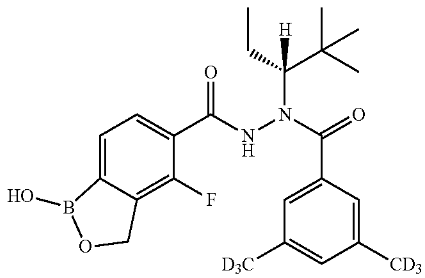 [SMILES: [2H]C([2H])([2H])c1cc(C(=O)N(NC(=O)c2ccc3c(c2F)COB3O)[C@H](CC)C(C)(C)C)cc(C([2H])([2H])[2H])c1] | (R)-N'-(3,5-bis(methyl-d3)benzoyl)-N'-(2,2-dimethylpentan-3-yl)-4-fluoro-1-hydroxy-1,3-dihydrobenzo[c][1,2]oxaborole-5-carbohydrazide |

TABLE 2-continued

| Structure | Name |
|---|---|
| 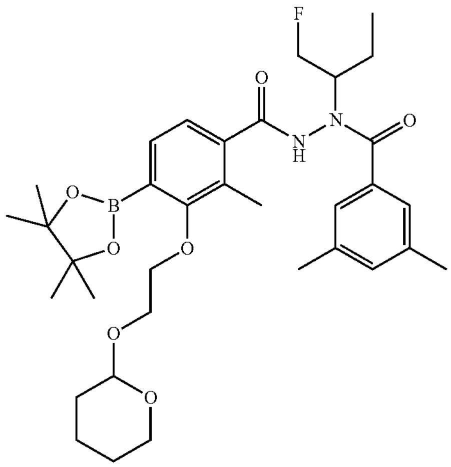 | N'-(3,5-dimethylbenzoyl)-N'-(1-fluorobutan-2-yl)-2-methyl-3-(2-((tetrahydro-2H-pyran-2-yl)oxy)ethoxy)-4-(4,4,5,5-tetramethyl-1,3,2-dioxaborolan-2-yl)benzohydrazide |
| 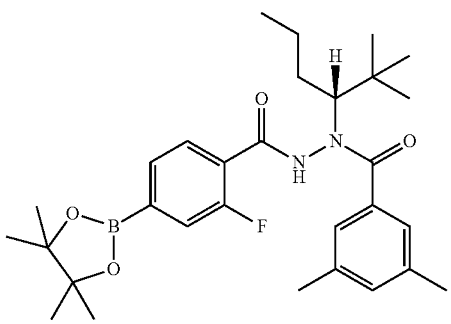 | (R)-N'-(3,5-dimethylbenzoyl)-N'-(2,2-dimethylhexan-3-yl)-2-fluoro-4-(4,4,5,5-tetramethyl-1,3,2-dioxaborolan-2-yl)benzohydrazide |
| 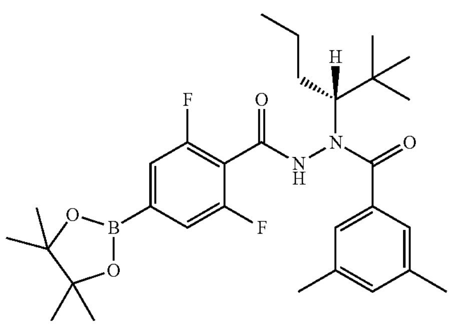 | (R)-N'-(3,5-dimethylbenzoyl)-N'-(2,2-dimethylhexan-3-yl)-2,6-difluoro-4-(4,4,5,5-tetramethyl-1,3,2-dioxaborolan-2-yl)benzohydrazide |
| 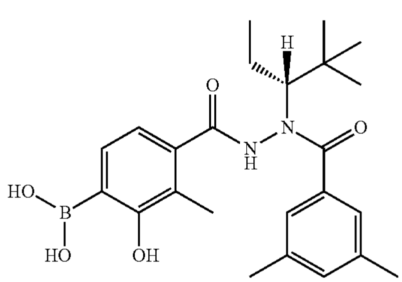 [SMILES: CC[C@@H](N(NC(=O)c1ccc(B(O)O)c(O)c1C)C(=O)c1cc(C)cc(C)c1)C(C)(C)C] | (R)-(4-(2-(3,5-dimethylbenzoyl)-2-(2,2-dimethylpentan-3-yl)hydrazine-1-carbonyl)-2-hydroxy-3-methylphenyl)boronic acid |

TABLE 2-continued

| Structure | Name |
|---|---|
| 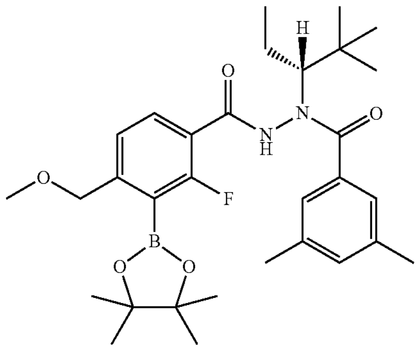 | (R)-N'-(3,5-dimethylbenzoyl)-N'-(2,2-dimethylpentan-3-yl)-2-fluoro-4-(methoxymethyl)-3-(4,4,5,5-tetramethyl-1,3,2-dioxaborolan-2-yl)benzohydrazide |
| 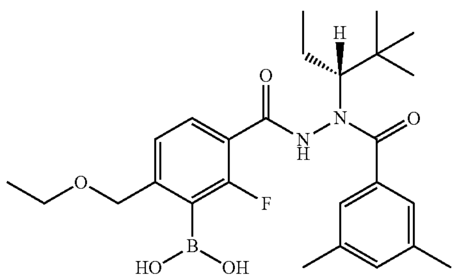 [SMILES: CCOCc1ccc(C(=O)NN(C(=O)c2cc(C)cc(C)c2)[C@H](CC)C(C)(C)C)c(F)c1B(O)O] | (R)-(3-(2-(3,5-dimethylbenzoyl)-2-(2,2-dimethylpentan-3-yl)hydrazine-1-carbonyl)-6-(ethoxymethyl)-2-fluorophenyl)boronic acid |
| 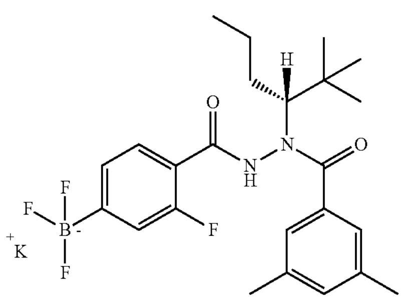 | potassium (R)-(4-(2-(3,5-dimethylbenzoyl)-2-(2,2-dimethylhexan-3-yl)hydrazine-1-carbonyl)-3-fluorophenyl)trifluoroborate |
| 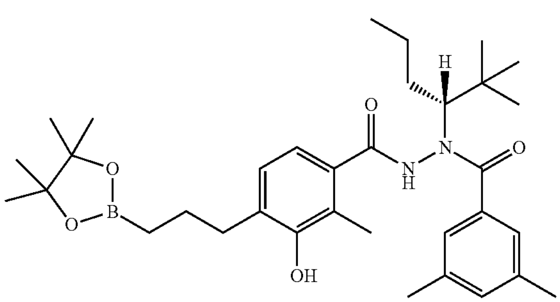 | (R)-N'-(3,5-dimethylbenzoyl)-N'-(2,2-dimethylhexan-3-yl)-3-hydroxy-2-methyl-4-(3-(4,4,5,5-tetramethyl-1,3,2-dioxaborolan-2-yl)propyl)benzohydrazide |
| 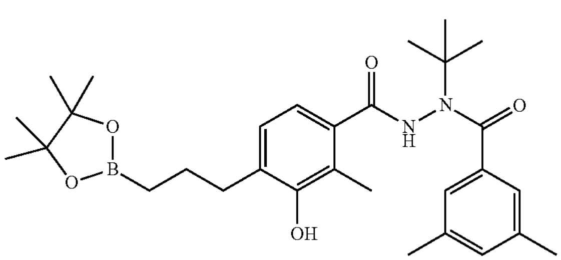 | N'-(tert-butyl)-N'-(3,5-dimethylbenzoyl)-3-hydroxy-2-methyl-4-(3-(4,4,5,5-tetramethyl-1,3,2-dioxaborolan-2-yl)propyl)benzohydrazide |

TABLE 2-continued

| Structure | Name |
|---|---|
| 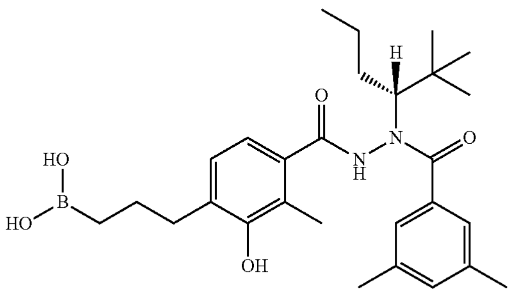 [SMILES: CCC[C@@H](N(NC(=O)c1ccc(CCCB(O)O)c(O)c1C)C(=O)c1cc(C)cc(C)c1)C(C)(C)C] | (R)-(3-(4-(2-(3,5-dimethylbenzoyl)-2-(2,2-dimethylhexan-3-yl)hydrazine-1-carbonyl)-2-hydroxy-3-methylphenyl)propyl)boronic acid |
| 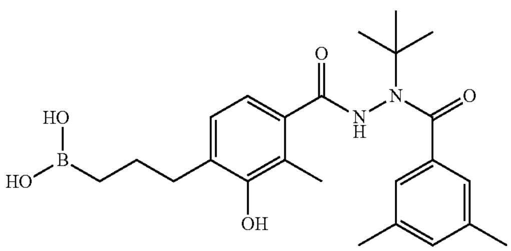 [SMILES: Cc1cc(C)cc(C(=O)N(NC(=O)c2ccc(CCCB(O)O)c(O)c2C)C(C)(C)C)c1] | (3-(4-(2-(tert-butyl)-2-(3,5-dimethylbenzoyl)hydrazine-1-carbonyl)-2-hydroxy-3-methylphenyl)propyl)boronic acid |
| 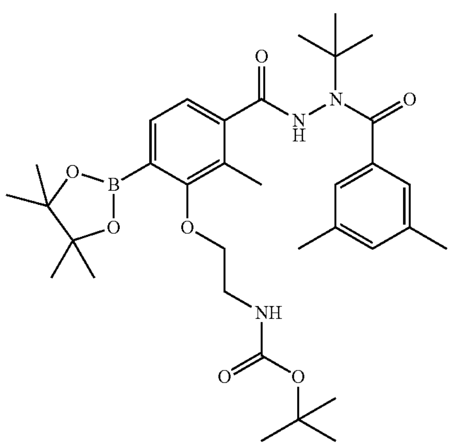 | tert-butyl (2-(3-(2-(tert-butyl)-2-(3,5-dimethylbenzoyl)hydrazine-1-carbonyl)-2-methyl-6-(4,4,5,5-tetramethyl-1,3,2-dioxaborolan-2-yl)phenoxy)ethyl)carbamate |
| 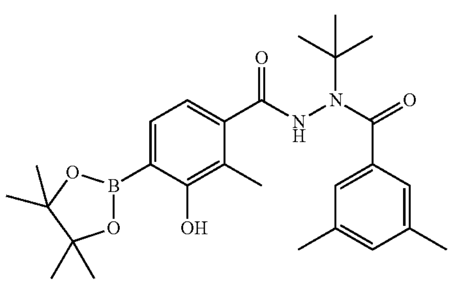 | N'-(tert-butyl)-N'-(3,5-dimethylbenzoyl)-3-hydroxy-2-methyl-4-(4,4,5,5-tetramethyl-1,3,2-dioxaborolan-2-yl)benzohydrazide |
|  | (4-(2-(2,2-dimethyl-1-phenylpropyl)-2-(3,5-dimethylbenzoyl)hydrazine-1-carbonyl)-3-methyl-2-(2-(((tetrahydro-2H-pyran-2-yl)oxy)ethoxy)phenyl)boronic acid |

TABLE 2-continued

| Structure | Name |
|---|---|

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{3-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{3-4}$ alkyl group. In another embodiment, the alkyl group is chosen from a straight or branched chain $C_{3-4}$ alkyl group. In another embodiment, the alkyl group is partially or completely deuterated, i.e., one or more hydrogen atoms of the alkyl group are replaced with deuterium atoms. Non-limiting exemplary $C_{1-10}$ alkyl groups include methyl (including —$CD_3$), ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —$CH_2CH_2NO_2$, —$CH_2CH_2CO_2H$, —$CH_2CH_2SO_2CH_3$, —$CH_2CH_2COPh$, —$CH_2C_6H_{11}$, and the like.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent.

For the purpose of the present disclosure, the term "cycloalkenyl" as used by itself or part of another group refers to a partially unsaturated cycloalkyl group as defined above. In one embodiment, the cycloalkenyl has one carbon-to-carbon double bond. In another embodiment, the cycloalkenyl group is chosen from a $C_{4-8}$ cycloalkenyl group. Exemplary cycloalkenyl groups include cyclopentenyl, cyclohexenyl and the like.

For the purpose of the present disclosure, the term "optionally substituted cycloalkenyl" as used by itself or as part of another group means that the cycloalkenyl as defined above is either unsubstituted or substituted with one, two, or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkenyl is substituted with two substituents. In another embodiment, the optionally substituted cycloalkenyl is substituted with one substituent. In another embodiment, the cycloalkenyl is unsubstituted.

For the purpose of the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —SCH$_3$, and —SCH$_2$CH$_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. Non-limiting exemplary heteroalkyl groups include —CH$_2$OCH$_2$CH$_2$OCH$_3$, —OCH$_2$CH$_2$OCH$_2$CH$_2$OCH$_3$, —CH$_2$NHCH$_2$CH$_2$OCH$_2$, —OCH$_2$CH$_2$NH$_2$, —NHCH$_2$CH$_2$N(H)CH$_3$, and —OCH$_2$CH$_2$OCH$_3$.

For the purpose of the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl. In one embodiment, the aryl group is phenyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, or (heteroaryl)alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-difluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Examples include:

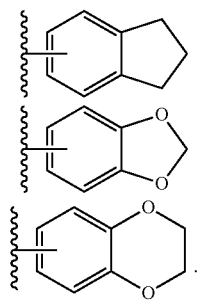

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "heteroaryloxy" as used by itself or as part of another group refers to an optionally substituted heteroaryl attached to a terminal oxygen atom.

For the purpose of the present disclosure, the term "aralkyloxy" or "arylalkyloxy" as used by itself or as part of another group refers to an aralkyl group attached to a terminal oxygen atom. A non-limiting exemplary aralkyloxy group is $PhCH_2O$—.

For the purpose of the present disclosure, the term "heteroaryl" or "heteroaromatic" refers to monocyclic and bicyclic aromatic ring systems having 5 to 14 ring atoms (i.e., $C_5$-$C_{14}$ heteroaryl) and 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In one embodiment, the heteroaryl is a $C_5$ heteroaryl. In another embodiment, the heteroaryl is a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide and the like.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted heteroaryl has one substituent. In one embodiment, the optionally substituted is an optionally substituted pyridyl, i.e., 2-, 3-, or 4-pyridyl. Any available carbon or nitrogen atom can be substituted. In another embodiment, the optionally substituted heteroaryl is an optionally substituted indole.

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) and at least one heteroatom. Each heteroatom is independently selected from the group consisting of oxygen, sulfur, including sulfoxide and sulfone, and/or nitrogen atoms, which can be quaternized. The term "heterocyclo" is meant to include cyclic ureido groups such as 2-imidazolidinone and cyclic amide groups such as β-lactam, γ-lactam, δ-lactam and ε-lactam. The term "heterocyclo" is also meant to include groups having fused optionally substituted aryl groups, e.g., indolinyl. In one embodiment, the heterocyclo group is chosen from a 5- or 6-membered cyclic group containing one ring and one or two oxygen and/or nitrogen atoms. The heterocyclo can be optionally linked to the rest of the molecule through a carbon or nitrogen atom. Non-limiting exemplary heterocyclo groups include 2-oxopyrrolidin-3-yl, 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, and the like. Substitution may occur on any available carbon or nitrogen atom, and may form a spirocycle.

For the purpose of the present disclosure, the term "amino" as used by itself or as part of another group refers to —NH$_2$.

For the purpose of the present disclosure, the term "alkylamino" as used by itself or as part of another group refers to —NHR$^{22}$, wherein R$^{22}$ is alkyl.

For the purpose of the present disclosure, the term "dialkylamino" as used by itself or as part of another group refers to —NR$^{23a}$R$^{23b}$, wherein R$^{23a}$ and R$^{23b}$ are each independently alkyl or R$^{23a}$ and R$^{23b}$ are taken together to form a 3- to 8-membered optionally substituted heterocyclo.

For the purpose of the present disclosure, the term "hydroxyalkylamino" as used by itself or as part of another group refers to —NHR$^{24}$, wherein R$^{24}$ is hydroxyalkyl.

For the purpose of the present disclosure, the term "cycloalkylamino" as used by itself or as part of another group refers to —NR$^{25a}$R$^{25b}$, wherein R$^{25a}$ is optionally substituted cycloalkyl and R$^{25b}$ is hydrogen or alkyl.

For the purpose of the present disclosure, the term "(amino)alkyl" as used by itself or as part of another group refers to an alkyl group substituted with an amino group. Non-limiting exemplary amino alkyl groups include —CH$_2$CH$_2$NH$_2$, —CH$_2$CH$_2$CH$_2$NH$_2$, —CH$_2$CH$_2$CH$_2$CH$_2$NH$_2$ and the like.

For the purpose of the present disclosure, the term "(alkylamino)alkyl" as used by itself or as part of another group refers to an alkyl group substituted with an alkylamino group. A non-limiting exemplary (alkylamino)alkyl group is —CH$_2$CH$_2$N(H)CH$_3$.

For the purpose of the present disclosure, the term "(dialkylamino)alkyl" as used by itself or as part of another group refers to an alkyl group substituted by a dialkylamino group. A non-limiting exemplary (dialkylamino)alkyl group is —CH$_2$CH$_2$N(CH$_3$)$_2$.

For the purpose of the present disclosure, the term "(cycloalkylamino)alkyl" as used by itself or as part of another group refers to an alkyl group substituted by a cycloalkylamino group. Non-limiting exemplary (cycloalkylamino) alkyl groups include —CH$_2$N(H)cyclopropyl, —CH$_2$N(H)cyclobutyl, and —CH$_2$N(H)cyclohexyl.

For the purpose of the present disclosure, the term "(cyano)alkyl" as used by itself or as part of another group refers to an alkyl group substituted with one or more cyano, e.g., —CN, groups. Non-limiting exemplary (cyano)alkyl groups include —CH$_2$CH$_2$CN, —CH$_2$CH$_2$CH$_2$CN, and —CH$_2$CH$_2$CH$_2$CH$_2$CN.

For the purpose of the present disclosure, the term "carboxamido" as used by itself or as part of another group refers to a radical of formula —C(=O)NR$^{26a}$R$^{26b}$, wherein R$^{26a}$ and R$^{26b}$ are each independently hydrogen, optionally substituted alkyl, optionally substituted aryl, or optionally substituted heteroaryl, or R$^{26a}$ and R$^{26b}$ taken together with the nitrogen to which they are attached from a 3- to 8-membered heterocyclo group. In one embodiment, R$^{26a}$ and R$^{26b}$ are each independently hydrogen or optionally substituted alkyl. Non-limiting exemplary carboxamido groups include —CONH$_2$, —CON(H)CH$_3$, CON(CH$_3$)$_2$, and CON(H)Ph.

For the purpose of the present disclosure, the term "(carboxamido)alkyl" as used by itself or as part of another group refers to an alkyl group substituted with a carboxamido group. Non-limiting exemplary (carboxamido)alkyl groups include —CH$_2$CONH$_2$, —C(H)CH$_3$—CONH$_2$, and —CH$_2$CON(H)CH$_3$.

For the purpose of the present disclosure, the term "sulfonamido" as used by itself or as part of another group refers to a radical of the formula —SO$_2$NR$^{27a}$R$^{27b}$, wherein R$^{27a}$ and R$^{27b}$ are each independently hydrogen, optionally substituted alkyl, or optionally substituted aryl, or R$^{27a}$ and R$^{27b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

For the purpose of the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

For the purpose of the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

For the purpose of the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

For the purpose of the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the term "alkoxycarbonyl" as used by itself or as part of another group refers to a carbonyl group, i.e., —C(=O)—, substituted by an alkoxy group. Non-limiting exemplary alkoxycarbonyl groups are —CO$_2$Me and —CO$_2$Et.

For the purpose of the present disclosure, the term "aralkyl" as used by itself or as part of another group refers to an alkyl group substituted with one, two, or three optionally substituted aryl groups. In one embodiment, the aralkyl group is a $C_{1-4}$ alkyl substituted with one optionally substituted aryl group. Non-limiting exemplary aralkyl groups include benzyl, phenethyl, —$CHPh_2$, and —$CH(4\text{-F-Ph})_2$.

For the purpose of the present disclosure, the term "ureido" as used by itself or as part of another group refers to a radical of the formula —$NR^{30a}$—$C(=O)$—$NR^{30b}R^{30c}$, wherein $R^{22a}$ is hydrogen, alkyl, or optionally substituted aryl, and $R^{30b}$ and $R^{30c}$ are each independently hydrogen, alkyl, or optionally substituted aryl, or $R^{30b}$ and $R^{30c}$ taken together with the nitrogen to which they are attached form a 4- to 8-membered heterocyclo group. Non-limiting exemplary ureido groups include —NH—C(C=O)—$NH_2$ and —NH—C(C=O)—$NHCH_3$.

For the purpose of the present disclosure, the term "guanidino" as used by itself or as part of another group refers to a radical of the formula —$NR^{28a}$—$C(=NR^{29})$—$NR^{28b}R^{28c}$, wherein $R^{28a}$, $R^{28b}$, and $R^{28c}$ are each independently hydrogen, alkyl, or optionally substituted aryl, and $R^{29}$ is hydrogen, alkyl, cyano, alkylsulfonyl, alkylcarbonyl, carboxamido, or sulfonamido. Non-limiting exemplary guanidino groups include —NH—C(C=NH)—$NH_2$, —NH—C(C=NCN)—$NH_2$, —NH—C(C=NH)—$NHCH_3$ and the like.

For the purpose of the present disclosure, the term "(heterocyclo)alkyl" as used by itself or as part of another group refers to an alkyl group substituted with one, two, or three optionally substituted heterocyclo groups. In one embodiment, the (heterocyclo)alkyl is a $C_{1-4}$ alkyl substituted with one optionally substituted heterocyclo group.

For the purpose of the present disclosure, the term "(heteroaryl)alkyl" as used by itself or as part of another group refers to an alkyl group substituted with one, two, or three optionally substituted heteroaryl groups. In one embodiment, the (heteroaryl)alkyl group is a $C_{1-4}$ alkyl substituted with one optionally substituted heteroaryl group.

For the purpose of the present disclosure, the term "alkylcarbonylamino" as used by itself or as part of another group refers to an alkylcarbonyl group attached to an amino. A non-limiting exemplary alkylcarbonylamino group is —$NHCOCH_3$.

For the purpose of the present disclosure, the term "pinacolborane" as used by itself or as part of another group refers a radical of the formula:

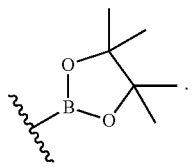

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$ (or deuterium (D)), $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, e.g., $^3H$, $^{11}C$, and $^{14}C$. In one embodiment, provided is a composition wherein substantially all of the atoms at a position within the Compound of the Disclosure are replaced by an atom having a different atomic mass or mass number. In another embodiment, provided is a composition wherein a portion of the atoms at a position within the Compound of the disclosure are replaced, i.e., the Compound of the Disclosure is enriched at a position with an atom having a different atomic mass or mass number." Isotopically-labelled Compounds of the Disclosure can be prepared by methods known in the art.

Compounds of the Disclosure may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well. For example, the following tautomers of $R^4$-5 of Formula I are encompassed by the present disclosure:

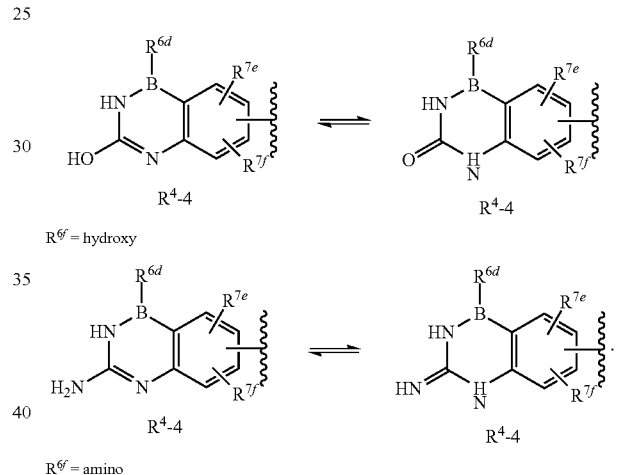

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure.

The present disclosure encompasses the preparation and use of salts of the Compounds of the Disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular Compound of the Disclosure with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The term "pharmaceutically acceptable salt" is meant to include boronic acid salts having the general formula:

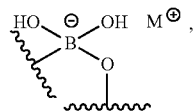

wherein $M^+$ is $H^+$ or a monovalent cation. By way of example, Compound 1 (see below) is converted to a pharmaceutically acceptable salt by reaction with NaOH according to the following scheme:

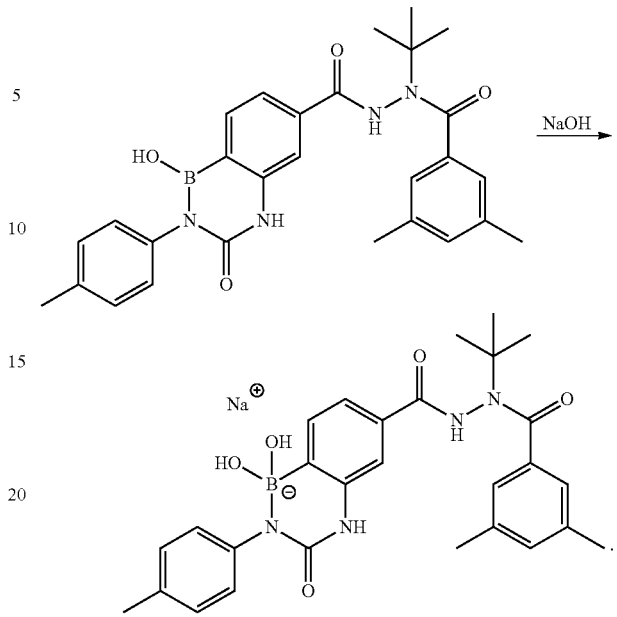

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure encompasses the preparation and use of hydroxy acid adducts of Compounds of the Disclosure. The term "hydroxy acid adduct" as used herein refers to the condensation product of a boronic acid having the general formula (R)(RO)B—OH and a hydroxy acid having formula HOOC—C(R')(R")—OH. R' and R" are each independently selected from hydrogen, carboxy, optionally substituted alkyl, aralkyl, aminoalkyl, haloalkyl, cyano, (cyano)alkyl, (carboxamido)alkyl, (carboxy)alkyl or hydroxyalkyl, and the like. R' and R" taken together with the carbon atom to which they are attached form a cycloalkyl or heterocyclo group. Non-limiting exemplary R'/R" groups include hydrogen, —CH$_3$, —OH, —CH(CH$_3$)$_2$, —CH(CH$_3$)(Et), —CH$_2$Ph, —CH$_2$CH$_2$SCH$_3$, —CH$_2$CO$_2$H, —CH$_2$CH$_2$CO$_2$H, —(CH$_2$)$_4$NH$_2$, —CH$_2$OH, —CH(CH$_3$)OH, —CH$_2$Ph-OH, —CH$_2$-imidazole, —CH$_2$SH, —CH$_2$C(O)NH$_2$, —CH$_2$CH$_2$C(O)NH$_2$, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, and —CH$_2$CH$_2$OCH$_2$CH$_2$—. In one embodiment, R' is selected from the group consisting of —CH$_2$Ph, —CO$_2$H, —CH$_2$CO$_2$H, and —CH$_2$CONH$_2$. The general structure of a hydroxy acid adduct is:

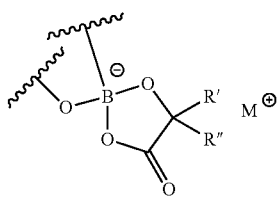

wherein M$^+$ is a monovalent cation.

The present disclosure encompasses the preparation and use of amino acid adducts of Compounds of the Disclosure. The term "amino acid adduct" as used herein refers to the condensation product of a boronic acid having the general formula (R)(RO)B—OH and a natural or unnatural, D- or L-, amino acid, including β-amino acids, e.g., an amino acid having formula HOOC—C(R''')(R'''')—NH$_2$. Suitable unnatural amino acids include, without limitation, the enantiomeric and racemic forms of 2-methylvaline, 2-methylalanine, (2-i-propyl)-β-alanine, phenylglycine, 4-methylphenylglycine, 4-isopropylphenylglycine, 3-bromophenylglycine, 4-bromophenylglycine, 4-chlorophenylglycine, 4-methoxyphenylglycine, 4-ethoxyphenylglycine, 4-hydroxyphenylglycine, 3-hydroxyphenylglycine, 3,4-dihydroxyphenylglycine, 3,5-dihydroxyphenylglycine, 2,5-dihydrophenylglycine, 2-fluorophenylglycine, 3-fluorophenylglycine, 4fluorophenylglycine, 2,3-difluorophenylglycine, 2,4-difluorophenylglycine, 2,5-difluorophenylglycine, 2,6-difluorophenylglycine, 3,4-difluorophenylglycine, 3,5-difluorophenylglycine, 2-(trifluoromethyl)phenylglycine, 3-(trifluoromethyl)phenylglycine, 4-(trifluoromethyl)phenylglycine, 2-(2-thienyl)glycine, 2-(3-thienyl)glycine, 2-(2-furyl)glycine, 3-pyridylglycine, 4-fluorophenylalanine, 4-chlorophenylalanine, 2-bromophenylalanine, 3-bromophenylalanine, 4-bromophenylalanine, 2-naphthylalanine, 3-(2-quinoyl)alanine, 3-(9-anthracenyl)alanine, 2-amino-3-phenylbutanoic acid, 3-chlorophenylalanine, 3-(2-thienyl)alanine, 3-(3-thienyl)alanine, 3-phenylserine, 3-(2-pyridyl)serine, 3-(3-pyridyl)serine, 3-(4-pyridyl)serine, 3-(2-thienyl)serine, 3-(2-furyl)serine, 3-(2-thiazolyl)alanine, 3-(4-thiazolyl)alanine, 3-(1,2,4-triazol-1-yl)-alanine, 3-(1,2,4-triazol-3-yl)-alanine, hexafluorovaline, 4,4,4-trifluorovaline, 3-fluorovaline, 5,5,5-trifluoroleucine, 2-amino-4,4,4-trifluorobutyric acid, 3-chloroalanine, 3-fluoroalanine, 2-amino-3-flurobutyric acid, 3-fluoronorleucine, 4,4,4-trifluorothreonine, L-allylglycine, tert-Leucine, propargylglycine, vinylglycine, S-methylcysteine, cyclopentylglycine, cyclohexylglycine, 3-hydroxynorvaline, 4-azaleucine, 3-hydroxyleucine, 2-amino-3-hydroxy-3-methylbutanoic acid, 4-thiaisoleucine, acivicin, ibotenic acid, quisqalic acid, 2-indanylglycine, 2-aminoisobutyric acid, 2-cyclobutyl-2-phenylglycine, 2-isopropyl-2-phenylglycine, 2-methylvaline, 2,2-diphenylglycine, 1-amino-1-cyclopropanecarboxylic acid, 1-amino-1-cyclopentanecarboxylic acid, 1-amino-1-cyclohexanecarboxylic acid, 3-amino-4,4,4-trifluorobutyric acid, 3-phenylisoserine, 3-amino-2-hydroxy-5-methylhexanoic acid, 3-amino-2-hydroxy-4-phenylbutyric acid, 3-amino-3-(4-bromophenyl)propionic acid, 3-amino-3-(4-chlorophenyl)propionic acid, 3-amino-3-(4-methoxyphenyl)propionic acid, 3-amino-3-(4-fluorophenyl)propionic acid, 3-amino-3-(2-fluorophenyl)propionic acid, 3-amino-3-(4-nitrophenyl)propionic acid, and 3-amino-3-(1-naphthyl)propionic acid. These non-natural amino acids are commercial available from the following commercial suppliers including Aldrich, Sigma, Fluka, Lancaster, ICN, TCI, Advanced ChemTech, Oakwood Products, Indofine Chemical Company, NSC Technology, PCR Research Chemicals, Bachem, Acros Organics, Celgene, Bionet Research, Tyger Scientific, Tocris, Research Plus, Ash Stevens, Kanto, Chiroscience, and Peninsula Lab. The following amino acids can be synthesized according to literature procedures: 3,3,3-trifluoroalanine (Sakai, T.; et al. Tetrahedron 1996, 52, 233) and 3,3-difluoroalanine (D'Orchymont, H. Synthesis 1993, 10, 961). Other N-protecting groups that can be used in the place of Z include Acetyl (Ac), tert-butoxycarbonyl (Boc), methoxycarbonyl. or ethoxycarbonyl. Non-limiting exemplary R'''/R'''' groups include hydrogen, CH$_3$, OH, —CH(CH$_3$)$_2$, —CH(CH$_3$)(Et), —CH$_2$Ph, —CH$_2$CH$_2$SCH$_3$, —CH$_2$CO$_2$H, —CH$_2$CH$_2$CO$_2$H, —(CH$_2$)$_4$NH$_2$, —CH$_2$OH, —CH(CH$_3$)OH, —CH$_2$Ph-OH, —CH$_2$-imidazole, —CH$_2$SH, —CH$_2$C(O)NH$_2$, and —CH$_2$CH$_2$C(O)NH$_2$. The general structure of a hydroxy acid adduct is:

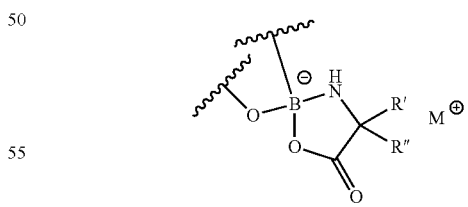

wherein M$^+$ is H$^+$ or a monovalent cation.

Compounds of the Disclosure containing a boronic acid, e.g., compounds having Formula I, wherein R$^4$ is R$^4$-1 and R$^{6a}$ is —B(OH)$_2$, are likely to display ionization equilibrium in water because of the acidic character of boronic acids. By way of illustration, certain Compounds of the Disclosure may exist either as an anionic trivalent species (Chart 1, Equation 1) or as an anionic tetrahedral species (Chart 1, Equation 2).

Chart 1

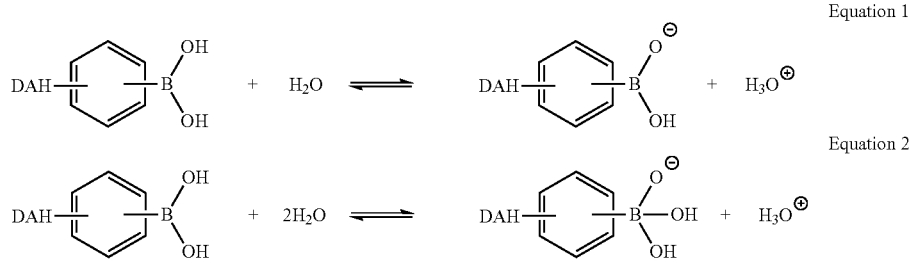

Equation 1

Equation 2

The present disclosure encompasses both anionic trivalent species and anionic tetrahedral species of boronic acids as illustrated in Chart 1. In one embodiment, Compounds of the Disclosure having a boronic acid substituent exist as an anionic tetrahedral species in water. For the purpose of the instant disclosure, the anionic tetrahedral species of a boronic acid in water is referred to as a "hydroxyboronate anionic form" of the boronic acid. Thus, in a pharmaceutical composition comprising a Compound of the Disclosure and water (and optionally one or more additional excipients), the Compound of the Disclosure may be present in the neutral (boronic acid) form, the hydroxyboronate anionic form, or both.

The present disclosure encompasses various forms of boron-containing rings, including open- and closed-ring forms which may exist in equilibria with one another depending on various conditions, e.g., solvent, pH, temperature, as illustrated in Chart 2. Compounds of the Disclosure are meant to include both open- and closed-ring forms that may exist under various conditions.

Compounds of the Disclosure are meant to include both open- and closed-ring forms of boron-containing rings as illustrated in Chart 2.

The present disclosure also encompasses various di- and trimeric forms of boronic acids and boron-containing rings, including boronic anhydrides (illustrated in Chart 3 as Formula Ia), dioxadiboretanes (illustrated in Chart 3 as Formula IIa), and boroxines (illustrated in Chart 3 as Formula IIb).

Chart 3

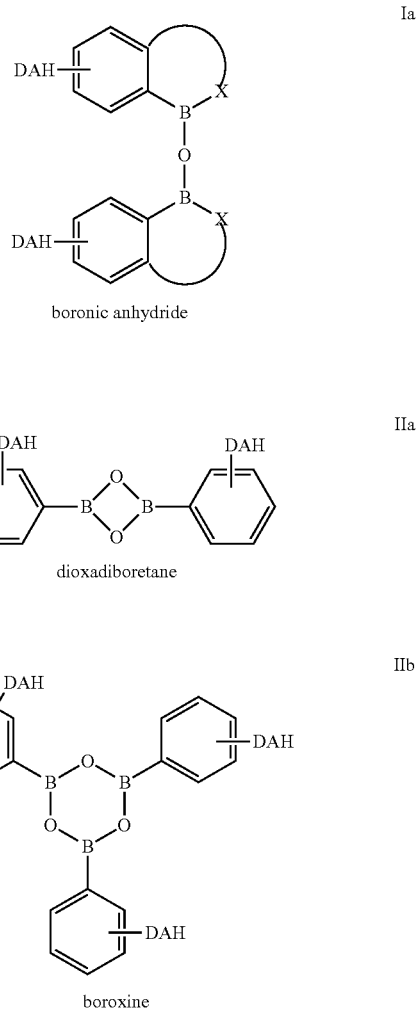

Chart 2

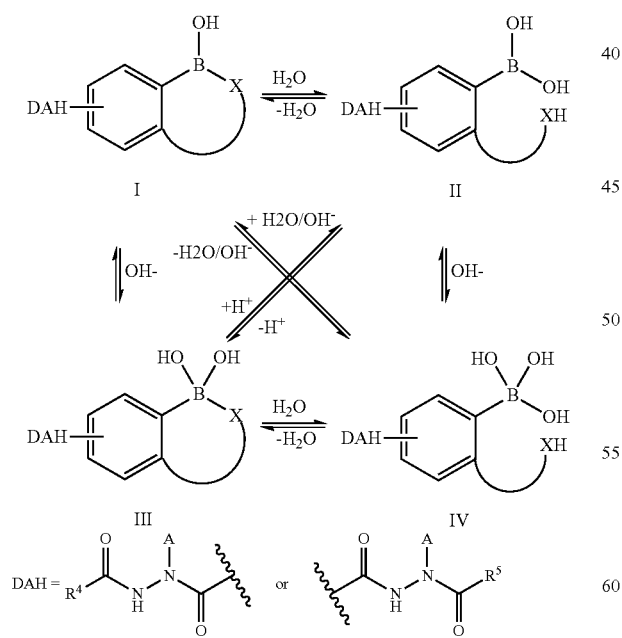

-continued

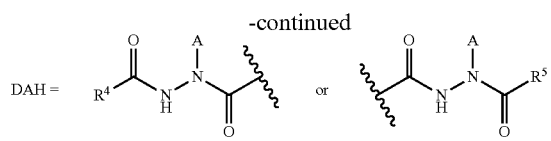

 = 2-5 atom connection as found in R⁴-3, R⁴-4, R⁴-5, R⁴-6, R⁴-7, R⁵-3, R⁵-4, R⁵-5, R⁵-6, or R⁵-7

X = O or NR (wherein R is hydrogen, alkyl, aryl, etc.)

Compounds of the Disclosure are meant to include the di- and trimeric forms of Compounds of the Disclosure illustrated in Chart 3 (collectively referred to "multimeric forms"). In one embodiment, Compounds of the Disclosure form boronic anyhydrides. In one embodiment, Compounds of the Disclosure form dioxadiboretanes. In one embodiment, Compounds of the Disclosure form boroxines. For the purpose of the instant disclosure, the term "boroxine" is meant to refer to a cyclotrimeric anhydride of a boronic acid of compound having Formula I.

The term "monovalent cation" as used herein refers to inorganic cations such as, but not limited to, alkaline metal ions, e.g., $Na^+$ and $K^+$, as well as organic cations such as, but not limited to, ammonium and substituted ammonium ions, e.g., $NH_4^+$, $NHMe_3^+$, $NH_2Me_2^+$, $NHMe_3^+$ and $NMe_4^+$.

As used herein, the term "micronization" refers to a process or method by which the size of a population of particles is reduced, typically to the micron scale.

As used herein, the term "micron" or "µm" refer to "micrometer," which is $1\times10^{-6}$ meter.

In another aspect, the present disclosure provides compositions comprising a Compound of the Disclosure and one or more excipients. In one embodiment, the excipient comprises dimethyl sulfoxide or acetone. In one embodiment, the composition comprises a pharmaceutically acceptable excipient, to provide a "pharmaceutically acceptable composition." In another embodiment, the composition comprises micronized Compounds of the Disclosure. In another embodiment, the pharmaceutically acceptable excipient comprises Miglyol 812, phospholipon 90G, or tocopheryl polyethylene glycol 1000 succinate, or a mixture thereof. In another embodiment, the pharmaceutically acceptable excipient consists essentially of Miglyol 812, phospholipon 90G, and tocopheryl polyethylene glycol 1000 succinate. In another embodiment, the pharmaceutically acceptable excipient comprises Labrasol®. In another embodiment, the pharmaceutically acceptable excipient comprises sorbitan monolaurate, hydroxypropylmethylcellulose acetate succinate, sodium taurocholate, Ethocel™ or palmitoyl-oleoyl-phosphatidylcholine, or a mixture thereof. In another embodiment, the pharmaceutically acceptable excipient comprises hydrogenated soy lecithin. Compound of the Disclosure can be admixed with one or more excipients using method well known to those of ordinary skill in the art.

In another embodiment, the excipient comprises ethanol, isopropanol, propylene glycol, benzyl alcohol, glycerin, sorbitol, sucrose, carbopol, maltodextrin, lycasin (maltitol), sodium benzoate, sodium saccharide, lutrol E, F, methyl paraben, propyl paraben, citric acid, capryol 90, Tween 80 (polysorbate 80), Kollidon® CL-M, polyoxyl stearate, hydroxypropyl methyl cellulose, Cremophor® RH 40, Cremophor® EL, sodium carboxymetyhl cellulose (CMC), guar gum, xanthan gum, polyethylene glycol, or polyvinyl pyrrolidone, or a mixture thereof.

In another embodiment, the excipient comprises Labrafil®, Labrasol®, Gelucire®, Labrafac®, Lauroglycol™ 90, Peceol™, Transcutol® Compritol®, Geloil®, Geleol™, or Precirol®, or a mixture thereof.

In another embodiment, the excipient comprises capmul, Captex®, or Acconon®, or a mixture thereof.

In another embodiment, the excipient comprises DYNACERIN®, DYNACET®, DYNASAN, GALENOL®, IMWITOR (Glyceryl Monooleate, Stearate, Caprylate), ISOFOL® (long chain alcohols), LIPDXOL® (Macrogol), MASSA ESTARINUM (Hydrogenated Coco-Glycerides), MIGLYOL (Caprylic/Capric Triglyceride), NACOL®, Nafol (alcohols), SOFTIGEN®, SOFTISAN®, WITEPSOL (Hydrogenated Coco-Glycerides), or WITOCAN® (Hydrogenated Coco-Gly), or a mixture thereof.

In another embodiment, the excipient comprises hypromellose acetate succinate.

In another embodiment, the excipient comprises Soluplus® (polyvinylcaprolactam-polyvinyl acetate-polyethylene glycol graft copolymer.

Compositions may contain from 0.01% to 99% by weight of a Compound of the Disclosure, e.g., about 1%, about 2%, about 3%, about 4%, about 5%, about 6%, about 7%, about 8%, about 9%, or about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. The amount in any particular composition will depend upon the effective dose, that is, the dose required to elicit the desired level of gene expression.

In another aspect, the present disclosure provides micronized Compounds of the Disclosure, and compositions thereof. In one embodiment, the average particle size distribution of the micronized form of a Compound of the Disclosure is about 20 µm or less, e.g., about 19 µm, about 18 µm, about 17 µm, about 16 µm, about 15 µm, about 14 µm, about 13 µm, about 12 µm, or about 11 µm, or less. In another embodiment, the average particle size distribution is about 10 µm or less, e.g., about 9 µm, about 8 µm, about 7 µm, about 6 µm, or about 5 µm, or less. In another embodiment, the average particle size distribution is about 5 µm or less, e.g., about 4 µm, about 3 µm, about 2 µm, or about 1 µm, or less. In another embodiment, the average particle size distribution is about 1 µm or less, e.g., about 0.9 µm, about 0.8 µm, about 0.7 µm, about 0.6 µm, about 0.5 µm, about 0.4 µm, about 0.3 µm, about 0.2 µm, about 0.1 µm, about 0.09 µm, about 0.08 µm, about 0.07 µm, about 0.06 µm, about 0.05 µm, about 0.04 µm, about 0.03 µm, about 0.02 µm, or about 0.01 µm or less.

In another aspect, the present disclosure provides methods of making a composition, comprising admixing a Compound of the Disclosure, or a micronized Compound of the Disclosure, with one or more excipients. In one embodiment, the excipient is a pharmaceutically acceptable excipient.

In another aspect, the present disclosure provides methods of regulating gene expression of a gene of interest in a host cell, comprising contacting the host cell with a Compound of the Disclosure, or a composition thereof. In one embodiment, the host cell comprises a polynucleotide encoding a gene switch comprising a ligand binding domain that binds a Compound of the Disclosure, wherein the level of expression of the gene of interest is increased, relative to the level of expression of the gene of interest in the absence of a Compound of the Disclosure. In another embodiment, the host cell is an isolated host cell. In certain other embodiments, an isolated host cell is genetically modified ex-vivo (e.g., transformed, transfected or infected) with a polynucleotide construct encoding a gene switch comprising a ligand binding domain that binds a Compound of the Disclosure. In another embodiment, the ex-vivo genetically modified host cell is administered to a subject. In certain embodiments, the expression of a gene of interest is under the control of the gene switch comprising a ligand binding domain that binds a Compound of the Disclosure. In another embodiment, the host cell is in a subject, e.g., an animal, e.g., a human. For example, one or more cells (host cells) in a subject may be genetically modified in-vivo by administering a viral vector to the subject (or a select population of host cells thereof), wherein the viral vector comprises a polynucleotide encoding a gene switch comprising a ligand binding domain that binds a Compound of the Disclosure. In yet other embodiments, the host cell is an autologous host cell obtained from a mammalian subject, wherein the autologous host cell is genetically modified with a polynucleotide construct encoding a gene switch comprising a ligand binding domain that binds a Compound of the Disclosure. In another embodiment, the host cell is an allogeneic stem cell or immune cell, wherein the allogenic host cell is genetically modified with a polynucleotide construct encoding a gene switch comprising a ligand binding domain that binds a Compound of the Disclosure. In another embodiment, a Compound of the Disclosure is administered to a subject as a pharmaceutically acceptable composition. In another embodiment, the gene switch comprises an ecdysone receptor (EcR) ligand binding domain that binds a Compound of the Disclosure. In another embodiment, the gene switch further comprises a second ligand binding domain that dimerizes with a first ligand binding domain (for example, an EcR ligand binding domain) that binds a Compound of the Disclosure. In one embodiment, an EcR ligand binding domain comprises one or more amino acid substitutions compared to the corresponding wild-type EcR polypeptide sequence. In another embodiment, the second ligand binding domain is a retinoic X receptor ligand binding domain. In another embodiment, the second ligand binding domain is a wild-type insect USP (Ultraspiracle protein). In another embodiment, the retinoic X receptor (RxR) ligand binding domain is a chimeric retinoic X receptor ligand binding domain. In another embodiment, the chimeric ligand binding domain is an mammalian RxR/invertebrate USP chimera. In another embodiment, the host cell further comprises a polynucleotide encoding a peptide, protein or polypeptide whose expression is regulated by the gene switch.

In another aspect, the present disclosure provides methods of treating a disease, disorder, injury, or condition in a subject, comprising administering to the subject a Compound of the Disclosure, or a composition thereof. In one embodiment, a vector (or two or more vectors) comprises a polynucleotide (or polynucleotides) encoding a gene switch that comprises a ligand binding domain that binds a Compound of the Disclosure. In one embodiment, the vector (or vectors) may be a DNA or RNA vector. In one embodiment, the vector (or vectors) may be a plasmid or viral vector (for example, an adenovirus vector or an adeno-associated viral vector). In one embodiment, a vector (or vectors) comprising a polynucleotide (or polynucleotides) encoding a gene switch that comprises a ligand binding domain that binds a Compound of the Disclosure is administered to a subject to treat a disease, disorder, injury, or condition in the subject. In one embodiment, following administration of a Compound of the Disclosure, a gene-of-interest (GOI) is expressed in vivo in a subject from a vector (or vectors) comprising a polynucleotide (or polynucleotides) encoding a GOI and comprising a gene switch that comprises a ligand binding domain that binds a Compound of the Disclosure. In one embodiment, a host cell within the subject or a non-human organism comprises a polynucleotide encoding a gene switch that comprises a ligand binding domain that binds a Compound of the Disclosure. In another embodiment, the subject is human. In another embodiment, the disease, disorder, injury, or condition is selected from the group consisting of cancer, metabolic-related disorder, kidney disease, anemia, autoimmune disorder, ocular disorder, blood disorder, neurological disorder, pulmonary (lung) disorder, rheumatologic disorder, cardiac disorder, hepatic (liver) disorder and infectious disease. In another embodiment, the disease, disorder, injury, or condition is cancer. In another embodiment, the cancer is melanoma. In another embodiment, the gene switch comprises an ecdysone receptor (EcR) ligand binding domain. In another embodiment, the gene switch further comprises a second ligand binding domain that dimerizes with a first ligand binding domain (for example, an EcR ligand binding domain) that binds a Compound of the Disclosure. In one embodiment, an EcR ligand binding domain comprises one or more amino acid substitutions compared to the corresponding wild-type EcR polypeptide sequence. In another embodiment, the second ligand binding domain is a wild-type insect USP (Ultraspiracle protein). In another embodiment, the second ligand binding domain is a retinoic X receptor ligand binding domain. In another embodiment, the retinoic X receptor (RxR) ligand binding domain is a chimeric retinoic X receptor ligand binding domain. In another embodiment, the chimeric ligand binding domain is a mammalian RxR/invertebrate USP chimera. In another embodiment, the host cell further comprises a polynucleotide encoding a peptide, protein, or polypeptide whose expression is regulated by the gene switch. In another embodiment, the gene switch regulates the expression of a polynucleotide encoding IL-12 or a subunit thereof (See, for example, US 2011/0268766).

In another embodiment, the present disclosure provides a Compound of the Disclosure, or a composition thereof, for use in treating a disease, disorder, injury, or condition in a subject.

In another embodiment, the present disclosure provides a Compound of the Disclosure, or a composition thereof, for use in the manufacture of a medicament for treating a disease, disorder, injury, or condition in a subject.

In another aspect, the present disclosure provides kits comprising a Compound of the Disclosure, or kits comprising a composition of a Compound of the Disclosure and one or more excipients. In one embodiment, the kit further comprises instructions for administering a Compound of the Disclosure to an isolated host cell or a subject. In another embodiment, the kit further comprises the R<small>HEO</small>S<small>WITCH</small> T<small>HERAPEUTIC</small> S<small>YSTEM</small>® (see, for example, the Instruction Manual for "R<small>HEO</small>S<small>WITCH</small>® Mammalian Inducible Expression System," New England BioLabs® Inc., Version 1.3, November 2007; Karzenowski, D. et al., *BioTechiques* 39:191-196 (2005); Dai, X. et al., *Protein Expr. Purif.* 42:236-245 (2005); Palli, S. R. et al., *Eur. J. Biochem.* 270:1308-1515 (2003); Dhadialla, T. S. et al., *Annual Rev. Entomol.* 43:545-569 (1998); Kumar, M. B, et al., *J. Biol. Chem.* 279:27211-27218 (2004); Verhaegent, M. and Christopoulos, T. K., *Annal. Chem.* 74:4378-4385 (2002); Katalam, A. K., et al., *Molecular Therapy* 13:S103 (2006); and Karzenowski, D. et al., *Molecular Therapy* 13:S194 (2006))

Compounds of the Disclosure may be administered to a subject in conjunction with other pharmaceutically active compounds. It will be understood by those skilled in the art that pharmaceutically active compounds to be used in combination the Compound of the Disclosure will be selected in order to avoid adverse effects on the recipient or undesirable interactions between the compounds. Examples of other pharmaceutically active compounds which may be used in combination a Compound of the Disclosure, for example, AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflammatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine $H_2$ receptor antagonists, hormones, hyperglycemic agents, hypolipidemics, immunosuppressants, laxatives, leprostatics, leukapheresis adjuncts, lung surfactants, migraine preparations, mucolytics, muscle relaxant antagonists, muscle relaxants, narcotic antagonists, nasal sprays, nausea medications nucleoside analogues, nutritional supplements, osteoporosis preparations, oxytocics, parasympatholytics, parasympathomimetics, Parkinsonism drugs, Penicillin adjuvants, phospholipids, platelet inhibitors, porphyria agents, prostaglandin analogues, prostaglandins, proton pump inhibitors, pruritus medications psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media. In some cases a Compound of the Disclosure may be useful as an adjunct to drug therapy, for example, to "turn off" a gene that produces an enzyme that metabolizes a particular drug.

For agricultural applications, Compounds of the Disclosure, or compositions thereof, may be used to control the expression of pesticidal proteins such as *Bacillus thuringiensis* (Bt) toxin. Such expression may be tissue or plant specific. In addition, particularly when control of plant pests is also needed, one or more pesticides may be combined with Compound of the Disclosure, or compositions thereof, thereby providing additional advantages and effectiveness, including fewer total applications, than if the pesticides are applied separately. When mixtures with pesticides are employed, the relative proportions of each component in the composition will depend upon the relative efficacy and the desired application rate of each pesticide with respect to the crops, pests, and/or weeds to be treated. Those skilled in the art will recognize that mixtures of pesticides may provide advantages such as a broader spectrum of activity than one pesticide used alone. Examples of pesticides which can be combined in compositions with Compounds of the Disclosure include fungicides, herbicides, insecticides, miticides, and microbicides.

In other agricultural embodiments, Compounds of the Disclosure may be used to control the expression of one or more genes of interest (GOIs). Exemplary GOIs include any desired trait, whether the trait is an agronomic trait, input trait, such as herbicide- or insecticide-resistance, nutritionally-desirable GOIs for the end consumer (animal or human), as well as desired GOIs for efficient processing of the plant product. Thus, in certain embodiments, a plant cell, a plant tissue, a whole plant and the like, is genetically modified with a polynucleotide encoding a gene switch, wherein the expression of one or more GOIs are under the control of the gene switch. Likewise, in certain embodiments, a fungal cell, a bacterial cell or a yeast cell is genetically modified with a polynucleotide encoding a gene switch, wherein the expression of one or more GOIs are under the control of the gene switch.

Ecdysone receptors in insects are naturally responsive to the ecdysone steroid hormone (molting hormone) and other steroidal compounds such as ponasterone A and muristerone A. (Graham et al., *Insect Biochemistry and Molecular Biology* 37:611-626 (2007); Dinan and Hormann, "Ecdysteroid Agonists and Antagonists," *Comprehensive Molecular Insect Science*, 1st ed.:197-242, (2005)). Diacylhydrazines having ecdysone receptor agonist activity have been described as insecticides. (See U.S. Pat. No. 5,530,028).

In another aspect, the present disclosure provides a method of controlling, e.g., reducing or preventing the spread of, or killing, insects comprising contacting the insects or their habitat with an insecticidally effective amount of a Compound of the Disclosure, or a composition thereof. In another embodiment, Compounds of the Disclosure, or a composition thereof, are insecticidally active against:

(1) insects from the order of the lepidopterans (Lepidoptera), for example, *Agrotis ipsilon, Agrotis segetum, Alabama argillacea, Anficarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalls, Dlatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Hellothis armigera, Hellothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalls, Panolls flammea, Pectinophora gossypiella, Peridroma saucia, Phalera bucephala, Phthorimaea operculella, Phyllocnistis citrella, Pieris brassicae, Plathypena scabs, Plutella xylostella, Pseudoplusia includens, Rhyacionia frustrana, Scrobipalpula absoluta, Sitotroga cerealella, Sparganothis pilleriana, Spodoptera fruglperda, Spodoptera littorals, Spodoptera litura, Thaumatopoea pityocampa, Tortrix viridana, Trichoplusia ni* and *Zeiraphera Canadensis;*

(2) beetles (Coleoptera), for example, *Agrilus sinuatus, Agriotes lineatus, Agriotes obscurus, Amphimallus solstitialis, Anisandrus dispar, Anthonomus grandis, Anthonomus*

*pomorum, Aphthona euphoridae, Athous haemorrhoidals, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hiirtpennis, Eutinobothrus brasiilensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;*

(3) flies, mosquitoes (Diptera), for example, *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discails, Chrysops silacea, Chrysops allanticus, Cochliomyla hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Della radicum, Dermatobia hominis, Fannia canicularis, Geomyza Tripunctata, Gasterophilus intestinalis, Glossina morsiftans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilla sericata, Lycoria pectoralis, Mansonia titillanus, Mayetiola destructor, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimullum mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola,* and *Tabanus similis, Tipula oleracea,* and *Tipulapaludosa:*

(4) thrips (Thysanoptera), for example, *Dichromothrips corbetti, Dichromothrips* ssp, *Frankliniella fusca, Frankllniella occidentalls, Frankllniella tritici, Scirtothrlps citri, Thrips olyzae, Thrips palmi* and *Thrips tabaci,*

(5) termites (Isoptera), for example, *Calotermes flavicollis, Leucotermes flavipes, Heterotermes aureus, Reticulltermes flavipes, Retfculltermes virginicus, Reticulltermes lucifugus, Termes natalensis,* and *Coptotermes formosanus,*

(6) cockroaches (Blattaria-Blattodea), for example, *Blattella germanica, Blattella asahinae, Periplaneta americana, Periplaneta japonica, Periplaneta brunnea, Periplaneta fulligginosa, Periplaneta australasiae,* and *Blatta orientalis;*

(7) true bugs (Hemiptera), for example, *Acrosternum hilare, Blissus leucopterus, Cyrtopeltis notatus, Dysdercus cingulatus, Dysdercus intermedius, Eurygaster integriceps, Euschistus impictivenfris, Leptoglossus phyllopus, Lygus llneolaris, Lygus pratensis, Nezara viriduia, Piesma quadrata, Solubea insularis, Thyanta perditor, Acyrthosiphon onobrychis, Adelges laricis, Aphidula nasturti; Aphis fabae, Aphis forbesi, Aphis pomi, Aphis gossypii, Aphis grossulariae, Aphis schneideri, Aphis spiraecola, Aphis sambuci, Acyrthosiphon pisum, Aulacofthum solani, Bemisia argentifolii, Brachycaudus cardui, Brachycaudus helichrysi, Brachycaudus persicae, Brachycaudus prunicola, Brevicoryne brassicae, Capifiophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum inserfum, Sappaphis mala, Sappaphis mali, Schizaphis graminum, Schizoneura lanuginosa, Sitobion avenae, Trialeurodes vaporariorum, Toxoptera aurantiiand, Viteus vitifolli, Cimex lectularius, Cimex hemipterus, Reduvius senilis, Triatoma* spp., and *Arilus critatus;*

(8) ants, bees, wasps, sawflies (Hymenoptera), for example, *Athalia rosae, Atta cephalotes, Atta capiguara, Atta cephalotes, Afta laevigata, Atta robusta, Atta sexdens, Atta texana, Crematogaster* spp., *Hoplocampa minuta, Hoplocampa testudinea, Monomorium pharaonls, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;*

(9) crickets, grasshoppers, locusts (Orthoptera), for example, *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americans, Schistocerca gregaria, Dociostaurus maroccanus, Tachycines asynamorus, Oedaleus senegalensis, Zonozerus variegatus, Hieroglyphus daganensis, Kraussaria angulifera, Calliptamus itallcus, Chortoicetes terminifera,* and *Locustana pardalina;*

(10) Arachnoidea, such as arachnids (Acarina), for example, of the families Argasidae, Ixodidae and Sarcoptidae, such as *Amblyomma americanum, Amblyomma variegatum, Amblyomma maculatum, Argas persicus, Boophilus annulatus, Boophilus decoloratus, Boophilus microplus, Dermacentor silvarum, Dermacentor andersoni, Dermacentor variabllis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni, Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus*

*urticae, Panonychus ulmi, Panonychus citri,* and *Oligonychus pratensis; Araneida,* e.g., *Lafrodectus mactans,* and *Loxosceles reclusa,*

(11) fleas (Siphonaptera), for example, *Ctenocephalides felis, Ctenocephalides canis, Xenopsylla cheopis, Pulex irritans, Tunga penefrans,* and *Nosopsyllus fasciatus;*

(12) silverfish, firebrat (Thysanura), for example, *Lepisma saccharins* and *Thermobia domestics:*

(13) centipedes (Chilopoda), for example, *Scutigera coleoptrata,*

(14) millipedes (Diplopoda), for example, *Narceus* spp.,

(15) Earwigs (Dermaptera), for example, *forifcula auricularia*; and/or

(16) lice (Phthiraptera), for example, *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

In another embodiment, Compounds of the Disclosure, or compositions thereof, are insecticidally active against insects of the order Diptera, Hemiptera, and/or Lepidoptera. In another embodiment, Compounds of the Disclosure, or a composition thereof, are insecticidally active against insects of the order Lepidoptera. In another embodiment, Compound of the Disclosures, or a composition thereof, are insecticidally active against insects of the order Hemiptera.

Compounds of the Disclosure, or compositions thereof, can be applied to plant foliage as aqueous sprays by methods commonly employed, such as conventional high-liter hydraulic sprays, low-liter sprays, air-blast, and aerial sprays. The dilution and rate of application will depend upon the type of equipment employed, the method and frequency of application desired, and the ligand application rate. It may be desirable to include additional adjuvants in the spray tank. Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/Functional Materials,* and *McCutcheon's Functional Materials,* all published annually by McCutcheon Division of MC Publishing Company (New Jersey). Compounds of the Disclosure, or compositions thereof, can also be mixed with fertilizers or fertilizing materials before their application. Compounds of the Disclosure, or compositions thereof, and solid fertilizing material can also be admixed in mixing or blending equipment, or they can be incorporated with fertilizers in granular formulations. Any relative proportion of fertilizer can be used which is suitable for the crops and weeds to be treated. Compounds of the Disclosure, or compositions thereof, will commonly comprise from 5% to 50% of the fertilizing composition. These compositions provide fertilizing materials which promote the rapid growth of desired plants, and at the same time control gene expression.

As used herein, the term "therapeutically effective amount," refers to the amount of a Compound of the Disclosure sufficient to treat one or more symptoms of a disease, condition, injury, or disorder, or prevent advancement of disease, condition, injury, or disorder, or cause regression of the disease, condition, injury, or disorder. For example, with respect to the treatment of cancer, in one embodiment, a therapeutically effective amount will refer to the amount of a Compound of the Disclosure that decreases the rate of tumor growth, decreases tumor mass, decreases the number of metastases, increases time to tumor progression, or increases survival time by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%.

As used herein, the term "insecticidally effective amount" refers to the amount of a Compound of the Disclosure sufficient to control, e.g., reduce or prevent the spread of, or kill, insects. For example, an insecticidally effect amount will refer to the amount of a Compound of the Disclosure that induces premature molting and death in an insect.

The terms "a" and "an" refer to one or more than one.

The term "about," as used herein, includes the recited number±10%. Thus, "about 10" means 9 to 11.

As used herein, the term "excipient" refers to any ingredient in a composition other than the Compound of the Disclosure. An excipient is typically an inert substance added to a composition to facilitate processing, handling, administration, etc., of Compound of the Disclosure. Useful excipients include, but are not limited to, adjuvants, antiadherents, binders, carriers, disintegrants, fillers, flavors, colors, diluents, lubricants, glidants, preservatives, sorbents, solvents, surfactants, and sweeteners.

Conventional pharmaceutical excipients are well known to those of skill in the art. In particular, one of skill in the art will recognize that a wide variety of pharmaceutically acceptable excipients can be used in admixture with Compounds of the Disclosure, including those listed in the *Handbook of Pharmaceutical Excipients*, Pharmaceutical Press 4th Ed. (2003), and *Remington: The Science and Practice of Pharmacy*, Lippincott Williams & Wilkins, 21st ed. (2005). In one embodiment, the composition comprises one or more of the following excipients: water, Labrasol, Lauroglycol 90, Phosal 53 MCT, Miglyol, Cremophor® EL, polysorbate 80, Crillet 1 HP, Isopropyl myristate, Oleic acid, and/or PEG 400 NF. In another embodiment, the composition comprises a lipid.

Pharmaceutically acceptable carriers include fillers such as saccharides, for example, trehalose, lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate or calcium stearate, and/or polyethylene glycol. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the is dissolved or suspended in suitable liquids, such as fatty oils, or liquid paraffin, optionally with stabilizers.

Fatty oils may comprise mono-, di- or triglycerides. Mono-, di- and triglycerides include those that are derived from $C_6$, $C_8$, $C_{10}$, $C_{12}$, $C_{14}$, $C_{16}$, $C_{18}$, $C_{20}$ and $C_{22}$ acids. Exemplary diglycerides include, in particular, diolein, dipalmitolein, and mixed caprylin-caprin diglycerides. Preferred triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

In one embodiment, the triglyceride is the medium chain triglyceride available under the trade name LABRAFAC CC. Other triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX® 355. Other triglycerides are caprylic-capric acid triglycerides such as known and commercially available under the trade name MYRITOL, including the product MYRITOL 813. Further triglycerides of this class are CAPMUL MCT, CAPTEX® 200, CAPTEX® 300, CAPTEX® 800, NEOBEE M5 and MAZOL 1400.

Pharmaceutical compositions comprising triglycerides may further comprise lipophilic and/or hydrophilic surfactants which may form clear solutions upon dissolution with an aqueous solvent. One such surfactant is tocopheryl polyethylene glycol 1000 succinate (vitamin E TPGS). Examples of such compositions are described in U.S. Pat. No. 6,267,985.

In another embodiment, the pharmaceutically acceptable carrier comprises LABRASOL (Gattefosse SA), which is PEG-8 caprylic/capric glycerides. In another embodiment, the pharmaceutically acceptable carrier comprises PL90G, vitamin E TPGS, and Miglyol 812N.

As used herein, the term "treat," "treating," or "treatment" is meant to encompass administering to a subject a Compound of the Disclosure, or a composition thereof, for the purposes of amelioration or cure of a disease, disorder, injury, or condition, including preemptive treatment.

As used herein, the term "subject" refers to an insect, plant, algae, or animal, e.g., human or veterinary animal, e.g., cow, sheep, pig, horse, dog, or cat. In one embodiment, a host cell of the subject comprises a polynucleotide encoding a gene switch that comprises a ligand binding domain that binds a Compound of the Disclosure.

As used herein, the term "gene of interest" is any gene that one wishes to express that encodes a peptide, protein, or polypeptide.

As used herein, the term "gene expression" refers to the transcription of DNA to messenger RNA (mRNA), and/or the translation of mRNA to amino acid sequence.

As used herein, the term "regulating gene expression" refers to increasing the level of gene expression in response to contact of a Compound of the Disclosure with the ligand binding domain that binds a Compound of the Disclosure, relative to the level of gene expression in the absence of contacting the ligand binding domain that binds a Compound of the Disclosure.

As used herein, the term "gene switch" refers to peptide, protein, or polypeptide complex that functions to (a) bind a Compound of the Disclosure, i.e., the ligand, and (b) regulate the transcription of a gene of interest in a ligand-dependent fashion. Gene switches are useful for various applications such as gene therapy, production of proteins in cells, cell based high throughput screening assays, functional genomics, and regulation of traits in transgenic plants and animals.

In one embodiment, the polynucleotide encoding a gene switch is a recombinant polynucleotide, i.e., a polynucleotide, that has been engineered, by molecular biological manipulation, to encode the gene switch. In another embodiment, the recombinant polynucleotide is a synthetic polynucleotide. See, e.g., US Pat. Appl. Pub. Nos. 2012/0322148, 2012/0185954, and 2011/0059530.

As used herein, the term "gene" refers to a polynucleotide comprising nucleotides that encode a functional molecule, including functional molecules produced by transcription only (e.g., a bioactive RNA species) or by transcription and translation (e.g. a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" or "exogenous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

In one embodiment, Compounds of the Disclosure are administered to an isolated host cell or a subject as a composition. In another embodiment, Compounds of the Disclosure are administered to an isolated host cell or a subject as a pharmaceutically acceptable composition.

As used herein, the term "dimerizes with the ligand binding domain that binds a Compound of the Disclosure" refers to a selective protein-protein interaction.

In one embodiment, the gene switch efficacy or "$EC_{50}$" of a Compound of the Disclosure is about 20 µM or less, about 10 µM or less, about 5 µM or less, about 3 µM or less, about 2 µM or less, about 1 µm or less, about 500 nM or less, about 300 nM or less, about 200 nM or less, or about 100 nM or less, e.g., about 75 nM about 50 nM, about 25 nM, about 15 nM, about 10 nM, about 9 nM, about 8 nM, about 7 nM, about 6 nM, about 5 nM, about 4 nM, about 3 nM, about 2 nM, about 1 nM, about 0.5 nM, or less in a cellular gene switch assay. Examples of in vitro assays for measuring gene switch-regulated gene expression are well known to those of ordinary skill in the art. See, for example, Karzenowski et al., *BioTechniques* 39: 191-200 (2005).

As used herein, the "$EC_{50}$" is the "half maximal effective concentration," which refers to the concentration of a Compound of the Disclosure that induces a gene switch-regulated change in expression of a polynucleotide encoding an gene of interest that is halfway between the baseline level of expression and the maximum level of expression after a specified exposure time.

As used herein, the term "ligand binding domain that binds a Compound of the Disclosure" refers to an amino acid sequence that selectively binds a Compound of the Disclosure. In the methods disclosed herein, a Compound of the Disclosure binds to a ligand binding domain, e.g., an ecdysone receptor ligand binding domain, that is part of a ligand-dependent transcriptional activation complex that regulates the expression of a polynucleotide sequence that encodes a gene of interest. Hence, the expression of the gene of interest is regulated in a ligand (Compound of the Disclosure) dependent fashion.

In one embodiment, the ligand binding domain that binds a Compound of the Disclosure, e.g., an ecdysone receptor ligand binding domain, dimerizes with another ligand binding domain, e.g., a retinoid X receptor ligand binding domain, to form a protein-protein complex.

In one embodiment, the expression of the gene of interest is regulated by a Compound of the Disclosure in an on/off fashion that is independent of the concentration or dosage of the Compound of the Disclosure. In another embodiment, the expression of the gene of interest is regulated by a Compound of the Disclosure in a concentration (or dosage)-dependent fashion, i.e., there is a dose-response relationship between the concentration (or dosage) of a Compound of the Disclosure and the level of gene expression of the gene of interest. See, e.g., US 2009/0123441.

The term "operably linked" refers to the association of polynucleotide sequences on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

In one embodiment, the host cell is an isolated host cell. In one embodiment, an "isolated" host cell refers to a cell that is not present in a subject. In one embodiment, an "isolated" host cell refers to one or more host cells in a cell culture apparatus or in a cell culture preparation.

In one embodiment, the host cell is within a subject, and the host cell is contacted by a Compound of the Disclosure by administering the Compound of the Disclosure, or a composition thereof, to the subject. In another embodiment, the host cell is contacted with a Compound of the Disclosure, or a composition thereof, in vitro. In another embodiment, the host cell is contacted with a Compound of the Disclosure, or a composition thereof, ex vivo. In another embodiment, the host cell is in a human subject. In another embodiment, the host cell is in an animal subject. In another embodiment, the host cell is in a plant subject. In another embodiment, the host cell is in an algae subject.

In one embodiment, Compounds of the Disclosure, or compositions thereof, are administered to a subject. In one embodiment, Compounds of the Disclosure, or compositions thereof, are administered to a subject orally. In another embodiment, Compounds of the Disclosure, or compositions thereof, are administered to a subject parenterally. In another embodiment, Compounds of the Disclosure, or compositions thereof, are administered subcutaneously, intramuscularly, intravenously, intraperitoneally or intratumorally.

In addition to or together with the above modes of administration, Compounds of the Disclosure, or compositions thereof, can be added to food consumed by a subject. In one embodiment, Compounds of the Disclosure, or compositions thereof, are combined, blended, or admixed with food material to provide a "food product." The term "food material" is used in its broadest possible sense, and includes any form, e.g., solid, emulsion, liquid, of ingestible materials consumed by an animal, e.g., a human. Food products may be formulated so the subject takes in an appropriate quantity of a Compound of the Disclosure, or composition thereof, with its diet. In another embodiment, a Compound of the Disclosure, or composition thereof, is formulated as a premix for addition to food material. In one embodiment, the food product or premix comprises a Compound of the Disclosure, or composition thereof, and one or more lipids.

In one embodiment, the ligand binding domain in the gene switch that binds a Compound of the Disclosure is a Group H nuclear receptor ligand binding domain, or a mutant thereof, that binds a Compound of the Disclosure. In another embodiment, the Group H nuclear receptor ligand binding domain is selected from the group consisting of an ecdysone receptor ligand binding domain, a ubiquitous receptor ligand binding domain, an orphan receptor-1 ligand binding domain, an NER-1 ligand binding domain, a receptor-interacting protein-15 ligand binding domain, a liver X receptor-3 ligand binding domain, a steroid hormone receptor-like protein ligand binding domain, a liver X receptor ligand binding domain, a liver X receptor ligand binding domain, a farnesoid X receptor ligand binding domain, a receptor-interacting protein-14 ligand binding domain, and a farnesol receptor ligand binding domain ligand binding domain, or a mutant thereof, that binds a Compound of the Disclosure.

In another embodiment, the Group H nuclear receptor ligand binding domain is an ecdysone receptor ligand binding domain, or a mutant thereof, that binds a Compound of the Disclosure. In another embodiment, the ecdysone receptor ligand binding domain is selected from the group consisting of an Arthropod ecdysone receptor ligand binding domain a Lepidopteran ecdysone receptor ligand binding domain, a Dipteran ecdysone receptor ligand binding domain, an Orthopteran ecdysone receptor ligand binding domain, a Homopteran ecdysone receptor ligand binding domain and a Hemipteran ecdysone receptor ligand binding domain, a spruce budworm *Choristoneura fumiferana* ecdysone receptor ligand binding domain, a beetle *Tenebrio* molitor ecdysone receptor ligand binding domain, a *Manduca sexta* ecdysone receptor ligand binding domain, a *Heliothies virescens* ecdysone receptor ligand binding domain, a midge *Chironomus tentans* ecdysone receptor ligand binding domain, a silk moth *Bombyx mori* ecdysone receptor ligand binding domain, a squinting bush brown *Bicyclus anynana* ecdysone receptor ligand binding domain, a buckeye *Junonia coenia* ecdysone receptor ligand binding domain, a fruit fly *Drosophila melanogaster* ecdysone receptor ligand binding domain, a mosquito *Aedes aegypti* ecdysone receptor ligand binding domain, a blowfly *Lucilia capitata* ecdysone receptor ligand binding domain, a blowfly *Lucilia cuprina* ecdysone receptor ligand binding domain, a blowfly *Calliphora vicinia* ecdysone receptor ligand binding domain, a Mediterranean fruit fly *Ceratitis capitata* ecdysone receptor ligand binding domain, a locust *Locusta migratoria* ecdysone receptor ligand binding domain, an aphid *Myzus persicae* ecdysone receptor ligand binding domain, a fiddler crab *Celuca pugilator* ecdysone receptor ligand binding domain, an ixodid tick *Amblyomma americanum* ecdysone receptor ligand binding domain, a whitefly *Bamecia argentifoli* ecdysone receptor ligand binding domain, a leafhopper *Nephotetix cincticeps* ecdysone receptor ligand binding domain, or a mutant thereof, that binds a Compound of the Disclosure. In another embodiment, the ecdysone receptor ligand binding domain is a spruce budworm *Choristoneura fumiferana* ecdysone receptor ligand binding domain, for which the amino acid sequence is set forth in U.S. Patent Publication No. 2006/0100416 A1.

In another embodiment, the ecdysone receptor ligand binding domain is a mutant of the spruce budworm *Choristoneura fumiferana* ecdysone receptor ligand binding domain that binds a Compound of the Disclosure.

Suitable ecdysone receptor ligand binding domains include those disclosed, for example, in U.S. Pat. Nos. 7,935,510; 7,919,269; 7,563,879; and in U.S. Patent Publication No. 2006/0100416 A1.

In one embodiment, the gene switch comprises a ligand binding domain that dimerizes with the ligand binding domain that binds a Compound of the Disclosure. In one embodiment, the ligand binding domain that dimerizes with the ligand binding domain that binds a Compound of the Disclosure is a Group B nuclear receptor ligand binding domain. In another embodiment, the Group B nuclear receptor ligand binding domain is selected from the group consisting of a retinoid X receptor ligand binding domain, an H-2 region II binding protein ligand binding domain, a nuclear receptor co-regulator-1 ligand binding domain, an ultraspiracle protein ligand binding domain, a 2Cl nuclear receptor ligand binding domain, and a chorion factor 1 ligand binding domain. In another embodiment, a ligand binding domain that dimerizes with the ligand binding domain that binds a Compound of the Disclosure is not an ecdysone receptor ligand binding domain.

In one embodiment, the ligand binding domain that dimerizes with the ligand binding domain that binds a Compound of the Disclosure is a retinoic X receptor ligand binding domain. In another embodiment, the retinoic X receptor ligand binding domain is a vertebrate retinoic X receptor ligand binding domain. In another embodiment, the retinoic X receptor ligand binding domain is a *Homo sapiens* retinoic X receptor ligand binding domain. In another embodiment, the retinoic X receptor ligand binding domain is a retinoic X receptor α isoform. In another embodiment, the retinoic X receptor ligand binding domain is a retinoic X receptor β isoform. In another embodiment, the retinoic X receptor ligand binding domain is a retinoic X receptor γ isoform.

In another embodiment, the retinoic X receptor ligand binding domain is an invertebrate retinoic X receptor ligand binding domain. In another embodiment, the invertebrate retinoic X receptor ligand binding domain is a *Locusta migratoria* retinoic X receptor ligand binding domain.

In another embodiment, the invertebrate retinoic X receptor ligand binding domain is a non-Lepidopteran, non-Dipteran retinoic X receptor ligand binding domain.

In one embodiment, the retinoid receptor ligand binding domain is a vertebrate retinoid X receptor ligand binding domain, an invertebrate retinoid X receptor ligand binding domain, an ultraspiracle protein ligand binding domain, or a chimeric retinoid X receptor ligand binding domain.

In one embodiment, the chimeric retinoid X receptor ligand binding domain comprises two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, a different invertebrate retinoid X receptor ligand binding domain, or a different ultraspiracle protein ligand binding domain.

In another embodiment, the chimeric retinoid X receptor ligand binding domain is one that is disclosed in U.S. Pat. No. 7,531,326.

In another embodiment, the first polypeptide fragment of the chimeric retinoid X receptor ligand binding domain comprises helices 1-6, helices 1-7, helices 1-8, helices 1-9, helices 1-10, helices 1-11, or helices 1-12 of a first species of retinoid X receptor, and the second polypeptide fragment of the chimeric retinoid X receptor ligand binding domain comprises helices 7-12, helices 8-12, helices 9-12, helices 10-12, helices 11-12, helix 12, or F domain of a second species of retinoid X receptor, respectively.

In another embodiment, the first polypeptide fragment of the chimeric retinoid X receptor ligand binding domain comprises helices 1-6 of a first species RXR according to the disclosure, and the second polypeptide fragment of the chimeric retinoid X receptor ligand binding domain comprises helices 7-12 of a second species of retinoid X receptor.

In another embodiment, the first polypeptide fragment of the chimeric retinoid X receptor ligand binding domain comprises helices 1-7 of a first species retinoid X receptor according to the disclosure, and the second polypeptide fragment of the chimeric retinoid X receptor ligand binding domain comprises helices 8-12 of a second species retinoid X receptor.

In another embodiment, the first polypeptide fragment of the chimeric retinoid X receptor ligand binding domain comprises helices 1-8 of a first species of retinoid X receptor, and the second polypeptide fragment of the chimeric retinoid X receptor ligand binding domain comprises helices 9-12 of a second species of retinoid X receptor.

In another embodiment, the first polypeptide fragment of the chimeric retinoid X receptor ligand binding domain comprises helices 1-9 of a first species of retinoid X receptor, and the second polypeptide fragment of the chimeric retinoid X receptor ligand binding domain comprises helices 10-12 of a second species of retinoid X receptor.

In another embodiment, the first polypeptide fragment of the chimeric retinoid X receptor ligand binding domain comprises helices 1-10 of a first species of retinoid X receptor, and the second polypeptide fragment of the chimeric retinoid X receptor ligand binding domain comprises helices 11-12 of a second species of retinoid X receptor.

In another embodiment, the first polypeptide fragment of the chimeric retinoid X receptor ligand binding domain comprises helices 1-11 of a first species of retinoid X receptor, and the second polypeptide fragment of the chimeric retinoid X receptor ligand binding domain comprises helix 12 of a second species of retinoid X receptor.

In another preferred embodiment, the first polypeptide fragment of the chimeric retinoid X receptor ligand binding domain comprises helices 1-12 of a first species of retinoid X receptor, and the second polypeptide fragment of the chimeric retinoid X receptor ligand binding domain comprises an F domain of a second species of retinoid X receptor.

In one embodiment, the first polypeptide fragment in the chimeric retinoid X receptor ligand binding domain is human retinoid X receptor sequence, and the second polypeptide fragment in the chimeric retinoid X receptor ligand binding domain is invertebrate retinoid X receptor sequence. In another embodiment, the invertebrate retinoid X receptor sequence is *Locusta migratoria* retinoid X receptor sequence.

In another embodiment, the first polypeptide fragment of the chimeric retinoid X receptor ligand binding domain comprises helices 1-8 of a human retinoid X receptor, and the second polypeptide fragment of the chimeric retinoid X receptor ligand binding domain comprises helices 9-12 of *Locusta migratoria* retinoid X receptor.

In one embodiment, the gene switch further comprises a DNA binding domain ("DBD"). In another embodiment, the DBD is selected from the group consisting of a GAL4 DBD, a LexA DBD, a transcription factor DBD, a steroid/thyroid hormone nuclear receptor superfamily member DBD, a bacterial LacZ DBD, and a yeast DBD.

In one embodiment, the gene switch further comprises a transactivation domain ("TD"). In another embodiment, the transactivation domain is selected from the group consisting of a VP16 TD, a GAL4 TD, an NF-κB TD, a BP64 TD, and a B42 acidic TD.

In one embodiment, a DNA binding domain, the ligand binding domain that binds a Compound of the Disclosure, a ligand binding domain that dimerizes with the ligand binding domain that binds a Compound of the Disclosure, and a transactivation domain are encoded by polynucleotide sequences that are contained in the same polynucleotide.

In another embodiment, a DNA binding domain, a ligand binding domain that binds a Compound of the Disclosure, a ligand binding domain that dimerizes with the ligand binding domain that binds a Compound of the Disclosure, and a transactivation domain are encoded by polynucleotide sequences that are contained in one or more separate polynucleotide sequences.

In another embodiment, a DNA binding domain, a ligand binding domain that binds a Compound of the Disclosure, a ligand binding domain that dimerizes with the ligand binding domain that binds a Compound of the Disclosure, and a transactivation domain are encoded by polynucleotide sequences that are contained in two separate polynucleotide sequences.

In another embodiment, a DNA binding domain and a ligand binding domain that binds a Compound of the Disclosure are encoded by polynucleotide sequences that are contained in a first polynucleotide sequence, and a ligand binding domain that dimerizes with the ligand binding domain that binds a Compound of the Disclosure and a transactivation domain are encoded by polynucleotide sequences that are contained in a second polynucleotide sequence.

In another embodiment, a DNA binding domain and a ligand binding domain that dimerizes with the ligand binding domain that binds a Compound of the Disclosure are encoded by polynucleotide sequences that are contained in a first polynucleotide sequence, and a ligand binding domain that binds a Compound of the Disclosure and a transactivation domain are encoded by polynucleotide sequences that are contained in a second polynucleotide sequence.

In embodiments in which one or more of the DNA binding domain, a ligand binding domain that binds a Compound of the Disclosure, a ligand binding domain that dimerizes with the ligand binding domain that binds a Compound of the Disclosure, and a transactivation domain are encoded by polynucleotide sequences that are contained in one or more separate polynucleotide sequences, then the one or more separate polynucleotide sequences is operably linked to one or more separate promoters. In another embodiment, the one or more separate polynucleotide sequences are operably linked to one or more separate enhancer elements. In another embodiment, the promoter(s) and/or the enhancer(s) are constitutively active. In another embodiment, the promoter(s) and/or the enhancer(s) are tissue specific promoters and/or enhancers.

In one embodiment, the gene switch comprises a DNA binding domain, an ecdysone receptor ligand binding domain, a ligand binding domain that dimerizes with the ecdysone receptor ligand binding domain, and a transactivation domain.

In another embodiment, the gene switch comprises a DNA binding domain, an ecdysone receptor ligand binding domain, a retinoid X receptor ligand binding domain, and a transactivation domain.

In another embodiment, the gene switch comprises a DNA binding domain, an ecdysone receptor ligand binding domain, a chimeric vertebrate/invertebrate retinoid X receptor ligand binding domain, and a transactivation domain.

In another embodiment, the gene switch comprises a first polypeptide comprising a DNA binding domain (DBD) and a first ligand binding domain (LBD) and comprises a second polypeptide comprising a transactivation domain (TAD) and a second LBD. In one embodiment, the first LBD is an EcR ligand binding domain. In one embodiment the first LBD is an RxR, a USP, a chimeric LBD, or a chimeric RxR/USP LBD. In one embodiment, the second LBD is an EcR ligand binding domain. In one embodiment the second LBD is an RxR, a USP, a chimeric LBD, or a chimeric RxR/USP LBD. In one embodiment, the DBD is a Gal4 DNA binding domain. In one embodiment, the TAD is a VP16 transactivation domain. In one embodiment, the gene switch comprises a first polypeptide comprising a Gal4 DNA binding domain and an EcR ligand binding domain (LBD) and comprises a second polypeptide comprising a VP16 transactivation domain and chimeric RxR/USP ligand binding domain. In one embodiment, the EcR ligand binding domain comprises one or more amino acid substitutions compared to the corresponding wild-type EcR polypeptide sequence.

In another embodiment, the gene switch comprises a GAL4 DNA binding domain, a *Choristoneura fumiferana* ecdysone receptor ligand binding domain that is engineered to contain the mutations V107I and Y127E of the *Choristoneura fumifrana* ecdysone receptor sequence set forth in U.S. Patent Publication No. 2006/0100416 A1, a chimeric *Homo sapiens/Locusta migratoria* retinoid X receptor ligand binding, and a VP16 transactivation domain.

The term "V107I" means that the valine amino acid residue at position 107 in the *Choristoneura fumifrana* ecdysone receptor sequence set forth in U.S. Patent Publication No. 2006/0100416 A1 is changed to isoleucine. The term "Y127E" means that the tyrosine amino acid residue at position 127 in the *Choristoneura fumifrana* ecdysone receptor sequence set forth in U.S. Patent Publication No. 2006/0100416 A1 is changed to glutamate.

In another embodiment, the host cell further comprises a polynucleotide encoding a peptide, protein or polypeptide whose expression is regulated by the gene switch. A promoter that binds the gene switch complex is operably linked to the polynucleotide encoding a peptide, protein or polypeptide whose expression is regulated by the gene switch.

In another embodiment, the polynucleotide encoding a peptide, protein or polypeptide whose expression is regulated by the gene switch is contained in the same polynucleotide as a polynucleotide that encodes one or more of a DNA binding domain, the ligand binding domain that binds a Compound of the Disclosure, a ligand binding domain that dimerizes with the ligand binding domain that binds a Compound of the Disclosure, and a transactivation domain. Such constructs are disclosed, for example, in U.S. Patent Publication No. 2009/0123441.

In another embodiment, the polynucleotide encoding a peptide, protein or polypeptide whose expression is regulated by the gene switch is contained in a different polynucleotide than a polynucleotide that encodes one or more of a DNA binding domain, the ligand binding domain that binds a Compound of the Disclosure, a ligand binding domain that dimerizes with the ligand binding domain that binds a Compound of the Disclosure, and a transactivation domain.

In one embodiment, the gene switch is more sensitive to a Compound of the Disclosure than to a steroid hormone. In another embodiment, the gene switch is more sensitive to a Compound of the Disclosure than to another diacylhydrazine compound.

The sensitivity of a gene switch to a Compound of the Disclosure, relative to another ligand, can readily be determined in an in vitro assay, for example, an in vitro assay that employs a reporter gene, such as firefly luciferase. Examples of such in vitro assays are well known to those of ordinary skill in the art. See, for example, Karzenowski et al., *BioTechniques* 39: 191-200 (2005).

In one embodiment, the polynucleotide encoding the gene switch is contained in a vector. In one embodiment, the vector selected from the group consisting of a plasmid, an expression vector, a replicon, a phage vector, a cosmid, a viral vector, a liposome, an electrically charged lipid (e.g., a cytofectin), a DNA-protein complex, and a biopolymer.

In another embodiment, the vector is a retroviral vector. In another embodiment, the vector is selected from the group consisting of an adeno-associated viral vector, a pox viral vector, a baculoviral vector, a vaccinia viral vector, a herpes simplex viral vector, an Epstein-Barr viral vector, an adenoviral vector, a gemini viral vector, and a caulimo viral vector.

In one embodiment, the host cell is a prokaryotic host cell. In another embodiment, the host cell is a eukaryotic host cell. In other embodiments, the host cell is an immune cell (e.g., a T-cell, a B-cell, a Natural Killer cell and the like) or a stem cell (e.g., a mesenchymal stem cell (MSC), an endometrial derived stem cell, an endometrial regenerative cell and the like).

In another embodiment, the host cell is a vertebrate host cell. In another embodiment, the host cell is an invertebrate host cell.

In another embodiment, the host cell is selected from the group consisting of a bacterial cell, a fungal cell, a yeast cell, a nematode cell, an insect cell, a fish cell, a plant cell, an avian cell, an algae cell, an animal cell, and a mammalian cell.

In another embodiment, the host cell is selected from the group consisting of a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, and a human cell.

In another embodiment, the host cell is selected from the group consisting of an *Aspergillus* cell, a *Trichoderma* cell, a *Saccharomyces* cell, a *Pichia* cell, a *Candida* cell, a *Hansenula* cell.

In another embodiment, the host cell is selected from the group consisting of a *Synechocystis* cell, a *Synechococcus* cell, a *Salmonella* cell, a *Bacillus* cell, a *Acinetobacter* cell, a *Rhodococcus* cell, a *Streptomyces* cell, an *Escherichia* cell, a *Pseudomonas* cell, a *Methylomonas* cell, a *Methylobacter* cell, a *Alcaligenes* cell, a *Synechocystis* cell, a *Anabaena* cell, a *Thiobacillus* cell, a *Methanobacterium* cell and a *Klebsiella* cell.

In another embodiment, the host cell is selected from the group consisting of an apple cell, an *Arabidopsis* cell, a bajra cell, a banana cell, a barley cell, a bean cell, a beet cell, a blackgram cell, a chickpea cell, a chili cell, a cucumber cell, an eggplant cell, a favabean cell, a maize cell, a melon cell, a millet cell, a mungbean cell, an oat cell, an okra cell, a *Panicum* cell, a papaya cell, a peanut cell, a pea cell, a pepper cell, a pigeonpea cell, a pineapple cell, a *Phaseolus* cell, a potato cell, a pumpkin cell, a rice cell, a sorghum cell, a soybean cell, a squash cell, a sugarcane cell, a sugarbeet cell, a sunflower cell, a sweet potato cell, a tea cell, a tomato cell, a tobacco cell, a watermelon cell, a mushroom cell, and a wheat cell.

In another embodiment, the host cell is selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid (or vector) transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art. Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification (e.g., glycosylation, cleavage (e.g., of signal sequence)) of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

In one embodiment, the host cell comprises two or more orthogonal gene switches. Two or more individually operable gene regulation systems are said to be "orthogonal" when (a) modulation of each of the given gene switches by its respective ligand results in a measurable change in the magnitude of expression of the gene that is regulated by that gene switch, and (b) the change is statistically significantly different than the change in expression of all other gene switches that are in the host cell. In one embodiment, regulation of each individually operable gene switch system effects a change in gene expression at least 2-fold, 3-fold, 4-fold, 5-fold, 10-fold, 20-fold, 50-fold, 70-fold, 100-fold, 200-fold, 300 fold, 400-fold or 500-fold greater than all of the other operable gene switches in the host cell. Non-limiting examples of orthogonal gene switch systems are set forth in U.S. Patent Publication No. US 2002/0110861 A1.

In another embodiment, a Compound of the Disclosure, or composition thereof, is administered to a subject to treat cancer in the subject, for example, a cancer selected from the group consisting of myelodysplasia, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, mesothelioma, osteogenic sarcoma, primary macroglobulinemia, and retinoblastoma, and the like.

In another embodiment, a Compound of the Disclosure, or composition thereof, is administered to a subject to treat a metabolic-related disorder in the subject, for example, a metabolic disorder selected from the group consisting of dyslipidemia, atherosclerosis, insulin resistance, diabetes (e.g., diabetes type I, diabetes type II, MODY, and gestational diabetes), obesity, impaired glucose tolerance, atheromatous disease, hypertension, heart disease (which includes, but is not limited to, coronary heart disease, stroke, cardiac insufficiency, coronary insufficiency, and high blood pressure), hyperlipidemia, glucose intolerance, insulin resistance, hyperglycemia, hyperinsulinemia, metabolic syndrome X (or syndrome X, or insulin resistance syndrome, or Reaven's syndrome, or the metabolic cardiovascular risk syndrome), hypertension, chronic fatigue, accelerated aging, degenerative disease, endocrine deficiencies of aging, $G_m1$ gangliosidosis, Morquio-B disease, Krabbe's disease, Fabry's disease, Gaucher's disease, Tay-Sachs disease, Sandhoff disease, fucosidosis, disorders of carbohydrate metabolism (e.g., glycogen storage disease), disorders of amino acid metabolism (e.g., phenylketonuria, maple syrup urine disease, glutaric acidemia type 1), disorders of organic acid metabolism (e.g., alcaptonuria), disorders of fatty acid oxidation and mitochondrial metabolism (e.g., medium chain acyl dehydrogenase deficiency), disorders of porphyrin metabolism (e.g., acute intermittent porphyria), disorders of purine or pyrimidine metabolism (e.g., Lesch-Nyhan syndrome), disorders of steroid metabolism (e.g., congenital adrenal hyperplasia), disorders of mitochondrial function (e.g., Kearns-Sayre syndrome), and disorders of peroxisomal function (e.g., Zellweger syndrome).

In another embodiment, a Compound of the Disclosure, or composition thereof, is administered to a subject to treat kidney disease in the subject. In one embodiment, the kidney disease is renal failure. In another embodiment, the kidney disease is chronic renal failure.

In another embodiment, a Compound of the Disclosure, or composition thereof, is administered to a subject to treat anemia in the subject. In one embodiment, the anemia is anemia associated with kidney disease, for example, renal failure or chronic renal failure. In another embodiment, the anemia is associated with cancer therapy with, for example, one or more chemotherapeutic agents. In another embodiment, the anemia is associated with advanced age. In another embodiment, the anemia is associated with impaired lung function. In another embodiment, the anemia is associated with myelodisplasia. In another embodiment, the anemia is associated with radiation therapy. In another embodiment, the anemia is associated with a critical illness. In another embodiment, the anemia is associated with cardiac disease. In another embodiment, the anemia is not a cardiac disease. Nonlimiting types of "cardiac disease" are congestive heart failure, hypoxia, ischemic heart disease, hypertensive heart disease, coronary artery disease, peripheral vascular disease and ischemic cardiac events, e.g., myocardial infarction, heart attack, heart failure, arrhythmia, myocardial rupture, pericarditis, cardiogenic shock, thrombosis, embolism, atherosclerosis, and arterial stenosis.

In another embodiment, a Compound of the Disclosure, or composition thereof, are administered to a subject to treat an autoimmune disorder in the subject, for example, an autoimmune disorder selected from the group consisting of Achlorhydra Autoimmune Active Chronic Hepatitis, Acute Disseminated Encephalomyelitis, Acute hemorrhagic leukoencephalitis, Addison's Disease, gammaglobulinemia, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chronic Fatigue Immune Dysfunction Syndrome, chronic inflammatory demyelinating polyneuropathy, Chronic recurrent multifocal ostomyelitis, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease, Cushing's Syndrome, Cutaneous leukocytoclastic angiitis, Dego's disease, Dermatitis herpetiformis, Dermatomyositis, Diabetes mellitus type 1, Diffuse cutaneous systemic sclerosis, Dressler's syndrome, Discoid lupus erythematosus, eczema, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyositis, Fibrosing aveolitis, Gastritis, Gastrointestinal pemphigoid, Giant cell arteritis, Goodpasture's syndrome, Graves' disease, Guillain-Barré syndrome (GBS), Hashimoto's encephalitis, Hashimoto's thyroiditis, Hemolytic anaemia, Henoch-Schonlein purpura, Herpes gestationis, Hughes syndrome (or Antiphospholipid syndrome), Hypogammaglobulinemia, Idiopathic Inflammatory Demyelinating Diseases, Idiopathic pulmonary fibrosis, Idiopathic thrombocytopenic purpura, IgA nephropathy (or Berger's disease), Inclusion body myositis, ory demyelinating polyneuopathy, Juvenile idiopathic arthritis, Juvenile rheumatoid arthritis, Lambert-Eaton myasthenic syndrome, Leukocytoclastic vasculitis, Lichen planus, Lichen sclerosus, Linear IgA disease (LAD), Lou Gehrig's Disease, Lupoid hepatitis, Lupus erythematosus, Majeed syndrome, Meniere's disease, Microscopic polyangiitis, Miller-Fisher syndrome, Mixed Connective Tissue Disease, Mucha-Habermann disease, Muckle-Wells syndrome, Multiple Myeloma, Myasthenia gravis, Myositis, Narcolepsy, Neuromyelitis optica (also Devic's Disease), Occular cicatricial pemphigoid, Ord thyroiditis, Palindromic rheumatism, PANDAS (Pediatric Autoimmune Neuropsychiatric Disorders Associated with *Streptococcus*), Paraneoplastic cerebellar degeneration, Paraneoplastic cerebellar degeneration, Parry Romberg syndrome, Parsonnage-Turner syndrome, Pars planitis, *Pemphigus, Pemphigus vulgaris*, Pernicious anaemia, Perivenous encephalomyelitis, POEMS syndrome, Polyarteritis nodosa, Polymyalgia rheumatica, Polymyositis, Primary biliary cirrhosis, psoriasis, psoriatic arthritis, Pyoderma gangrenosum, pure red cell aplasia, Rasmussen's encephalitis, Raynaud phenomenon, Relapsing polychondritis, Reiter's syndrome, Retroperitoneal fibrosis, Rheumatoid arthritis, Rheumatoid fever, Schmidt syndrome, Schnitzler syndrome, Scleritis, Sjögren's syndrome, Spondyloarthropathy, sticky blood syndrome, Still's Disease, Subacute bacterial endocarditis (SBE), Susac's syndrome, Sweet syndrome, Sydenham Chorea, Sympathetic ophthalmia, Takayasu's arteritis, Temporal arteritis, Tolosa-Hunt syndrome, Transverse Myelitis, Ulcerative Colitis, Undifferentiated connective tissue disease, Undifferentiated spondyloarthropathy, vasculitis, Wegener's granulomatosis, Wilson's syndrome, and Wiskott-Aldrich syndrome.

In another embodiment, a Compound of the Disclosure, or composition thereof, is administered to a subject to treat an ocular disorder in the subject, for example, an ocular disorder selected from the group consisting of glaucoma including Open Angle Glaucoma (e.g., Primary Open Angle Glaucoma, Pigmentary Glaucoma, and Exfoliative Glaucoma, Low Tension Glaucoma), Angle Closure Glaucoma (also known clinically as closed angle glaucoma, narrow angle glaucoma, pupillary block glaucoma, and ciliary block glaucoma) (e.g., Acute Angle Closure Glaucoma and Chronic Angle Closure Glaucoma), Aniridic Glaucoma, Congenital Glaucoma, Juvenile Glaucoma, Lens-Induced Glaucoma, Neovascular Glaucoma (e.g., using vectors composed of Vascular Endothelial Growth Factor (VEGF) decoy, Pigment Derived Growth Factor (PDGF), Endostatin, Angiostatin, or Angiopoetin-1), Post-Traumatic Glaucoma, Steroid-Induced Glaucoma, Sturge-Weber Syndrome Glaucoma, and Uveitis-Induced Glaucoma, diabetic retinopathy (e.g., using vectors composed of VEGF decoy, PDGF, Endostatin, Angiostatin, or Angiopoetin-1), macular degeneration (e.g., vectors composed of VEGF decoy, PDGF, Endostatin, Angiostatin, Angiopoetin-1, ATP Binding Casette Subfamily A Member 4), macular degeneration (e.g., using vectors composed of VEGF decoy, PDGF, Endostatin, Angiostatin, Angiopoetin-1, ATP Binding Casette Subfamily A Member 4), choroidal neovascularization, (e.g., using vectors composed of VEGF decoy, PDGF, Endostatin, Angiostatin, or Angiopoetin-1), vascular leak, and/or retinal edema, bacterial conjunctivitis, fungal conjunctivitis, viral conjunctivitis, uveitis, keratic precipitates, macular edema (e.g., using vectors composed of VEGF decoy, PDGF, Endostatin, Angiostatin, or Angiopoetin-1), inflammation response after intra-ocular lens implantation, uveitis syndromes (for example, chronic iridocyclitis or chronic endophthalmitis), retinal vasculitis (for example, as seen in rheumatoid arthritis, juvenile rheumatoid arthritis, systemic lupus erythymatosus, progressive systemic sclerosis, polyarteritis nodosa, Wegener's granulomatosis, termporal arteritis, Adamantiades Bechcet disease, Sjorgen's, relapsing polychondritis and HLA-B27 associated spondylitis), sarcoidosis, Eales disease, acute retinal necrosis, Vogt Koyanaki Harada syndrome, occular toxoplasmosis, radiation retinopathy, proliferative vitreoretinopathy, endophthalmitis, ocular glaucomas (for example, inflammatory glaucomas), optic neuritis, ischemic optic neuropathy (e.g., vectors composed of Allotopic NADH dehydrogenase Unit 4), thyroid associated orbitopathy, orbital pseudotumor, pigment dispersion syndrome (pigmentary glaucoma), scleritis, episcleritis choroidopathies (for example, "White-dot" syndromes including, but not limited to, acute multifocal posterior placoid), retinopathies (for example, cystoid macular edema, central serous choroidopathy and presumed ocular histoplasmosis syndrome (e.g., vectors composed of Glial Cell Derived Neurotropic Factor, Peripherin-2)), retinal vascular disease (for example, diabetic retinopathy, Coat's disease and retinal arterial macroaneurysm), retinal artery occlusions, retinal vein occlusions, retinopathy of prematurity, retinitis pigmentosa (e.g., vectors composed of Retinal Pigment Specific 65 kDa protein), familial exudative vitreoretinopathy (FEVR), idiopathic polypoidal choroidal vasculopathy, epiretinal macular membranes and cataracts.

In another embodiment, a Compound of the Disclosure, or composition thereof, is administered to a subject to treat an ocular disorder in the subject, wherein the ocular disorder is selected from the group consisting of glaucoma, wet and dry age-related macular degeneration, diabetic retinopathy, and macular oedema.

In another embodiment, a Compound of the Disclosure, or composition thereof, is administered to a subject to treat a blood disorder in the subject, for example, a blood disorder selected from the group consisting of a blood disorder selected from the group consisting of anemia, bleeding and clotting disorders (e.g., disseminated intravascular coagulation (DIC), hemophilia, Henoch-Schonlien Purpura, hereditary hemorrhagic telangiectasia, thrombocytopenia (ITP, TTP), thrombophilia, Von Willebrand's disease), leukemias (e.g., acute lymphocytic leukemia, acute myelocytic leukemia, chronic lymphocytic leukemia, chronic myelocytic leukemia), lymphomas (e.g., Hodgkin lymphoma, non-Hodgkin lymphoma), myeloproliferative disorders (e.g., myelofibrosis, Polycythemia Vera, thrombocythemia), plasma cell disorders (e.g., macroglobulinemia, monoclonal gammopathies of undetermined significance, multiple lyeloma), spleen disorders, white blood cell disorders (e.g., basophilic disorder, eosinophilic disorder, lymphocytopenia, monocyte disorders, neutropenia, neutrophillic leukocytosis), thrombosis, deep vein thrombosis (DVT), hemochromatosis, menorrhagia, sickle cell disease, and thalassemia.

In another embodiment, a Compound of the Disclosure, or composition thereof, is administered to a subject to treat a neurological disorder in the subject, for example, a neurological disorder selected from the group consisting of Gaucher disease, Parkinson's disease, Alzheimer's disease, amyotrophic lateral sclerosis (ALS), multiple sclerosis (MS), Huntington's disease, Fredrich's ataxia, Mild Cognitive Impairment, Cerebral Amyloid Angiopathy, Parkinsonism Disease, Lewy Body Disease, Frontotemporal Dementia (FTD) Multiple System Atrophy (MSA), Progressive Supranuclear Palsy, and movement disorders (including ataxia, cerebral palsy, choreoathetosis, dystonia, Tourette's syndrome, kernicterus) and tremor disorders, and leukodystrophies (including adrenoleukodystrophy, metachromatic leukodystrophy, Canavan disease, Alexander disease, Pelizaeus-Merzbacher disease), neuronal ceroid lipofucsinoses, ataxia telangectasia, Rett Syndrome, alpha-synucleinopathy (e.g., Lewy Body Disease, Multiple System Atrophy, Hallervorden-Spatz disease, or Frontotemporal Dementia), Niemann-Pick Type C disease (NPCD), spinocerebellar ataxia Type 1, Type 2, and Type 3, and dentatorubral pallidoluysian atrophy (DRLPA).

In another embodiment, a Compound of the Disclosure, or composition thereof, is administered to a subject to treat a lung disorder in the subject, for example, a lung disorder selected from the group consisting of asthma, atelectasis, bronchitis, COPD (chronic obstructive pulmonary disease), emphysema, Lung cancer, mesothelioma, pneumonia, asbestosis, Aspergilloma, Aspergillosis, Aspergillosis—acute invasive, bronchiectasis, bronchiolitis obliterans organizing pneumonia (BOOP), eosinophilic pneumonia, necrotizing pneumonia, ral effusion, pneumoconiosis, pneumothorax, pulmonary actinomycosis, monary alveolar proteinosis, pulmonary anthrax, pulmonary arteriovenous malformation, pulmonary fibrosis, pulmonary embolus, pulmonary histiocytosis X (eosinophilic granuloma), pulmonary hypertension, pulmonary edema, pulmonary hemorrhage, pulmonary nocardiosis, pulmonary tuberculosis, pulmonary veno-occlusive disease, rheumatoid lung disease, sarcoidosis, radiation fibrosis, hypersensitivity pneumonitis, acute respiratory distress syndrome (ARDS), infant respiratory distress syndrome, idiopathic pulmonary fibrosis, idiopathic interstitial pneumonia, lymphangioleiomyomatosis, pulmonary Langerhans' cell histiocytosis, pulmonary alveolar proteinosis, sinusitis, tonsillitis, otitis media, pharyngitis, laryngitis, Pulmonary hamartoma, pulmonary sequestration, congenital cystic adenomatoid malformation (CCAM), and cystic fibrosis.

In another embodiment, a Compound of the Disclosure, or composition thereof, is administered to a subject to treat a rheumatologic disorder in the subject, for example, a rheumatologic disorder selected from the group consisting of systemic lupus erythematosus, dermatomyositis, scleroderma, systemic necrotizing arteritis, cutaneous necrotizing venulitis, rheumatoid arthritis, Sjogren's Syndrome, Raynaud's phenomenon, Reiter's syndrome, arthritis, psoriatic arthritis, seronegative spondyloarthropathies, Sjogren's syndrome, systemic sclerosis, dermatomyositis/polymyositis, mixed connective tissue disease, and ankylosing spondylitis.

In another embodiment, a Compound of the Disclosure, or composition thereof, is administered a subject to treat an infectious disease in the subject, for example, an infectious disease selected from the group consisting of fungal diseases such as dermatophytosis (e.g., trichophytosis, ringworm or tinea infections), athletes foot, paronychia, *pityriasis versicolor*, erythrasma, intertrigo, fungal diaper rash, *candida vulvitis, candida balanitis*, otitis externa, candidiasis (cutaneous and mucocutaneous), chronic mucocandidiasis (e.g., thrush and vaginal candidiasis), cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and fungemia, *Acinetobacter* infections, Actinomycosis, African sleeping sickness, AIDS (Acquired immune deficiency syndrome), Amebiasis, Anaplasmosis, Anthrax, *Arcanobacterium haemolyticum* infection, Argentine hemorrhagic fever, Ascariasis, Aspergillosis, atrovirus infection, Babesiosis, *Bacillus cereus* infection, Bacterial pneumonia, Bacterial vaginosis (BV), *Bacteroides* infection, Balantidiasis, *Baylisascaris* infection, BK virus infection, Black piedra, *Blastocystis hominis* infection, *Borrelia* infection, Botulism (and Infant botulism), Brazilian hemorrhagic fever, Brucellosis, *Burkholderia* infection, Buruli ulcer, Calcivirus infection (Norovirus and Sapovirus), Candidiasis, Cat-scratch disease, Cellulitis, Chagas Disease (American trypanosomiasis), Chancroid, Chickenpox, Chlamydia, Cholera, Chromoblastomycosis, Clonorchiasis, *Clostridium difficile*, Coccidioidomycosis, Colorado tick fever (CTF), Common cold (Acute viral rhinopharyngitis; Acute coryza), Creutzfeldt-Jakob disease (CJD), Cryptococcosis, Cryptosporidiosis, ous larva migrans (CLM), Dengue fever, Dientamoebiasis, Diphtheria, Diphyllobothriasis, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum, Exanthem subitum, Fasciolopsiasis, Fasciolosis, Fatal familial insomnia (FFI), Filariasis, *Fusobacterium* infection, Gas gangrene (Clostridial myonecrosis), Geotrichosis, Gerstmann-Sträussler-Scheinker syndrome (GSS), Giardiasis Glanders, Gnathostomiasis, Gonorrhea, Granuloma inguinale (Donovanosis), Group A streptococcal infection, Group B streptococcal infection, *Haemophilus influenzae*, Hand, foot and mouth disease (HFMD), Hantavirus Pulmonary Syndrome (HPS) *Helicobacter pylori* infection, ic-uremic syndrome (HUS), Hemorrhagic fever with renal syndrome (HFRS), Hepatitis A, B, C, D, E, Herpes simplex, Histoplasmosis, Hookworm infection, n bocavirus infection, Human ewingii ehrlichiosis, Human granulocytic anaplasmosis (HGA), Human granulocytic anaplasmosis (HGA), Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Melioidosis (Whitmore's disease), Meningitis, Meningococcal disease, Metagonimiasis, Microsporidiosis, Molluscum contagiosum (MC), Mumps, Murine typhus (Endemic typhus), Mycoplasma pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, Pneumocystis pneumonia (PCP), Pneumonia, Poliomyelitis, Poliomyelitis, *Prevotella* infection, mary amoebic meningoencephalitis (PAM), Progressive multifocal leukoencephalopathy, Psittacosis, Q fever, Rabies, Rat-bite fever, Respiratory syncytial virus infection, Rhinosporidiosis, inovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, tanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea unguium (Onychomycosis), Tinea versicolor (*Pityriasis versicolor*), Toxocariasis (Visceral Larva Migrans (VLM)), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, viral pneumonia, West Nile Fever, White piedra (Tinea blanca), *Yersinia pseudotuberculosis* infection, Yersiniosis, Yellow fever, and Zygomycosis.

In another embodiment, a Compound of the Disclosure, or composition thereof, is administered to a subject to treat angioedema in the subject. In another embodiment, the angioedema is hereditary angioedema.

In another embodiment, a Compound of the Disclosure, or composition thereof, is administered to a subject treat a disease, condition or disorder selected from the group consisting of sepsis, hypercoagulability, pulmonary dysfunction, hypoxemia, hemorrhagic pancreaitis, myocardial infarction, lung transplantation, trauma, thermal injury and vascular leak in the subject.

In another embodiment, a Compound of the Disclosure, or composition thereof, is administered to a subject to treat a disease, condition or disorder in which inhibition of kallikrein provides a therapeutically beneficial effect. Examples of such diseases, conditions or disorders include, but are not limited to, disease, conditions or disorders of the contact system. See e.g., Shariat-Madar et al., *Innate Immunity*, vol. 10, no. 1, 3-13 (2004) and Frick, et al., *EMBO J*., (2006) 25, 5569-5578 (2006). In another embodiment, a Compound of the Disclosure, or composition thereof, is administered a subject to treat a disease, condition or disorder selected from the group consisting of atherothrombosis, coronary artery disease, Alzheimer's Disease, inflammatory bowel disease (for example, Crohn's Disease), vascular leak, acute respiratory distress syndrome and bradykinin-mediated inflammation in the subject.

In another embodiment, a Compound of the Disclosure, or composition thereof, is administered to a subject to treat a disease, condition or disorder in which inhibition of bradykinin B2 receptor provides a therapeutically beneficial effect. In another embodiment, a Compound of the Disclosure, or composition thereof, is administered to a subject treat a disease, condition or disorder selected from the group consisting of glomerulosclerosis, Alzheimer's Disease, cerebral edema, vascular leak, acute respiratory distress syndrome, pain, inflammation, trauma, burns, shock, allergy, and cardiovascular disease in the subject.

In another embodiment, a Compound of the Disclosure, or composition thereof, is administered to a subject to treat an infectious disease in the subject, for example, an infectious disease selected from the group consisting of Bovine respiratory disease, Porcine respiratory disease, Avian influenza, Avian infectious bronchitis, Bovine spongiform encephalopathy, Canine leishmaniasis, Chronic wasting disease, human immune deficiency virus (HIV), hepatitis, hepatitis A, hepatitis B, hepatitis C, Classical swine fever, *Echinococcus*, Enzootic pneumonia, FIP, Foot-and-mouth disease, Jaagsiekte, Maedi-Visna, Mastitis in animals, *Microsporum canis*, Orf (animal disease), Peste des petits ruminants, Pox diseases, Psittacine beak and feather disease, Rabies, Mediterranean fever (Brucellosis) or Bang's disease or undulant fever, Malta fever, contagious abortion, epizootic abortion, *Salmonella* food poisoning, enteric paratyphosis, Bacillary dysentery, *Pseudotuberculosis*, plague, pestilential fever, Tuberculosis, Vibrios, Circling disease, Weil's disease (Leptospirosis) or canicola fever, Hemorrhagic jaundice (*Leptospira icterohaemorrhagiae*), dairy worker fever (*L. hardjo*), Relapsing fever, tick-borne relapsing fever, spirochetal fever, vagabond fever, famine fever, Lyme arthritis, Bannworth's syndrome (lime disease), tick-borne meningopolyneuritis, erythema chronicum migrans, Vibriosis, Colibacteriosis, colitoxemia, white scours, gut edema of swine, enteric paratyphosis, Staphylococcal alimentary toxicosis, staphylococcal gastroenteritis, Canine Corona Virus (CCV) or canine parvovirus enteritis, feline infectious peritonitis virus, transmissible gastroenteritis (TGE) virus, Hagerman Redmouth Disease (ERMD), Infectious Hematopoietic necrosis (IHN), porcine *Actinobacillus* (*Haemophilus*) pleuropneumonia, Hansen's disease, Streptotrichosis, Mycotic Dermatitis of Sheep, Pseudoglanders, Whitmore's disease, Francis' disease, deer-fly fever, rabbit fever, O'Hara disease, Streptobacillary fever, Haverhill fever, epidemic arthritic erythema, sodoku, Shipping or transport fever, hemorrhagic septicemia, Ornithosis, Parrot Fever, Chlamydiosis, North American blastomycosis, Chicago disease, Gilchrist's disease, Cat Scratch Fever, Benign Lymphoreticulosis, Benign nonbacterial Lymphadenitis, Bacillary Angiomatosis, Bacillary Peliosis Hepatis, Query fever, Balkan influenza, Balkan grippe, abattoir fever, Tick-borne fever, pneumorickettsiosis, American Tick Typhus, Tick-borne Typhus Fever, Vesicular Rickettsiosis, Kew Gardens Spotted Fever, Flea-borne Typhus Fever, Endemic Typhus Fever, Urban Typhus, Ringworm, Dermatophytosis, Tinea, Trichophytosis, Microsporosis, Jock Itch, Athlete's Foot, *Sporothrix schenckii*, dimorphic fungus, Cryptococcosis and histoplasmosis, Benign Epidermal Monkeypox, BEMP, Herpesvirus simiae, Simian B Disease, Venezuelan equine encephalitis, Type C lethargic encephalitis choriomeningitis, California encephalitis/La crosse encephalitis, African Hemorrhagic, Yellow fever, Black Vomit, hantavirus pulmonary syndrome, Korean Hemorrhagic Fever, Nephropathia Epidemica, Epidemic Hemorrhagic Fever, Hemorrhagic Nephrosonephritis, lymphocytic Fever, Green or Vervet Monkey Disease, Hydrophobia, Lyssa, Infectious hepatitis, Epidemic hepatitis, Epidemic jaundice, Rubeola, Morbilli, Swine and Equine Influenza, Fowl Plague, Newcastle disease, Piroplasmosis, toxoplasmosis, African Sleeping Sickness, Gambian Trypanosomiasis, Rhodesian Trypanosomiasis, Chagas's Disease, Chagas-Mazza Disease, South American Trypanosomiasis, *Entamoeba histolytica*, Balantidial dysentery, cryptosporidiosis, giardiasis, Cutaneous leishmaniasis: Chiclero ulcer, espundia, pianbols, uta, and buba (in the Americas); oriental sore, Aleppo boil (in the Old World); Bagdad boil, Delhi boil, Baum ulcer, Visceral leishmaniasis: kala-azar, Microsporidiosis, Anisakiasis, Trichinosis, Angiostrongylosis, eosinophilic meningitis or meningoencephalitis (*A. cantonensis*), abdominal angiostrongylosis (*A. costaricensis*), Uncinariasis, Necatoriasis, Hookworm Disease, Capillariasis, Brugiasis, Toxocariasis, Oesophagostomiasis, Strongyloidiasis, Trichostrongylosis, Ascaridiasis, Diphyllobothriasis, Sparganosis, Hydatidosis, Hydatid Disease, *Echinococcus granulosus*, Cystic hydatid disease, Tapeworm Infection, and *Schistosoma*.

In another embodiment, a Compound of the Disclosure, or composition thereof, is administered to a subject to treat chronic renal disease, osteoarthritis, oncology, viral upper respiratory infection, feline plasma cell stomatitis, feline eosinophillic granulomas, feline leukemia virus infection, canine distemper infection, systemic fungal infections, cardiomyopathy, and mucopolysaccharidosis VII in the subject.

In the methods of the present disclosure, the gene switch regulates the expression of a polynucleotide encoding a peptide, protein, or polypeptide. In one embodiment, gene switch regulates the expression of a polynucleotide encoding a peptide, protein, or polypeptide of therapeutic interest for the treatment of a disease, condition, or disorder in a subject, e.g., a human. In another embodiment, the peptide, protein, or polypeptide of interest is selected from the group consisting of Her-2/neu (ERBB2/c-erbB-2), Osteocalcin, stromelysin-1, prostate specific antigen, human sodium-iodide symporter, H19, IF-1, IGF-2, thymosin β15, T cell factor, cartilage-derived retinoic acid-sensitive protein, Prostasin, telomerase catalytic subunit, cyclin-A, midkine; c-erbB-2, prostate-specific membrane antigen, p51, telomerase RNA, prostatic acid phosphatase, PCA3dd3, DF3/MUC1, hex II, cyclooxygenase-2, super PSA, skp2, PRL-3, CA125/M17S2, IAI.3B, CRG-L2, TRPM4, RTVP, TARP, telomere reverse transcriptase, A4 amyloid protein, amyloid β-protein precursor, precursor of the Alzheimer's Disease A4 amyloid protein, neuropeptide FF, endoplasmic reticulum stress elements, urocortin II, tyrosine hydroxylase, complement factor 3; serum amyloid A3, tissue inhibitor of metalloproteinase-3 (TIMP-3), p75 tumor necrosis factor receptor, tumor necrosis factor-α, TRPM4, RTVP, TARP, telomere reverse transcriptase, A4 amyloid protein, amyloid β-protein precursor, precursor of the Alzheimer's Disease A4 amyloid protein, neuropeptide FF, endoplasmic reticulum stress elements, urocortin II, tyrosine hydroxylase, complement factor 3; serum amyloid A3, tissue inhibitor of metalloproteinase-3 (TIMP-3), p75 tumor necrosis factor receptor, tumor necrosis factor-α, peroxisome proliferator activated receptor/IIA-1 nonpancreatic secreted phospholipase A2, SOCS-3, SR-BI, Ob, site-1 protease, TIGR, VL30, excitatory amino acid transporter-2, MDTS9, LIM, pyrroline 5-carboxylate reductase, SIM2, Bax, Fas, bbc3, PINK-1, troponin T, myoD, Actin, smooth muscle 22a, Utrophin, Myostatin, smooth muscle myosin heavy chain, cardiac ankyrin repeat protein, MLP, Smoothelin, MYBPC3, Tα1 α-tubulin, intercellular adhesion molecule-4 (ICAM-4), γ-aminobutyric acid type A receptor β1 subunit, neuronal nicotinic acetylcholine receptor β2-subunit, presenilin-1, calcium-calmodulin-dependent kinase IIα, CRF2α receptor, nerve growth factor, GLP-2 receptor, type I transglutaminase, K14, stearoyl-CoA desaturase, Megsin, Prolactin, GDF-9, PSP94, NRL, NGAL, long whey acidic protein, mammary associated amyloid A, endothelin-1, Serglycin, platelet-endothelial cell adhesion molecule-1 (PECAM-1), Tie receptor tyrosine kinase, KDR/flk-1, Endoglin, CCR5, CD11d, platelet glycoprotein IIb, preproendothelin-1, interleukin-18 binding protein, CD34, Tec tyrosine kinase, MLH1, MSH2, MSH6, PMS1, APC, LEF-1, F2 receptor, TGF-β type II receptor, EYA4, PCA3, K2, PROST 03, PCAM-1, PCADM-1, PCA3dd3, PCAV, PAcP, $ATB_0$, CSA-1, SYG972, Urb-ctf, BCU399, TBX2, Cyr61, DIAPH3, BEHAB, IL-8, BLSA, BP1, DAP-kinase, HOXA9, ARP, Nbk, CD43, β7-hcG, β6-hCG, β6e-hCG, β5-hCG, β8-hcG, β3-hCG, MTAls, Old-35, Old-64, LAGE-1, CIF150/hTAFII150, P65 oncofetal protein, Telomerase, CYP1B1, 14-3-3σ, NEST, CAR-1, HMGI, MAG, ELL2, Ephrin B2, WAF1, CIF130, C35, BMP2, BUB3, Polymerase kappa, EAG1, EAG2, HMG I, HLTF, Barx2, Pp 32r1, BMP4, TS10q23.3, Nuclear spindle-associating protein, PFTAIRE, SEMA3B, MOGp, Fortilin, IGFBP-3, Polyhomeotic 2, PNQALRE, SCN5A, miR15, miR16, Headpin, PAOh1/SMO, Hippo, Mst2, PSMA-like, JAB1, NF-AT, P28ING5, MTG16, ErbB-2, HDAC9, GPBP, MG20, KLF6, ARTS1, Dock 3, Annexin 8, MH15, DELTA-N p73, RapR6, StarD10, Ciz1, HLJ1, RapR7, A34, Sef, Killin, SGA-1M, TGFβ Type II receptor, GCA-associated genes, PRV-1, Vezf1, MLP, VEGI, PRO256, AOP2, Remodelin, Phosphodiesterase 4D, Prostaglandin receptor subtype EP3, CARP, HOP, PLTP, UCP-2, FLJ11011, Codanin-1, Resistin, Archipelin, Neuronatin, Ncb5or, 7B2, PTHrP, PEX, KChIP1, SLIT-3, CX3CR1, SMAP-2, IC-RFX, E2IG4, UCP2, Ob receptor, Ob, Dp1, NRG-1, Synapsin III, NRG1AG1, AL-2, Proline dehydrogenase, MNR2, ATM, Ho-1, CON202, Ataxin-1, NR3B, NIPA-1, DEPP, adrenomedullin, csdA, Inf-20, EOPA, SERT, FRP-1, Serum amyloid A, BMP2, BMPR1A, ACLP, Resistin-like molecule β, Dlg5, TRANCE, Matrilin-3, Synoviolin, HIV LTR, SHIVA, EBI 1, EBI 2, EBI 3, NM23, Eps8, Beta-10, Hair follicle growth factor, Corneodesmosin, GCR9, Bg, FGF23, BBSR, MIC-1, MIA-2, IL-17B, Formylglycine generating enzyme, LPLA2, CXCL1O, HFE2A, IL-1, IL-2, IL-3, IL-4, IL-5, IL-7, IL-8, IL-9, IL-10R DN or a subunit thereof, IL-15, IL-18, IL-21, IL-23, IL-24, IL-27, GM-CSF, IFN-alpha, IFN-gamma, IFN-alpha 1, IFN alpha 2, IL-15-R-alpha, CCL3 (MIP-1α), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, IFN-beta, TNF-alpha, dnFADD, BCG, TGF-alpha, PD-L1 RNAi, a PD-L1 antisense oligonucleotide, TGFbRII DN, ICOS-L, S100, CD40L, p53, survivin, p53-survivin fusion, MAGE3, myelin basic protein, PSA and PSMA.

In another embodiment, the peptide, protein, or polypeptide of interest is ciliary neurotrophic factor, vasohibin, IL-10, Erythro-poietin, VEGF trap, or PDGF.

In another embodiment, the peptide, protein, or polypeptide of interest is a JUN-kinase inhibitor, vasoinhibin, EPO, or CTNF.

In another embodiment, the gene switch regulates the expression of a polynucleotide encoding an IL-12 or a subunit thereof. In another embodiment, the IL-12 or subunit thereof is human IL-12 or subunit thereof.

In another embodiment, the gene switch regulates the expression of a polynucleotide encoding a C1 esterase inhibitor (for example, a human C1 esterase inhibitor), a kallikrein inhibitor, or a bradykinin B2 receptor antagonist.

Examples of kallikrein inhibitors include, but are not limited to, ecallantide and those kallikrein inhibitors set forth U.S. Patent Publication Nos. 2010/0034805, 2009/0264350, 2009/0234009, 2008/0221031, 2007/0213275, 2006/0264603 and 2005/0089515.

Examples of bradykinin B2 receptor inhibitors include, but are not limited to, helokinestatin and anti-bradykinin B2 receptor antibodies. The amino acid sequence of helokinestatin is set forth in Kwok, H. F. et al., *Peptides* 29I 65-72 (2008). Nonlimiting examples of anti-bradykinin B2 receptor antibodies are set forth in Alla, S. A. et al., *J. Biol. Chem.* 271: 1748-1755 (1996).

In another embodiment, the gene switch regulates the expression of a polynucleotide encoding an IL-12 or a subunit thereof for the treatment of cancer, e.g., melanoma, in a subject, e.g., a human.

In another embodiment, a polynucleotide encodes (a) a gene switch that comprises a GAL4 DNA binding domain, the *Choristoneura fumiferana* ecdysone receptor ligand binding domain having the mutations V107I and Y127E (relative to the *Choristoneura fumifrana* ecdysone receptor sequence set forth in U.S. Patent Publication No. 2006/0100416 A1), a chimeric RXR ligand binding domain consisting of helices 1-8 of *Homo sapiens* RXR and helices 9-12 of *Locusta migratoria* RXR, the VP16 transactivation domain, and (b) human IL-12, and the gene switch encoded by the polynucleotide regulates the expression of human IL-12 when the ecdysone receptor ligand binding domain in the gene switch binds a Compound of the Disclosure. In a further embodiment, the polynucleotide is administered to a subject having a cancer such as melanoma. The polynucleotide may be administered intratumorally either in a pharmaceutically acceptable carrier, or contained by an immune cell such as a dendritic cell. In one embodiment, the polynucleotide is administered to a subject followed by administration of a Compound of the Disclosure, or composition thereof. In another embodiment, a Compound of the Disclosure, or composition thereof, is administered to a subject followed by administration of the polynucleotide. For example, a Compound of the Disclosure, or composition thereof, may be administered to the subject on day −1, 0, +1, +2, +3, +4, +5, +6, +7, or more, relative to the day the polynucleotide is administered to the subject.

In another embodiment, the gene switch regulates the expression of a polynucleotide encoding a transcription factor, e.g., GATA-1, friend of GATA (FOG-1), EKLF (a Kruppel-like transcription factor), p45/nuclear factor-erythroid 2 (NF-E2), stem cell leukemia (SCL) or T-cell acute lymphocytic leukemia-1, OCT4, or Sry-related high-mobility group box transcription factor (Sox6), or growth factor, e.g., IGFII, bFGF, Flt3, stem cell factor (SCF), thrombopoietin (TPO), bone morphogenetic protein 4 (BMP4), recombinant human vascular endothelial growth factor (VEGF-A165), interleukin-3 (IL-3) interleukin-6 (IL-6), or interleukin-11 (IL-11), or erythropoietin, for use in regenerative medicine, e.g., differentiation, trans-differentiation, reprogramming, self-renewal, or expansion of hematopoietic stem cells, haematopoietic progenitor cells, or induced pluripotent stem cells in the process of blood pharming, i.e., production of red blood cells or other blood products, in a subject.

General Synthetic Methods

Compounds of the Disclosure are prepared using methods known to those skilled in the art in view of this disclosure (see, e.g., U.S. Pat. Nos. 8,076,517, 7,456,315, 7,304,161, and 6,258,603), and/or by the illustrative methods shown in the General Schemes below.

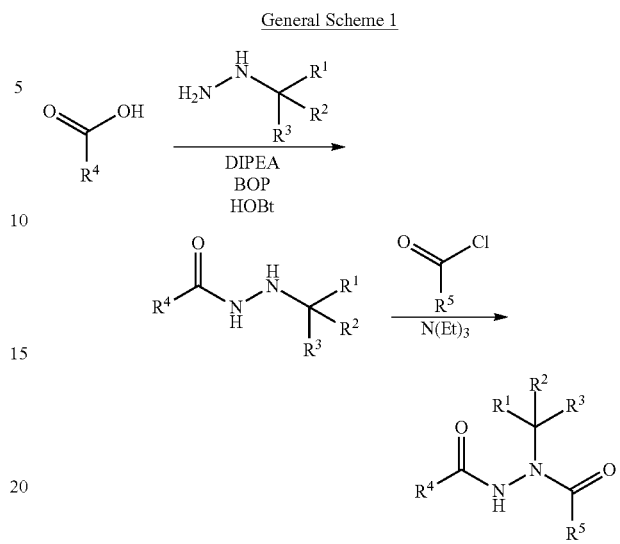

General Scheme 1

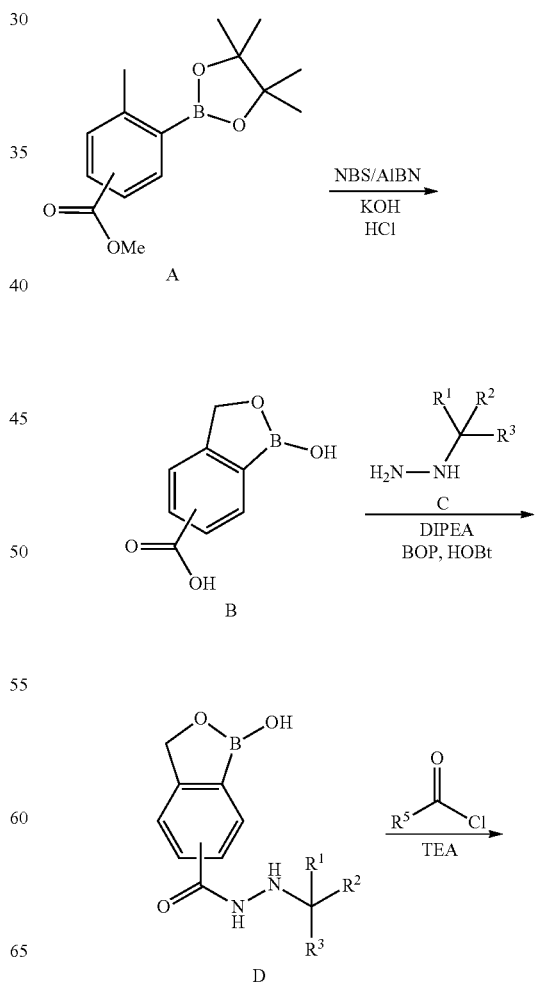

General Scheme 2

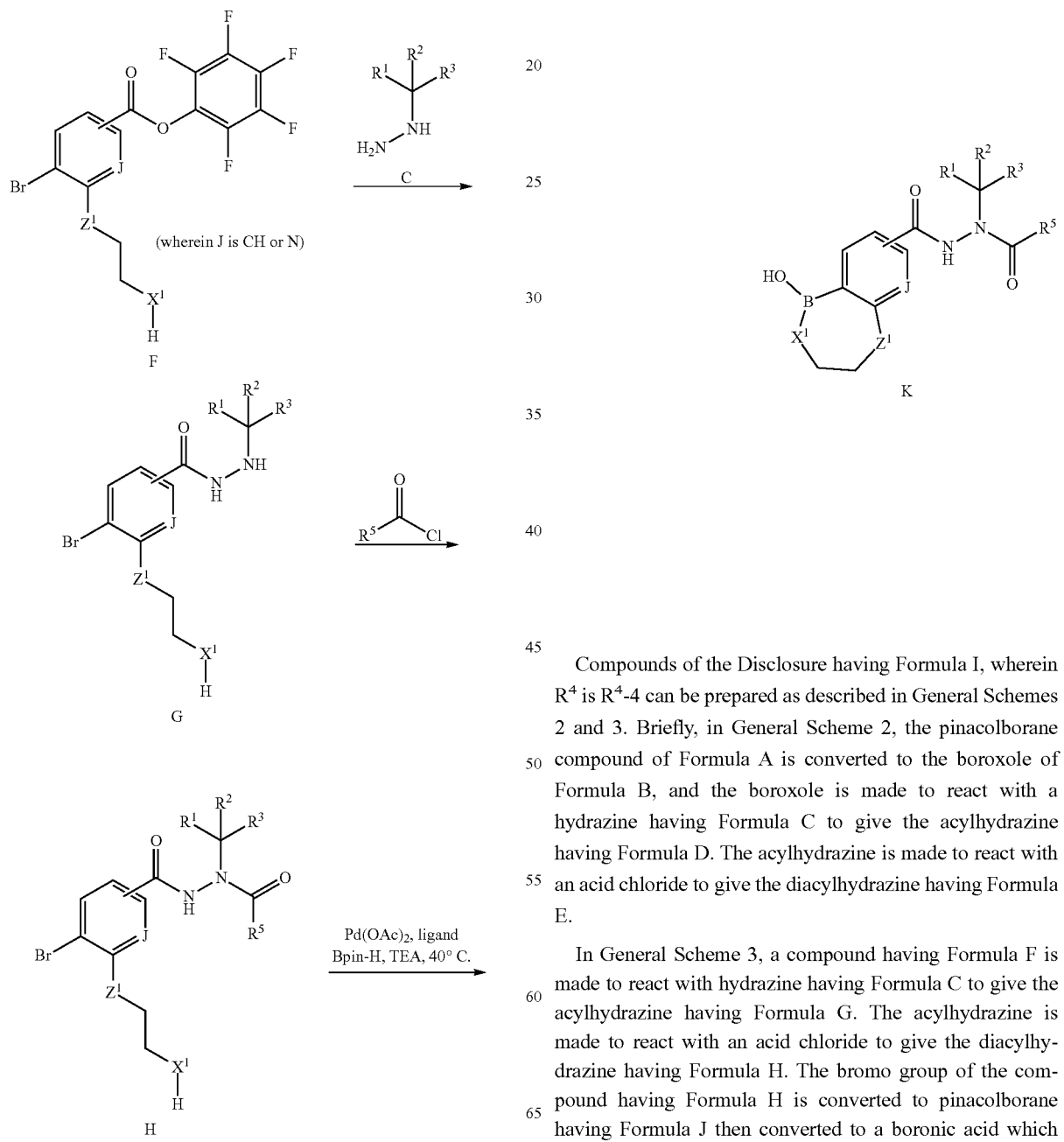

Compounds of the Disclosure having Formula I, wherein $R^4$ is $R^4$-4 can be prepared as described in General Schemes 2 and 3. Briefly, in General Scheme 2, the pinacolborane compound of Formula A is converted to the boroxole of Formula B, and the boroxole is made to react with a hydrazine having Formula C to give the acylhydrazine having Formula D. The acylhydrazine is made to react with an acid chloride to give the diacylhydrazine having Formula E.

In General Scheme 3, a compound having Formula F is made to react with hydrazine having Formula C to give the acylhydrazine having Formula G. The acylhydrazine is made to react with an acid chloride to give the diacylhydrazine having Formula H. The bromo group of the compound having Formula H is converted to pinacolborane having Formula J then converted to a boronic acid which cyclizes to give diacylhydrazines having Formula K.

General Scheme 4
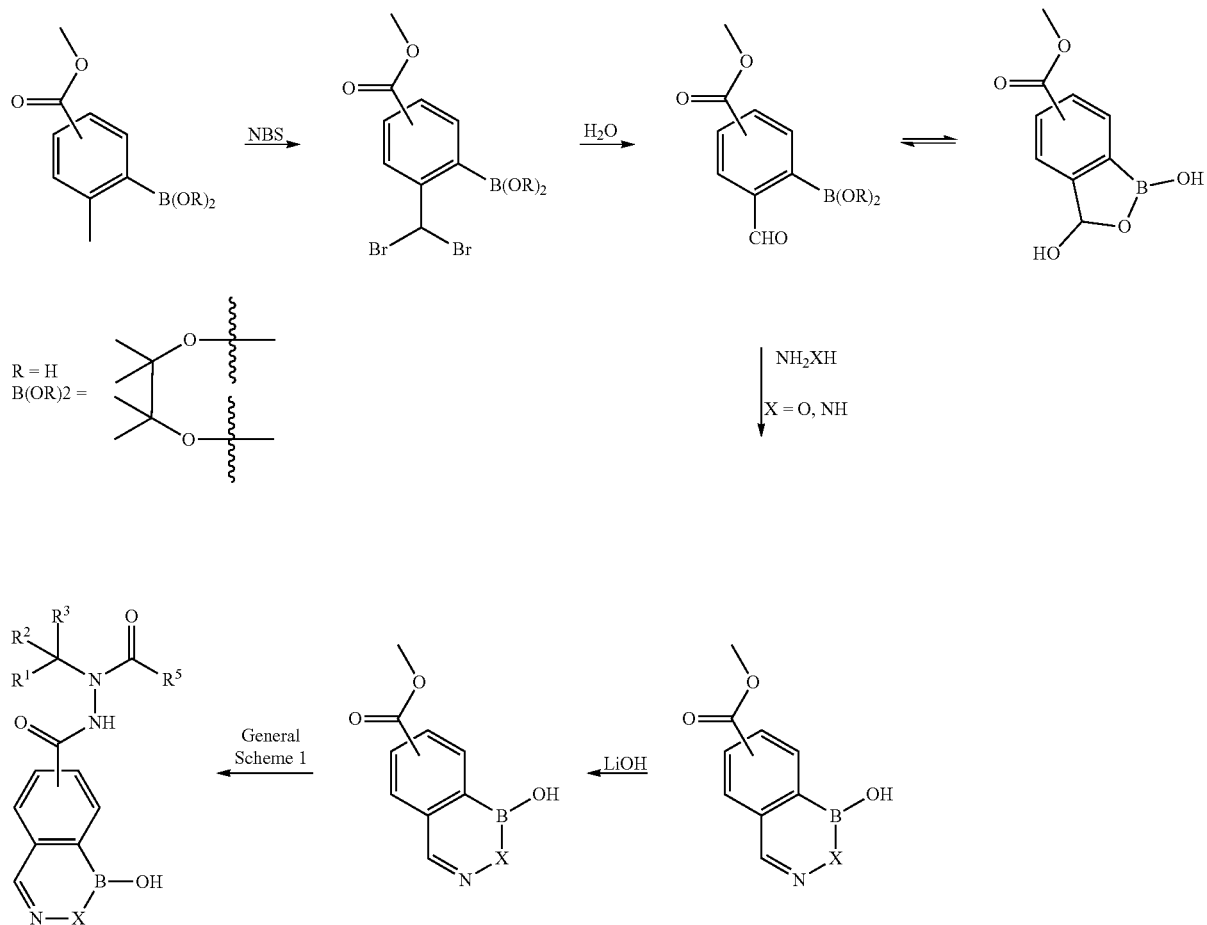
Compounds of the Disclosure having Formula I, wherein $R^4$ is $R^4$-3 and $R^{7a}$ and $R^{7b}$ are hydrogen, can be prepared as described in General Scheme 4.
General Scheme 5
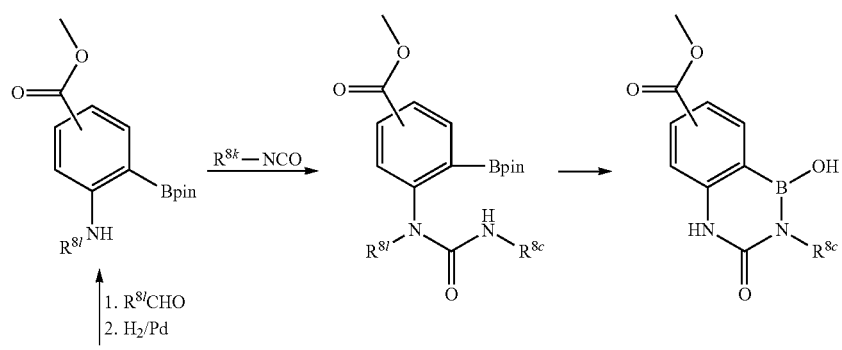

-continued
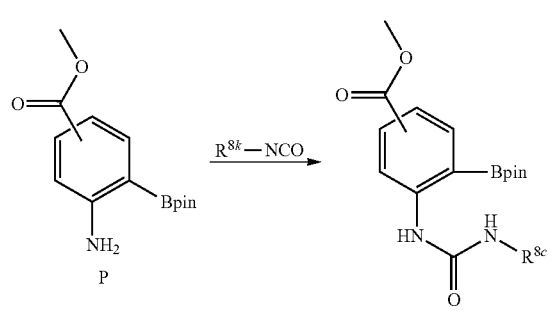
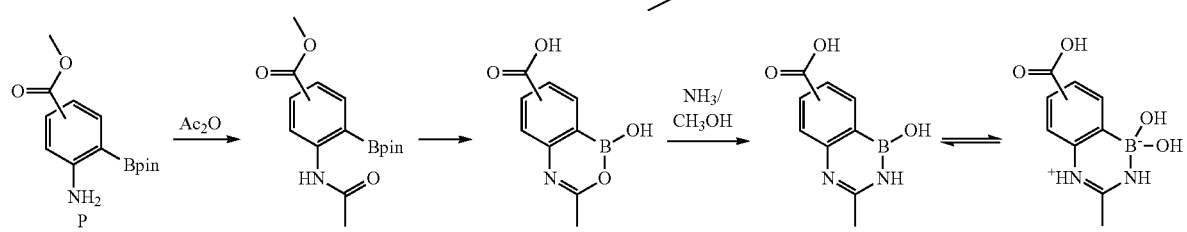
General Scheme 6
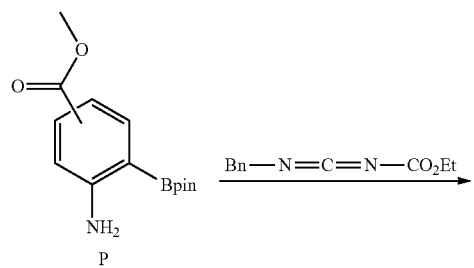
General Scheme 7
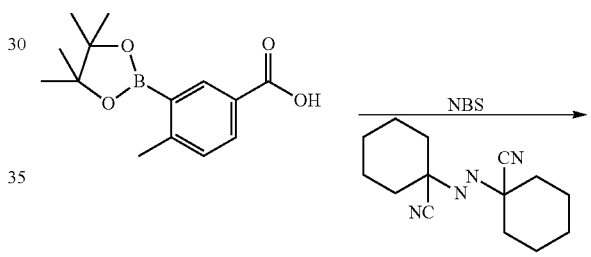
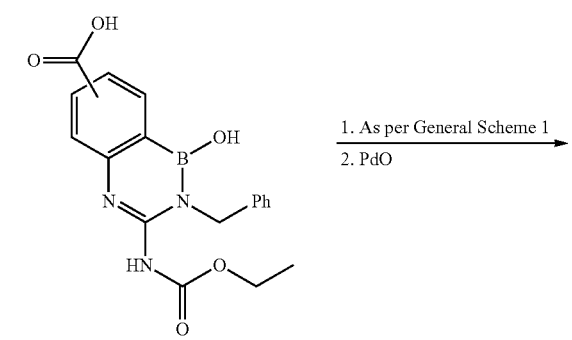
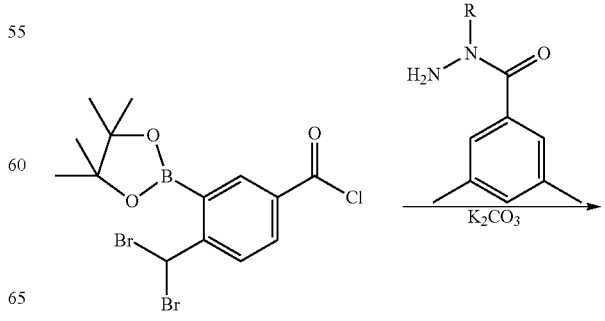

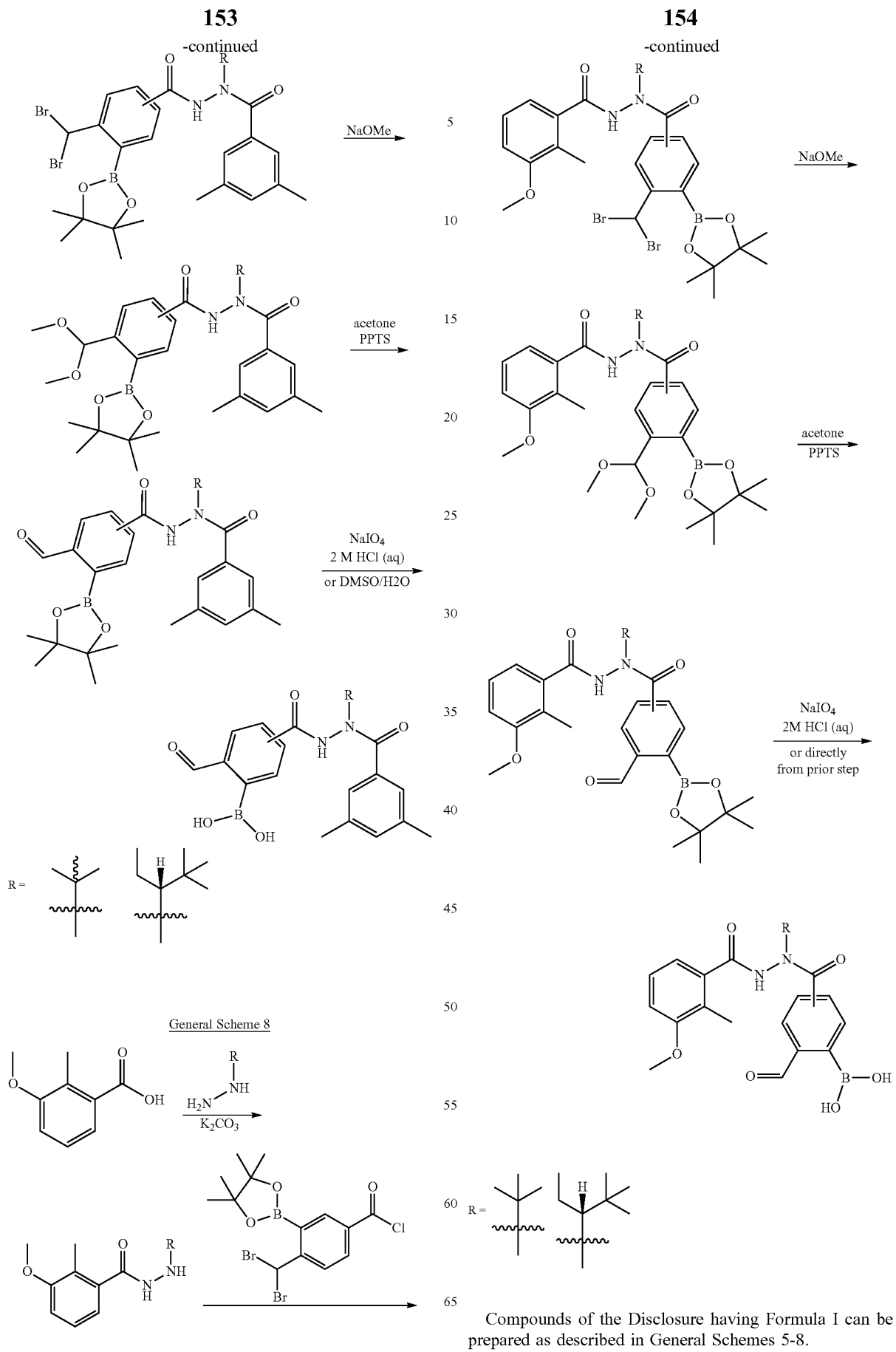
Compounds of the Disclosure having Formula I can be prepared as described in General Schemes 5-8.

EXAMPLES

Example 1

Synthesis of 4-(dibromomethyl)-3-(4,4,5,5-tetramethyl-1,3,2-dioxaborolan-2-yl)benzoic Acid

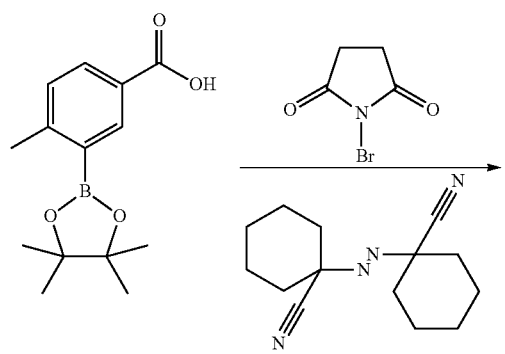

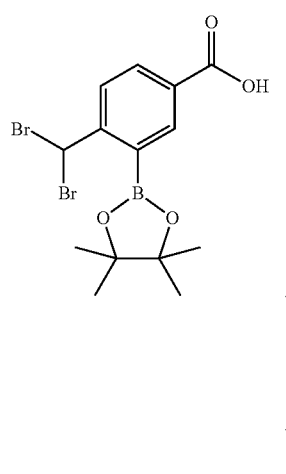

To a solution of 4-methyl-3-(4,4,5,5-tetramethyl-1,3,2-dioxaborolan-2-yl)benzoic acid (10.00 g, 38.2 mmol) in CCl$_4$ (110 mL) was added NBS (13.58 g, 76 mmol) and the resulting solution was heated at reflux while adding (E)-1,1'-(diazene-1,2-diyl)dicyclohexanecarbonitrile (0.932 g, 3.82 mmol) in portions over 10 min. The resulting solution was stirred at 82° C. for 30 h and cooled to 23° C., H$_2$O (40 mL) added and stirred for 1 h. The organic layer was collected and washed with water, brine, dried (MgSO$_4$) filtered and concentrated under reduced pressure on a rotary evaproator. The resulting off-white solids were triturated with hexanes and filtered to give 4-(dibromomethyl)-3-(4,4,5,5-tetramethyl-1,3,2-dioxaborolan-2-yl)benzoic acid (18.56 g, 44.2 mmol, 116% yield) as off-white powder containing residual succinamide. $^1$H NMR (400 MHz, DMSO-d6) δ 11.06 (br s, 1H), 8.24 (s, 1H), 8.19-8.16 (app dd, 1H), 8.09-8.07 (d, 1H), 7.74 (s, 1H), 1.36 (s, 12H) ppm; LCMS for Chemical Formula: LCMS for C$_{14}$H$_{17}$B$^{79}$Br$_2$O$_4$ (M+H)$^+$=419.

Example 2

Synthesis of 3-(dibromomethyl)-4-(4,4,5,5-tetramethyl-1,3,2-dioxaborolan-2-yl)benzoic Acid

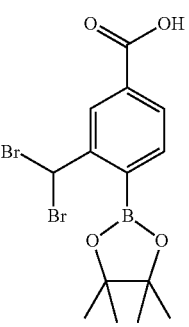 [SMILES: CC1(C)OB(c2ccc(C(=O)O)cc2C(Br)Br)OC1(C)C]

In a similar manner to 4-(CHBr$_2$—)-3-Bpin-benzoic acid, 3-(dibromomethyl)-4-(4,4,5,5-tetramethyl-1,3,2-dioxaborolan-2-yl)benzoic acid was prepared by filtration of precipitated product from the reaction mixture, washing with water, and drying: 1H NMR (400 MHz, DMSO-d6) δ 8.48 (d, J=1.4 Hz, 1H), 7.91 (dd, J=7.8, 1.5 Hz, 1H), 7.78 (d, J=7.8 Hz, 1H), 7.73 (s, 1H), 3.31 (br s, 1H), 1.35 (s, 12H) ppm.

Example 3

Synthesis of 4-(dibromomethyl)-3-(4,4,5,5-tetramethyl-1,3,2-dioxaborolan-2-yl)benzoyl chloride To an ice cooled solution of 4-(dibromomethyl)-3-(4,4,5,5-tetramethyl-1,3,2-dioxaborolan-2-yl)benzoic acid (16.02 g, 38.2 mmol) in CH$_2$Cl$_2$ (120 mL) was added oxalyl chloride (6.68 ml, 76 mmol), followed by DMF (0.148 ml, 1.908 mmol). The reaction mixture was stirred for 5 min. at 0° C. and 16 h at 23° C. The reaction mixture was stirred for an additional 1.5 h at 40° C. to complete the reaction. Concentration of the reaction mixture afforded a pale yellow solid which was azeotroped from CHCl₃ (3×30 ml) and dried under high vacuum for 2 h to give 4-(dibromomethyl)-3-(4,4,5,5-tetramethyl-1,3,2-dioxaborolan-2-yl)benzoyl chloride (16.83 g, 38.4 mmol, 101% yield). $^1$H NMR was consistent with the assigned chemical structure. LCMS of the residue in MeOH gave the mass of the methyl ester. $^1$H NMR (400 MHz, DMSO-d6) δ $^1$H NMR (400 MHz, DMSO) δ 8.24 (s, 1H), 8.17-8.16 (d, 1H), 8.09-8.07 (s, 1H), 7.74 (s, 1H), 2.74 (s, 3H), 1.36 (s, 12H) ppm; LCMS (M+H)$^+$ for methyl ester=433.

Example 4

Synthesis of 3-(dibromomethyl)-4-(4,4,5,5-tetramethyl-1,3,2-dioxaborolan-2-yl)benzoyl chloride

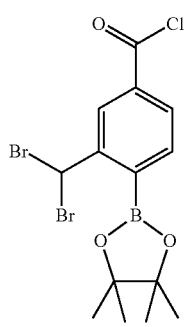 [SMILES: CC1(C)OB(c2ccc(C(=O)Cl)cc2C(Br)Br)OC1(C)C]

In a similar manner, the 3,4-regioisomer was prepared: $^1$H NMR (400 MHz, CDCl₃) δ 8.74 (dd, J=1.8, 0.5 Hz, 1H), 7.97 (d, J=1.7 Hz, 1H), 7.91 (d, J=0.6 Hz, 1H), 7.82 (s, 1H), 1.40 (s, 12H) ppm.

Example 5

Synthesis of N'-(tert-butyl)-4-(dibromomethyl)-N'-(3,5-dimethylbenzoyl)-3-(4,4,5,5-tetramethyl-1,3,2-dioxaborolan-2-yl)benzohydrazide

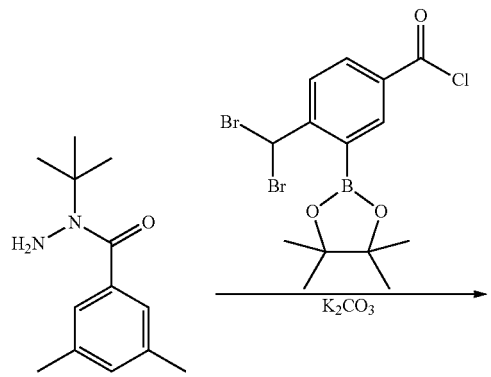

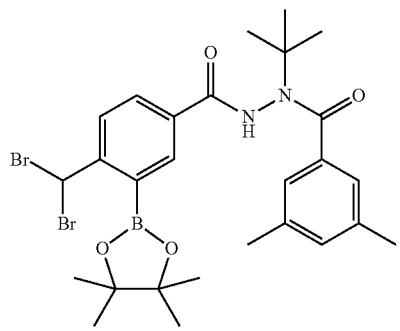

A solution of N'-(tert-butyl)-3,5-dimethylbenzohydrazide (4.57 g, 20.74 mmol) was dissolved in CH₂Cl₂ (30 mL) and cooled in an ice bath. The resulting solution was treated with a solution of K₂CO₃ (8.60 g, 62.2 mmol) in H₂O (30 mL) and stirred for 5 min at 0-5° C. A solution of 4-(dibromomethyl)-3-(4,4,5,5-tetramethyl-1,3,2-dioxaborolan-2-yl)benzoyl chloride (10 g, 22.81 mmol) in CH₂Cl₂ (30 mL) was added slowly with vigorous stirring. The reaction mixture was stirred for 16 h at 23° C. and the white voluminous precipitate that resulted was filtered with suction, washed with water and cold (0° C.) CH₂Cl₂ (3×10 mL) and air dried to give the desired product (8.02 g) as a white solid. The organic layer was collected and the aqueous layer was extracted with CH₂Cl₂ (2×50 mL) and the combined organic layer was dried (MgSO₄), filtered and concentrated. The resulting yellow residue was purified by flash column chromatography on the ISCO over a 40 g RediSep silica gel column, eluting with 0-100% EtOAc—hexanes affording more of the desired product (4.63 g). The $^1$H NMR and LCMS of the two samples were identical and therefore were combined giving N'-(tert-butyl)-4-(dibromomethyl)-N'-(3,5-dimethylbenzoyl)-3-(4,4,5,5-tetramethyl-1,3,2-dioxaborolan-2-yl)benzohydrazide (12.65 g, 20.33 mmol, 98% yield) as a white fluffy solid. $^1$H NMR (400 MHz, DMSO) δ $^1$H NMR (400 MHz, DMSO) δ 10.75 (s, 1H—NH), 7.95 (br s, 1H), 7.75-7.66 (br s, 1H), 7.65 (app d, 1H), 7.09 (s, 2H), 6.95 (s, 1H), 2.24 (s, 6H), 1.48 (s, 9H), 1.45-1.24 (br s, 12H) ppm; LCMS for C₂₇H₃₅BBr₂N₂O₄ (M+H)$^+$=621.

Example 6

Synthesis of N'-(tert-butyl)-N'-(3,5-dimethylbenzoyl)-4-formyl-3-(4,4,5,5-tetramethyl-1,3,2-dioxaborolan-2-yl)benzohydrazide

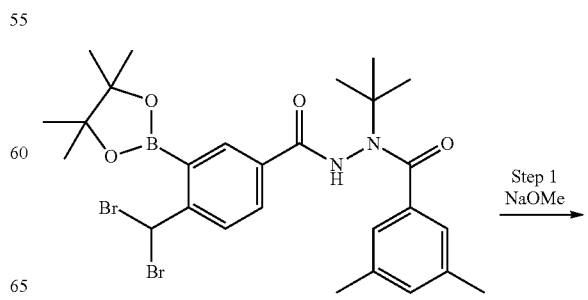

-continued

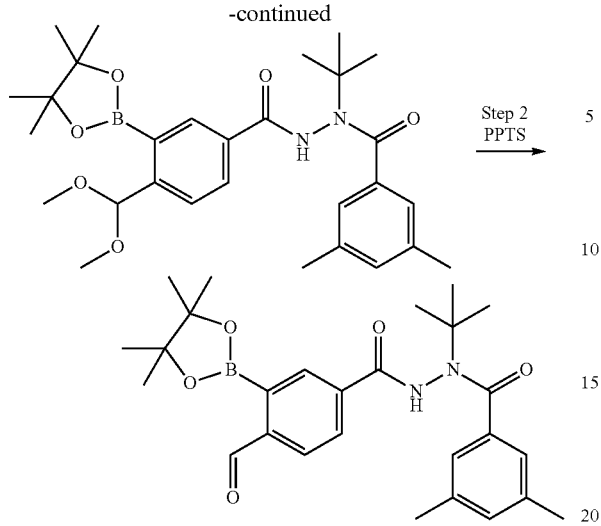

Step 1 (Acetal Formation):

To a stirred solution of N'-(tert-butyl)-4-(dibromomethyl)-N'-(3,5-dimethylbenzoyl)-3-(4,4,5,5-tetramethyl-1,3,2-dioxaborolan-2-yl)benzohydrazide (8 g, 12.86 mmol) in MeOH (100 mL) at 23° C., was added sodium methanolate (6.11 g, 28.3 mmol). The reaction mixture was heated at 65° C. for 2 h, cooled to 23° C. and the MeOH was removed on a rotary evaporator. The residue was dissolved in $CH_2Cl_2$ (100 mL) and washed with brine, dried ($MgSO_4$), filtered and concentrated to give N'-(tert-butyl)-4-(dimethoxymethyl)-N'-(3,5-dimethylbenzoyl)-3-(4,4,5,5-tetramethyl-1,3,2-dioxaborolan-2-yl)benzohydrazide (6.20 g, 11.82 mmol, 92% yield). The crude residue was used in the next step without further purification as a white solid and as white solid. $^1$H NMR (400 MHz, DMSO) δ 10.67, 10.61, 7.89, 7.61, 7.60, 7.59, 7.58, 7.57, 7.56, 7.55, 7.51, 7.49, 7.46, 7.41, 7.11, 7.10, 6.95, 6.93, 5.78, 5.67, 5.59, 3.95, 3.35, 3.26, 3.25, 3.24, 2.53, 2.53, 2.52, 2.52, 2.51, 2.24, 2.23, 1.53, 1.52, 1.50, 1.47, 1.39, 1.36, 1.33, 1.29, 1.26, 1.12, 1.09 ppm; LCMS for $C_{29}H_{41}BN_2O_6$ $(M+H)^+=525$.

Step 2 (Trans-Acetalization in Acetone):

To a stirred solution of N'-(tert-butyl)-4-(dimethoxymethyl)-N'-(3,5-dimethylbenzoyl)-3-(4,4,5,5-tetramethyl-1,3,2-dioxaborolan-2-yl)benzohydrazide (6.20 g, 11.82 mmol, 92% yield) in acetone (100 mL) at 23° C., was added PPTS (0.364 g, 1.446 mmol). The reaction mixture was stirred at 23° C. for 16-18 h. The reaction was only about 10% complete. Then heated at 40° C. for 2 h, and finally at 60 C for 16 h. The reaction was complete by LCMS and was cooled to 23° C., concentrated on a rotary evaporator and the resulting residue was dissolved with $CH_2Cl_2$ (100 mL). The organic layer was washed with $H_2O$, brine, dried ($MgSO_4$), filtered and concentrated to give crude (5-(2-(tert-butyl)-2-(3,5-dimethylbenzoyl)hydrazinecarbonyl)-2-(dimethoxymethyl)phenyl)boronic acid (5.47 g, 12.37 mmol, 96% yield) as a off-white foam which was used in the next step without further purification. $^1$H NMR (400 MHz, DMSO) δ 10.84, 10.64, 10.34, 8.88, 8.87, 8.86, 8.86, 7.96, 7.94, 7.94, 7.93, 7.92, 7.91, 7.70, 7.70, 7.68, 7.68, 7.65, 7.64, 7.57, 7.56, 7.56, 7.55, 7.49, 7.47, 7.12, 7.11, 7.08, 6.95, 6.93, 6.27, 2.52, 2.51, 2.51, 2.50, 2.50, 2.29, 2.23, 1.52, 1.50, 1.48, 1.47, 1.36, 1.31, 1.24, 1.15, 1.10, 1.08 ppm. LCMS for $C_{27}H_{35}BN_2O_5$ $(M+H)^+=477$.

Example 7

Synthesis of (5-(2-(tert-butyl)-2-(3,5-dimethylbenzoyl)hydrazinecarbonyl)-2-formylphenyl)boronic Acid

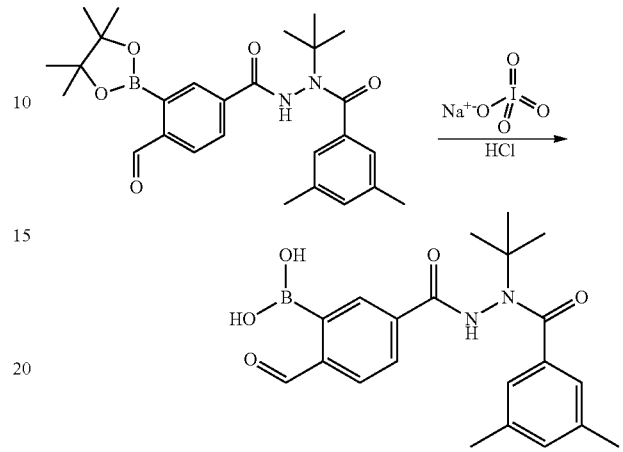

A solution of N'-(tert-butyl)-N'-(3,5-dimethylbenzoyl)-4-formyl-3-(4,4,5,5-tetramethyl-1,3,2-dioxaborolan-2-yl)benzohydrazide (150 mg, 0.314 mmol) in 4 mL of THF and 1 ml $H_2O$ was treated with sodium periodate (67.1 mg, 0.314 mmol). The reaction mixture was stirred with cooling at 0° C. before adding hydrogen chloride (0.157 ml, 0.314 mmol) and the reaction mixture was stirred for 1 h. THF was removed on a rotary evaporator under vacuum and the residue was dissolved in DMSO (approx. 3 mL) and purified by reverse phase chromatography on the ISCO using a 15.5 g C18 RediSep ISCO column and eluted with 0-100% $CH_3CN$—$H_2O$. The desired fractions were pooled and lyophilized over 18 h to give (5-(2-(tert-butyl)-2-(3,5-dimethylbenzoyl) hydrazinecarbonyl)-2-formylphenyl)boronic acid (79 mg, 0.199 mmol, 63.6% yield) as a pale yellow powder. $^1$H NMR (400 MHz, DMSO) δ 10.52 and 10.37 (two rotomer s, 1H), 7.93-7.90 (overlapping d, 1H), 7.77-7.67 (m, 3H), 7.15-7.10 (m, 1H), 6.99-6.97 (m, 1H), 6.46-6.30 (2 rotomers d, 1H), 4.44-4.23 (two rotomers d, 1H), 3.73-3.72 (d, 3H), 1.77-1.42 (m, 5H), 1.36 (s, 12H), 1.12-1.05 (m, 12H) ppm; LCMS for $C_{21}H_{25}BN_2O_5$ $(M+H)^+=397$.

Example 8

Synthesis of (R)—N'-(tert-butyl)-4-(dibromomethyl)-N'-(3,5-dimethylbenzoyl)-3-(4,4,5,5-tetramethyl-1,3,2-dioxaborolan-2-yl)benzohydrazide

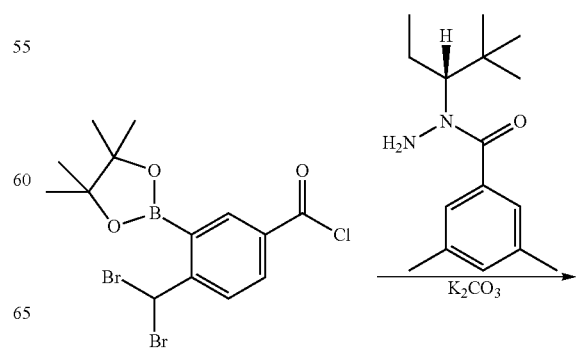

161
-continued

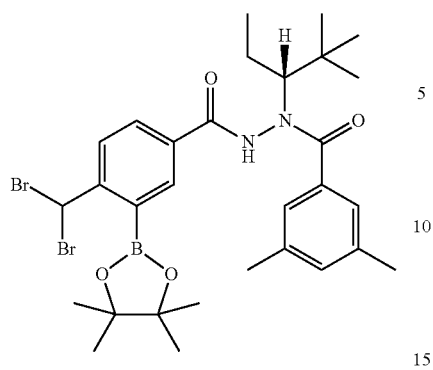

A solution of (R)—N'-(2,2-dimethylpentan-3-yl)-3,5-dimethylbenzohydrazide (3.99 g, 15.21 mmol) dissolved in CH$_2$Cl$_2$ (30 mL) and cooled in an ice bath. The resulting solution was treated with a solution of potassium carbonate (6.31 g, 45.6 mmol) in H$_2$O (30 mL) and stirred for 5 min at 0-5° C. A solution of 4-(dibromomethyl)-3-(4,4,5,5-tetramethyl-1,3,2-dioxaborolan-2-yl)benzoyl chloride (8 g, 18.25 mmol) in CH$_2$Cl$_2$ (30 mL) was added slowly with vigorous stirring. The reaction mixture was stirred for 16 h at 23° C. and then diluted with CH$_2$Cl$_2$ (20 mL). The organic layer was collected and the aqueous layer was extracted with CH$_2$Cl$_2$ (2×50 mL) and the combined organic layer was dried (MgSO$_4$), filtered and concentrated. The resulting yellow residue was purified by reverse phase column chromatography on the ISCO over a 150 g RediSep C18 column, eluting with 0-100% CH$_3$CN—H2O. The desired fractions were lyophilized to remove H$_2$O affording (R)-4-(dibromomethyl)-N'-(3,5-dimethylbenzoyl)-N'-(2,2-dimethylpentan-3-yl)-3-(4,4,5,5-tetramethyl-1,3,2-dioxaborolan-2-yl) benzohydrazide (8.006 g, 12.05 mmol, 79% yield) as a tanned solids. $^1$H NMR (400 MHz, DMSO) δ 10.44 and 10.25 (rotomers d, 1H, amide NH), 8.13-8.09 and 7.99-7.97 (rotomers two d, 1H), 7.73-7.46 (rotomers m, 3H), 7.12-6.96 (rotomers m, 3H), 4.45-4.25 (dd, 1H-chiral CH), 2.32-2.23 (rotomers—m of s, 6H), 1.72-1.50 (br m, 2H), 1.36-1.34 (m, 12H), 1.10-0.90 (m, 12H); LCMS C$_{30}$H$_{41}$BBr$_2$N$_2$O$_4$ (M+H)$^+$=663.

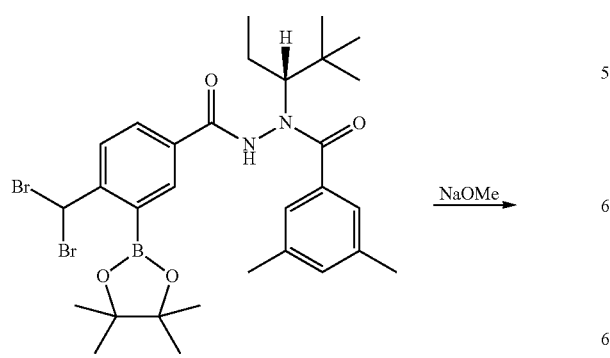

162
-continued

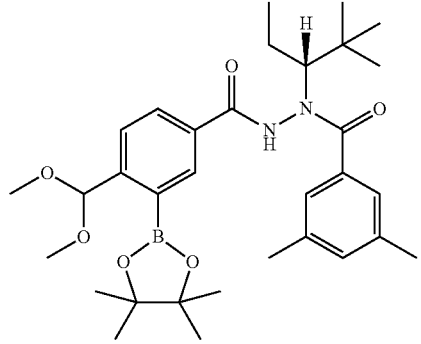

To a stirred solution of (R)-4-(dibromomethyl)-N'-(3,5-dimethylbenzoyl)-N'-(2,2-dimethylpentan-3-yl)-3-(4,4,5,5-tetramethyl-1,3,2-dioxaborolan-2-yl)benzohydrazide (2.979 g, 4.48 mmol) in MeOH (36 mL) at 23° C., was added sodium methanolate (2.132 ml, 9.87 mmol). The reaction mixture was heated at 65° C. for 2 h, cooled to 23° C. and the MeOH was removed on a rotary evaporator. The residue was dissolved in CH$_2$Cl$_2$ (100 mL) and washed with brine, dried (MgSO$_4$), filtered and concentrated to give (R)-4-(dimethoxymethyl)-N'-(3,5-dimethylbenzoyl)-N'-(2,2-dimethylpentan-3-yl)-3-(4,4,5,5-tetramethyl-1,3,2-dioxaborolan-2-yl)benzohydrazide. The crude residue was used in the next step without further purification as a white solid and as white solid. LCMS C$_{32}$H$_{47}$BN$_2$O$_6$ (M+H)$^+$=567.

Example 9

Synthesis of (R)—N'-(3,5-dimethylbenzoyl)-N'-(2,2-dimethylpentan-3-yl)-4-formyl-3-(4,4,5,5-tetramethyl-1,3,2-dioxaborolan-2-yl)benzohydrazide

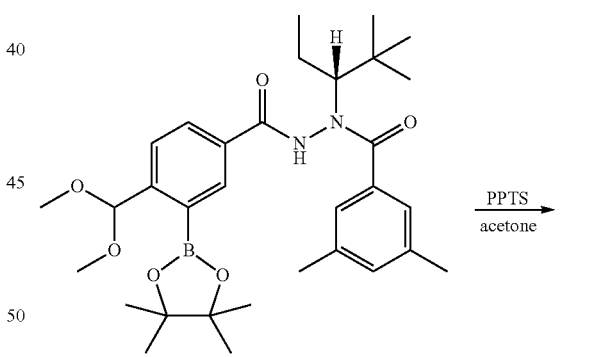

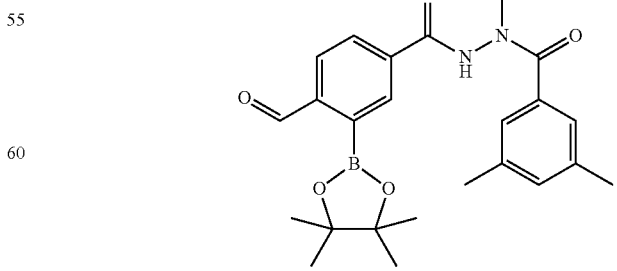

To a stirred solution of (R)-4-(dimethoxymethyl)-N'-(3,5-dimethylbenzoyl)-N'-(2,2-dimethylpentan-3-yl)-3-(4,4,5,5-tetramethyl-1,3,2-dioxaborolan-2-yl)benzohydrazide in acetone (100 mL) at 23° C., was added PPTS (0.364 g, 1.446 mmol). The reaction mixture was stirred at 23° C. for 16-18 h. The reaction was only about 10% complete. Then heated at 40° C. for 2 h, and finally at 60 C for 16 h. The reaction was complete by LCMS and was cooled to 23° C., concentrated on a rotary evaporator and the resulting residue was dissolved with $CH_2Cl_2$ (100 mL). The organic layer was washed with $H_2O$, brine, dried ($MgSO_4$), filtered and concentrated to give crude (R)—N'-(3,5-dimethylbenzoyl)-N'-(2,2-dimethylpentan-3-yl)-4-formyl-3-(4,4,5,5-tetramethyl-1,3,2-dioxaborolan-2-yl)benzohydrazide (5.47 g, 12.37 mmol, 96% yield) as a off-white foam which was used in the next step without further purification. $^1$H NMR (400 MHz, DMSO) δ 10.56-10.12 (four overlapping s, 2H; NH and CH of aldehyde), 7.94-7.42 overlapping m, 3H), 7.17-6.95 (overlapping m of s, 3H), 4.47-4.26 (dd, 1H—CH chiral), 2.55-2.33 (m of s, 6H), 1.75-1.52 (m, 2H), 1.38-1.31 (m of s, 9H), 1.22-0.92 (m, 12H) ppm; LCMS $C_{30}H_{41}BN_2O_5$ (M+H)$^+$=521.

Example 10

Synthesis of (R)—N'-(3,5-dimethylbenzoyl)-N'-(2,2-dimethylpentan-3-yl)-4-formyl-3-(4,4,5,5-tetramethyl-1,3,2-dioxaborolan-2-yl)benzohydrazide

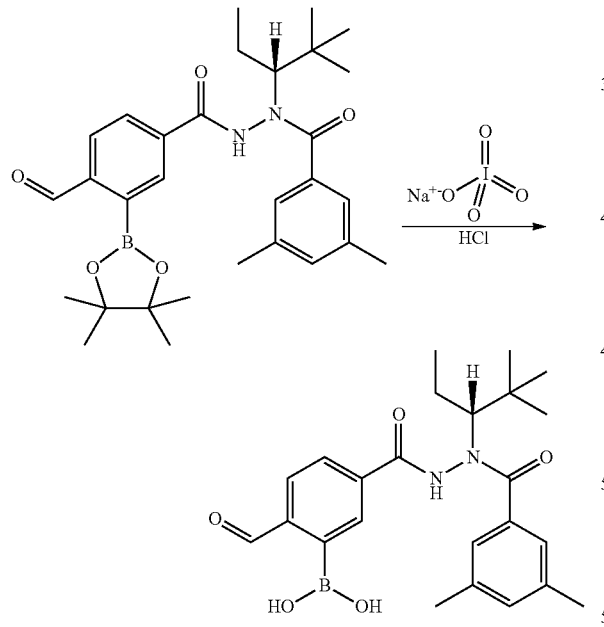

A solution of (R)—N'-(3,5-dimethylbenzoyl)-N'-(2,2-dimethylpentan-3-yl)-4-formyl-3-(4,4,5,5-tetramethyl-1,3,2-dioxaborolan-2-yl)benzohydrazide (1.565 g, 3.01 mmol) in 4 mL of THF and 1 ml $H_2O$ was treated with sodium periodate (0.643 g, 3.01 mmol). The reaction mixture was stirred with cooling at 0° C. before adding HCl (1.503 ml, 3.01 mmol) and the reaction mixture was stirred for 1 h at 0° C. THF was removed on a rotary evaporator under vacuum and the residue was dissolved in DMSO (approx. 3 mL) and purified by reverse phase chromatography on the ISCO using a 15.5 g C-18 RediSep ISCO column and eluted with 0-100% $CH_3CN$—$H_2O$. The desired fractions were pooled and lyophilized over 18 h to give (R)—N'-(3,5-dimethylbenzoyl)-N'-(2,2-dimethylpentan-3-yl)-4-formyl-3-(4,4,5,5-tetramethyl-1,3,2-dioxaborolan-2-yl)benzohydrazide as a white powder. $^1$H NMR (400 MHz, DMSO) δ 10.48-10.12 (overlapping s, 2H, amide NH and aldehyde CH), 8.45-7.63 (br m, 3H), 7.57-7.06 (overlapping br m, 4H), 6.95 (s, 1H), 4.48-4.26 (apparent dd, 1H), 2.23 (s, 6H), 1.81-1.15 (m, 2H), 1.11-0.98 (m, 12H) ppm; LCMS $C_{24}H_{31}BN_2O_5$ (M+H)$^+$=439.

Example 11

Synthesis of N'-(tert-butyl)-3-(dibromomethyl)-N'-(3,5-dimethylbenzoyl)-4-(4,4,5,5-tetramethyl-1,3,2-dioxaborolan-2-yl)benzohydrazide

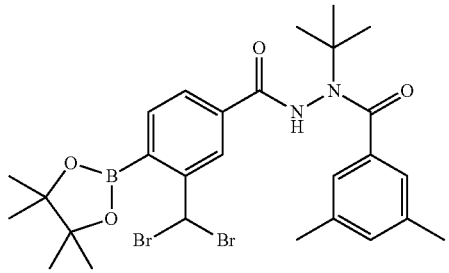

In a similar manner to N'-(tert-butyl)-4-(dibromomethyl)-N'-(3,5-dimethylbenzoyl)-3-(4,4,5,5-tetramethyl-1,3,2-dioxaborolan-2-yl)benzohydrazide, the 3,4-regioisomer was prepared by filtration of the precipitated product from the reaction mixture, washing with water and hexanes, and then drying: $^1$H NMR (400 MHz, DMSO-$d_6$) δ 10.82 (s, 1H), 7.92 (s, 1H), 7.67 (s, 1H), 7.66 (d, J=7.8 Hz, 1H), 7.45 (d, J=7.8 Hz, 1H), 7.07 (s, 2H), 6.94 (s, 1H), 2.22 (s, 6H), 1.50 (s, 9H), 1.33 (s, 12H) ppm.

Example 12

Synthesis of N'-(tert-butyl)-N'-(3,5-dimethylbenzoyl)-3-formyl-4-(4,4,5,5-tetramethyl-1,3,2-dioxaborolan-2-yl)benzohydrazide

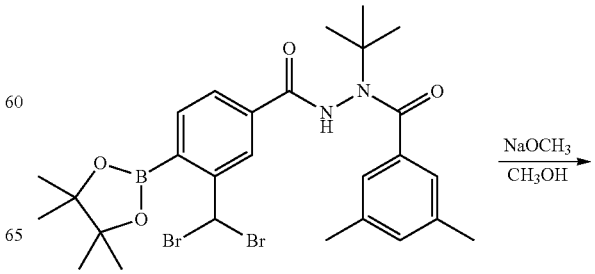

165

-continued

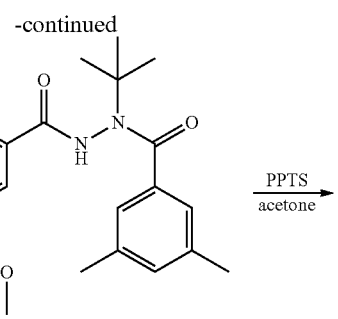

PPTS
acetone
→

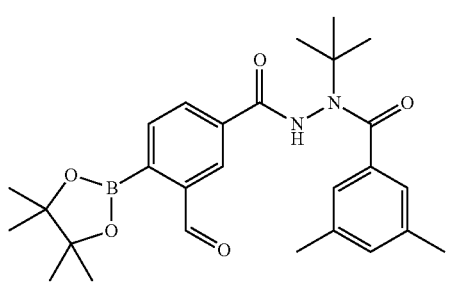

In a manner similar to (R)—N'-(3,5-dimethylbenzoyl)-N'-(2,2-dimethylpentan-3-yl)-4-formyl-3-(4,4,5,5-tetramethyl-1,3,2-dioxaborolan-2-yl)benzohydrazide, the 4,3 regioisomer was prepared. $^1$H NMR (400 MHz, DMSO-d$_6$) δ 10.85 (s, 1H), 10.32 (s, 1H), 7.96 (t, J=1.1 Hz, 1H), 7.75 (dd, J=2.0, 1.1 Hz, 2H), 7.08 (d, J=1.6 Hz, 2H), 6.91 (s, 1H), 2.20 (s, 6H), 1.49 (s, 9H), 1.33 (s, 12H) ppm.

Example 13

Synthesis of (4-(2-(tert-butyl)-2-(3,5-dimethylbenzoyl)hydrazine-1-carbonyl)-2-formylphenyl)boronic Acid

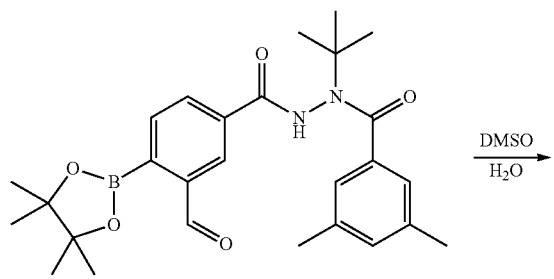

DMSO
H$_2$O
→

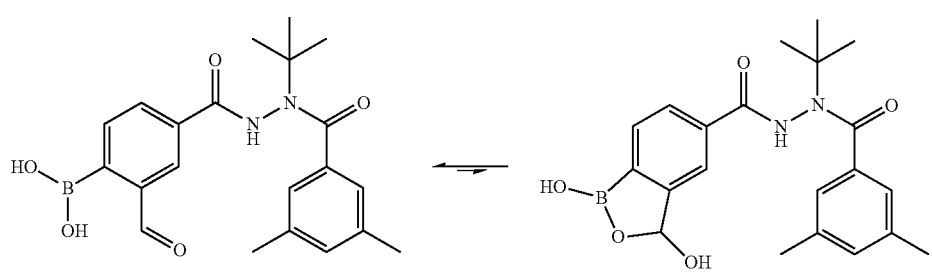

166

840 mg (1.76 mmol) N'-(tert-butyl)-N'-(3,5-dimethylbenzoyl)-3-formyl-4-(4,4,5,5-tetramethyl-1,3,2-dioxaborolan-2-yl)benzohydrazide were dissolved in 2.25 mL DMSO in a 20 mL vial. Water (0.6 mL) was added, whereupon a slight exotherm ensued. Dissolution was assisted by dilution with an additional 2.2 mL DMSO and sonication for 15 min at 38 C. The mixture was stirred with heating at 40 C for 1 hour and then at room temperature for 20 hours. The resultant pale yellow solution was purified by reverse phase chromatography using a water-CAN (0.1% formic acid) gradient. Lyophilization of the product yielded 567 mg (81% yield) (4-(2-(tert-butyl)-2-(3,5-dimethylbenzoyl)hydrazine-1-carbonyl)-2-formylphenyl)boronic acid as a white powder. $^1$H NMR (400 MHz, DMSO-d$_6$) δ 10.78 (s, 1H, exchangeable with D$_2$O), 10.10 (s, 1H), 8.34 (s, 2H, exchangeable with D$_2$O), 7.95 (d, J=1.7 Hz, 1H), 7.70 (dd, J=7.6, 1.7 Hz, 1H), 7.61 (d, J=7.6 Hz, 1H), 7.09 (s, 2H), 6.91 (s, 1H), 2.21 (s, 6H), 1.49 (s, 9H) ppm. Approximately 5% of the corresponding 1,3-dihydroxy oxaborole in equilibrium was observed from the acetal methine multiplet at δ 6.17, as well as an exchangeable B—OH singlet at δ 9.39 and aromatic multiplets at δ 7.56-7.46 and 7.21-7.11 ppm.

Example 14

Synthesis of (R)-3-(dibromomethyl)-N'-(3,5-dimethylbenzoyl)-N'-(2,2-dimethylpentan-3-yl)-4-(4,4,5,5-tetramethyl-1,3,2-dioxaborolan-2-yl)benzohydrazide

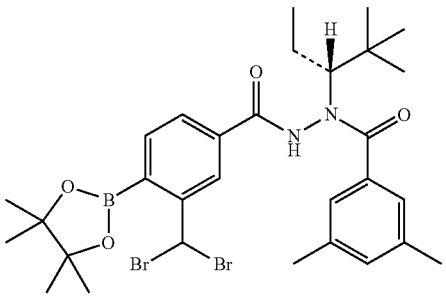

Example 15

Synthesis of N'-(tert-butyl)-N'-(4-(dibromomethyl)-3-(4,4,5,5-tetramethyl-1,3,2-dioxaborolan-2-yl)benzoyl)-3-methoxy-2-methylbenzohydrazide

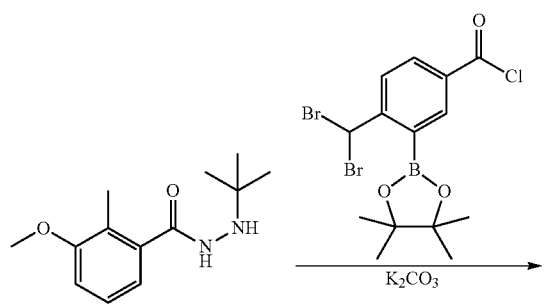

A solution of impure N'-(tert-butyl)-3-methoxy-2-methylbenzohydrazide (3.56 g, 15.06 mmol) was dissolved in CH$_2$Cl$_2$ (30 mL) and cooled in an ice bath. The resulting solution was treated with a solution of K$_2$CO$_3$ (6.24 g, 45.2 mmol) in H$_2$O (20 mL) followed by a solution of 4-(dibromomethyl)-3-(4,4,5,5-tetramethyl-1,3,2-dioxaborolan-2-yl) benzoyl chloride (7.92 g, 18.07 mmol) in CH$_2$Cl$_2$ (10 mL), added slowly with vigorous stirring resulting. The reaction mixture was stirred for 18 h at 23° C. to afford a voluminous precipitate and the organic layer was diluted with 20 mL hexanes with vigorous stirring for 5 min. The resulting mixture was filtered through a disposable plastic funnel with suction. The resulting solid was washed with hexanes (2×10 mL), water (2×40 mL) and hexanes (2×40 mL), air dried with suction for 2 h, and dried to a constant weight under high vacuum to give N'-(tert-butyl)-N'-(4-(dibromomethyl)-3-(4,4,5,5-tetramethyl-1,3,2-dioxaborolan-2-yl)benzoyl)-3-methoxy-2-methylbenzohydrazide (9.61 g, 15.06 mmol, 100% yield) as a white fluffy solid. $^1$H NMR (400 MHz, DMSO) δ 10.60 (s, 1H, NH), 7.94-7.92 (d, J=4 Hz, 1H), 7.75 (s, 1H), 7.70 (s, 1H), 7.67-7.65 (d, J=4 Hz, 1H), 7.09-7.05 (t, J=4 Hz, 1H), 6.97-6.95 (d, J=4 Hz, 1H), 6.21-6.19 (d, J=4 Hz, 1H), 3.73 (s, 3H), 1.63 (s, 3H), 1.52 (s, 9H), 1.34 (s, 12H) ppm; LCMS for C$_{27}$H$_{35}$BBr$_2$N$_2$O$_5$ (M+H)$^+$=637.

Example 16

Synthesis of N'-(tert-butyl)-N'-(4-(dimethoxymethyl)-3-(4,4,5,5-tetramethyl-1,3,2-dioxaborolan-2-yl)benzoyl)-3-methoxy-2-methylbenzohydrazide

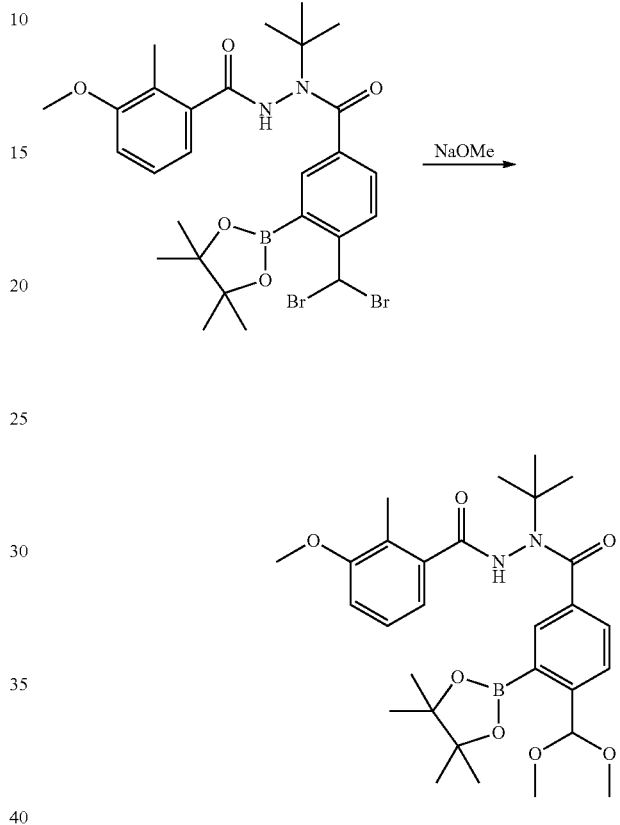

To a stirred solution of N'-(tert-butyl)-N'-(4-(dibromomethyl)-3-(4,4,5,5-tetramethyl-1,3,2-dioxaborolan-2-yl)benzoyl)-3-methoxy-2-methylbenzohydrazide (5 g, 7.83 mmol) in MeOH (60 mL) at 23° C., was added sodium methanolate (3.94 ml, 17.24 mmol). The reaction mixture was heated at 65° C. for 2 h, cooled to 0° C., quenched acetic acid (0.090 ml, 1.567 mmol) and the MeOH was removed on a rotary evaporator. The residue was dissolved in CH$_2$Cl$_2$ (100 mL) and washed with brine, dried (MgSO$_4$), filtered and concentrated to give N'-(tert-butyl)-N'-(4-(dimethoxymethyl)-3-(4,4,5,5-tetramethyl-1,3,2-dioxaborolan-2-yl)benzoyl)-3-methoxy-2-methylbenzohydrazide (3.59 g, 6.64 mmol, 85% yield). The crude residue was used in the next step without further purification as a white solid. $^1$H NMR (400 MHz, DMSO) δ 10.54-10.52 (d, 1H, NH rotomers), 7.52-7.36 (br m, 3H), 7.06-7.03 (apparent t, J=4 Hz, 1H), 6.98-6.96 (d, J=4 Hz, 1H), 6.24-6.15 (apparent dd, 1H, rotomers), 5.71 and 5.41 (two s, 1H, rotomers), 3.75-3.74 (apparent d, 3H rotomers), 3.26-3.24 (apparent q, 6H, rotomers), 1.69-1.66 (apparent d, 3H, CH$_3$ rotomer), 1.51 (s, 9H), 1.31 (s, 12H) ppm; LCMS for C$_{29}$H$_{41}$BN$_2$O$_7$ (M+H)$^+$=541.

Example 17

Synthesis of N'-(tert-butyl)-N'-(4-formyl-3-(4,4,5,5-tetramethyl-1,3,2-dioxaborolan-2-yl)benzoyl)-3-methoxy-2-methylbenzohydrazide

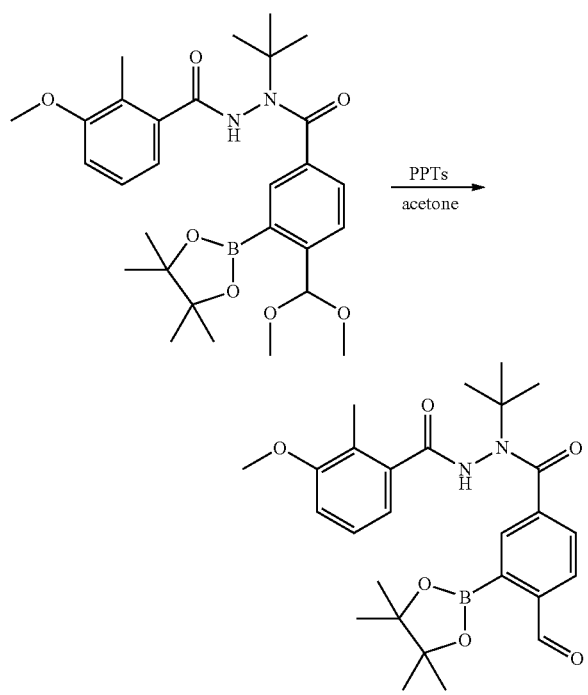

To a stirred solution of N'-(tert-butyl)-N'-(4-(dimethoxymethyl)-3-(4,4,5,5-tetramethyl-1,3,2-dioxaborolan-2-yl)benzoyl)-3-methoxy-2-methylbenzohydrazide (3.59 g, 6.64 mmol, 85% yield) in acetone (100 mL) at 23° C., was added PPTS (0.364 g, 1.446 mmol). The reaction mixture was heated at 40° C. for 2 h, cooled to 23° C., concentrated on a rotary evaporator and the resulting residue was dissolved with CH$_2$Cl$_2$ (100 mL). The organic layer was washed with H$_2$O, brine, dried (MgSO$_4$), filtered and concentrated to give crude N'-(tert-butyl)-N'-(4-formyl-3-(4,4,5,5-tetramethyl-1,3,2-dioxaborolan-2-yl)benzoyl)-3-methoxy-2-methylbenzohydrazide (3.21 g, 6.49 mmol, 83% yield) as a off-white foam which was used in the next step without further purification. LCMS for C$_{27}$H$_{35}$BN$_2$O$_6$ (M+H)$^+$=495.

Example 18

Synthesis of (5-(1-(tert-butyl)-2-(3-methoxy-2-methylbenzoyl)hydrazinecarbonyl)-2-formylphenyl) boronic Acid

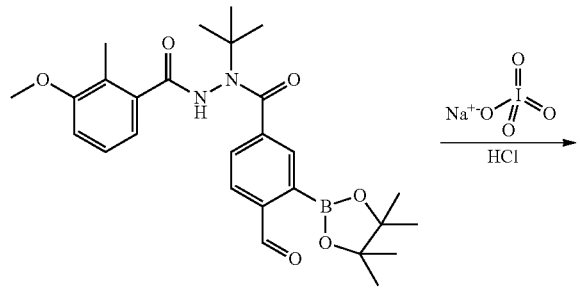

A solution of N'-(tert-butyl)-N'-(4-formyl-3-(4,4,5,5-tetramethyl-1,3,2-dioxaborolan-2-yl)benzoyl)-3-methoxy-2-methylbenzohydrazide (1.36 g, 2.75 mmol) in 20 mL of THF and 5 ml H$_2$O was treated with sodium periodate (0.588 g, 2.75 mmol). The reaction mixture was stirred with cooling at 0° C. before adding hydrogen chloride (1.375 ml, 2.75 mmol) and the reaction mixture was stirred for 1 h at 0° C. THF was removed on a rotary evaporator under vacuum and the residue was dissolved in DMSO (approx. 3 mL) and purified by reverse phase chromatography on the ISCO using a 15.5 g C-18 RediSep ISCO column and eluted with 0-100% CH$_3$CN—H$_2$O. The desired fractions were pooled and lyophilized over 18 h to give (5-(1-(tert-butyl)-2-(3-methoxy-2-methylbenzoyl)hydrazinecarbonyl)-2-formylphenyl)boronic acid as a pale yellow powder. $^1$H NMR (400 MHz, DMSO) δ 10.79, 10.58 and 10.55 (three s, 1H, NH rotamers), 10.22 and 10.19 (two s, 1H, aldehyde rotamers), 8.34 (br s, 1H), 7.85-7.83 (d, J=4 Hz, 1H), 7.70-7.69 (d, J=2 Hz, 1H), 7.57-7.55 (d, J=4 Hz, 1H), 7.11-7.07 (t, J=4 Hz, 1H), 6.98-6.96 (overlapping d, J=4 Hz, 1H), 6.31-6.29 (d, J=4 Hz, 1H), 3.73 (s, 3H), 1.65 (s, 3H), 1.52 (s, 9H) ppm; LCMS for C$_{21}$H$_{25}$BN$_2$O$_6$(M+H)$^+$=413.

Example 19

Synthesis of 3-methoxy-2-methylbenzoyl chloride

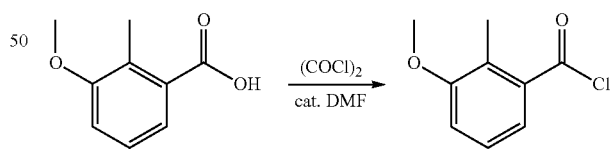

A suspension of 3-methoxy-2-methylbenzoic acid (30 g, 181 mmol) in dry toluene (200 mL) was treated with DMF (0.126 ml, 1.625 mmol) followed by oxalyl chloride (31.6 ml, 361 mmol) and stirred at room temperature for 1 hr then at 82° C. for 16 h. The resulting pale yellow solution was evaporated in vacuo. The residue was azeotroped 3 times from 50 ml of dry chloroform and used in the subsequent reaction without further purification to give 3-methoxy-2-methylbenzoyl chloride (33.3 g, 180 mmol, 100% yield) as a light brown solid. LCMS for C$_{10}$H$_{12}$O$_3$ (M+H)$^+$=181 in MeOH was good for the methyl ester.

Example 20

Synthesis of (R)—N'-(2,2-dimethylpentan-3-yl)-3-methoxy-2-methylbenzohydrazide

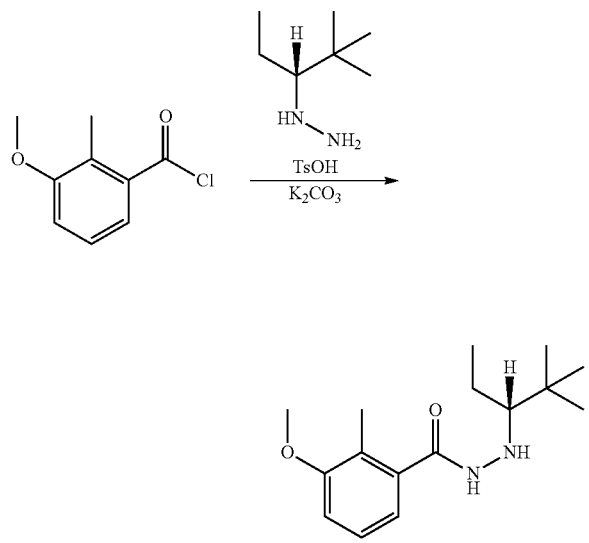

A solution of (R)-(2,2-dimethylpentan-3-yl)hydrazine 4-methylbenzenesulfonate (65.5 g, 217 mmol) suspended in $CH_2Cl_2$ (150 mL) and cooled in an ice-salt water bath. The resulting suspension was treated with a solution of potassium carbonate (62.4 g, 451 mmol) in $H_2O$ (150 mL) and stirred for 5 min at 0-5° C. An additional 50 mL $H_2O$ was added to dissolve the precipitate. A solution of 3-methoxy-2-methylbenzoyl chloride (33.3 g, 180 mmol, 100% yield) in $CH_2Cl_2$ (250 mL) was cooled in dry ice with stirring for 5 min and added slowly with vigorous stirring to the hydrazine solution via a plastic funnel. The reaction mixture was stirred at 0-5° C. for 1 h and then for 16 h at 23° C. LCMS of an aliquot of the reaction mixture in MeOH shows no starting material remaining. The organic layer was collected and the aqueous layer was extracted with $CH_2Cl_2$ (2×50 mL) and the combined organic layer was dried ($MgSO_4$), filtered and concentrated. A small portion of the resulting oily yellow residue was purified by flash column chromatography on the ISCO over a 360 g RediSep C-18 reverse phase column, eluting with 0-100% $CH_3CN$—$H^2O$ affording (R)—N'-(2,2-dimethylpentan-3-yl)-3-methoxy-2-methylbenzohydrazide (1.68 g) after lyophilization as a light yellow gum which was transferred to a 20 mL scintillation vial with $CH_2Cl_2$ and dried on the high vacuum to give a light yellow crystalline material. The remaining crude material was seeded purified compound and crystallized from pentanes to give the additional product (35.58 g, 72.8%) as tanned solids. $^1H$ NMR (400 MHz, DMSO) δ 9.57 (s, 1H, amide NH), 7.23-7.19 (t, J=4 Hz, 1H), 7.03-7.01 (d, J=4 Hz, 1H), 6.85-6.83 (d, J=4 Hz, 1H), 3.80 (s, 3H), 2.37-2.35 (t, J=2 Hz, 1H), 2.07 (s, 3H), 1.61-1.51 (m, 1H), 1.34-1.23 (m, 1H), 1.06-1.02 (t, J=4 Hz, 3H), 0.94 (s, 9H) ppm; LCMS for $C_{16}H_{26}N_2O_2$ $(M+H)^+$=279.

Example 21

Synthesis of (R)—N'-(4-(dibromomethyl)-3-(4,4,5,5-tetramethyl-1,3,2-dioxaborolan-2-yl)benzoyl)-N'-(2,2-dimethylpentan-3-yl)-3-methoxy-2-methylbenzohydrazide

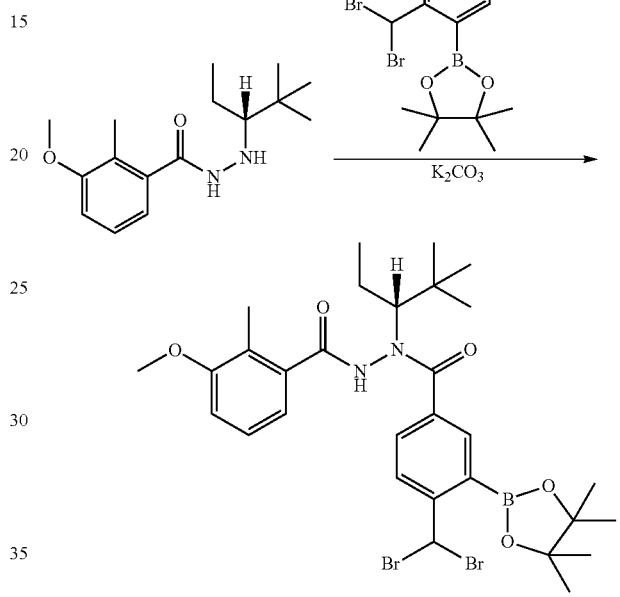

A solution of (R)—N'-(2,2-dimethylpentan-3-yl)-3-methoxy-2-methylbenzohydrazide (0.854 g, 3.07 mmol) dissolved in $CH_2Cl_2$ (30 mL) and cooled in an ice bath. The resulting solution was treated with a solution of potassium carbonate (1.273 g, 9.21 mmol) in $H_2O$ (30 mL) and stirred for 5 min at 0-5° C. A solution of 4-(dibromomethyl)-3-(4,4,5,5-tetramethyl-1,3,2-dioxaborolan-2-yl)benzoyl chloride (1.48 g, 3.38 mmol) in $CH_2Cl_2$ (30 mL) was added slowly with vigorous stirring. The reaction mixture was stirred for 16 h at 23° C. and diluted with water and $CH_2Cl_2$. The $CH_2Cl_2$ layer was collected and washed with saturated Na2CO3 solution, water, brine, dried ($MgSO_4$), filtered and concentrated. The resulting yellow residue was purified by trituration using hexanes under vigorous stirring. The clean product was isolated by filtration under suction affording N'-(tert-butyl)-4-(dibromomethyl)-N'-(3,5-dimethylbenzoyl)-3-(4,4,5,5-tetramethyl-1,3,2-dioxaborolan-2-yl)benzohydrazide (12.65 g, 20.33 mmol, 98% yield) as a white fluffy solid. $^1H$ NMR (400 MHz, DMSO) δ 10.44-10.25 (two s, 1H, NH rotomers), 8.13-7.97 (d, 1H, rotomers), 7.74-7.46 (overlapping m, 3H), 7.12-6.96 (overlapping s, 3H), 4.45-4.25 (dd, 1H, chiral CH, 2.32-2.23 (overlapping s, 6H), 1.76-1.62 (m, 1H), 1.57-1.50 (m, 1H), 1.36-1.34 (3 overlapping s, 12H), 1.10-0.90 (overlapping s, 12H) ppm; LCMS for $C_{30}H_{41}BBr_2N_2O_5$ $(M+H)^+$=679.

Example 22

Synthesis of (R)—N'-(4-(dimethoxymethyl)-3-(4,4,5,5-tetramethyl-1,3,2-dioxaborolan-2-yl)benzoyl)-N'-(2,2-dimethylpentan-3-yl)-3-methoxy-2-methylbenzohydrazide

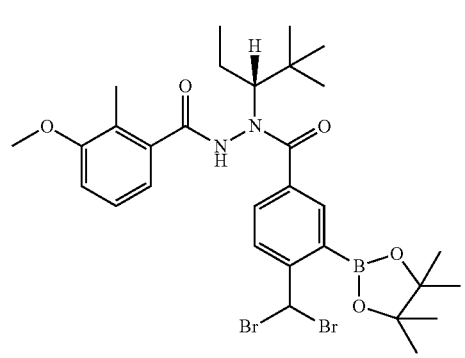

To a stirred solution of (R)—N'-(4-(dibromomethyl)-3-(4,4,5,5-tetramethyl-1,3,2-dioxaborolan-2-yl)benzoyl)-N'-(2,2-dimethylpentan-3-yl)-3-methoxy-2-methylbenzohydrazide (1.84 g, 2.70 mmol) in MeOH (36 mL) at 23° C., was added sodium methanolate (1.286 g, 5.95 mmol). The reaction mixture was heated at 65° C. for 2 h, cooled to 23° C. and the MeOH was removed on a rotary evaporator. The residue was dissolved in $CH_2Cl_2$ (100 mL) and washed with brine, dried ($MgSO_4$), filtered and concentrated to give (R)—N'-(4-(dimethoxymethyl)-3-(4,4,5,5-tetramethyl-1,3,2-dioxaborolan-2-yl)benzoyl)-N'-(2,2-dimethylpentan-3-yl)-3-methoxy-2-methylbenzohydrazide as a yellow powder. The crude residue was used in the next step without further purification as a yellow gum. $^1$H NMR (400 MHz, DMSO) δ 10.46-10.24 (m, 1H), 7.88-7.39 (br m, 3H), 7.11-7.07 (m, 1H), 7.01-6.95 (m, 1H), 6.48-6.29 (m, 1H), 5.76-5.69 (m, 1H), 4.46-4.23 (dd, 1H, chiral CH), 3.74-3.71 (m, 1H), 3.32-3.23 (m, 6H), 1.90-1.40 (m, 5H), 1.32 (s, 9H), 1.12-0.96 (m, 15H) ppm; LCMS for $C_{32}H_{47}BN_2O_7$ $(M+H)^+$=583.

Example 23

Synthesis of (R)—N'-(2,2-dimethylpentan-3-yl)-N'-(4-formyl-3-(4,4,5,5-tetramethyl-1,3,2-dioxaborolan-2-yl)benzoyl)-3-methoxy-2-methylbenzohydrazide To a stirred solution of (R)—N'-(4-(dimethoxymethyl)-3-(4,4,5,5-tetramethyl-1,3,2-dioxaborolan-2-yl)benzoyl)-N'-(2,2-dimethylpentan-3-yl)-3-methoxy-2-methylbenzohydrazide (1.488 g, 2.55 mmol, 94% yield) in acetone (20 mL) at 23° C., was added pyridine 4-methylbenzenesulfonate (0.068 g, 0.270 mmol). The reaction mixture was stirred at 56° C. for 16-18 h. The reaction was complete by LCMS and was cooled to 23° C., concentrated on a rotary evaporator and the resulting residue was dissolved with $CH_2Cl_2$ (40 mL). The organic layer was washed with saturated $NH_4Cl$, $H_2O$, brine, dried ($MgSO_4$), filtered and concentrated to give crude (R)—N'-(2,2-dimethylpentan-3-yl)-N'-(4-formyl-3-(4,4,5,5-tetramethyl-1,3,2-dioxaborolan-2-yl)benzoyl)-3-methoxy-2-methylbenzohydrazide (1.311 g, 2.444 mmol, 90% yield) as a yellow gum and was used in the next step without further purification. $^1$H NMR (400 MHz, DMSO) δ 10.57-10.22 (m, 2H, amide NH+aldehyde rotomers), 7.89-7.59 (m, 3H), 7.16-7.10 (m, 1H), 7.00-6.98 (m, 1H), 6.55-6.36 (m, 1H), 4.46-4.24 (dd, 1H, chiral methine), 3.73-3.72 (two s, 3H), 1.83-1.40 (br m, 5H), 1.38-1.36 (m, 9H), 1.13-0.98 (m, 15H) ppm; LCMS for $C_{30}H_{41}BN_2O_6$ $(M+H)^+$=538.

Example 24

Synthesis of (R)-(5-(1-(2,2-dimethylpentan-3-yl)-2-(3-methoxy-2-methylbenzoyl)hydrazine-1-carbonyl)-2-formylphenyl)boronic Acid

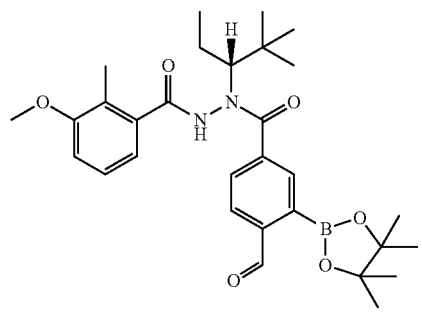
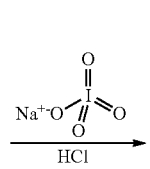
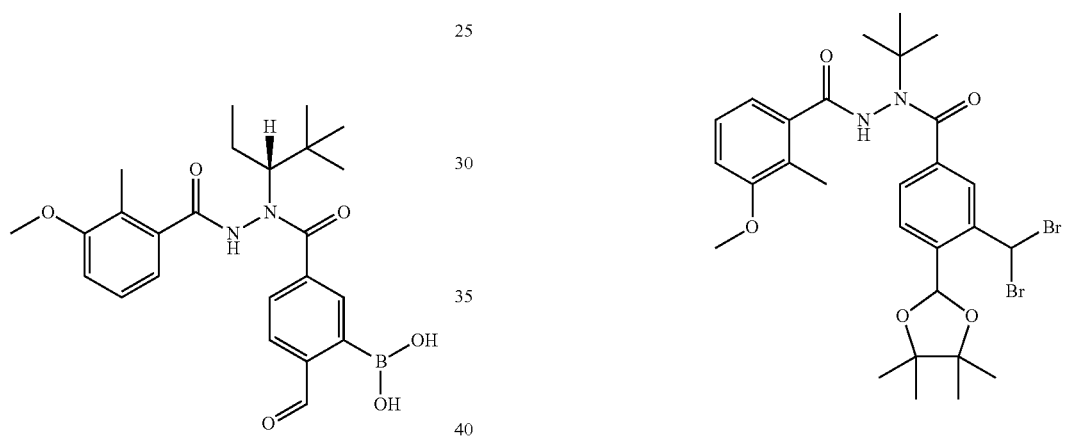

A solution of sodium periodate (0.498 g, 2.330 mmol) in 12 mL of THF and 3 ml of H₂O was treated with sodium periodate (0.498 g, 2.330 mmol). The reaction mixture was stirred with cooling at 0° C. before adding HCl (1.165 ml, 2.330 mmol) and the reaction mixture was stirred for 1 h at 0° C. THF was removed on a rotary evaporator under vacuum and the residue was dissolved in DMSO (approx. 3 mL) and purified by reverse phase chromatography on the ISCO using a 15.5 g C-18 RediSep ISCO column and eluted with 0-100% CH₃CN—H₂O. The desired fractions were pooled and lyophilized over 18 h to give [Products] as a pale yellow powder. LCMS for $C_{24}H_{31}BN_2O_6$ (M+H)$^+$=455.

Example 25

Synthesis of N'-(tert-butyl)-N'-(3-(dibromomethyl)-4-(4,4,5,5-tetramethyl-1,3-dioxolan-2-yl)benzoyl)-3-methoxy-2-methylbenzohydrazide

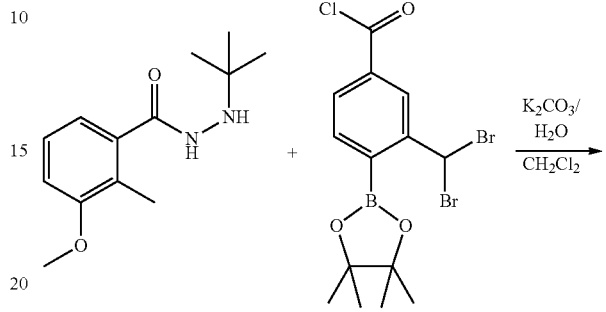

N'-(tert-butyl)-3-methoxy-2-methylbenzohydrazide (1.55 g, 6.57 mmol) was dissolved in 5 mL CH₂Cl₂ in a round bottom flask. A solution of K2CO3 (1.73 g, 12.5 mmol) in 10 mL water was added. The biphasic mixture was stirred magnetically with ice cooling. A solution of 3-(dibromomethyl)-4-(4,4,5,5-tetramethyl-1,3,2-dioxaborolan-2-yl)benzoyl chloride in 8 mL was added to the mixture dropwise over 5 min. The mixture was allowed to warm to room temperature and was stirred for 22 hours. The mixture was diluted with water and H2Cl2 to ca. 50 mL in each phase. The aqueous phase was removed, and the organic phase was washed once with water, once with brine, and dried over Na2SO4/MgSO4. The solution was filtered and solvent was removed in vacuo, to yield a yellow-beige solid. The solid was triturated thrice with a total of ca. 80 mL 10% ether in hexanes. Drying in air overnight yielded 3.86 g (96% yield) of a light beige, powdery solid, N'-(tert-butyl)-N'-(3-(dibromomethyl)-4-(4,4,5,5-tetramethyl-1,3-dioxolan-2-yl)benzoyl)-3-methoxy-2-methylbenzohydrazide. ¹H NMR (400 MHz, DMSO-d₆) δ 10.63 (s, 1H), 8.00 (d, J=1.4 Hz, 1H), 7.73 (s, 1H), 7.60 (d, J=7.7 Hz, 1H), 7.40 (dd, J=7.7, 1.6 Hz, 1H), 7.08 (d, J=7.9 Hz, 1H), 6.96 (dd, J=8.4, 1.1 Hz, 1H), 6.36 (dd, J=7.6, 1.1 Hz, 1H), 3.72 (s, 3H), 2.50 (s, 6H), 1.57 (s, 3H), 1.55 (s, 9H), 1.35 (s, 12H) ppm.

Example 26

Synthesis of (4-(1-(tert-butyl)-2-(3-methoxy-2-methylbenzoyl)hydrazine-1-carbonyl)-2-formylphenyl)boronic Acid

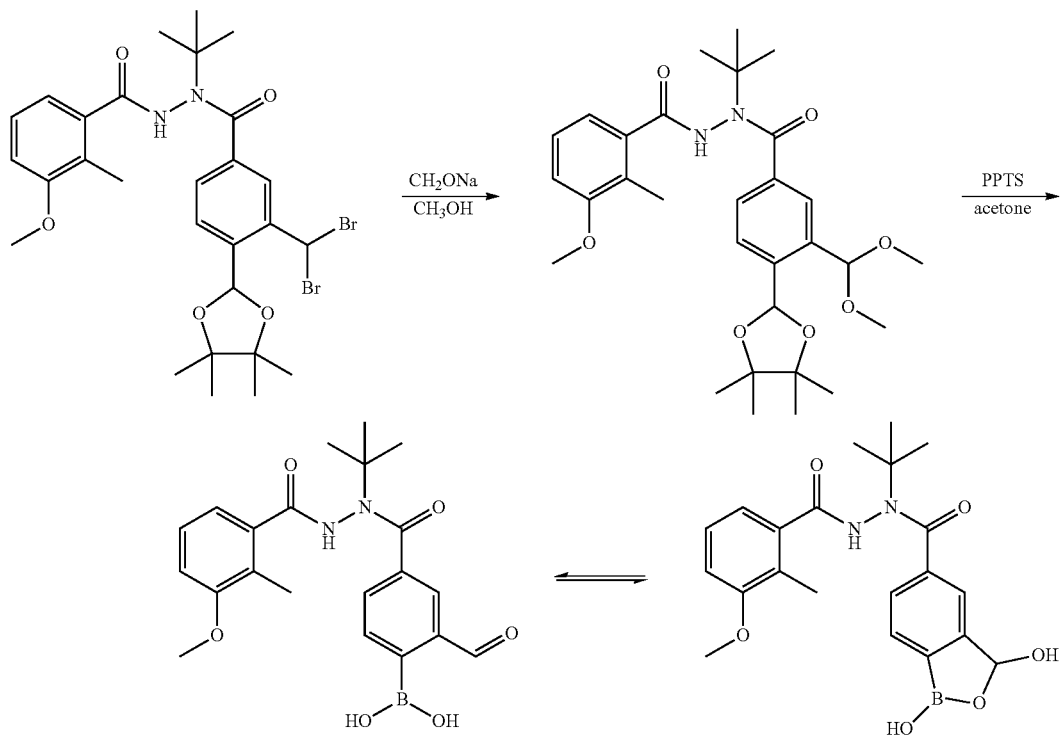

N'-(tert-butyl)-N'-(3-(dibromomethyl)-4-(4,4,5,5-tetramethyl-1,3-dioxolan-2-yl)benzoyl)-3-methoxy-2 methylbenzohydrazide (3.65 g, 5.7 mmole) was dissolved in 40 mL methanol at room temp. Sodium methoxide in methanol (2.75 g of a 25% solution, ca. 2.2 eq.) was added and the solution was stirred magnetically and heated at 65 C for 2 hr. The solvent was removed in vacuo and the residue was dissolved in 30 mL CH2Cl2, washed with brine, dried over MgSO4, filtered, and concentrated to dryness on rotary evaporator to yield 3.09 g (100% mass recovery) foamy, cream-colored solid. $^1$H NMR (400 MHz, DMSO-$d_6$) δ 10.52 (s, 1H), 7.55 (d, J=1.5 Hz, 1H), 7.49 (d, J=7.6 Hz, 1H), 7.36 (dd, J=7.6, 1.7 Hz, 1H), 7.05 (t, 1H), 6.97 (d, J=1.2 Hz, 1H), 6.26 (dd, J=7.5, 1.1 Hz, 1H), 3.23 (s, 1H), 3.20 (s, 1H) 1.50 (s, 9H), 1.31 (s, 12H) ppm. Singlets at 1.07 (pinacol) and 7.87 (B(OH)2 indicated the presence of pinacol hydrolysis. This material was used for the next step without purification.

The acetal (3.09 g, 5.7 mmole) was dissolved in 24 mL acetone. Pyridinium p-toluenesulfonate (144 mg, 0.57 mmole) was added. The mixture was stirred at reflux for 4.5 hr and then concentrated on a rotary evaporator. The residue was dissolved in 30 mL CH2Cl2, and the resultant solution was washed with water and brine, and finally dried over MgSO4. Filtration and concentration to dryness on a rotary evaporator yielded a cream-colored, sticky solid. $^1$H NMR indicated a substantial quantity of the free boronic acid as well as the boron pinacolate. The product mixture was purified by reverse phase flash chromatography, using a water-ACN gradient with 0.1% formic acid. After lyophilization, 1.24 g (52% yield) pure (4-(1-(tert-butyl)-2-(3-methoxy-2-methylbenzoyl)hydrazine-1-carbonyl)-2-formylphenyl)boronic acid was obtained a white solid. $^1$H NMR (400 MHz, DMSO-$d_6$) δ 10.63 (s, 1H, exchangeable), 10.17 (s, 1H), 8.34 (br s, 2H, exchangeable), 7.94 (s, 1H), 7.65 (d, J=1.7 Hz, 1H), 7.60 (d, 1H), 7.10 (t, 1H), 6.95 (d, 1H), 6.30 (dd, J=7.6, 1.1 Hz, 1H), 3.73 (s, 3H), 1.60 (s, 3H), 1.52 (s, 9H) ppm. By 1H NMR, approximately 5% of the corresponding 1,3-dihydroxy oxaborole in equilibrium was observed from the acetal methine multiplet at δ 6.25, as well as an exchangeable B—OH singlet at δ 9.34, aromatic multiplets at δ 7.8 and 6.85 ppm, and doubling of the methoxy and t-butyl signals. These signals coalesced in a DMSO-$d_6$ D$_2$O mixture.

Example 27

Synthesis of N'-(tert-butyl)-N'-(3,5-dimethylbenzoyl)-1-hydroxy-1H-benzo[d][1,2,6]oxazaborinine-7-carbohydrazide

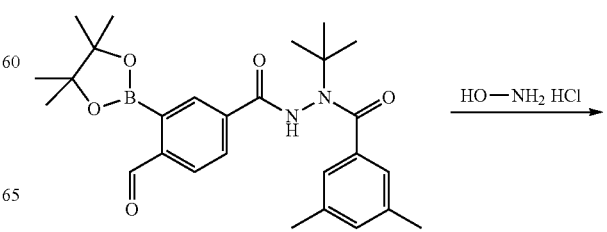

-continued

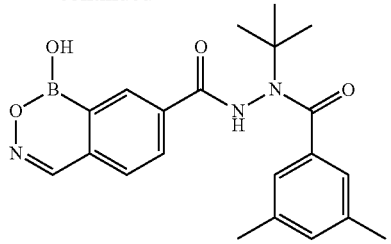

A solution of N'-(tert-butyl)-N'-(3,5-dimethylbenzoyl)-4-formyl-3-(4,4,5,5-tetramethyl-1,3,2-dioxaborolan-2-yl)benzohydrazide (150 mg, 0.314 mmol) in 4 mL of H$_2$O was treated with hydroxylamine hydrochloride (65.4 mg, 0.941 mmol). The pH of the reaction mixture was adjusted to 4 with 1 N NaOH solution resulting in a voluminous white precipitate. Four drops of 95% EtOH was added to the reaction mixture to dissolve most of the solid. The reaction mixture was stirred with heating at 70° C. for 16 h affording a white precipitate, and upon cooling to room temperature, the white precipitate was collected by suction filtration and washed with cold water and then CH$_2$Cl$_2$ to afford N'-(tert-butyl)-N'-(3,5-dimethylbenzoyl)-1-hydroxy-1H-benzo[d][1,2,6]oxazaborinine-7-carbohydrazide (92 mg, 0.234 mmol, 74.6% yield) as a white solid. $^1$H NMR (400 MHz, DMSO) δ 10.95-10.78 ((s, 1H), 9.61-9.44 ((s, 1H), 8.80-8.56 (s, 1H), 8.22-8.03 (s, 1H), 7.91-7.69 (m, 2H), 7.22-7.00 (s, 2H), 7.02-6.83 (s, 1H), 2.28-2.17 (s, 6H), 1.56-1.46*s, 9H) ppm; LCMS for C$_{24}$H$_{31}$BN$_2$O$_6$ (M+H)$^+$=394.

Example 28

Synthesis of N'-(tert-butyl)-N'-(3,5-dimethylbenzoyl)-1-hydroxy-1,2-dihydrobenzo[d][1,2,3]diazaborinine-7-carbohydrazide

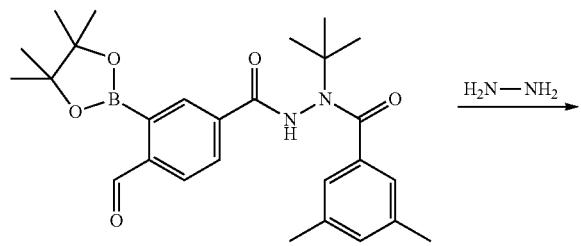

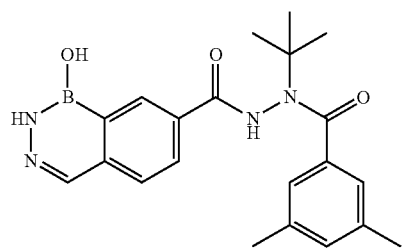

A solution of N'-(tert-butyl)-N'-(3,5-dimethylbenzoyl)-4-formyl-3-(4,4,5,5-tetramethyl-1,3,2-dioxaborolan-2-yl)benzohydrazide (150 mg, 0.314 mmol) in 4 mL of 95% EtOH was treated with hydrazine (30.1 mg, 0.941 mmol). The reaction mixture was stirred with 70° C. for 16 h, and upon cooling to room temperature, the reaction mixture was concentrated, the residue was transferred to a 30 g RediSep C18 reverse phase column and eluted with 0-100% CH$_3$CN—H$_2$O on an ISCO HPLC system to afford N'-(tert-butyl)-N'-(3,5-dimethylbenzoyl)-1-hydroxy-1,2-dihydrobenzo[d][1,2,3]diazaborinine-7-carbohydrazide (87 mg, 0.222 mmol, 70.7% yield) as a white solid. $^1$H NMR (400 MHz, DMSO) δ 10.76 (s, 1H), 10.01 (s, 1H), 8.37-8.31 (apparent d, 2H), 8.02 (s, 1H), 7.74-7.66 (m, 2H), 7.11 (s, 2H), 6.92 (s, 1H), 2.22 (s, 6H), 1.49 (s, 9H) ppm; LCMS for C$_{21}$H$_{25}$BN$_4$O$_3$ (M+H)$^+$=393.

Example 29

Synthesis of N'-(tert-butyl)-N'-(3,5-dimethylbenzoyl)-1-hydroxy-2-methyl-1,2-dihydrobenzo[d]-[1,2,3]diazaborinine-7-carbohydrazide

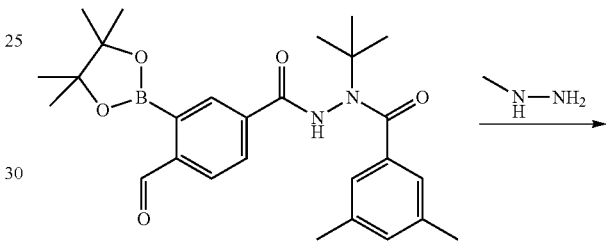

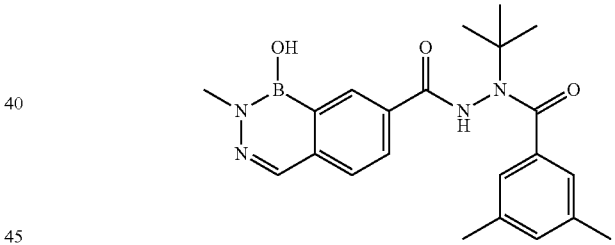

A solution of N'-(tert-butyl)-N'-(3,5-dimethylbenzoyl)-4-formyl-3-(4,4,5,5-tetramethyl-1,3,2-dioxaborolan-2-yl)benzohydrazide (150 mg, 0.314 mmol) in 95% EtOH was treated with methylhydrazine (0.050 ml, 0.941 mmol). The reaction mixture was stirred with heating at 70° C. for 16 h, and upon cooling to room temperature, the precipitate was collected by suction filtration and washed with cold water and then CH$_2$Cl$_2$ to afford N'-(tert-butyl)-N'-(3,5-dimethylbenzoyl)-1-hydroxy-2-methyl-1,2-dihydrobenzo[d][1,2,3]diazaborinine-7-carbohydrazide (47 mg, 0.116 mmol, 36.9% yield) as a white solid. $^1$H NMR (400 MHz, DMSO) δ 10.74 (s, 1H), 8.66 (s, 1H), 8.50 (s, 1H), 8.02 (s, 1H), 7.75-7.73 (d, J=4 Hz, 1H), 7.63-7.62 (d, J=4 Hz, 1H), 7.61-7.60 (d, J=4 Hz, 1H), 7.11 (s, 2H), 6.93 (s, 1H), 3.52 (s, 3H), 2.22 (s, 6H), 1.52-1.47 (s, 9H) ppm; LCMS for C$_{22}$H$_{27}$BN$_4$O$_3$ (M+H)$^+$=393.

Example 30

Synthesis of N'-(tert-butyl)-N'-(3,5-dimethylbenzoyl)-1-hydroxy-2-isopropyl-1,2-dihydrobenzo-[d][1,2,3]diazaborinine-7-carbohydrazide

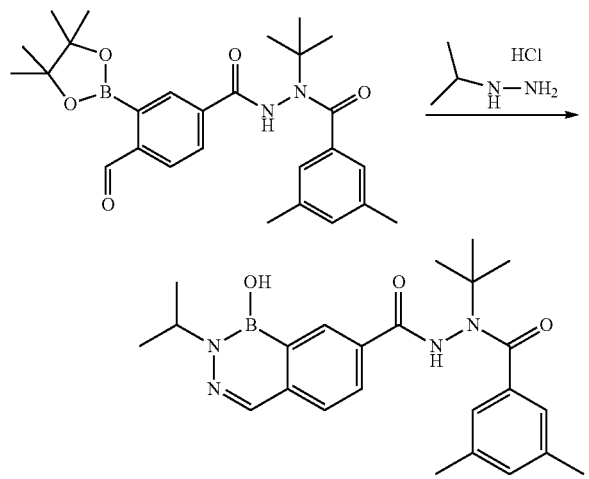

A solution of N'-(tert-butyl)-N'-(3,5-dimethylbenzoyl)-4-formyl-3-(4,4,5,5-tetramethyl-1,3,2-dioxaborolan-2-yl)benzohydrazide (150 mg, 0.314 mmol) in 95% EtOH was treated with isopropylhydrazine hydrochloride (34.7 mg, 0.314 mmol) and the resulting the solution was adjusted to pH 4 by the addition of 1 N NaOH. The reaction mixture was stirred with heating at 70° C. for 16 h, and upon cooling to room temperature, the precipitate was collected by suction filtration and washed with cold water and then CH$_2$Cl$_2$ to afford N'-(tert-butyl)-N'-(3,5-dimethylbenzoyl)-1-hydroxy-2-isopropyl-1,2-dihydrobenzo[d][1,2,3]diazaborinine-7-carbohydrazide (69 mg, 0.159 mmol, 50.7% yield) as a white solid. $^1$H NMR (400 MHz, DMSO) δ 10.72 (s, 1H), 8.62 (s, 1H), 8.52 (s, 1H) 8.10 (s, 1H), 7.73-7.71 (d, J=4 Hz, 1H), 7.63-7.60 (d, J=4 Hz, 1H), 7.11 (s, 2H), 6.92 (s, 1H), 4.68-4.62 (q, 1H), 2.21 (s, 6H), 1.52-1.49 (s, 9H), 1.27-1.26 (d, J=4 Hz, 6H) ppm; LCMS for C$_{24}$H$_{31}$BN$_4$O$_3$ (M+H)$^+$=435.

Example 31

Synthesis of N'-(tert-butyl)-N'-(3,5-dimethylbenzoyl)-1-hydroxy-2-phenyl-1,2-dihydrobenzo[d]-[1,2,3]diazaborinine-7-carbohydrazide

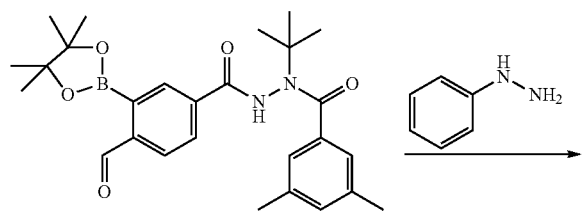

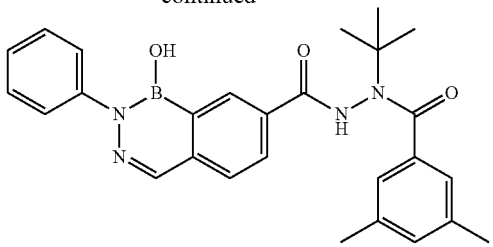

A solution of N'-(tert-butyl)-N'-(3,5-dimethylbenzoyl)-4-formyl-3-(4,4,5,5-tetramethyl-1,3,2-dioxaborolan-2-yl)benzohydrazide (150 mg, 0.314 mmol) in 95% EtOH was treated with phenylhydrazine (67.8 mg, 0.627 mmol). The reaction mixture was stirred with heating at 70° C. for 16 h, and upon cooling to room temperature, the precipitate was collected by suction filtration and washed with cold water and then CH$_2$Cl$_2$ to afford N'-(tert-butyl)-N'-(3,5-dimethylbenzoyl)-1-hydroxy-2-phenyl-1,2-dihydrobenzo[d][1,2,3]diazaborinine-7-carbohydrazide (83 mg, 0.177 mmol, 56.5% yield) as a white solid. $^1$H NMR (400 MHz, DMSO) δ 10.82, 8.47, 8.29, 8.12, 7.89, 7.87, 7.73, 7.72, 7.43, 7.41, 7.09, 6.92, 3.32, 2.52, 2.51, 2.51, 2.50, 2.50, 2.38, 2.22, 2.08, 1.50, 1.48 ppm; LCMS for C$_{27}$H$_{29}$BN$_4$O$_3$ (M+H)$^+$=469.

Example 32

Synthesis of N'-(tert-butyl)-N'-(3,5-dimethylbenzoyl)-1-methyl-2-(methylsulfonyl)-1,2-dihydrobenzo[d]-[1,2,3]-diazaborinine-7-carbohydrazide

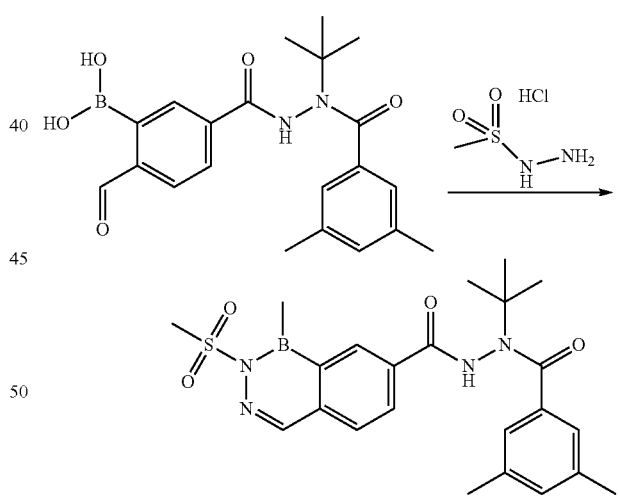

A solution of (5-(2-(tert-butyl)-2-(3,5-dimethylbenzoyl)hydrazinecarbonyl)-2-formylphenyl)boronic acid (200 mg, 0.505 mmol) in 4 mL of 95% EtOH was treated with methanesulfonohydrazide hydrochloride (148 mg, 1.009 mmol). The reaction mixture was stirred with heating at 70° C. for 16 h, and upon cooling to room temperature, the precipitate was collected by suction filtration and washed with cold water and then CH$_2$Cl$_2$ to afford N'-(tert-butyl)-N'-(3,5-dimethylbenzoyl)-1-methyl-2-(methylsulfonyl)-1,2-dihydrobenzo[d][1,2,3]diazaborinine-7-carbohydrazide as a white solid. $^1$H NMR (400 MHz, DMSO) δ 10.86 (s, 1H), 8.36-8.28 (br s, 2H), 8.26 (s, 1H), 7.84-7.78 (m, 2H), 7.10

(s, 2H), 6.93 (s, 1H), 3.38 (s, 3H), 2.22 (s, 6H), 1.51 (s, 9H) ppm; LCMS for $C_{22}H_{27}BN_4O_5S$ (M+H)$^+$=471.

Example 33

Synthesis of N'-(tert-butyl)-N'-(3,5-dimethylbenzoyl)-1-hydroxy-2-tosyl-1,2-dihydrobenzo[d]-[1,2,3]diazaborinine-7-carbohydrazide

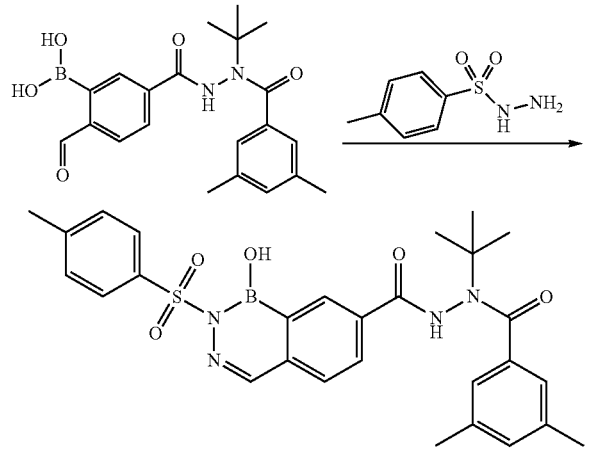

A solution of N'-(tert-butyl)-N'-(3,5-dimethylbenzoyl)-4-formyl-3-(4,4,5,5-tetramethyl-1,3,2-dioxaborolan-2-yl)benzohydrazide (150 mg, 0.314 mmol) in 4 mL of 95% EtOH was treated with 4-methylbenzenesulfonohydrazide (117 mg, 0.627 mmol). The reaction mixture was stirred with heating at 70° C. for 16 h, and upon cooling to room temperature, the precipitate was collected by suction filtration and washed with cold water and then $CH_2Cl_2$ to afford N'-(tert-butyl)-N'-(3,5-dimethylbenzoyl)-1-hydroxy-2-tosyl-1,2-dihydrobenzo[d][1,2,3]diazaborinine-7-carbohydrazide as a white solid. LCMS for $C_{28}H_{31}BN_4O_5S$ (M+H)$^+$=547.

Example 34

Synthesis of N'-(tert-butyl)-3-cyano-N'-(3,5-dimethylbenzoyl)-1-hydroxy-1,3-dihydrobenzo[c][1,2]-oxaborole-6-carbohydrazide

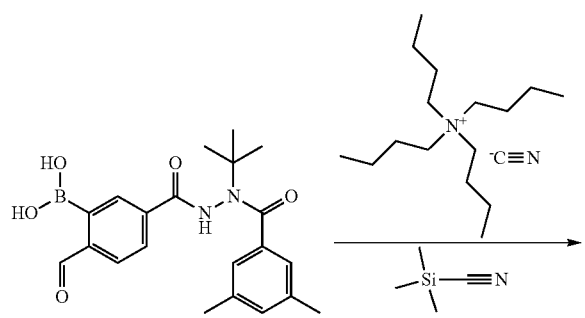

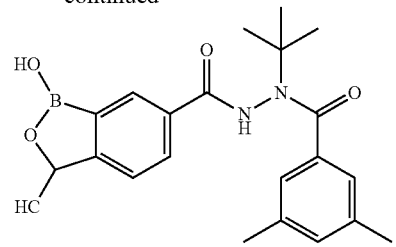

A solution of (5-(2-(tert-butyl)-2-(3,5-dimethylbenzoyl)hydrazinecarbonyl)-2-formylphenyl)boronic acid (500 mg, 1.262 mmol) in dry DCM (2 mL) was added trimethylsilanecarbonitrile (0.186 ml, 1.388 mmol) under argon at 0° C. followed by a solution of tetrabutylammonium cyanide (50.8 mg, 0.189 mmol) in dry DCM (4 mL). The reaction mixture was stirred at 0° C. for 1 h, quenched with saturated aqueous NaHCO$_3$ solution (10.3 mL), and extracted with DCM. The combined organic layers were dried with MgSO$_4$, filtered and concentrated on a rotary evaporator. The N'-(tert-butyl)-3-cyano-N'-(3,5-dimethylbenzoyl)-1-hydroxy-1,3-dihydrobenzo[c][1,2]oxaborole-6-carbohydrazide as a white solid. $^1$H NMR (400 MHz, DMSO) δ 10.74 and 10.73 (overlapping s, 1H), 9.99 (s, 1H), 7.94-7.91 (d, 1H), 7.68-7.65 (m, 2H), 7.09 (s, 2H), 6.93 (s, 1H), 6.31 (s, 1H), 2.22 (s, 6H), 1.50 (s, 9H) ppm; LCMS for $C_{22}H_{24}BN_3O_4$ (M+H)$^+$=406.

Example 35

Synthesis of (R)—N'-(3,5-dimethylbenzoyl)-N'-(2,2-dimethylpentan-3-yl)-1-hydroxy-1H-benzo[d][1,2,6]-oxazaborinine-7-carbohydrazide

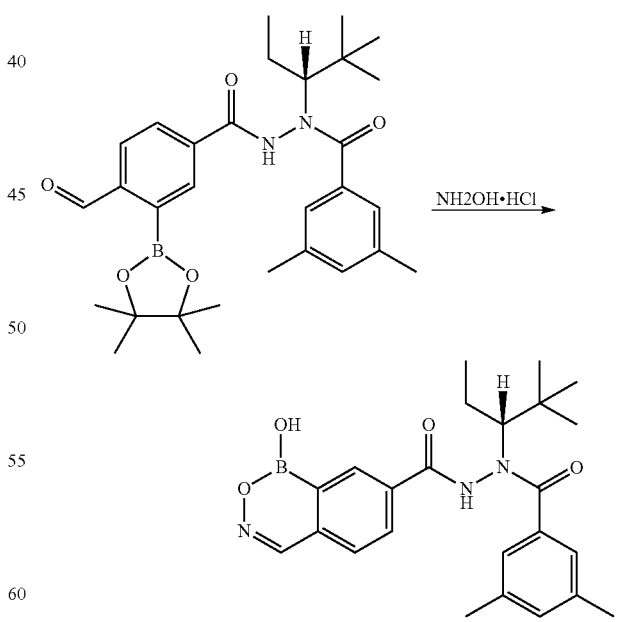

A solution of (R)—N'-(3,5-dimethylbenzoyl)-N'-(2,2-dimethylpentan-3-yl)-4-formyl-3-(4,4,5,5-tetramethyl-1,3,2-dioxaborolan-2-yl)benzohydrazide (200 mg, 0.384 mmol) in 4 mL of 95% EtOH was treated with hydroxylamine hydrochloride (40.1 mg, 0.576 mmol). The reaction mixture was stirred with heating at 70° C. for 16 h, and upon cooling to room temperature, the precipitate was collected by suction filtration and washed with cold water and then CH$_2$Cl$_2$ to afford (R)—N'-(3,5-dimethylbenzoyl)-N'-(2,2-dimethylpentan-3-yl)-1-hydroxy-1H-benzo[d][1,2,6]oxazaborinine-7-carbohydrazide (121 mg, 0.278 mmol, 72.3% yield). $^1$H NMR (400 MHz, DMSO) δ 10.56 and 10.37 (combined two s, 1H, NH rotomers), 9.55-9.51 (app. d, 1H, rotomers), 8.77-8.55 (combined three s, 1H), 8.22-8.06 (m, 1H), 7.91-7.67 (m, 2H), 7.18-7.07 (m, 2H), 6.96-6.95 (overlapping s, 1H), 4.49-4.28 (two partial d, J=8 Hz, 1H, CH chiral), 2.34 and 2.23 (combined two s, 1H, benzylic), 1.90-1.25 (m, 2H), 1.23-0.87 (m, 12H) ppm; LCMS for C$_{24}$H$_{30}$BN$_3$O$_4$ (M+H)$^+$=436.

Example 36

Synthesis of (R)—N'-(3,5-dimethylbenzoyl)-N'-(2,2-dimethylpentan-3-yl)-1-hydroxy-1,2-dihydrobenzo[d]-[1,2,3]-diazaborinine-7-carbohydrazide

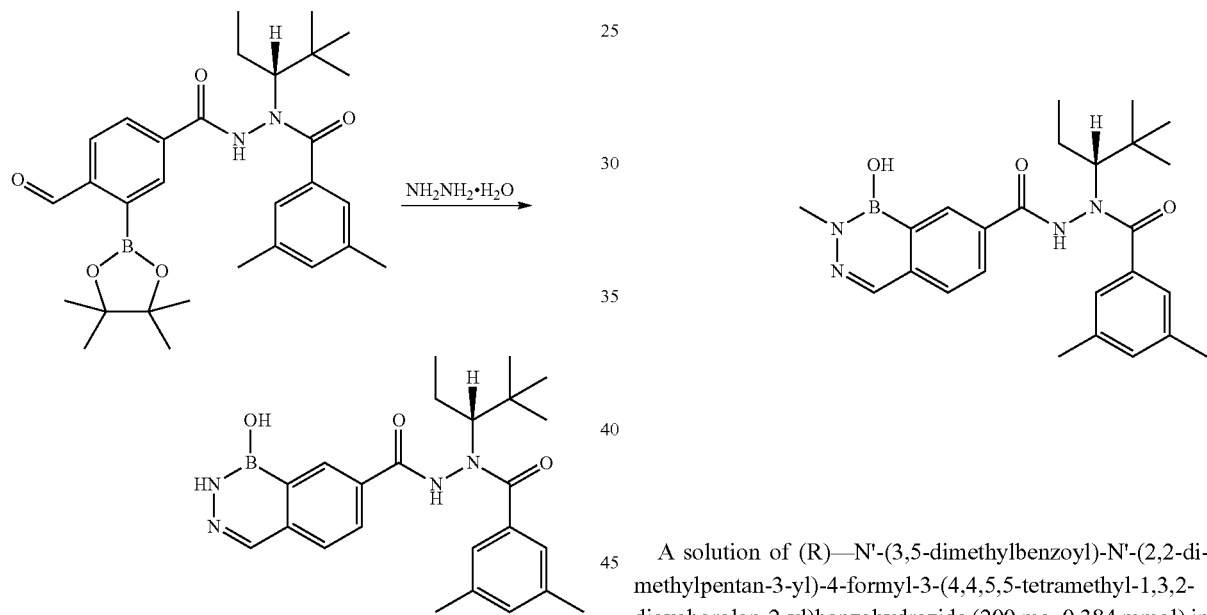

A solution of (R)—N'-(3,5-dimethylbenzoyl)-N'-(2,2-dimethylpentan-3-yl)-4-formyl-3-(4,4,5,5-tetramethyl-1,3,2-dioxaborolan-2-yl)benzohydrazide (200 mg, 0.384 mmol) in 4 mL of 95% EtOH was treated with hydrazine hydrate (28.9 mg, 0.576 mmol). The reaction mixture was stirred with heating at 70° C. for 16 h, and upon cooling to room temperature, the precipitate was collected by suction filtration and washed with cold water and then CH$_2$Cl$_2$ to afford (R)—N'-(3,5-dimethylbenzoyl)-N'-(2,2-dimethylpentan-3-yl)-1-hydroxy-1,2-dihydrobenzo[d][1,2,3]diazaborinine-7-carbohydrazide (111 mg, 0.256 mmol, 66.5% yield) as a white solid. $^1$H NMR (400 MHz, DMSO) δ 10.45 and 10.27 (combined two s, 1H, NH rotomers), 10.03-10.02 (overlapping s, 1H), 8.33-8.29 (m, 2H), 8.02 (s, 1H), 7.17-7.71 (m, 1H), 7.67-7.56 (br m, 1H), 7.19-7.07 (m, 2H), 7.01-6.88 (two overlapping s, 1H), 4.50-4.28 (two combined d, J=12 Hz, 1H, CH chiral), 2.23 (s, 6H), 1.97-1.29 (4 partial br m, 2H), 1.21-0.88 (m, 12H) ppm; LCMS for C$_{24}$H$_{31}$BN$_4$O$_3$ (M+H)$^+$=435.

Example 37

Synthesis of (R)—N'-(3,5-dimethylbenzoyl)-N'-(2,2-dimethylpentan-3-yl)-1-hydroxy-2-methyl-1,2-dihydrobenzo[d][1,2,3]diazaborinine-7-carbohydrazide

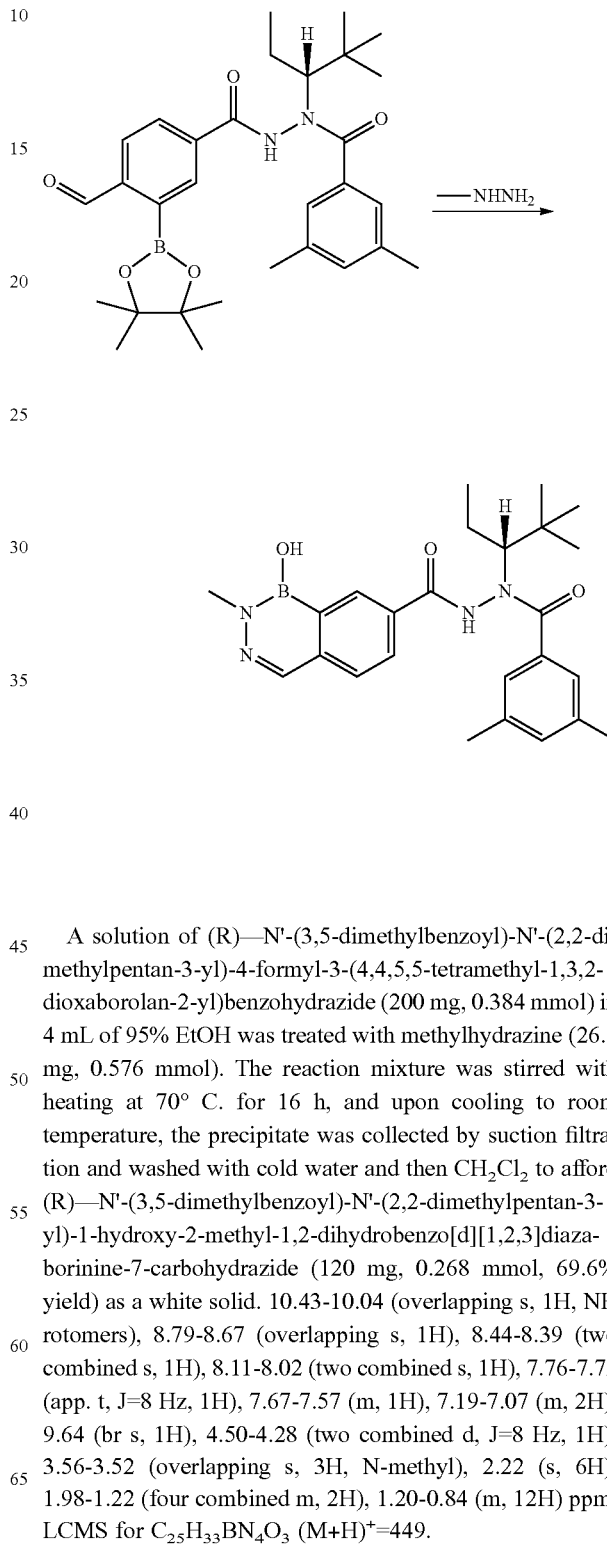

A solution of (R)—N'-(3,5-dimethylbenzoyl)-N'-(2,2-dimethylpentan-3-yl)-4-formyl-3-(4,4,5,5-tetramethyl-1,3,2-dioxaborolan-2-yl)benzohydrazide (200 mg, 0.384 mmol) in 4 mL of 95% EtOH was treated with methylhydrazine (26.6 mg, 0.576 mmol). The reaction mixture was stirred with heating at 70° C. for 16 h, and upon cooling to room temperature, the precipitate was collected by suction filtration and washed with cold water and then CH$_2$Cl$_2$ to afford (R)—N'-(3,5-dimethylbenzoyl)-N'-(2,2-dimethylpentan-3-yl)-1-hydroxy-2-methyl-1,2-dihydrobenzo[d][1,2,3]diazaborinine-7-carbohydrazide (120 mg, 0.268 mmol, 69.6% yield) as a white solid. 10.43-10.04 (overlapping s, 1H, NH rotomers), 8.79-8.67 (overlapping s, 1H), 8.44-8.39 (two combined s, 1H), 8.11-8.02 (two combined s, 1H), 7.76-7.72 (app. t, J=8 Hz, 1H), 7.67-7.57 (m, 1H), 7.19-7.07 (m, 2H), 9.64 (br s, 1H), 4.50-4.28 (two combined d, J=8 Hz, 1H), 3.56-3.52 (overlapping s, 3H, N-methyl), 2.22 (s, 6H), 1.98-1.22 (four combined m, 2H), 1.20-0.84 (m, 12H) ppm; LCMS for C$_{25}$H$_{33}$BN$_4$O$_3$ (M+H)$^+$=449.

Example 38

Synthesis of (R)—N'-(3,5-dimethylbenzoyl)-N'-(2,2-dimethylpentan-3-yl)-1-hydroxy-2-(methylsulfonyl)-1,2-dihydrobenzo[d][1,2,3]diazaborinine-7-carbohydrazide

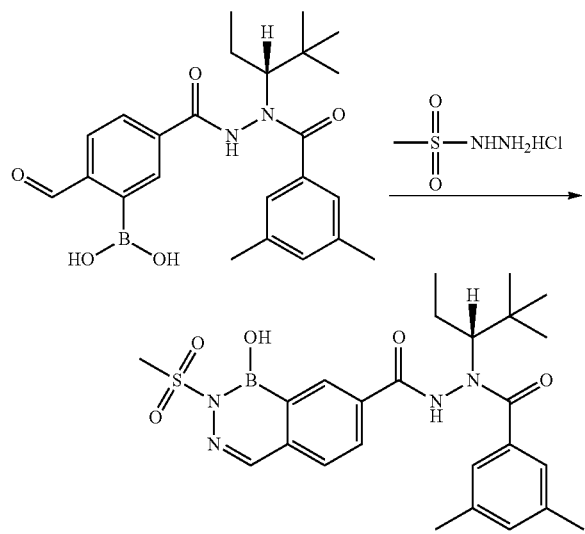

A solution of (R)—N'-(3,5-dimethylbenzoyl)-N'-(2,2-dimethylpentan-3-yl)-4-formyl-3-boronic acid benzohydrazide (200 mg, 0.384 mmol) in 4 mL of 95% EtOH was treated with methanesulfonohydrazide hydrochloride (84 mg, 0.576 mmol). The reaction mixture was stirred with heating at 70° C. for 16 h, and upon cooling to room temperature, was purified by reverse phase ISCO chromatography using 0-100% $CH_3CN$—$H_2O$ as eluent affording (R)—N'-(3,5-dimethylbenzoyl)-N'-(2,2-dimethylpentan-3-yl)-1-hydroxy-2-(methylsulfonyl)-1,2-dihydrobenzo[d][1,2,3]diazaborinine-7-carbohydrazide as a pale yellow solid. 10.56 and 10.37 (two s, 1H, NH rotomers), 8.68-8.34 (m, 1H), 8.28-8.18 (m, 2H), 7.96-7.68 (m, 2H), 7.18-7.07 (m, 2H), 6.96 (br s, 1H), 4.50-4.28 (two combined d, J=12 Hz, 1H), 3.41 and 3.38 (overlapping s, 3H), 2.34-2.23 (overlapping s, 6H), 1.94-1.20 (four br multiplets, 2H), 1.21-0.81 (m, 12H) ppm; LCMS for $C_{25}H_{33}BN_4O_5S$ $(M+H)^+=513$.

Example 39

Synthesis of (R)—N'-(3,5-dimethylbenzoyl)-N'-(2,2-dimethylpentan-3-yl)-1-hydroxy-2-tosyl-1,2-dihydrobenzo[d]-[1,2,3]diazaborinine-7-carbohydrazide

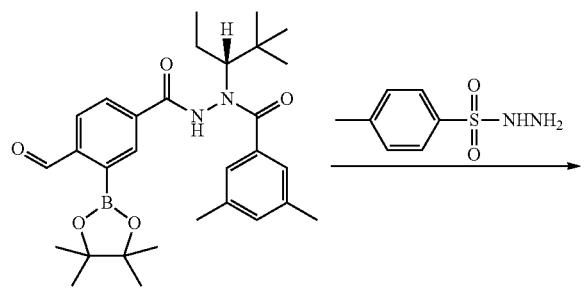

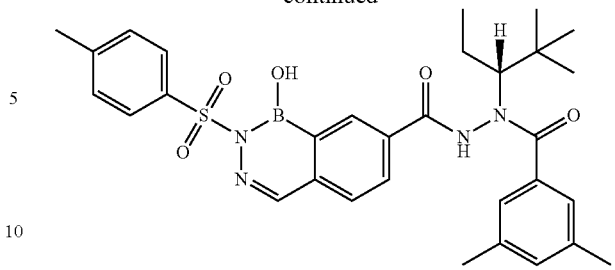

A solution of (R)—N'-(3,5-dimethylbenzoyl)-N'-(2,2-dimethylpentan-3-yl)-4-formyl-3-(4,4,5,5-tetramethyl-1,3,2-dioxaborolan-2-yl)benzohydrazide (200 mg, 0.384 mmol) in 4 mL of 95% EtOH was treated with [Reactants]. The reaction mixture was stirred with heating at 70° C. for 16 h, and upon cooling to room temperature, the precipitate was collected by suction filtration and washed with cold water and then $CH_2Cl_2$ to afford (R)—N'-(3,5-dimethylbenzoyl)-N'-(2,2-dimethylpentan-3-yl)-1-hydroxy-2-tosyl-1,2-dihydrobenzo[d][1,2,3]diazaborinine-7-carbohydrazide as a white solid. 10.52 and 10.34 (two combined s, 1H, NH rotomers), 8.72-8.51 (m, 1H), 8.25-8.20 (two combined s, 1H), 8.13 (s, 1H), 7.92-7.87 (m, 2H), 7.74-7.61 (m, 2H), 7.43-7.41 (m, 2H), 7.16-7.01 (m, 2H), 6.94 (s, 1H), 4.49-4.27 (two combined distinct d, J=12 Hz, 1H), 2.38-2.33 (m, 3H), 2.22 (s, 6H), 1.90-1.20 (m, 2H), 1.12-0.92 (m, 12H) ppm; LCMS for $C_{25}H_{33}BN_4O_5S$ $(M+H)^+=513$.

Example 40

Synthesis of N'-(tert-butyl)-N'-(3,5-dimethylbenzoyl)-1-hydroxy-1H-benzo[d]-[1,2,6]oxazaborinine-6-carbohydrazide

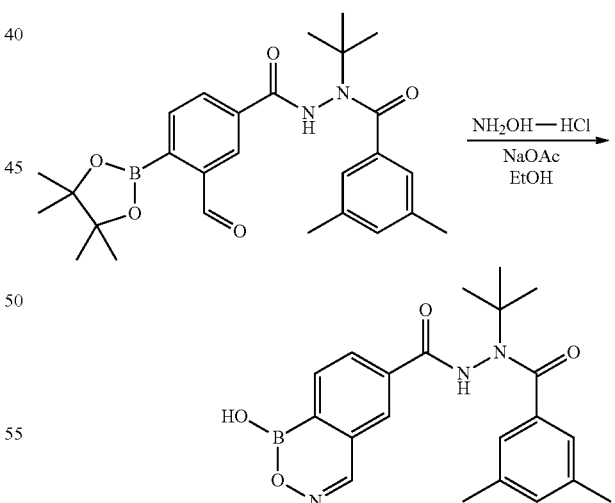

By analogy to (R)—N'-(3,5-dimethylbenzoyl)-N'-(2,2-dimethylpentan-3-yl)-1-hydroxy-1H-benzo[d][1,2,6]-oxazaborinine-7-carbohydrazide and mixing hydroxylamine HCl, NaOAc and the Bpin aldehyde in abs. ethanol at room temperature for 45 hours, N'-(tert-butyl)-N'-(3,5-dimethylbenzoyl)-1-hydroxy-1H benzo[d][1,2,6]oxazaborinine-6-carbohydrazide was obtained after reverse phase chromatography using a water-ACN gradient with 0.1% formic acid: ¹H NMR (400 MHz, DMSO-d₆) δ 10.83 (s, 1H, exchangeable with D₂O), 9.48 (s, 1H, exchangeable with D₂O), 8.62 (s, 1H), 8.06 (d, J=7.7 Hz, 1H), 7.81 (d, J=1.5 Hz, 1H), 7.70 (dd, J=7.7, 1.6 Hz, 1H), 7.08 (s, 2H), 6.94 (s, 1H), 2.21 (s, 6H), 1.50 (s, 9H) ppm.

Example 41

Synthesis of N'-(tert-butyl)-N'-(3,5-dimethylbenzoyl)-1-hydroxy-1,2-dihydrobenzo[d]-[1,2,3]diazaborinine-6-carbohydrazide

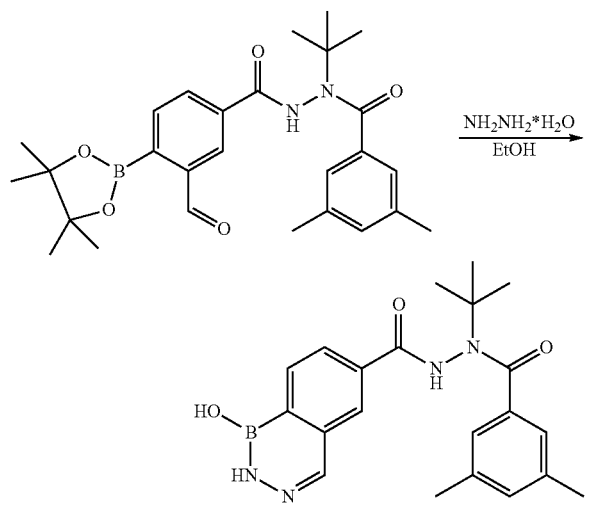

By analogy to (R)—N'-(3,5-dimethylbenzoyl)-N'-(2,2-dimethylpentan-3-yl)-1-hydroxy-1,2-dihydrobenzo[d]-[1,2,3]-diazaborinine-7-carbohydrazide and mixing hydrazine hydrate and the Bpin aldehyde in abs. ethanol at room temperature for 24 hours, N'-(tert-butyl)-N'-(3,5-dimethylbenzoyl)-1-hydroxy-1,2-dihydrobenzo[d][1,2,3]diazaborinine-6-carbohydrazide was obtained after reverse phase chromatography using a water-ACN gradient with 0.1% formic acid: ¹H NMR (400 MHz, DMSO-d₆) δ 10.76 (s, 1H, exchangeable with D₂O), 10.11 (s, 1H, exchangeable with D₂O), 8.32 (s, 1H, exchangeable with D₂O), 8.19 (d, J=7.9 Hz, 1H), 7.96 (s, 1H), 7.74 (d, J=1.4 Hz, 1H), 7.58 (dd, J=7.9, 1.6 Hz, 1H), 7.11 (s, 2H), 6.94 (s, 1H), 2.22 (s, 6H), 1.51 (s, 9H) ppm.

Example 42

Synthesis of N'-(tert-butyl)-N'-(3,5-dimethylbenzoyl)-1-hydroxy-2-methyl-1,2-dihydrobenzo[d][1,2,3]diazaborinine-6-carbohydrazide

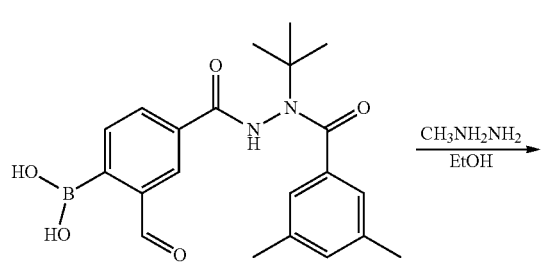

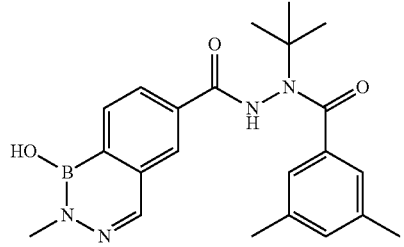

By analogy to (R)—N'-(3,5-dimethylbenzoyl)-N'-(2,2-dimethylpentan-3-yl)-1-hydroxy-2-methyl-1,2-dihydrobenzo[d][1,2,3]diazaborinine-7-carbohydrazide and mixing methylhydrazine and the boronic aldehyde in abs. ethanol at room temperature for hours, N'-(tert-butyl)-N'-(3,5-dimethylbenzoyl)-1-hydroxy-2-methyl-1,2-dihydrobenzo[d][1,2,3]diazaborinine-6-carbohydrazide was obtained after reverse phase chromatography using a water-ACN gradient with 0.1% formic acid: ¹H NMR (400 MHz, DMSO-d₆) δ 10.75 (s, 1H, exchangeable), 8.65 (s, 1H, exchangeable), 8.25 (d, J=8.0 Hz, 1H), 7.96 (s, 1H), 7.75 (d, J=1.5 Hz, 1H), 7.62-7.55 (m, 1H), 7.16-7.07 (m, 2H), 6.94 (s, 1H), 3.50 (s, 3H), 2.21 (s, 6H), 1.49 (d, J=14.4 Hz, 10H) ppm.

Example 43

Synthesis of 2-acetyl-N'-(tert-butyl)-N'-(3,5-dimethylbenzoyl)-1-hydroxy-1,2-dihydrobenzo[d][1,2,3]diazaborinine-6-carbohydrazide

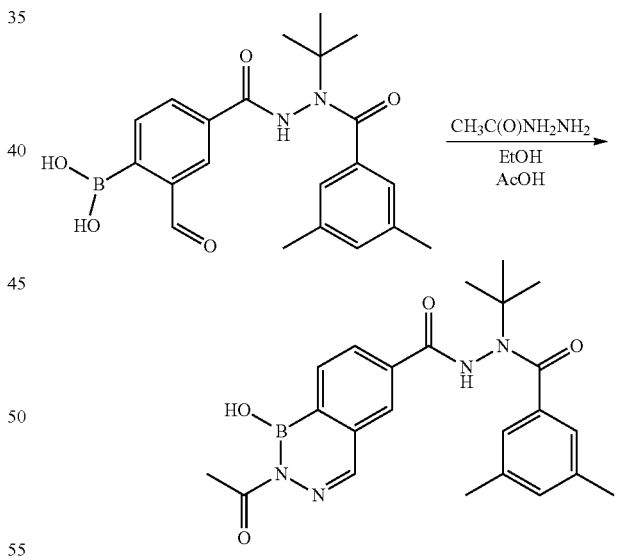

By analogy to N'-(tert-butyl)-N'-(3,5-dimethylbenzoyl)-1-hydroxy-2-methyl-1,2-dihydrobenzo[d][1,2,3]diazaborinine-6-carbohydrazide and mixing acetylhydrazine, the boronic aldehydes, and 2% w/w AcOH/aldehyde in abs. ethanol at room temperature for hours, 2-acetyl-N'-(tert-butyl)-N'-(3,5-dimethylbenzoyl)-1-hydroxy-1,2-dihydrobenzo[d][1,2,3]diazaborinine-6-carbohydrazide was obtained after reverse phase chromatography using a water-ACN gradient with 0.1% formic acid: ¹H NMR (400 MHz, DMSO-d₆), 2 conformers, tautomers, or hydrate/dehydrate in a ca. 3:1 ratio, δ 10.69+10.69 (2s, 1H, exchangeable), 8.13+8.11 (2s, 1H), 7.77+7.71 (2s, 1H), 7.61+7.53 (2dt, 2H), 7.09 (s, 2H), 6.93 (s, 1H), 2.37 (s, 3H)), 2.22 (s, 6H), 1.50 (s, 9H) ppm.

Example 44

Synthesis of N'-(tert-butyl)-N'-(3,5-dimethylbenzoyl)-1-hydroxy-2-phenyl-1,2-dihydrobenzo[d][1,2,3]diazaborinine-6-carbohydrazide

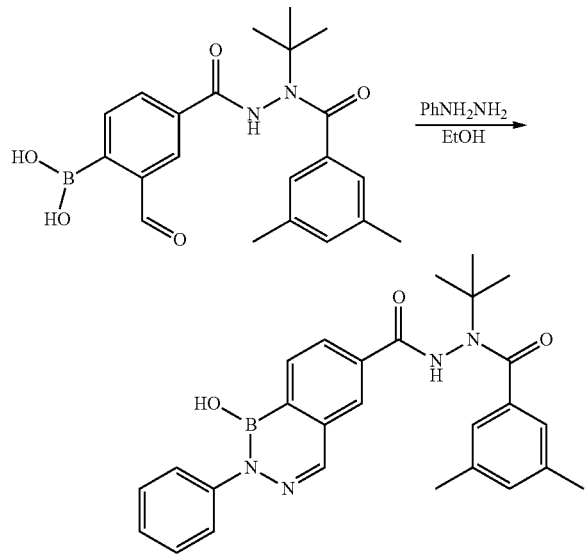

By analogy to N'-(tert-butyl)-N'-(3,5-dimethylbenzoyl)-1-hydroxy-2-phenyl-1,2-dihydrobenzo[d]-[1,2,3]diazaborinine-7-carbohydrazide and mixing phenylhydrazine, the boronic aldehyde, and 2.5% w/w AcOH/aldehyde in abs. ethanol at room temperature for hours, N'-(tert-butyl)-N'-(3,5-dimethylbenzoyl)-1-hydroxy-2-phenyl-1,2-dihydrobenzo[d][1,2,3]diazaborinine-6-carbohydrazide was obtained after reverse phase chromatography using a water-ACN gradient with 0.1% formic acid: $^1$H NMR (400 MHz, DMSO-$d_6$) δ 10.81 (s, 1H, exchangeable), 9.08 (s, 1H, exchangeable), 8.40 (d, J=8.0 Hz, 1H), 8.17 (s, 1H), 7.85 (s, 1H), 7.66 (d, J=1.5 Hz, 1H), 7.56 (d, 2H), 7.41 (t, 2H), 7.23 (t, 1H), 7.12 (s, 2H), 6.95 (s, 1H), 2.23 (s, 6H), 1.52 (s, 6H) ppm.

Example 45

Synthesis of N'-(tert-butyl)-N'-(3,5-dimethylbenzoyl)-1-hydroxy-2-(methylsulfonyl)-1,2-dihydrobenzo[d][1,2,3]diazaborinine-6-carbohydrazide

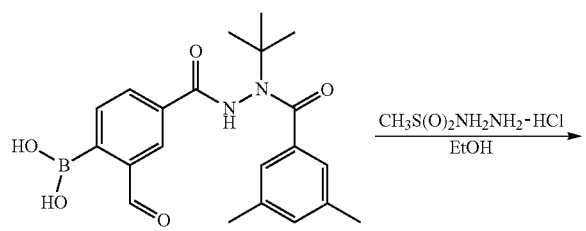

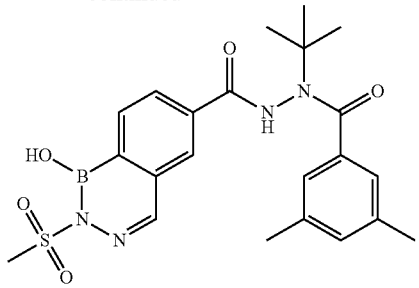

By analogy to (R)—N'-(3,5-dimethylbenzoyl)-N'-(2,2-dimethylpentan-3-yl)-1-hydroxy-2-(methylsulfonyl)-1,2-dihydrobenzo[d][1,2,3]diazaborinine-7-carbohydrazide and mixing methanesulfonylhydrazine HCl and the boronic aldehyde in abs. ethanol at room temperature for 9 days, N'-(tert-butyl)-N'-(3,5-dimethylbenzoyl)-1-hydroxy-2-(methylsulfonyl)-1,2-dihydrobenzo[d][1,2,3]diazaborinine-6-carbohydrazide was obtained after reverse-phase chromatography using a water-ACN gradient with 0.1% formic acid: $^1$H NMR (400 MHz, DMF-$d_7$) δ 10.82 (s, 1H, exchangeable), 8.45 (s, 1H, exchangeable), 8.16 (s, 1H), 8.16 (d, 1H), 7.82 (s, 1H), 7.68 (d, 1H), 7.09 (s, 2H), 6.93 (s, 1H), 3.35 (s, 3H), 2.21 (s, 6H), 1.51 (s, 9H) ppm.

Example 46

Synthesis of N-(tert-butyl)-1-hydroxy-N'-(3-methoxy-2-methylbenzoyl)-1H-benzo[d][1,2,6]oxazaborinine-7-carbohydrazide

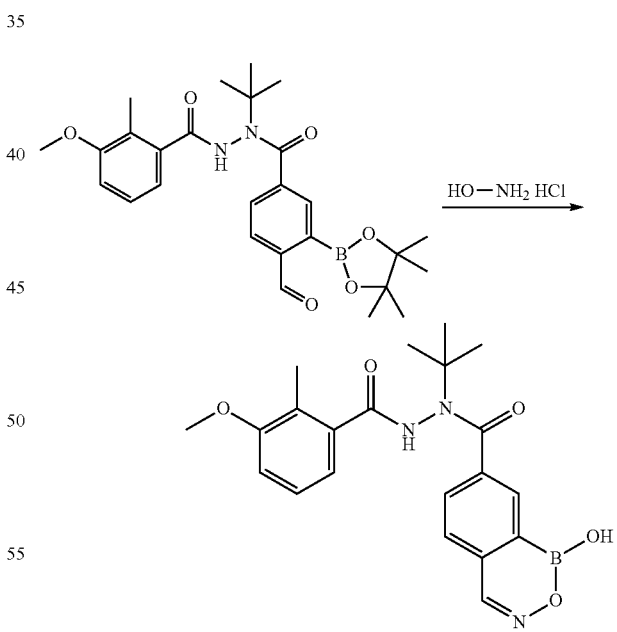

A solution of N'-(tert-butyl)-N'-(4-formyl-3-(4,4,5,5-tetramethyl-1,3,2-dioxaborolan-2-yl)benzoyl)-3-methoxy-2-methylbenzohydrazide (300 mg, 0.607 mmol) in 4 mL of H$_2$O was treated with hydroxylamine hydrochloride (127 mg, 1.820 mmol). The pH of the reaction mixture was adjusted to 4 with 1 N NaOH solution resulting in a voluminous white precipitate. Then added 4 drops of 95% EtOH to dissolve most of the solid. The reaction mixture was stirred at 23° C. for 16 h and then at with heating at 70° C. for 0.5 h affording a white precipitate, and upon cooling to room temperature, the white precipitate was collected by suction filtration and washed with cold water and then 40% aqueous EtOH to afford a white solid. The product was air dried with suction for 2 h and then at 40° C. under high vacuum for 18 h to give N-(tert-butyl)-1-hydroxy-N'-(3-methoxy-2-methylbenzoyl)-1H-benzo[d][1,2,6]oxazaborinine-7-carbohydrazide as a white powder. $^1$H NMR (400 MHz, DMSO) δ 11.39, 11.34, 10.67, 10.55, 9.48, 8.69, 8.16, 8.15, 8.15, 8.15, 7.84, 7.83, 7.82, 7.81, 7.75, 7.73, 7.58, 7.56, 7.47, 7.45, 7.11, 7.10, 7.08, 7.06, 6.98, 6.96, 6.94, 6.33, 6.31, 6.25, 6.23, 3.74, 3.74, 3.71, 3.32, 2.52, 2.51, 2.51, 2.50, 2.50, 1.58, 1.54, 1.51, 1.50, 1.49, 1.47 ppm; LCMS for $C_{21}H_{24}BN_3O_5$ (M+H)$^+$=410.

Example 47

Synthesis of N-(tert-butyl)-1-hydroxy-N'-(3-methoxy-2-methylbenzoyl)-1,2-dihydrobenzo[d][1,2,3]diazaborinine-7-carbohydrazide

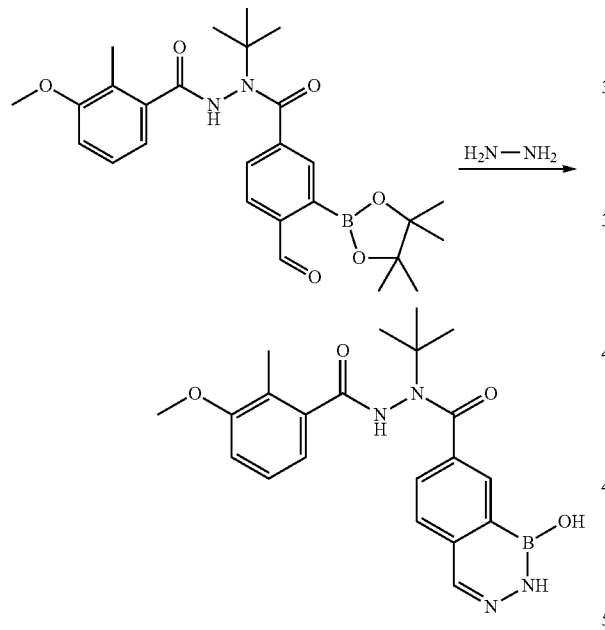

A solution of N'-(tert-butyl)-N'-(4-formyl-3-(4,4,5,5-tetramethyl-1,3,2-dioxaborolan-2-yl)benzoyl)-3-methoxy-2-methylbenzohydrazide (300 mg, 0.607 mmol) in 4 mL of EtOH was treated with hydrazine (38.9 mg, 1.214 mmol). The reaction mixture was stirred with 70° C. for 16 h, and upon cooling to room temperature, the precipitate was collected by suction filtration and washed with cold water and then $CH_2Cl_2$ to afford N-(tert-butyl)-1-hydroxy-N'-(3-methoxy-2-methylbenzoyl)-1,2-dihydrobenzo[d][1,2,3]diazaborinine-7-carbohydrazide as a white solid. $^1$H NMR (400 MHz, DMSO) δ 10.59, 9.99, 8.31, 8.31, 8.31, 8.22, 8.02, 7.75, 7.74, 7.73, 7.72, 7.69, 7.67, 7.06, 7.04, 7.02, 6.94, 6.92, 6.22, 6.21, 3.70, 3.31, 2.52, 2.51, 2.51, 2.50, 2.50, 1.55, 1.53, 1.51, 1.45 ppm; LCMS for $C_{21}H_{25}BN_4O_4$ (M+H)$^+$=409.

Example 48

Synthesis of N-(tert-butyl)-1-hydroxy-N'-(3-methoxy-2-methylbenzoyl)-2-methyl-1,2-dihydrobenzo[d][1,2,3]diazaborinine-7-carbohydrazide

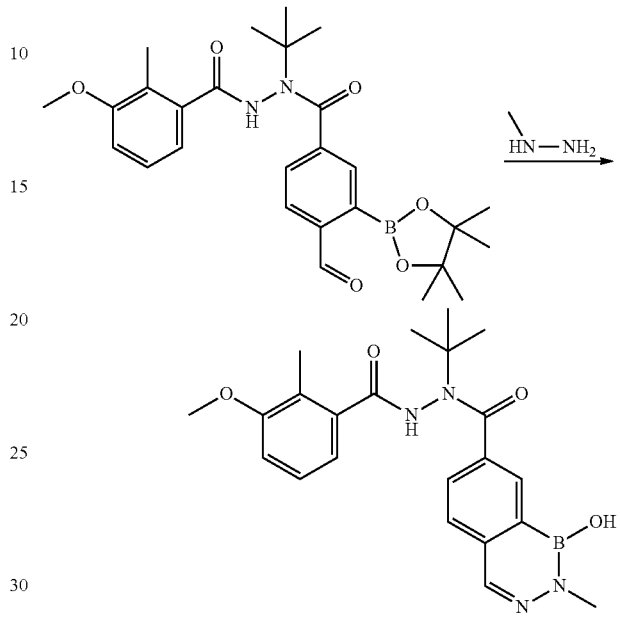

A solution of N'-(tert-butyl)-N'-(4-formyl-3-(4,4,5,5-tetramethyl-1,3,2-dioxaborolan-2-yl)benzoyl)-3-methoxy-2-methylbenzohydrazide (300 mg, 0.607 mmol) in 4 mL of EtOH was treated with methylhydrazine (55.9 mg, 1.214 mmol). The reaction mixture was stirred with 70° C. for 16 h, and upon cooling to room temperature, the precipitate was collected by suction filtration and washed with cold water and then $CH_2Cl_2$ to afford N-(tert-butyl)-1-hydroxy-N'-(3-methoxy-2-methylbenzoyl)-2-methyl-1,2-dihydrobenzo[d][1,2,3]diazaborinine-7-carbohydrazide as a white solid. $^1$H NMR (400 MHz, DMSO) δ 10.58, 10.52, 10.04, 8.59, 8.41, 8.02, 7.90, 7.74, 7.73, 7.72, 7.71, 7.70, 7.68, 7.64, 7.45, 7.42, 7.40, 7.06, 7.04, 7.02, 6.98, 6.96, 6.94, 6.92, 6.21, 6.19, 3.74, 3.73, 3.70, 3.52, 3.32, 3.18, 2.83, 2.52, 2.51, 2.51, 2.50, 1.59, 1.57, 1.55, 1.53, 1.50, 1.45 ppm; LCMS for $C_{22}H_{27}BN_4O_4$ (M+H)$^+$=423.

Example 49

Synthesis of N-(tert-butyl)-1-hydroxy-2-isopropyl-N'-(3-methoxy-2-methylbenzoyl)-1,2-dihydrobenzo[d][1,2,3]diazaborinine-7-carbohydrazide

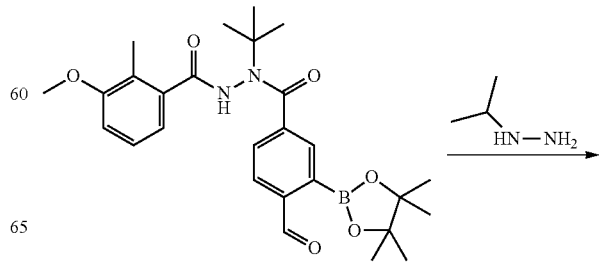

-continued

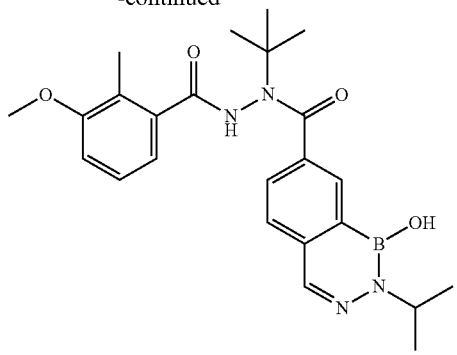

A solution of N'-(tert-butyl)-N'-(4-formyl-3-(4,4,5,5-tetramethyl-1,3,2-dioxaborolan-2-yl)benzoyl)-3-methoxy-2-methylbenzohydrazide (300 mg, 0.607 mmol) in 4 ml of 95% EtOH was treated with isopropylhydrazine (90 mg, 1.214 mmol). The reaction mixture was stirred with 70° C. for 16 h, and upon cooling to room temperature, the precipitate was collected by suction filtration and washed with cold water and then $CH_2Cl_2$ to afford N-(tert-butyl)-1-hydroxy-2-isopropyl-N'-(3-methoxy-2-methylbenzoyl)-1,2-dihydrobenzo[d][1,2,3]diazaborinine-7-carbohydrazide as a white solid. $^1$H NMR (400 MHz, DMSO) δ 10.62, 10.56, 10.48, 10.04, 8.53, 8.42, 8.42, 8.42, 8.09, 7.92, 7.90, 7.74, 7.74, 7.72, 7.72, 7.68, 7.66, 7.64, 7.62, 7.08, 7.08, 7.06, 7.04, 7.02, 6.98, 6.96, 6.94, 6.92, 6.91, 6.20, 6.19, 4.68, 4.67, 4.65, 4.63, 4.62, 3.74, 3.73, 3.73, 3.70, 3.68, 3.32, 2.55, 2.52, 2.51, 2.51, 2.50, 2.50, 1.73, 1.70, 1.70, 1.66, 1.65, 1.60, 1.57, 1.55, 1.53, 1.52, 1.51, 1.50, 1.48, 1.43, 1.43, 1.39, 1.33, 1.29, 1.27, 1.14, 1.12, 1.11, 1.10, 1.10, 1.09, 1.09, 1.08, 1.05, 1.04, 1.03, 1.02, 0.98, 0.98 ppm; LCMS for $C_{24}H_{31}BN_4O_4$ (M+H)$^+$=451.

Example 50

Synthesis of N-(tert-butyl)-1-hydroxy-N'-(3-methoxy-2-methylbenzoyl)-2-phenyl-1,2-dihydrobenzo[d][1,2,3]diazaborinine-7-carbohydrazide

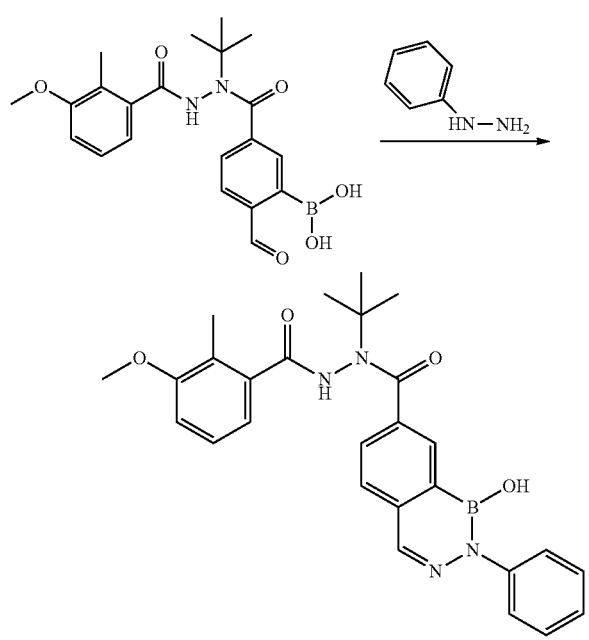

A solution of (5-(1-(tert-butyl)-2-(3-methoxy-2-methylbenzoyl)hydrazinecarbonyl)-2-formylphenyl)boronic acid (100 mg, 0.243 mmol) in 4 mL of EtOH was treated with phenylhydrazine (52.5 mg, 0.485 mmol). The reaction mixture was stirred with 70° C. for 16 h, and upon cooling to room temperature, the precipitate was collected by suction filtration and washed with cold water and then $CH_2Cl_2$ to afford N-(tert-butyl)-1-hydroxy-N'-(3-methoxy-2-methylbenzoyl)-2-phenyl-1,2-dihydrobenzo[d][1,2,3]diazaborinine-7-carbohydrazide as a white solid. $^1$H NMR (400 MHz, DMSO) δ 10.62, 9.05, 8.56, 8.23, 7.82, 7.82, 7.80, 7.80, 7.79, 7.77, 7.58, 7.58, 7.56, 7.43, 7.42, 7.40, 7.25, 7.23, 7.22, 7.09, 7.07, 7.05, 6.96, 6.94, 6.25, 6.23, 3.71, 3.32, 2.52, 2.51, 2.51, 2.50, 1.56, 1.52 ppm; LCMS for $C_{27}H_{29}BN_4O_4$ (M+H)$^+$=485.

Example 51

Synthesis of N-(tert-butyl)-1-hydroxy-N'-(3-methoxy-2-methylbenzoyl)-2-(methylsulfonyl)-1,2-dihydrobenzo[d]-[1,2,3]diazaborinine-7-carbohydrazide

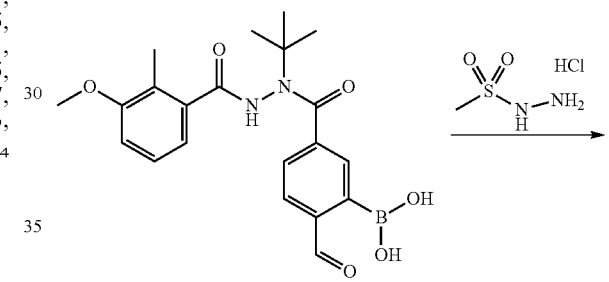

A solution of (5-(1-(tert-butyl)-2-(3-methoxy-2-methylbenzoyl) hydrazinecarbonyl)-2-formylphenyl)boronic acid (100 mg, 0.243 mmol) in 4 mL of 95% EtOH was treated with methanesulfonohydrazide hydrochloride (71.1 mg, 0.485 mmol). The reaction mixture was stirred with heating at 70° C. for 16 h, and upon cooling to room temperature, the precipitate was collected by suction filtration and washed with cold water and then CH$_2$Cl$_2$ to afford N-(tert-butyl)-1-hydroxy-N'-(3-methoxy-2-methylbenzoyl)-2-(methylsulfonyl)-1,2-dihydrobenzo[d][1,2,3]diazaborinine-7-carbohydrazide as a white solid. $^1$H NMR (400 MHz, DMSO) δ 10.65, 10.59, 8.79, 8.32, 8.29, 8.02, 7.85, 7.82, 7.80, 7.69, 7.09, 7.07, 7.05, 6.96, 6.94, 6.24, 6.22, 3.71, 3.70, 3.46, 3.44, 3.40, 2.52, 2.51, 2.51, 2.50, 2.50, 1.55, 1.52, 1.50, 1.08, 1.06, 1.04 ppm; LCMS for LCMS for C$_{22}$H$_{27}$BN$_4$O$_6$S (M+H)$^+$=487.

-continued

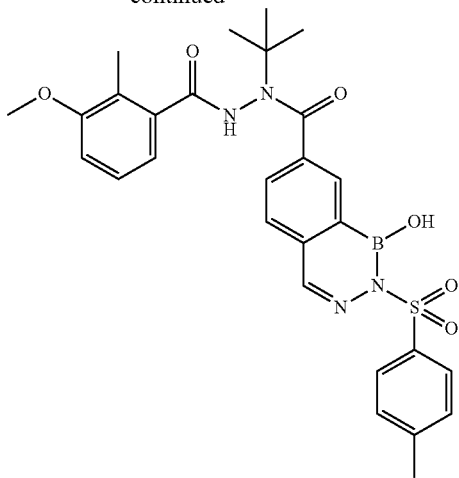

Example 52

Synthesis of N-(tert-butyl)-1-hydroxy-N'-(3-methoxy-2-methylbenzoyl)-2-tosyl-1,2-dihydrobenzo[d][1,2,3]diazaborinine-7-carbohydrazide

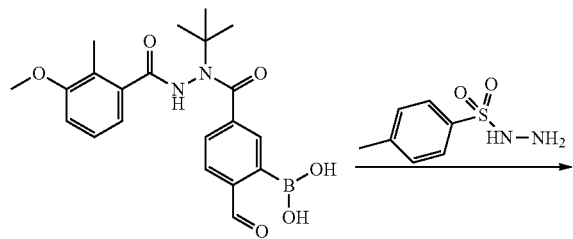

A solution of (5-(1-(tert-butyl)-2-(3-methoxy-2-methylbenzoyl) hydrazinecarbonyl)-2-formylphenyl)boronic acid (100 mg, 0.243 mmol) in 4 mL of EtOH was treated with 4-methylbenzenesulfonohydrazide (90 mg, 0.485 mmol) and one drop of glacial acetic acid. The reaction mixture was stirred with 70° C. for 16 h, and upon cooling to room temperature, the precipitate was collected by suction filtration and washed with cold water and then CH$_2$Cl$_2$ to afford N-(tert-butyl)-1-hydroxy-N'-(3-methoxy-2-methylbenzoyl)-2-tosyl-1,2-dihydrobenzo[d][1,2,3]diazaborinine-7-carbohydrazide as a white solid. $^1$H NMR (400 MHz, DMSO) δ 10.62, 8.97, 8.30, 8.18, 7.88, 7.86, 7.79, 7.79, 7.77, 7.77, 7.73, 7.71, 7.44, 7.42, 7.05, 7.03, 7.01, 6.95, 6.93, 6.21, 6.19, 3.71, 3.32, 2.51, 2.51, 2.50, 2.39, 1.54, 1.44 ppm; LCMS for C$_{28}$H$_{31}$BN$_4$O$_6$S (M+H)$^+$=563.

Example 53

Synthesis of N'-(tert-butyl)-3-cyano-N'-(3,5-dimethylbenzoyl)-1-hydroxy-1,3-dihydrobenzo[c][1,2]oxaborole-6-carbohydrazide

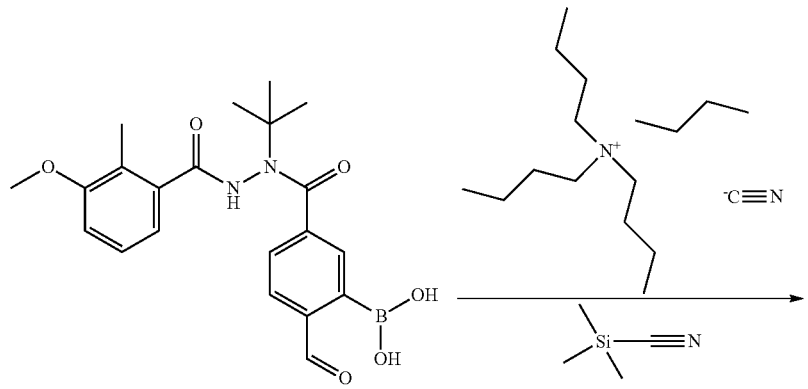

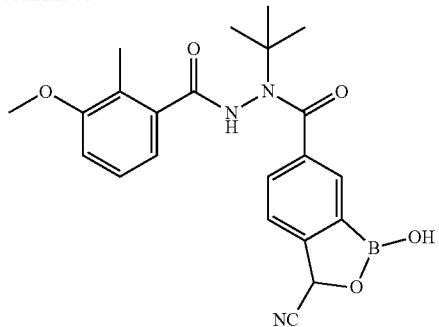

A solution of (5-(1-(tert-butyl)-2-(3-methoxy-2-methylbenzoyl) hydrazinecarbonyl)-2-formylphenyl)boronic acid (100 mg, 0.243 mmol) in dry DCM (1 mL) was added trimethylsilyl cyanide (0.036 ml, 0.267 mmol) under argon at 0° C. followed by a solution of tetrabutylammonium cyanide (9.77 mg, 0.036 mmol) in dry DCM (2 mL). The reaction mixture was stirred at 0° C. for 1 h, quenched with saturated aqueous NaHCO$_3$ solution (2 mL), and extracted with DCM. The combined organic layers were dried with MgSO$_4$, filtered and concentrated on a rotary evaporator. The N'-(tert-butyl)-3-cyano-N'-(3,5-dimethylbenzoyl)-1-hydroxy-1,3-dihydrobenzo[c][1,2]oxaborole-6-carbohydrazide as a white fluffy solid. $^1$H NMR (400 MHz, DMSO) δ 10.84, 10.82, 10.61, 10.58, 10.03, 10.01, 7.88, 7.86, 7.68, 7.67, 7.67, 7.66, 7.66, 7.65, 7.65, 7.64, 7.63, 7.61, 7.10, 7.08, 7.06, 7.05, 6.98, 6.96, 6.35, 6.35, 6.19, 6.17, 6.12, 6.10, 3.72, 3.72, 3.32, 2.55, 2.52, 2.51, 2.51, 2.50, 2.50, 1.54, 1.53, 1.51 ppm; LCMS for C$_{22}$H$_{24}$BN$_3$O$_5$ (M+H)$^+$=422.

Example 54

Synthesis of (R)—N-(2,2-dimethylpentan-3-yl)-1-hydroxy-N'-(3-methoxy-2-methylbenzoyl)-1,2-dihydrobenzo[d][1,2,3]diazaborinine-7-carbohydrazide A solution of (R)—N'-(2,2-dimethylpentan-3-yl)-N'-(4-formyl-3-(4,4,5,5-tetramethyl-1,3,2-dioxaborolan-2-yl)benzoyl)-3-methoxy-2-methylbenzohydrazide (150 mg, 0.280 mmol) in 4 mL of 95% EtOH was treated with hydrazine hydrate (28.0 mg, 0.559 mmol). The reaction mixture was stirred with heating at 70° C. for 16 h, and upon cooling to room temperature, the precipitate was collected by suction filtration and washed with 10% EtOH-cold water and then hexanes to afford (R)—N-(2,2-dimethylpentan-3-yl)-1-hydroxy-N'-(3-methoxy-2-methylbenzoyl)-1,2-dihydrobenzo[d][1,2,3]diazaborinine-7-carbohydrazide as a white solid. $^1$H NMR (400 MHz, DMSO) δ 11.44-10.00 (multiplet of overlapping s, 2H), 8.45-7.98 (m, 2H), 7.87-6.81 (overlapping m, 5H), 6.61-6.28 (m, 1H), 4.64-4.06 (m, 1H, chiral CH rotomers), 3.86-3.65 (m, 3H), 1.89-1.22 (m, 5H), 1.21-0.92 (m, 12H) ppm; LCMS for C$_{24}$H$_{31}$BN$_4$O$_4$ (M+H)$^+$=451.

Example 55

Synthesis of (R)—N-(2,2-dimethylpentan-3-yl)-1-hydroxy-N'-(3-methoxy-2-methylbenzoyl)-2-methyl-1,2-dihydrobenzo[d][1,2,3]diazaborinine-7-carbohydrazide

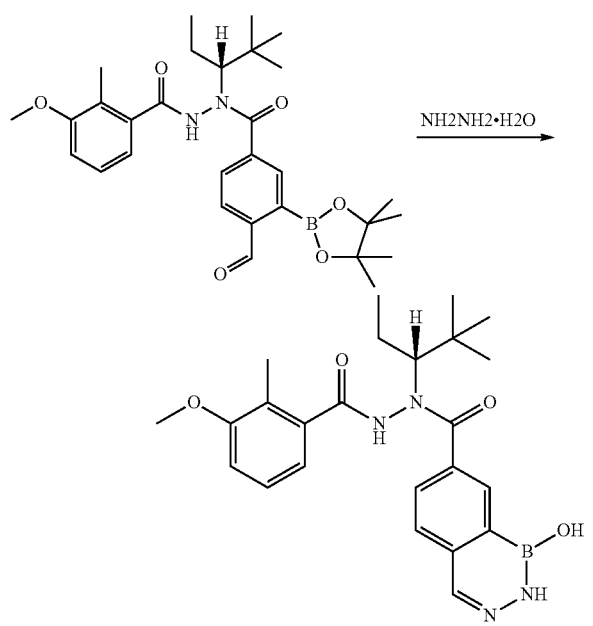

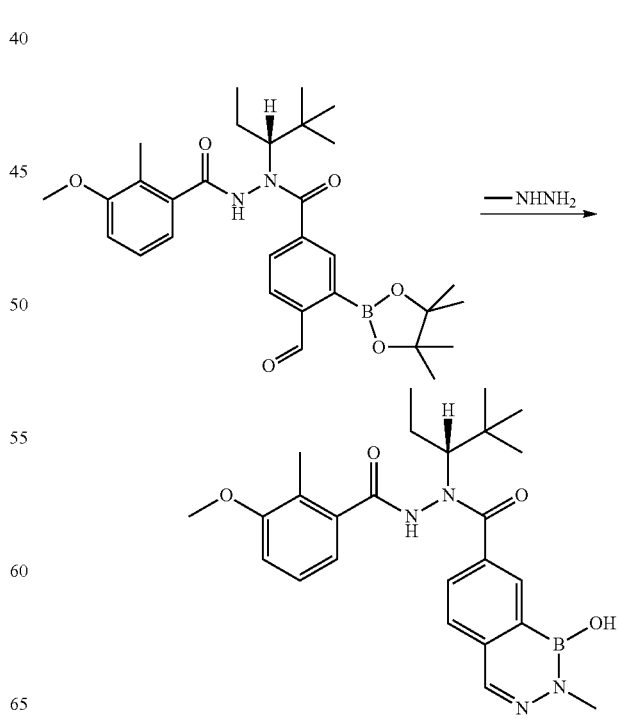

A solution of (R)—N'-(2,2-dimethylpentan-3-yl)-N'-(4-formyl-3-(4,4,5,5-tetramethyl-1,3,2-dioxaborolan-2-yl)benzoyl)-3-methoxy-2-methylbenzohydrazide (150 mg, 0.280 mmol) in 4 mL of 95% EtOH was treated with methylhydrazine (25.8 mg, 0.559 mmol). The reaction mixture was stirred with heating at 70° C. for 16 h, and upon cooling to room temperature, the precipitate was collected by suction filtration and washed with cold water and then $CH_2Cl_2$ to afford (R)—N-(2,2-dimethylpentan-3-yl)-1-hydroxy-N'-(3-methoxy-2-methylbenzoyl)-2-methyl-1,2-dihydrobenzo[d][1,2,3]diazaborinine-7-carbohydrazide as a white solid. LCMS for $C_{25}H_{33}BN_4O_4$ $(M+H)^+=465$.

Example 56

Synthesis of (R)—N-(2,2-dimethylpentan-3-yl)-1-hydroxy-N'-(3-methoxy-2-methylbenzoyl)-1H-benzo[d][1,2,6]oxazaborinine-7-carbohydrazide

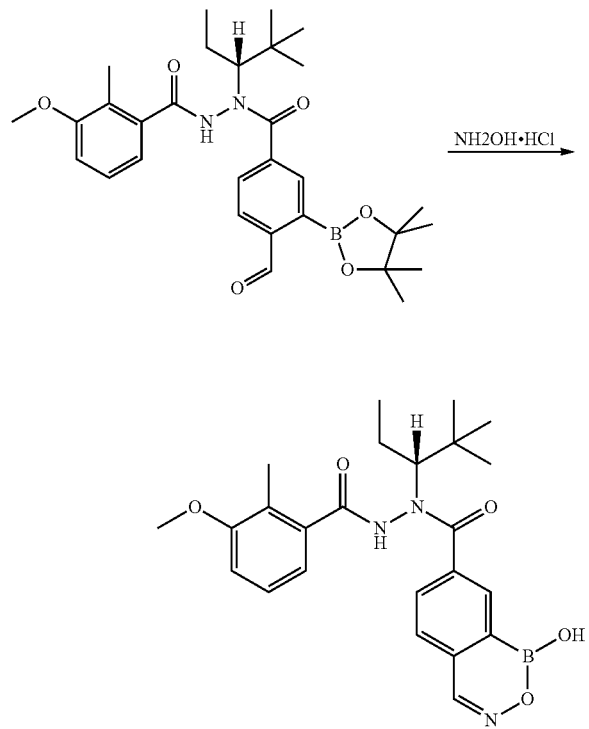

A solution of (R)—N'-(2,2-dimethylpentan-3-yl)-N'-(4-formyl-3-(4,4,5,5-tetramethyl-1,3,2-dioxaborolan-2-yl)benzoyl)-3-methoxy-2-methylbenzohydrazide (150 mg, 0.280 mmol) in 4 mL of 95% EtOH was treated with hydroxylamine hydrochloride (38.9 mg, 0.559 mmol). The reaction mixture was stirred with heating at 70° C. for 16 h, and upon cooling to room temperature, the precipitate was collected by suction filtration and washed with cold water and then $CH_2Cl_2$ to afford (R)—N-(2,2-dimethylpentan-3-yl)-1-hydroxy-N'-(3-methoxy-2-methylbenzoyl)-1H-benzo[d][1,2,6]oxazaborinine-7-carbohydrazide as a white solid. LCMS for $C_{24}H_{30}BN_3O_5$ $(M+H)^+=452$.

Example 57

Synthesis of 1,1'-oxybis(N'-(tert-butyl)-N'-(3,5-dimethylbenzoyl)-2-(pyridin-2-yl)-1,2-dihydrobenzo[d][1,2,3]diazaborinine-7-carbohydrazide)

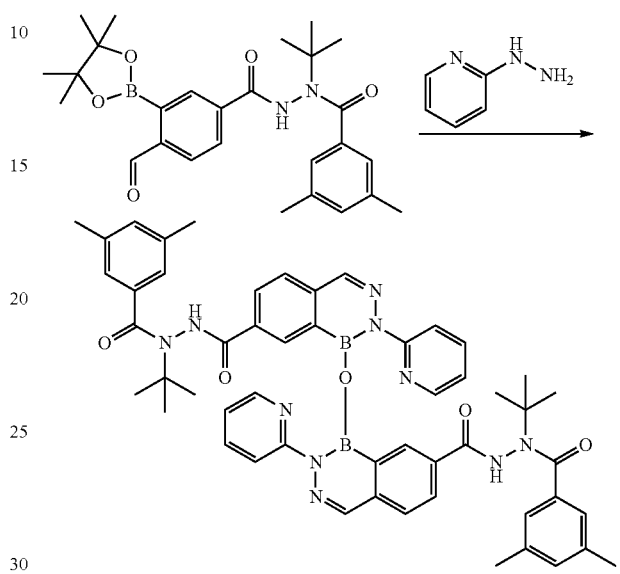

A solution of N'-(3,5-dimethylbenzoyl)-4-formyl-N'-isopropyl-3-(4,4,5,5-tetramethyl-1,3,2-dioxaborolan-2-yl)benzohydrazide (150 mg, 0.323 mmol) in 95% EtOH was treated with 2-hydrazinylpyridine (70.5 mg, 0.646 mmol). The reaction mixture was stirred with heating at 70° C. for 16 h, and upon cooling to room temperature, the precipitate was collected by suction filtration and washed with cold water and then $CH_2Cl_2$ to afford N'-(tert-butyl)-N'-(3,5-dimethylbenzoyl)-1-hydroxy-2-(pyridin-2-yl)-1,2-dihydrobenzo[d][1,2,3]diazaborinine-7-carbohydrazide (32 mg, 0.068 mmol, 21.11% yield) as a white solid. LCMS for $C_{52}H_{54}B_2N_{10}O_5$ $(M+H)^+=921$.

Example 58

Synthesis of N-(tert-butyl)-1-hydroxy-N'-(3-methoxy-2-methylbenzoyl)-1H-benzo[d][1,2,6]oxazaborinine-6-carbohydrazide

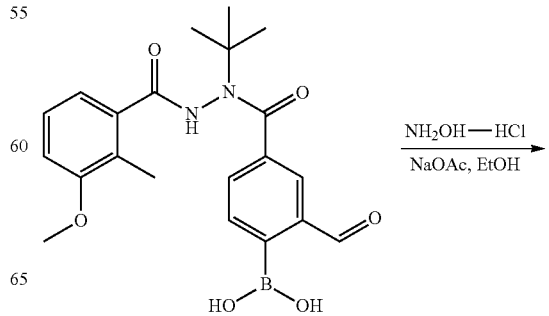

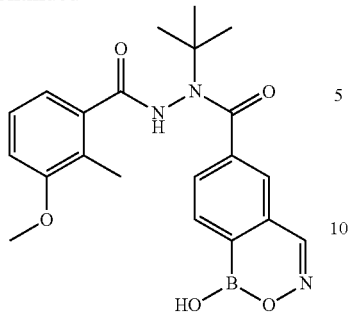

By analogy to (R)—N'-(3,5-dimethylbenzoyl)-N'-(2,2-dimethylpentan-3-yl)-1-hydroxy-1H-benzo[d][1,2,6]-oxazaborinine-7-carbohydrazide and mixing hydroxylamine HCl and the boronic aldehyde in abs. ethanol at room temperature for 8 hours, N-(tert-butyl)-1-hydroxy-N'-(3-methoxy-2-methylbenzoyl)-1H-benzo[d][1,2,6]oxazaborinine-6-carbohydrazide was obtained by washing the crude product with water and 5:1 hexanes:ether: $^1$H NMR (400 MHz, DMSO-$d_6$) δ 10.64 (s, 1H, exchangeable), 9.48 (s, 1H, exchangeable), 8.67 (d, J=0.6 Hz, 1H), 8.04 (d, J=7.7 Hz, 1H), 7.82 (s, 1H), 7.75 (dd, J=7.7, 1.5 Hz, 1H), 7.07 (t, 1H), 6.96 (d, J=1.1 Hz, 1H), 6.19 (dd, J=7.7, 1.1 Hz, 1H), 3.71 (s, 3H), 1.53 (s, 9H), 1.47 (s, 3H) ppm.

Example 59

Synthesis of N-(tert-butyl)-1-hydroxy-N'-(3-methoxy-2-methylbenzoyl)-1,2-dihydrobenzo[d][1,2,3]diazaborinine-6-carbohydrazide

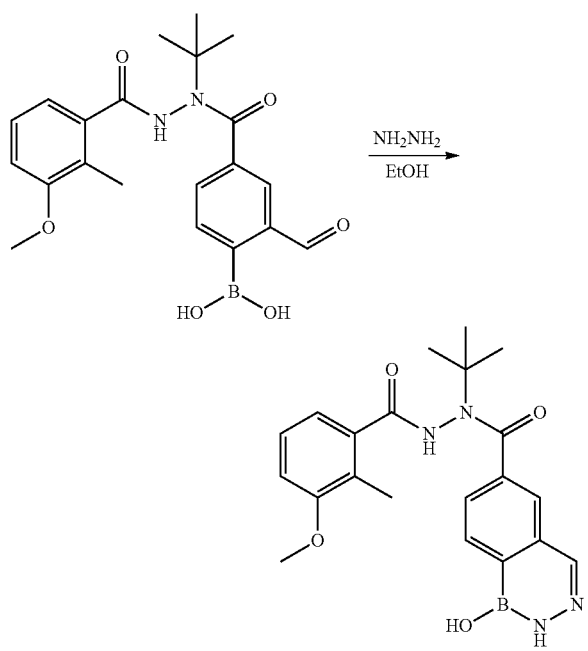

By analogy to (R)—N'-(3,5-dimethylbenzoyl)-N'-(2,2-dimethylpentan-3-yl)-1-hydroxy-1,2-dihydrobenzo[d]-[1,2,3]-diazaborinine-7-carbohydrazide and mixing hydrazine hydrate and the boronic aldehyde in abs. ethanol at room temperature for 6 hours, N-(tert-butyl)-1-hydroxy-N'-(3-methoxy-2-methylbenzoyl)-1,2-dihydrobenzo[d][1,2,3]diazaborinine-6-carbohydrazide was obtained by washing the crude product with water, ether, and hexanes: $^1$H NMR (400 MHz, DMSO-$d_6$) δ 10.58 (s, 1H, exchangeable), 10.00 (s, 1H, exchangeable), 8.22 (s, 1H, exchangeable), 8.14 (d, J=7.8 Hz, 1H), 7.99 (s, 1H), 7.78 (d, J=1.5 Hz, 1H), 7.59 (dd, J=7.8, 1.5 Hz, 1H), 7.03 (t, 1H), 6.93 (d, J=1.3 Hz, 1H), 6.18 (d, 1H), 3.69 (s, 3H), 1.54 (s, 9H), 1.43 (s, 3H) ppm.

Example 60

Synthesis of N-(tert-butyl)-1-hydroxy-N'-(3-methoxy-2-methylbenzoyl)-2-methyl-1,2-dihydrobenzo[d][1,2,3]diazaborinine-6-carbohydrazide

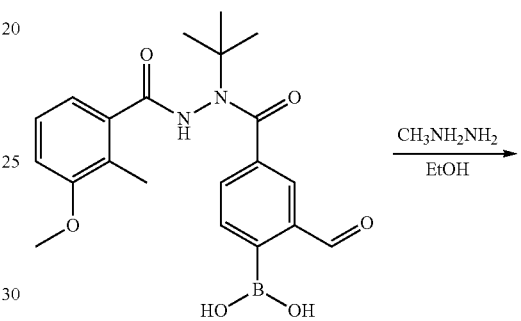

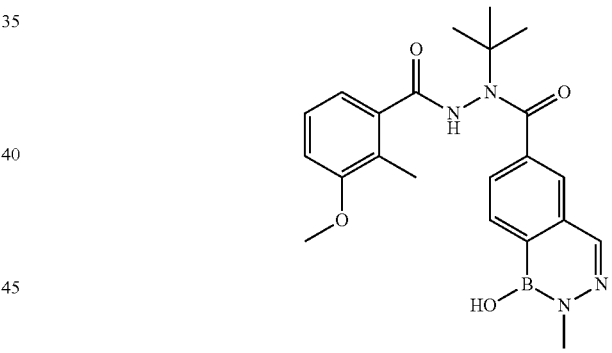

By analogy to N'-(tert-butyl)-N'-(3,5-dimethylbenzoyl)-1-hydroxy-2-methyl-1,2-dihydrobenzo[d]-[1,2,3]diazaborinine-7-carbohydrazide and mixing methylhydrazine hydrate and the boronic aldehyde in abs. ethanol at room temperature for 4.5 hours, N-(tert-butyl)-1-hydroxy-N'-(3-methoxy-2-methylbenzoyl)-2-methyl-1,2-dihydrobenzo[d][1,2,3]diazaborinine-6-carbohydrazide was obtained after reverse-phase chromatography using a water/acetonitrile gradient with 0.1% formic acid: $^1$H NMR (400 MHz, DMSO-$d_6$) δ 10.58 (s, 1H, exchangeable), 10.00 (s, 1H, exchangeable), 8.22 (s, 1H, exchangeable), 8.14 (d, J=7.8 Hz, 1H), 7.99 (s, 1H), 7.78 (d, J=1.5 Hz, 1H), 7.59 (dd, J=7.8, 1.5 Hz, 1H), 7.03 (t, 1H), 6.93 (d, J=1.3 Hz, 1H), 6.18 (d, 1H), 3.69 (s, 3H), 1.54 (s, 9H), 1.43 (s, 3H) ppm.

Example 61

Synthesis of 4-(bromomethyl)-3-(4,4,5,5-tetramethyl-1,3,2-dioxaborolan-2-yl)benzoic Acid

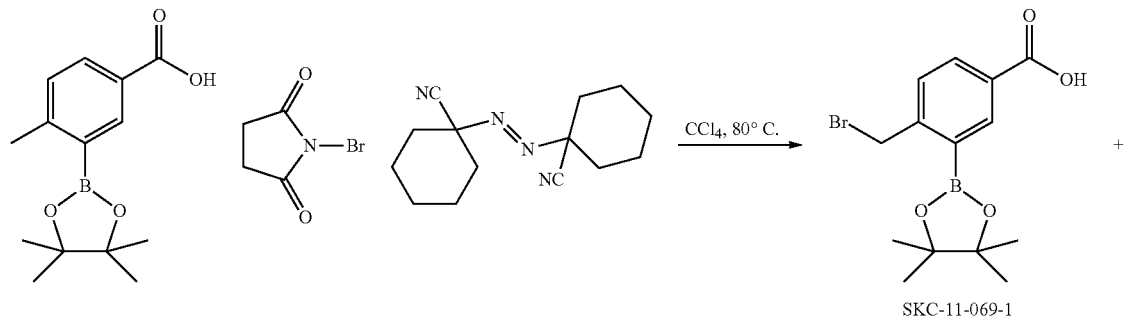

SKC-11-069-1

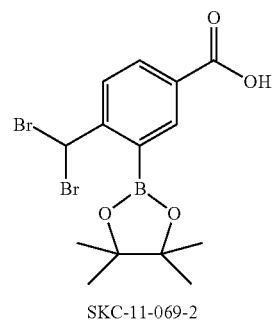

SKC-11-069-2

The reagents were added in 4 portions during 1 h to a stirred solution of the acid in anhydr.CCl$_4$ at 80° C. under argon. 4-methyl-3-(4,4,5,5-tetramethyl-1,3,2-dioxaborolan-2-yl)benzoic acid (commercial sample, 3.00 g, 11.45 mmol); 1-bromopyrrolidine-2,5-dione (2.06 g, 11.56 mmol) and [E]-1,1'[diazene-1,2-diyl)dicyclohexanecarbonitrile (0.280 g, 1.14 mmol) were used for the reaction. After the addition is completed, stirred the reaction mixture at 80° C. overnight under argon. A colorless suspension is noticed. Removed CCl$_4$ under vacuum and to the solid mixture was added DCM and water. Separated the layers and dried the org fractions over any MgSO$_4$, filtered and removed the solvent on a rotavapor. LCMS showed that the major pdt is the benzyl bromide, minor amount of dibromide also present. Dissolved the crude in DMSO and purified using 100 g of C18 column on ISCO in 4 batches. The first major peak was the pure monobromide (eluted with ~80% ACN/water solvent mixture, the less polar dibromide eluted in 90% acetonitrile/water. Both products are pure as judged by 1H NMR. 4-(bromomethyl)-3-(4,4,5,5-tetramethyl-1,3,2-dioxaborolan-2-yl)benzoic acid: $^1$H NMR (400 MHz, DMSO-d$_6$) δ 8.26 (s, 1H), 8.00 (dd, J=8.0, 2.0 Hz, 1H), 7.58 (m, 1H), 4.97 (s, 2H), 1.32 (s, 12H) ppm.

Example 62

Synthesis of 4-(bromomethyl)-3-(4,4,5,5-tetramethyl-1,3,2-dioxaborolan-2-yl)benzoyl chloride

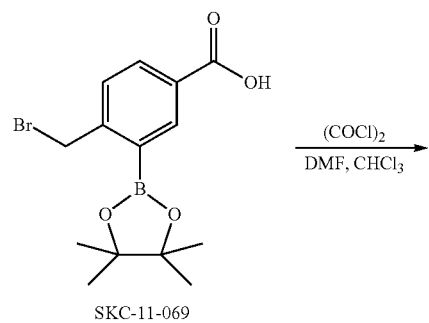

SKC-11-069

-continued

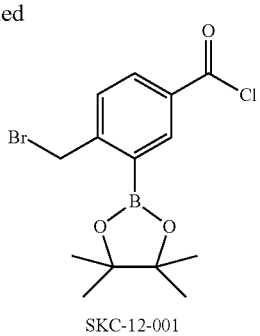

SKC-12-001

To a stirred solution of 4-(bromomethyl)-3-(4,4,5,5-tetramethyl-1,3,2-dioxaborolan-2-yl)benzoic acid (1.3 g, 3.81 mmol) in 8 ml of anhy. $CHCl_3$ in a 100 ml RB flask closed with a drying tube at room temperature was added oxalyl chloride (0.667 ml, 7.62 mmol) and one drop of anhy DMF. The mixture was stirred at RT for 2 hrs. LCMS of the sample was checked in $CH_3OH$, indicating quantitative conversion. The solvent was removed under vacuum on a rotavapor and dried using high vacuum pump. The solid was used as such for the next step. LC-MS (M+H)+ for methyl ester, $^{81}Br$=357.

Example 63

Synthesis of 4-(bromomethyl)-N'-(tert-butyl)-N'-(3,5-dimethylbenzoyl)-3-(4,4,5,5-tetramethyl-1,3,2-dioxaborolan-2-yl)benzohydrazide

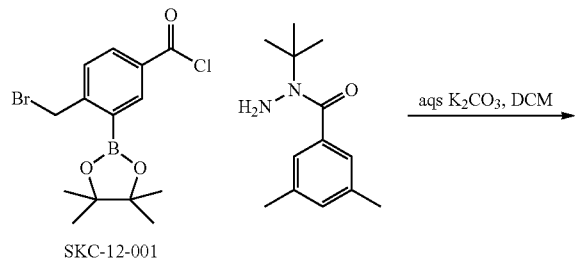

SKC-12-001

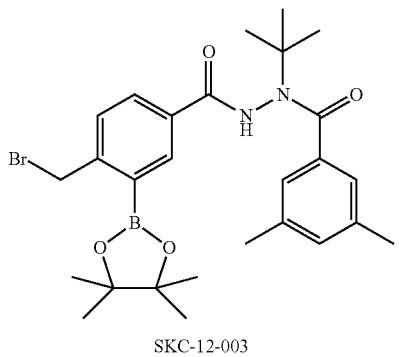

SKC-12-003

To a stirred solution of N-(tert-butyl)-3,5-dimethylbenzohydrazide (0.840 g, 3.81 mmol) in 17 ml DCM and 4.5 ml water (3.75:1 ratio) in a 100 ml RB flask was added potassium carbonate (1.58 g, 11.43 mmol) and stirred for few minutes. To this mixture, the above prepared benzoyl chloride (SKC-12-001, 1.37 g, 3.81 mmol) was added and continued to stir the reaction mixture overnight at rt. LCMS after 10 min showed formation of product, a peak with the expected product mass. After overnight stirring, diluted with water, extracted in DCM and a solid pdt obtained after evaporation of the solvent. Added ether and pentane, triturated and filtered to collect the pure solid sample as a colorless powder. $^1H$ NMR (400 MHz, DMSO-d6) δ 10.67 (s, 1H), 7.71 (s, 1H), 7.60-7.41 (dd, 2H), 7.08 (s, 2H), 6.93 (s, 1H), 4.92 (d, J=2.7 Hz, 2H), 2.23 (s, 6H), 1.48 (s, 9H), 1.33 (s, 12H). This material was used in the next step without purification.

Example 64

Synthesis of N'-(tert-butyl)-N'-(3,5-dimethylbenzoyl)-1-bydroxy-2,3-dihydro-1H-benzo[c][1,2]azaborole-6-carbohydrazide

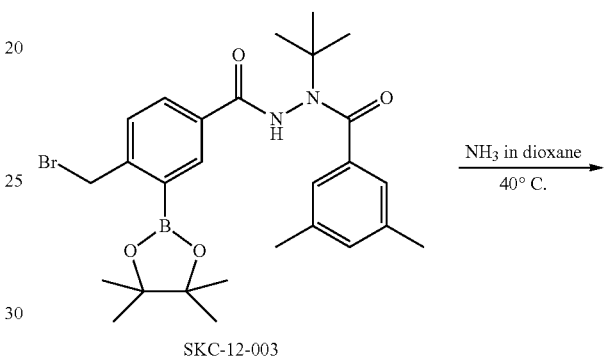

SKC-12-003

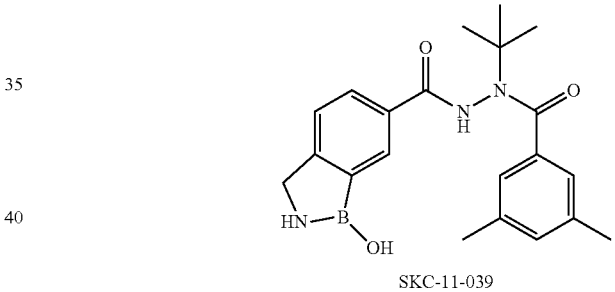

SKC-11-039

The above synthesized benzyl bromide (SKC-12-003, 300 mg, 0.552 mmol) was taken in a 100 ml RB flask fitted with a condenser. To this 20 ml of 0.5M solution of $NH_3$ in dioxane was added and stirred the mixture at 40° C. for 2 hours. LCMS checked in between, monitored the progress in the reaction, formation of the product with the expected mass of the azaborole and mass of the corresponding open chain form observed. The reaction mixture became light slurry, white color. After 2 h added another 15 ml of $NH_3$ solutions and heated for additional 2 h, LCMS showed a single peak. Removed the heating, cooled the clear solution in an ice bath and acidified to pH 3. The solvent was removed on a rotavapor without heating and the colorless crude solid product was finally purified on a reverse phase column (C18, ISCO, 0.1% solution of formic acid in water/acetonitrile solvent gradient). The first two peaks (A & B) gave the same mass on LCMS, (M+1)=380 as that of the expected azaborole. The peaks eluted with 100% water. From the $^1H$ NMR, it is found that there is some pinacol present. The solid product (SKC-11-039, 45 mg, 0.119 mmol) was treated with $NaIO_4$ (25.4 mg, 0.119 mmol) and 2.0 M HCl (0.059 ml, 0.119 mmol) at 0° C. for 30 min. and purified again on ISCO using C18 column. The single peak collected and dried to get pure N'-(tert-butyl)-N'-(3,5-dimethylbenzoyl)-1-bydroxy-2,3-dihydro-1H-benzo[c][1,2]azaborole-6-carbohydrazide. $^1$H NMR (400 MHz, DMSO-d6+ several drops D$_2$O) δ 7.61 (s, 1H), 7.29 (d, J=7.9, 1H), 7.12 (d, J=8.0 Hz, 1H), 7.05 (s, 2H), 6.89 (s, 1H), 3.91 (s, 2H), 2.18 (s, 6H), 1.45 (s, 9H). LC-MS (M+1)=380 found. The $^1$H NMR in DMSO-d6 without D$_2$O indicates several chemical species; these coalesce into mostly one species upon addition of D$_2$O. In D$_2$O alone, one species is observed: $^1$H NMR (400 MHz, D$_2$O) δ 7.34 (s, 1H), 7.2 (br, 2H), 7.02 (s, 1H), 7.01 (s, 2H), 4.1 (br, 2H), 2.19 (s, 6H), 1.51 (s, 9H) ppm. The primary species is assigned as the azaborole, in equilibrium with the tetrahedral zwitterionic borate and its open chain tautomer.

Example 65

Synthesis of (5-(2-(tert-butyl)-2-(3,5-dimethylbenzoyl)hydrazine-1-carbonyl)-2-((dimethylamino)-methyl)phenyl)boronic Acid

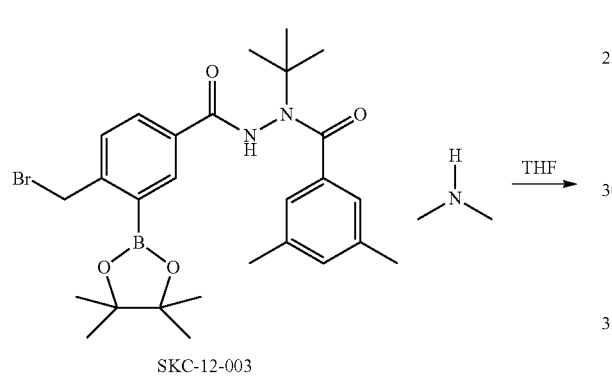

To a stirred solution of 4-(bromomethyl)-N'-(tert-butyl)-N'-(3,5-dimethylbenzoyl)-3-(4,4,5,5-tetramethyl-1,3,2-dioxaborolan-2-yl)benzohydrazide (SKC-12-003, 200 mg, 0.368 mmol) in THF (3 ml) in a scintillation vial at room temperature was added 2.0 M solution of dimethylamine in THF (0.368 ml, 0.736 mmol). The mixture was stirred for 1 hr. Reaction progress was checked by LCMS. After the reaction was complete, water was added, stirred for 10 min, the basic solution was cooled in an ice bath, and 2M HCl added slowly to adjust the pH 1-2. The mixture was stirred at ice temperature for ~1 h. The solvent was removed on a rotavapor without heating the water bath. Finally dissolved the colorless solid sample in DMSO and purified using a reverse phase C18 column (118 mg, 75% yield). $^1$H NMR (400 MHz, DMSO-d6+several drops D$_2$O) δ 8.17 (s, 1H), 7.57 (d, J=1.8 Hz, 1H), 7.27 (dd, J=7.8, 1.9 Hz, 1H), 7.07 (d, 1H), 7.05 (s, 2H), 6.90 (s, 1H), 3.73 (s, 2H), 2.27 (s, 6H), 2.19 (s, 6H), 1.45 (s, 9H). LC-MS (M+1)=426 found. The $^1$H NMR in DMSO alone indicated several species which coalesced into one upon addition of D$_2$O. Reference: JACS, 2006, 128, 1222-1232.

Example 66

Synthesis of (5-(2-(tert-butyl)-2-(3,5-dimethylbenzoyl)hydrazine-1-carbonyl)-2-((methylamino)-methyl)phenyl)boronic Acid

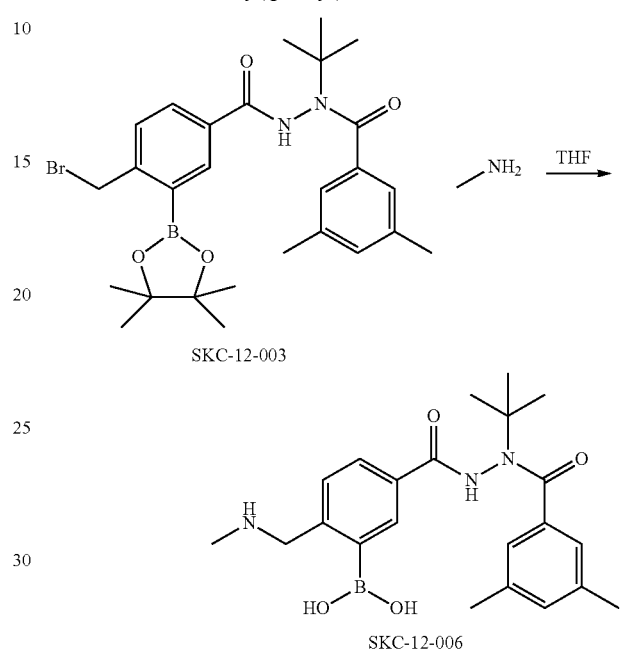

The experiment was performed as above using 4-(bromomethyl)-N'-(tert-butyl)-N'-(3,5-dimethylbenzoyl)-3-(4,4,5,5-tetramethyl-1,3,2-dioxaborolan-2-yl)benzohydrazide, SKC-12-003 (200 mg, 0.368 mmol) in 3 ml THF and 40% solution of methylamine in water (0.064 ml, 0.736 mmol) at room temperature for 1 h. After purification on ISCO using C18 column, the target compound was isolated (108 mg) in 71.3% yield. $^1$H NMR indicated primarily one species: $^1$H NMR (400 MHz, DMSO-d$_6$) δ 10.6 (m, 1H, exchangeable), 8.30 (br, 1H), 7.75 (s, 1H), 7.25 (m, 1H), 7.18 (d, J=7.9 Hz, 1H), 7.07 (s, 2H), 6.75 (m, 1H), 3.96 (s, 2H), 2.20 (s, 3H), 2.12 (s, 3H), 1.48 (s, 9H) ppm. LC-MS (M+1)=381, 412 found.

Example 67

Synthesis of N'-(tert-butyl)-4-(cyanomethyl)-N'-(3,5-dimethylbenzoyl)-3-(4,4,5,5-tetramethyl-1,3,2-dioxaborolan-2-yl)benzohydrazide

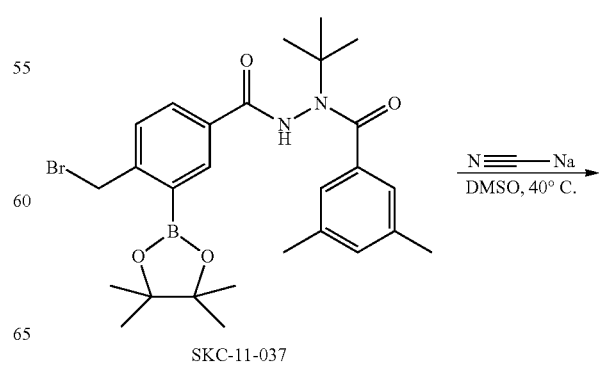

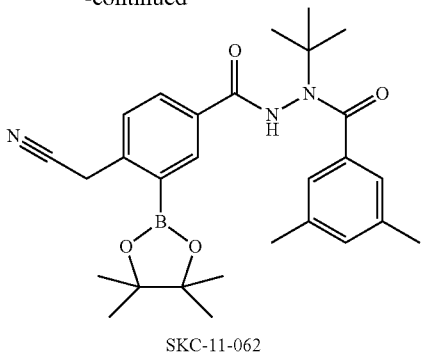

SKC-11-062

A solution of sodium cyanide (56.3 mg, 1.15 mmol) in DMSO (2 ml) at 40° C. was treated dropwise with a solution of 4-(bromomethyl)-N'-(tert-butyl)-N'-(3,5-dimethylbenzoyl)-3-(4,4,5,5-tetramethyl-1,3,2-dioxaborolan-2-yl)benzohydrazide (SKC-11-037, 347.0 mg, 0.639 mmol) in DMSO (3 ml) and stirred for 90 min at 40° C., cooled to room temperature, quenched with sat. aqs NaCl and extracted with ethyl acetate. See WO 2009/012252 and US 2007/0219240. The crude product was purified on ISCO using a C18 reverse phase column. The purified product was concentrated under vacuum to get 180.0 mg of sticky solid product, this is used as such for the hydrogenation step. $^1$H NMR (400 MHz, DMSO-$d_6$) δ 10.7 (s, 1H), 7.76 (d, J=2.0 Hz, 1H), 7.61 (dd, J=8.0, 2.0 Hz, 1H), 7.46 (d, J=8.0 Hz, 1H), 7.15 (s, 2H), 6.98 (s, 1H), 4.13 (s, 2H), 2.22 (s, 6H), 1.48 (s, 9H), 1.33 (s, 12H) ppm.

Example 68

Synthesis of N'-(tert-butyl)-N'-(3,5-dimethylbenzoyl)-1-hydroxy-1,2,3,4-tetrahydrobenzo[c][1,2]azaborinine-7-carbohydrazide

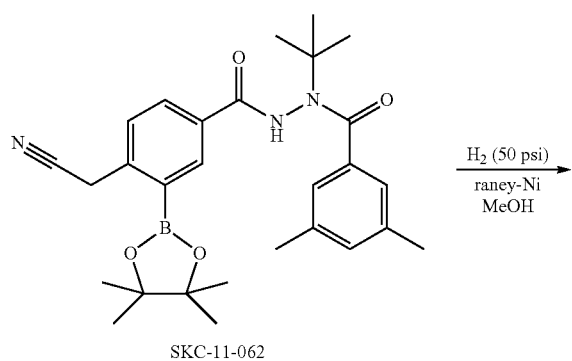

SKC-11-062

SKC-11-065
SKC-12-016

The reaction was performed using a Paar shaker hydrogenation apparatus. To a Paar bottle was added Raney-Nickel, the above synthesized N'-(tert-butyl)-4-(cyanomethyl)-N'-(3,5-dimethylbenzoyl)-3-(4,4,5,5-tetramethyl-1,3,2-dioxaborolan-2-yl)benzohydrazide (SKC-11-062, 105 mg) and 15 ml of CH$_3$OH. The mixture was flushed with argon. The bottle was fixed tightly on the hydrogenation apparatus, evacuated under vacuum and filled with H$_2$ up to 50 psi. The reaction mixture was shaken overnight at room temperature. LCMS showed the expected mass of the azaborinine, (M+1)=394 for an early-eluting product and a mass of (M+1)=494 for a later-eluting product corresponding to the ortho-aminoethyl pinacolate ester. The mixture was filtered through a short pad of Celite and the green solution removed on a rotavap under vacuum to get the crude product. KOH (7% aqueous) was added and the mixture was stirred for 20 min. The boron pinacolate ester hydrolyzed, thereby enriching the sample in the target azaborinine. The mixture was cooled and acidified using 2M HCl to pH 2-3; LCMS continued to indicate a major peak with (M+1)=394. Solvent was removed the under vacuum on a rotavapor. The product was dissolved in DMSO and purified using C18 column on ISCO. As some pinacolate remained, the product (40 mg) was treated with sodium periodate (21.7 mg, 0.102 mmol) and 2.0 M HCl (0.051 ml, 0.102 mmol) at 0° C. for 1 h in a scintillation vial. LCMS again showed (M+1)=394 for the expected azaborinine. The solvent was removed on a rotavapor under vacuum; dissolved in DMSO and purified using C18 column on ISCO. $^1$H NMR in DMSO with a small amount of D$_2$O indicated principally as one species: N'-(tert-butyl)-N'-(3,5-dimethylbenzoyl)-1-hydroxy-1,2,3,4-tetrahydrobenzo[c][1,2]azaborinine-7-carbohydrazide: $^1$H NMR (400 MHz, DMSO-$d_6$+D$_2$O) δ 7.63 (s, 1H), 7.16 (m, 1H), 7.08 (s, 2H), 6.98 (m, 1H), 6.88 (s, 1H), 2.96 (t, J=6.3 Hz, 2H), 2.81 (br m, 2H), 2.18 (s, 6H), 1.44 (s, 9H) ppm. The $^1$H NMR spectrum in DMSO alone indicates multiple equilibrating conformers or chemical species.

Example 69

Synthesis of (5-(2-(tert-butyl)-2-(3,5-dimethylbenzoyl)hydrazine-1-carbonyl)-2-(cyanomethyl)-phenyl)boronic Acid

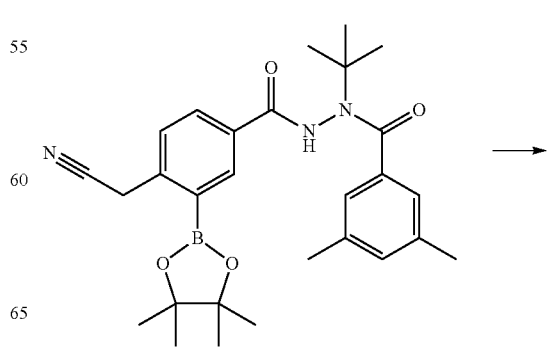

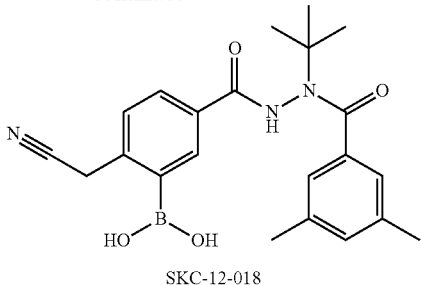

SKC-12-018

N'-(tert-butyl)-4-(cyanomethyl)-N'-(3,5-dimethylbenzoyl)-3-(4,4,5,5-tetramethyl-1,3,2-dioxaborolan-2-yl)benzohydrazide as a mixture with its boronic acid (45 mg) was dissolved in 2.5 mL 4:1 THF:water and chilled to 0° C. Sodium periodate (23.6 mg, 1 eq.) and 2N HCl (55 uL) were added. The mixture was stirred at 0 C for 1 hour. The solvent was removed on a rotovap, and the crude product was dissolved on DMSO and purified by reverse phase chromatography. $^1$H NMR (400 MHz, DMSO-$d_6$) δ 10.58 (s, 1H, exchangeable), 8.36 (s, 2H, exchangeable), 7.82 (d, J=2.0 Hz, 1H), 7.45 (dd, J=8.0, 2.0 Hz, 1H), 7.37 (d, J=8.1 Hz, 1H), 7.15 (s, 2H), 6.92 (s, 1H), 4.12+4.07 (s+br, 2H), 2.21 (s, 6H), 1.48 (s, 9H) ppm.

Example 70

Synthesis of N'-(4-(bromomethyl)-3-(4,4,5,5-tetramethyl-1,3,2-dioxaborolan-2-yl)benzoyl)-N'-(tert-butyl)-3-methoxy-2-methylbenzohydrazide

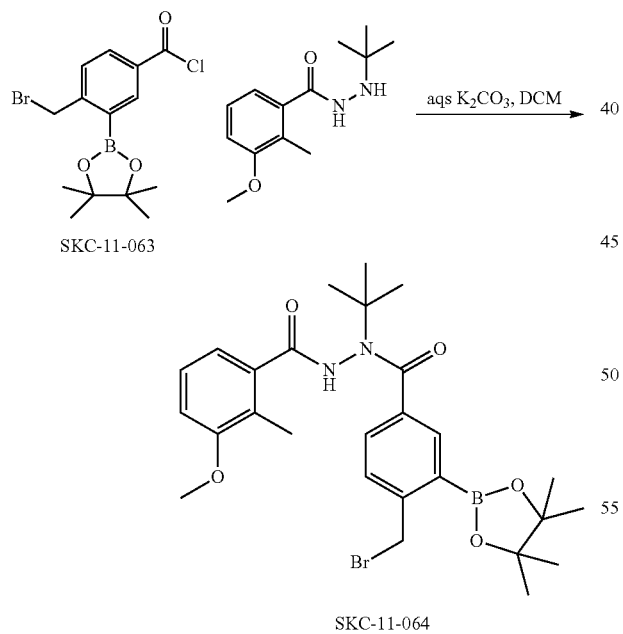

SKC-11-064

N'-(tert-butyl)-3-methoxy-2-methylbenzohydrazide (191 mg, 0.807 mmol) was taken in a 100 ml RB flask and added anhydrous K$_2$CO$_3$ (335 mg, 2.420 mmol), 4 ml Ch2Cl2 and 1 ml water and stirred the mixture at room temperature for few minutes. To this mixture, the above synthesized acid chloride (SKC-11-063, 290 mg) in 2 ml of CH2Cl2 was added and stirred at room temperature for 15 minutes. LCMS showed formation of product plus some monoacylhydrqazide remaining. The reaction mixture was stirred for several additional days. After aqueous work up and extraction in CH2Cl2, the crude mixture was ca. 85% pure. The crude product was purified on a reverse phase C18 column. After isolation and drying, $^1$H NMR indicated N'-(4-(bromomethyl)-3-(4,4,5,5-tetramethyl-1,3,2-dioxaborolan-2-yl) benzoyl)-N'-(tert-butyl)-3-methoxy-2-methylbenzohydrazide (SKC-11-064, 380 mg, 84% yield). $^1$H NMR (400 MHz, DMSO-$d_6$) δ 10.54 (s, 1H), 7.75 (s, 1H), 7.48 (dd, J=7.8, 2.0 Hz, 1H), 7.43 (d, J=7.9 Hz, 1H), 7.07 (t, J=8.0 Hz, 1H), 6.96 (d, J=8.1 Hz, 1H), 6.21 (d, J=7.5 Hz, 1H), 4.96 (s, 1H), 3.73 s, 3H), 1.65 (s, 3H), 1.50 (s, 9H), 1.33 (s, 12H) ppm.

Example 71

Synthesis of N-(tert-butyl)-1-hydroxy-N'-(3-methoxy-2-methylbenzoyl)-1,3-dihydrobenzo[c][1,2]oxaborole-6-carbohydrazide

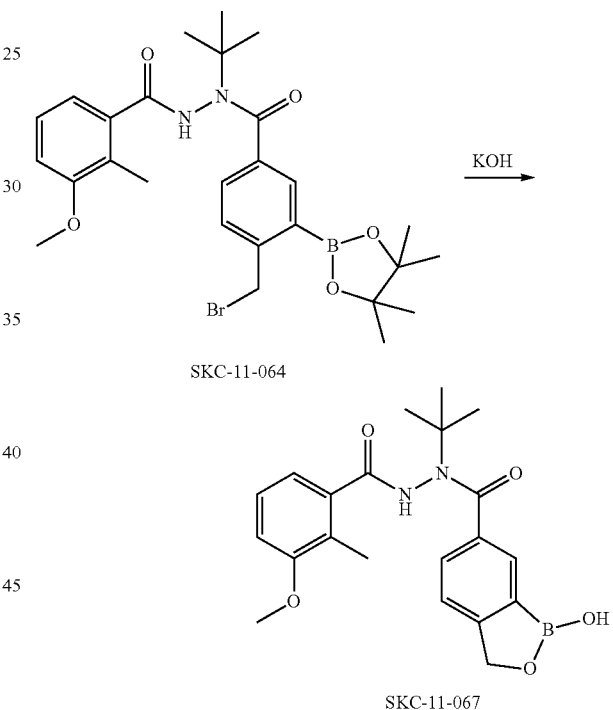

KOH (10 ml 7% aqueous solution) was added to N'-(4-(bromomethyl)-3-(4,4,5,5-tetramethyl-1,3,2-dioxaborolan-2-yl)benzoyl)-N'-(tert-butyl)-3-methoxy-2-methylbenzohydrazide (SKC-11-064, 140 mg, 0.250 mmol) in 6 ml water in a 100 ml RB flask. The mixture was stirred at room temperature for 30 min to 2 h. After 30 min, LCMS indicated the formation of product boroxole. After 2 hours, the mixture was cooled in an ice bath. 2M HCl was added slowly to adjust the pH to ~2. The crude mixture was filtered immediately and the solid was collected, rinsed with water, and washed with pentane. The filtrate was extracted in DCM and LCMS of both aqueous and organic fractions showed peak with the expected product mass. Both organic and aqueous portions were combined, the solvent was removed, and the residue was purified on a reverse phase C18 column. Pure N-(tert-butyl)-1-hydroxy-N'-(3-methoxy-2-methylbenzoyl)-

1,3-dihydrobenzo[c][1,2]oxaborole-6-carbohydrazide was isolated as a colorless solid (SKC-11-067, 61.0 mg, 61.5% yield). $^1$H NMR (400 MHz, DMSO-d$_6$) δ 10.54 (s, 1H), 9.21 (s, 1H), 7.83 (s, 1H), 7.53 (dd, J=7.8, 1.7 Hz, 1H), 7.38 (d, J=7.9 Hz, 1H), 7.08 (t, J=7.9 Hz, 1H), 6.95 (d, J=8.1 Hz, 1H), 6.23 (dd, J=7.6, 1.1 Hz, 1H), 5.01 (s, 2H), 3.72 (s, 3H), 1.65 (s, 3H), 1.52 (s, 9H) ppm.

Example 72

Synthesis of N-(tert-butyl)-1-hydroxy-N'-(3-methoxy-2-methylbenzoyl)-2,3-dihydro-1H-benzo[c][1,2]azaborole-6-carbohydrazide

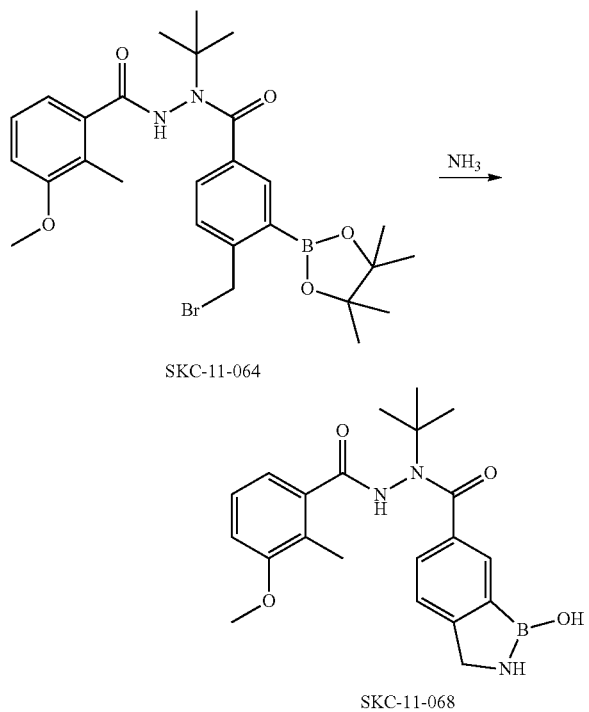

NH$_3$ in dioxane (30 ml 0.5M) was added to N'-(4-(bromomethyl)-3-(4,4,5,5-tetramethyl-1,3,2-dioxaborolan-2-yl)benzoyl)-N'-(tert-butyl)-3-methoxy-2-methylbenzohydrazide (SKC-11-064, 140 mg, 0.250 mmol). The mixture was stirred at 40° C. for 1 hour. After 1 hour, LCMS indicated the formation of product with (M+1)=396. The reaction mixture was cooled in an ice bath. 2M HCl was added slowly to adjust the pH to 3-4. A white precipitate formed, but was insufficient to filter. The solvent was removed on a rotavapor without heating and the crude product was purified by flash chromatography using a reverse phase C18 column. After solvent removal and lyophilization, 62 mg (62.7% yield) of colorless solid product was obtained. LC-MS (M+1)=396. $^1$H NMR (400 MHz, DMSO-d$_6$+several drops D$_2$O) δ 8.29 (s, 1H), 7.57 (s, 1H), 7.28 (dd, J=7.8, 1.8 Hz, 1H), 7.14 (d, J=7.9 Hz, 1H), 7.06 (t, J=7.9 Hz, 1H), 6.92 (dd, J=8.5, 1.1 Hz, 1H), 6.23 (dd, J=7.7, 1.1 Hz, 1H), 3.99 (s, 2H), 3.68 (s, 3H), 1.63 (s, 3H), 1.46 (s, 9H) ppm. $^1$H NMR in DMSO alone was more complex, suggestive of a more complex mixture of equilibrating conformations or acid/base, or tautomeric chemical species.

Example 73

Synthesis of 3-nitro-4-(4,4,5,5-tetramethyl-1,3,2-dioxaborolan-2-yl)benzoyl chloride

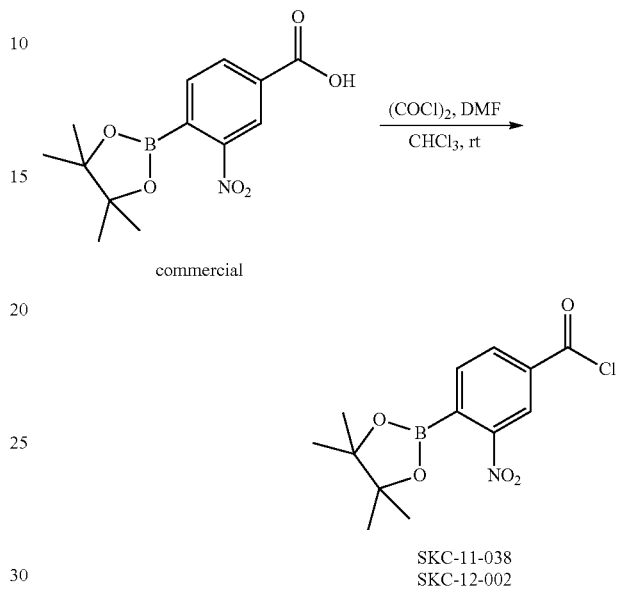

To a stirred solution of 3-nitro-4-(4,4,5,5-tetramethyl-1,3,2-dioxaborolan-2-yl)benzoic acid (5.0 g, 17.06 mmol) in 50 ml of anhydrous CHCl$_3$ in a 200 ml RB flask closed with a drying tube at room temperature was added oxalyl chloride (2.99 ml, 34.1 mmol) and one drop of anhydrous DMF. The mixture was stirred at room temperature for 2.5 hours. LCMS of the sample was checked by conversion to with methyl ester with CH$_3$OH, quantitative conversion. The solvent was removed under vacuum on a rotavapor and dried using high vacuum pump. The solid was used as such for the next step. $^1$H NMR (400 MHz, CDCl3) δ 8.86 (d, J=1.6 Hz, 1H), 8.36 (dt, J=7.8, 1.3 Hz, 1H), 7.73 (d, J=7.7 Hz, 1H), 1.44 (d, J=0.9 Hz, 12H) ppm.

Example 74

Synthesis of N'-(tert-butyl)-N'-(3,5-dimethylbenzoyl)-3-nitro-4-(4,4,5,5-tetramethyl-1,3,2-dioxaborolan-2-yl)benzohydrazide

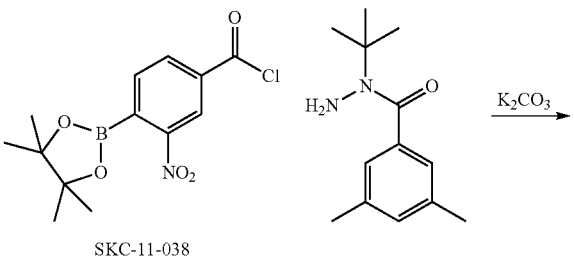

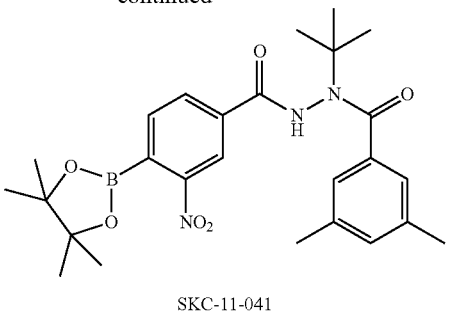

SKC-11-041

N-(tert-butyl)-3,5-dimethylbenzohydrazide (3.41 g, 15.47 mmol) was taken in a 500 ml RB flask and added anhydrous $K_2CO_3$ (6.41 g, 46.4 mmol), 70 ml CH2Cl2, and 23 ml water and stirred the mixture at room temperature for few minutes. To this mixture, 3-nitro-4-(4,4,5,5-tetramethyl-1,3,2-dioxaborolan-2-yl)benzoyl chloride (SKC-11-038, 5.3 g, 17.01 mmol) was added and the mixture was stirred at room temperature for 15 minutes. LCMS showed formation of product. After aqueous work up and extraction in CH2Cl2, the crude mixture was triturated with an ether/pentane mixture, the solid precipitate was collected & dried under vacuum and used for the next step (SKC-11-041, 7.0 g, 91% yield). N'-(tert-butyl)-N'-(3,5-dimethylbenzoyl)-3-nitro-4-(4,4,5,5-tetramethyl-1,3,2-dioxaborolan-2-yl)benzohydrazide: $^1$H NMR (400 MHz, DMSO-$d_6$) δ 10.97 (s, 1H), 8.15 (d, J=1.4 Hz, 1H), 7.90 (dd, J=7.6, 1.5 Hz, 1H), 7.70 (d, J=7.6 Hz, 1H), 7.07 (s, 2H), 6.92 (s, 1H), 2.21 (s, 6H), 1.49 (s, 9H), 1.33 (s, 12H) ppm.

Example 75

Synthesis of 3-amino-N'-(tert-butyl)-N'-(3,5-dimethylbenzoyl)-4-(4,4,5,5-tetramethyl-1,3,2-dioxaborolan-2-yl)benzohydrazide

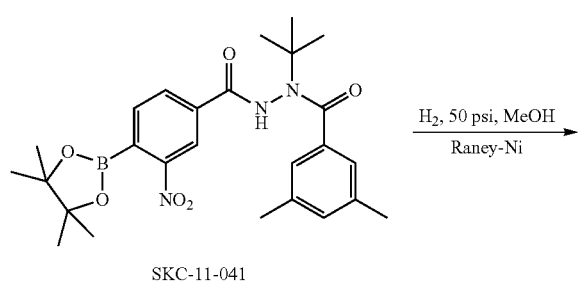

SKC-11-041

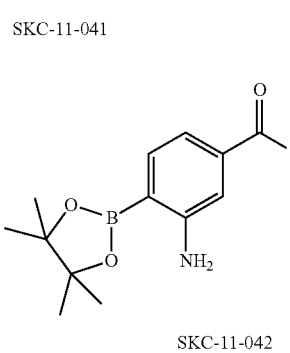

SKC-11-042

The reaction was performed using a Paar shaker hydrogenation apparatus. To the Paar bottle was added a tiny spatula tip of Raney-Nickel (neutral pH), the above synthesized N'-(tert-butyl)-N'-(3,5-dimethylbenzoyl)-3-nitro-4-(4,4,5,5-tetramethyl-1,3,2-dioxaborolan-2-yl)benzohydrazide (SKC-11-041, 5.0 g, 10.09 mmol) and 100 ml of $CH_3OH$. The mixture was flushed with argon. The bottle was fixed tightly on the hydrogenation apparatus, evacuated under vacuum and filled with $H_2$ up to 50 Psi. The reaction mixture was shaken overnight at room temperature. LCMS showed complete conversion to product. The crude mixture was filtered through a short pad of Celite and the solvent was removed on a rotavapor to obtain the crude 3-amino-N'-(tert-butyl)-N'-(3,5-dimethylbenzoyl)-4-(4,4,5,5-tetramethyl-1,3,2-dioxaborolan-2-yl)benzohydrazide as a light green solid (SKC-11-042, 4.6 g, 98% yield. $^1$H NMR (400 MHz, DMSO-$d_6$) δ 10.44 (s, 1H), 7.32 (d, J=7.7 Hz, 1H), 7.05 (m, 2H), 6.92 (m, 1H), 6.75 (d, J=1.5 Hz, 1H), 6.51 (dd, J=7.8, 1.5 Hz, 1H), 5.62 (s, 2H), 2.21 (s, 6H), 1.46 (s, 9H), 1.27 (s, 12H) ppm. The sample was stored under refrigeration until use for subsequent condensation reactions.

General procedure for addition or condensation reactions: see Groziak, M P; Chapter 1, boron Heterocycles as platforms for building new bioactive agents and JACS 116: 7597-7605 (1994). The reactions were performed in a scintillation vials in dioxane at 60-70° C., stirred for 30 min-120 min. The reactions were monitored by LCMS. After the reaction, the solvent was removed, the crude product was dissolved in DMSO and purified using C18 reverse phase flash chromatogroahy. The fractions for the major peak were collected, solvent was removed, and the product was dried under vacuum.

In many cases, the $^1$H NMR spectrum in DMSO was complex, suggestive of a mixture of equilibrating conformations, conjugate acid/base, or tautomeric (ring/chain; N, O) chemical species. Addition of a few drops of $D_2O$ to the DMSO-d6 solution frequently caused equilibrating species to coalesce into one form.

Example 76

Synthesis of N'-(tert-butyl)-N'-(3,5-dimethylbenzoyl)-1-hydroxy-3-methyl-1H-benzo[c][1,5,2]oxazaborinine-6-carbohydrazide

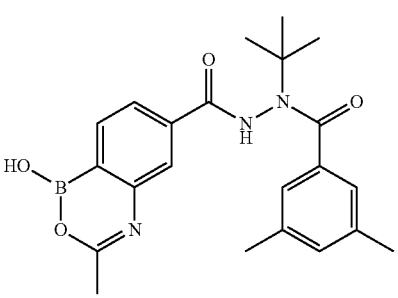 [SMILES: CC1=Nc2cc(C(=O)NN(C(=O)c3cc(C)cc(C)c3)C(C)(C)C)ccc2B(O)O1]

Following the general procedure and using 3-amino-N'-(tert-butyl)-N'-(3,5-dimethylbenzoyl)-4-(4,4,5,5-tetramethyl-1,3,2-dioxaborolan-2-yl)benzohydrazide (SKC-11-042, 200 mg, 0.430 mmol), acetic anhydride (0.608 ml, 6.45 mmol) and 2 ml of dioxane at 60° C. for 45 min, the title compound (lot SKC-11-053A) was isolated as a solid product (88 mg, 50% yield). $^1$H NMR (400 MHz, DMSO-$d_6$) δ 11.82 (s, 1H, exchangeable), 10.54 (s, 1H, exchangeable), 7.65 (s, 1H), 7.50 (d, J=7.5 Hz, 1H), 7.15 (d, J=7.8 Hz, 1H), 7.06 (s, 2H), 6.89 (s, 1H), 2.19 (s, 6H), 2.04 (s, 3H), 1.48 (s, 9H).

Hz, 1H), 7.59 (s, 1H), 7.38 (t, J=7.6 Hz, 2H), 7.35-7.24 (m, 1H), 7.17-7.04 (m, 5H), 6.95 (s, 1H), 2.22 (s, 6H), 1.51 (s, 9H) ppm.

Example 77

Synthesis of N'-(tert-butyl)-N'-(3,5-dimethylbenzoyl)-1-hydroxy-1H-benzo[c][1,5,2]oxazaborinine-6-carbohydrazide

Example 79

Synthesis of N'-(tert-butyl)-N'-(3,5-dimethylbenzoyl)-1-hydroxy-3-oxo-2-(p-tolyl)-1,2,3,4-tetrahydrobenzo[c][1,5,2]diazaborinine-6-carbohydrazide

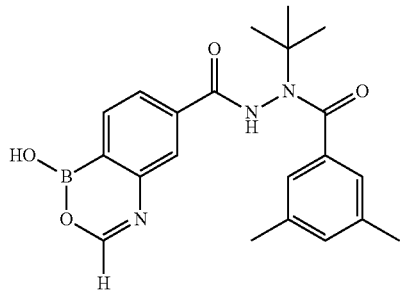 [SMILES: Cc1cc(C)cc(C(=O)N(NC(=O)c2ccc3c(c2)N=COB3O)C(C)(C)C)c1]

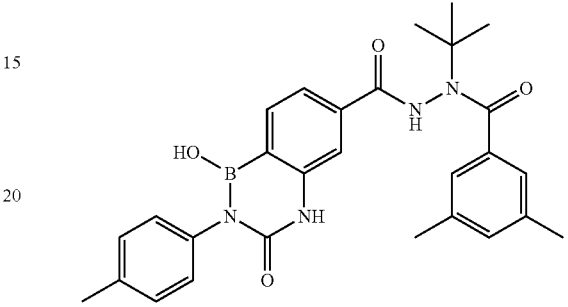

Following the general procedure and using 3-amino-N'-(tert-butyl)-N'-(3,5-dimethylbenzoyl)-4-(4,4,5,5-tetramethyl-1,3,2-dioxaborolan-2-yl)benzohydrazide (SKC-11-042, 200 mg, 0.430 mmol), formic acid (0.330 ml, 8.59 mmol) and 2 ml of dioxane at 60° C. for 45 min, the title compound (lot SKC-11-053B) was isolated as a solid product (58 mg, 34.3% yield). $^1$H NMR (400 MHz, DMSO-$d_6$+ $D_2O$) δ 8.30 (s, 1H), 8.07 (s, 1H), 7.60 (d, J=7.7 Hz, 1H), 7.09 (dd, J=7.7, 1.6 Hz, 1H), 7.02 (s, 2H), 6.92 (s, 1H), 2.18 (s, 6H), 1.45 (s, 9H) ppm.

Following the general procedure and using 3-amino-N'-(tert-butyl)-N'-(3,5-dimethylbenzoyl)-4-(4,4,5,5-tetramethyl-1,3,2-dioxaborolan-2-yl)benzohydrazide (SKC-11-042, 300 mg, 0.645 mmol), 1-isocyanato-4-methylbenzene (0.082 ml, 0.645 mmol) and 2 ml of dioxane at 70° C. for 2 h. The title compound SKC-11-054B was isolated as a solid product (105 mg, 32.7% yield). $^1$H NMR (400 MHz, DMSO-$d_6$) δ 10.65 (s, 1H, exchangeable), 10.50 (s, 1H, exchangeable), 9.07 (br, 1H, exchangeable), 7.97 (d, J=7.8 Hz, 1H), 7.26 (d, J=1.4 Hz, 1H), 7.17 (d, J=8.0 Hz, 2H), 7.08 (br s, 2H), 7.00 (dq, J=8.3, 2.6, 2.0 Hz, 3H), 6.94 (s, 1H), 2.33 (s, 3H), 2.22 (s, 6H), 1.50 (s, 9H) ppm.

Example 78

Synthesis of N'-(tert-butyl)-N'-(3,5-dimethylbenzoyl)-1-hydroxy-2-phenyl-3-thioxo-1,2,3,4-tetrahydrobenzo[c][1,5,2]diazaborinine-6-carbohydrazide

Example 80

Synthesis of N'-(3,5-dimethylbenzoyl)-1-hydroxy-3-(trifluoromethyl)-1H-benzo[c][1,5,2]oxazaborinine-6-carbohydrazide

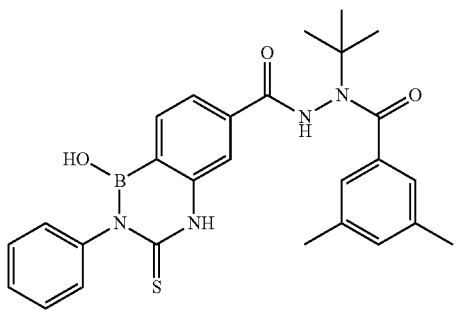

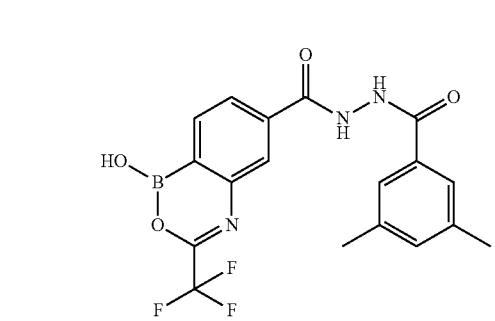 [SMILES: Cc1cc(C)cc(C(=O)NNC(=O)c2ccc3c(c2)N=C(C(F)(F)F)OB3O)c1]

Following the general procedure and using 3-amino-N'-(tert-butyl)-N'-(3,5-dimethylbenzoyl)-4-(4,4,5,5-tetramethyl-1,3,2-dioxaborolan-2-yl)benzohydrazide (SKC-11-042, 300 mg, 0.645 mmol), isothiocyanatobenzene (0.077 ml, 0.645 mmol) and 2 ml of dioxane at 60° C. for overnight. The title compound SKC-11-054A was isolated as a solid product (226 mg, 70.1% yield). $^1$H NMR (400 MHz, DMSO-$d_6$) δ 12.08 (s, 1H, exchangeable), 10.70 (s, 1H, exchangeable), 9.4 (br, 1H, exchangeable), 8.04 (d, J=7.8

The reagents 3-amino-N'-(tert-butyl)-N'-(3,5-dimethylbenzoyl)-4-(4,4,5,5-tetramethyl-1,3,2-dioxaborolan-2-yl) benzohydrazide (SKC-11-042, 200 mg, 0.430 mmol), trifluoroacetic anhydride (0.303 ml, 2.15 mmol) were mixed in a scintillation vial in dioxane (2 ml) at room temperature and stirred for 30 min. The clear solution became a thick suspension, LCMS did not show a product mass, so heated to 60° C. and stirred for 2 hrs. LCMS showed a peak with the mass of 406, indicating loss of the tert-butyl group.

Dioxane was removed and the product purified using reverse phase C18 flash chromatography to isolate the title compound SKC-11-056 (48.0 mg, 27.6% yield). $^1$H NMR (400 MHz, DMSO-$d_6$) δ 11.79 (s, 1H, exchangeable), 9.13 (s, 2H, exchangeable), 8.81 (d, J=2.6 Hz, 1H), 8.04 (m, 1H), 7.98 (m, 1H), 7.75 (s, 2H), 7.30 (s, 1H), 2.40 (6H) ppm.

Example 81

Synthesis of (4-(2-(tert-butyl)-2-(3,5-dimethylbenzoyl)hydrazine-1-carbonyl)-2-(phenylsulfonamido)phenyl)boronic Acid

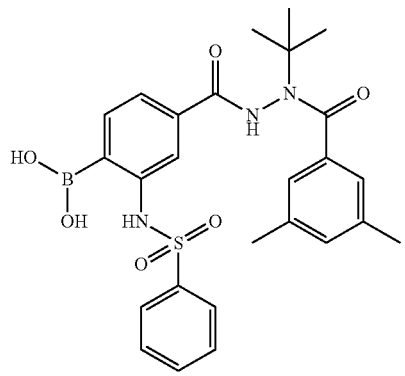 [SMILES: Cc1cc(C)cc(C(=O)N(NC(=O)c2ccc(B(O)O)c(NS(=O)(=O)c3ccccc3)c2)C(C)(C)C)c1]

Following the general procedure and using 3-amino-N'-(tert-butyl)-N'-(3,5-dimethylbenzoyl)-4-(4,4,5,5-tetramethyl-1,3,2-dioxaborolan-2-yl)benzohydrazide (SKC-11-042, 250 mg, 0.537 mmol), benzenesulfonyl chloride (0.083 ml, 0.645 mmol) and 2 ml of dioxane at 60° C. overnight. See BMCL 8: 843-846 (1998). LCMS showed one main peak with a mass of 524.36, corresponding to the open form. The solvent was removed and the crude mixture was purified using reverse phase C18 flash chromatography, twice in sequence to provide the title compound (lot SKC-11-058) as a solid (59.0 mg, 21% yield). $^1$H NMR (400 MHz, DMSO-$d_6$+$D_2$O) δ 7.64-7.49 (m, 3H), 7.49-7.35 (m, 3H), 7.01 (d, J=1.4 Hz, 1H), 6.98 (s, 2H), 6.93 (s, 1H), 2.18 (s, 6H), 1.43 (s, 9H) ppm. LC-MS (M+1)=524.

Example 82

Synthesis of (4-(2-(tert-butyl)-2-(3,5-dimethylbenzoyl)hydrazine-1-carbonyl)-2-((cyanomethyl)amino)-phenyl)boronic Acid

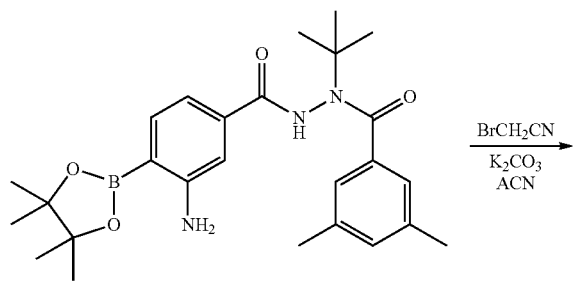

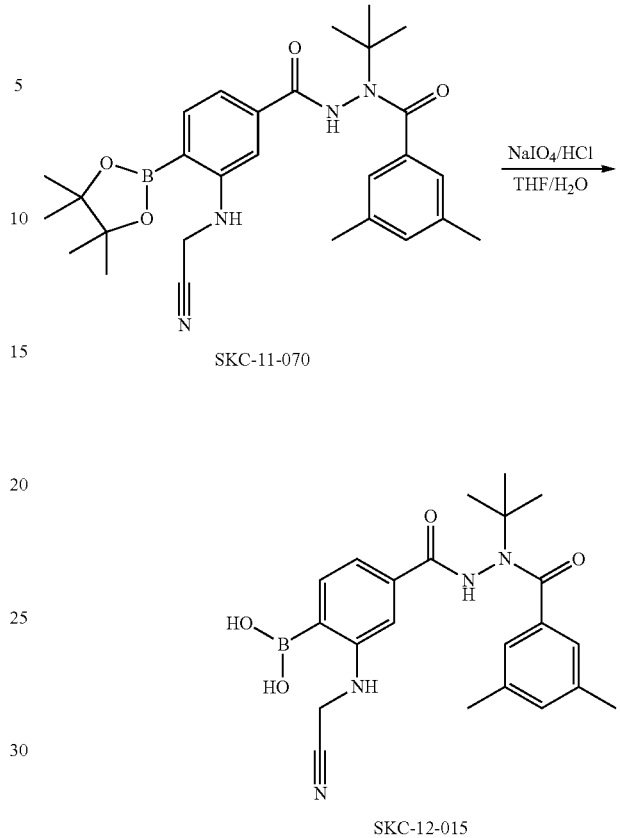

Step 1. Bromoacetonitrile (186 mg, 1.55 mmol) was added to a suspension of K2CO3 (267 mg, 1.93 mmol) and 3-amino-N'-(tert-butyl)-N'-(3,5-dimethylbenzoyl)-4-(4,4,5,5-tetramethyl-1,3,2-dioxaborolan-2-yl)benzohydrazide (600 mg, 1.29 mmol) in 6 mL acetonitrile. The reaction was heated at 40 C for 2 hours and then stirred overnight at room temperature. The mixture was diluted with water, extracted into ethyl acetate, and dried over MgSO4. After filtration and solvent removal in vacuo, the crude product was purified by reverse phase flash chromatography. $^1$H NMR (400 MHz, DMSO-$d_6$+$D_2$O) δ 7.45 (d, J=7.6 Hz, 1H), 7.00 (s, 2H), 6.91 (s, 1H), 6.81-6.62 (m, 2H), 4.26 (2s, 2H), 2.18 (s, 6H), 1.45 (s, 9H), 1.25 (s, 8H) ppm. A singlet at 1.05 indicated the presence of pinacol and therefore some pinacolate hydrolysis. LC-MS (M+1)=505.

Step 2. N'-(tert-butyl)-3-((cyanomethyl)amino)-N'-(3,5-dimethylbenzoyl)-4-(4,4,5,5-tetramethyl-1,3,2-dioxaborolan-2-yl)benzohydrazide (48 mg, 0.095 mmol) was mixed with NaIO4 (20.4 mg, 0.095 mmol) and HCl (48 uL of a 2N solution) in 2.5 mL of 4:1 THF:H2O. The reaction mixture was stirred for 1 hour at 0 C and monitored by 1C-Ms. The solvent was removed in vacuo and the crude product was purified by reverse phase flash chromatography. $^1$H NMR (400 MHz, DMSO-$d_6$) δ 10.47 (s, 1H, exchangeable), 8.51 (s, 2H, exchangeable), 7.60 (d, J=8.0 Hz, 1H), 7.07 (d, J=1.6 Hz, 2H), 6.92 (s, 1H), 6.87 (t, J=6.8 Hz, 1H), 6.74 (s, 1H), 6.73 (s, 1H, exchangeable), 4.32 (d, J=6.7 Hz, 2H), 2.21 (s, 6H), 1.48 (s, 9H) ppm.

Example 83

Synthesis of N'-(tert-butyl)-N'-(3,5-dimethylbenzoyl)-1-hydroxy-1,3,4,5-tetrahydrobenzo[c][1,5,2]oxazaborepine-7-carbohydrazide

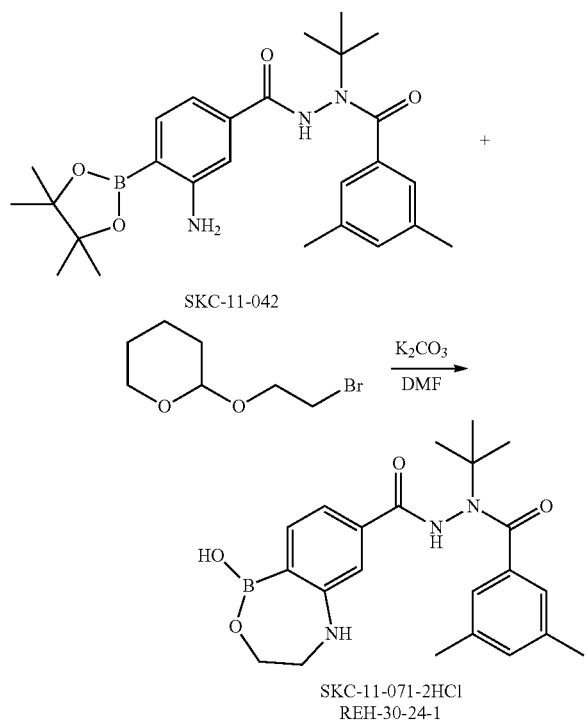

2-(2-bromoethoxy)tetrahydro-2H-pyran (270 mg, 1.29 mmole) was added to a stirred solution of 3-amino-N'-(tert-butyl)-N'-(3,5-dimethylbenzoyl)-4-(4,4,5,5-tetramethyl-1,3,2-dioxaborolan-2-yl)benzohydrazide (400 mg, 0.859 mmole), and potassium carbonate (238 mg, 1.7 mmole) in 5 mL DMF. The reaction was heated at 40 C for 2 hours, and then stirred overnight at room temperature. The mixture was diluted with water, extracted into ethyl acetate, and dried over MgSO4. After filtration and solvent removal in vacuo, the crude product was purified by reverse phase flash chromatography. Selected fractions representing combinations of THP protected- or Bpin'ylated intermediates, were treated with an acetonitrile/water solution containing 0.15% formic acid (RP HPLC mobile phase), the acidity of which was later fortified by the addition of 2M HCl at 0 C. When the deprotection was deemed to be complete, the solvent was removed in vacuo and the crude mixture was purified reverse phase flash chromatography to provide 78 mg of impure oxazaborepin (lot SKC-11-071-2 HCl). Re-chromatography under similar conditions provided N'-(tert-butyl)-N'-(3,5-dimethylbenzoyl)-1-hydroxy-1,3,4,5-tetrahydrobenzo[c][1,5,2]oxazaborepine-7-carbohydrazide (lot REH-30-24-1): $^1$H NMR (400 MHz, DMSO-d6) δ 10.46+10.43 (2s, 1H), 8.00+7.95 (2s, 1H), 7.77+7.63 (2d, J=7.9 Hz, 1H), 7.05 (s, 2H), 6.93 (s, 1H), 6.68+6.52 (2dd, J=7.9, 1.4 Hz, 1H), 4.03+3.51 (2m, 1H), 3.95+3.43 (2m, 1H), 2.21 (s, 6H), 1.48+1.46 (2s, 9H) ppm, as 2 conformers, tautomers, or conjugate acid-base forms.

Example 84

Synthesis of (R)—N'-(3,5-dimethylbenzoyl)-N'-(2,2-dimethylpentan-3-yl)-3-nitro-4-(4,4,5,5-tetramethyl-1,3,2-dioxaborolan-2-yl)benzohydrazide

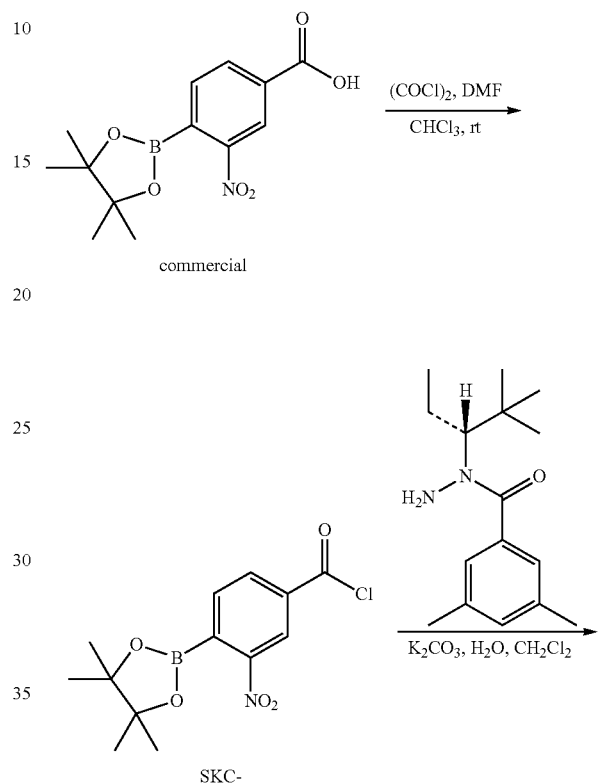

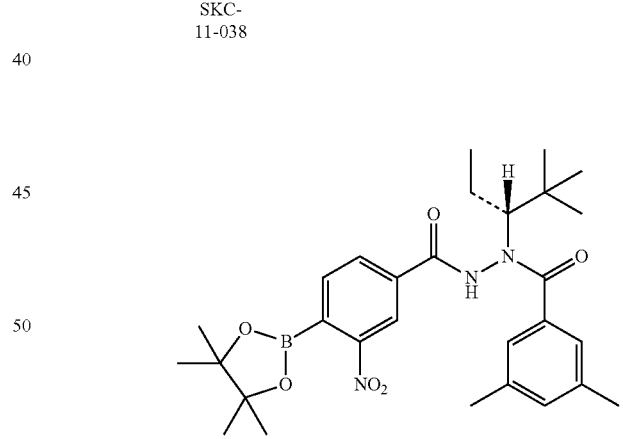

The title compound was prepared analogously to its t-butyl analog, N'-(tert-butyl)-N'-(3,5-dimethylbenzoyl)-3-nitro-4-(4,4,5,5-tetramethyl-1,3,2-dioxaborolan-2-yl)benzohydrazide (SKC-11-041). $^1$H NMR (400 MHz, DMSO-d$_6$) δ 10.56+10.4 (2s, 1H), 8.12+8.03 (2s, 1H), 7.85=7.7 (2m, 1H), 7.69 (dd, J=7.6, 1.9 Hz, 1H), 7.19-7.08 (m, 2H), 6.96 (br s, 1H), 4.46+4.27 (2d, 1H), 2.22 (s, 6H), 1.81-0.9 (multiplets, 26H) ppm. LC-MS (M+1)=538 found.

Example 85

Synthesis of (R)—N'-(3,5-dimethylbenzoyl)-N'-(2,2-dimethylpentan-3-yl)-3-hydroxy-1,3-dihydrobenzo[c][1,2,5]oxazaborole-6-carbohydrazide and (R)-3-amino-N'-(3,5-dimethylbenzoyl)-N'-(2,2-dimethylpentan-3-yl)-4-(4,4,5,5-tetramethyl-1,3,2-dioxaborolan-2-yl)benzohydrazide

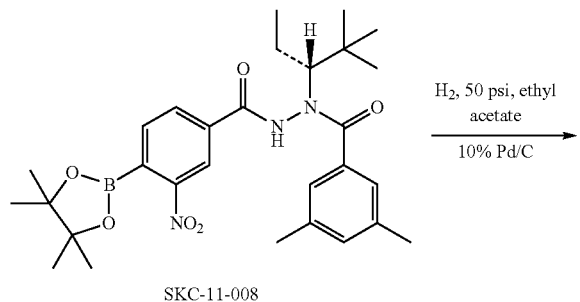

The title compounds were prepared using conditions analogous to the preparation of the t-butyl analog, 3-amino-N'-(tert-butyl)-N'-(3,5-dimethylbenzoyl)-4-(4,4,5,5-tetramethyl-1,3,2-dioxaborolan-2-yl)benzohydrazide (SKC-11-042). The reaction was performed using a Paar shaker hydrogenation apparatus. To a Paar bottle was added 20 ml of ethyl acetate, the above synthesized (R)—N'-(3,5-dimethylbenzoyl)-N'-(2,2-dimethylpentan-3-yl)-3-nitro-4-(4,4,5,5-tetramethyl-1,3,2-dioxaborolan-2-yl)benzohydrazide, (SKC-11-008, 3 g), and 10% Palladium on carbon 959 mg). The reaction mixture was shaken for 4 hr at 50 psi H2 at room temperature. LC-MS indicated masses of two major products at 424 and 426, the former of which is indicative of partial reduction of the nitro group, and the latter which is indicative of loss of pinacolate of the amino structure under LC-MS conditions. $^1$H NMR indicated the presence of a Bpin group. The mixture was filtered through a short pad of Celite and the solvent was removed under vacuum to get the crude product as a light green solid. This material was used for subsequent reactions with phenyl isocyanate and phenyl isothiocyanate. LC-MS: 2 products were observed with M+1=424 (oxazaborole) and M+1=426 (ortho-amino boronic acid). (R)—N'-(3,5-dimethylbenzoyl)-N'-(2,2-dimethylpentan-3-yl)-3-hydroxy-1,3-dihydrobenzo[c][1,2,5]oxazaborole-6-carbohydrazide was further purified: $^1$H NMR (400 MHz, DMSO-d$_6$) δ 10.4-10.1 (multiplets, 2H, exchangeable), 9.41+8.17 (2s, 1H, exchangeable), 7.59 (d, 1H), 7.1-6.8 (m, 5H), 4.45+4.23 (2d, 1H), 2.22 (s, 6H), 1.8-1.25 (m, 2H), 1.25-0.8 (m, 12H) ppm.

Example 86

Synthesis of (R)—N'-(3,5-dimethylbenzoyl)-N'-(2,2-dimethylpentan-3-yl)-1-hydroxy-3-oxo-2-phenyl-1,2,3,4-tetrahydrobenzo[c][1,5,2]diazaborinine-6-carbohydrazide and (R)—N'-(3,5-dimethylbenzoyl)-N'-(2,2-dimethylpentan-3-yl)-5-hydroxy-3-oxo-4-phenyl-1,3,4,5-tetrahydrobenzo[c][1,2,6,5]oxadiazaborepine-8-carbohydrazide

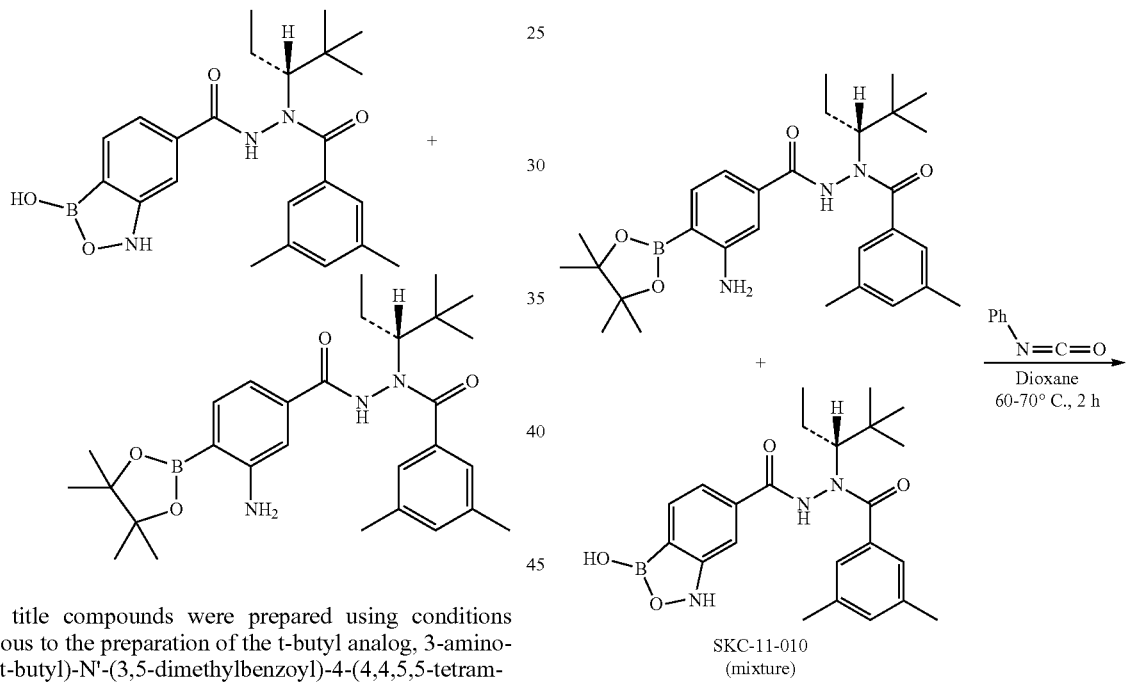

-continued

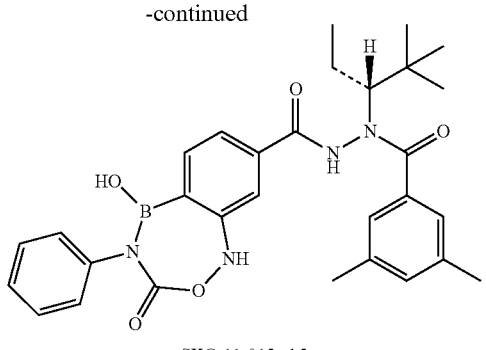

SKC-11-013 pk3

The SKC-11-010 mixture (oxazaborole+ortho-amino B-pinacolate, 300 mg, 0.591 mmole) was heated with phenyl isocyanate (70.4 mg) in 2 mL dioxane at 80 C for 45 min. Solvent was removed and the product mixture was purified by reverse phase flash chromatography. LC-MS: (M+1) 527 (diazaborinine) and 543 (oxadiazaborepine).

(R)—N'-(3,5-dimethylbenzoyl)-N'-(2,2-dimethylpentan-3-yl)-1-hydroxy-3-oxo-2-phenyl-1,2,3,4-tetrahydrobenzo[c][1,5,2]diazaborinine-6-carbohydrazide: $^1$H NMR (400 MHz, DMSO-d$_6$) δ 10.6-10.0 (multiple singlets, 2H), 9.6-8.5 (2s, 1H), 8.2-6.8 (multiplets, 11H), 4.5-4.2 (2d, 1H), 2.24 (s, 6H), 2-1.25 (m, 2H), 1.25-0.85 (m, 12H) ppm.

(R)—N'-(3,5-dimethylbenzoyl)-N'-(2,2-dimethylpentan-3-yl)-5-hydroxy-3-oxo-4-phenyl-1,3,4,5-tetrahydrobenzo[c][1,2,6,5]oxadiazaborepine-8-carbohydrazide: 10.5-10.0 (m, 2H), 9.5 (s, 1H), 8.25-6.8 (m, 1H), 4.5-4.2 (2m, 1H), 2.4-2.1 (2s, 6H), 1.9-1.25 (m, 2H), 1.25-0.8 (m, 12H) ppm.

Example 87

Synthesis of (R)—N'-(3,5-dimethylbenzoyl)-N'-(2,2-dimethylpentan-3-yl)-1-hydroxy-2-phenyl-3-thioxo-1,2,3,4-tetrahydrobenzo[c][1,5,2]diazaborinine-6-carbohydrazide

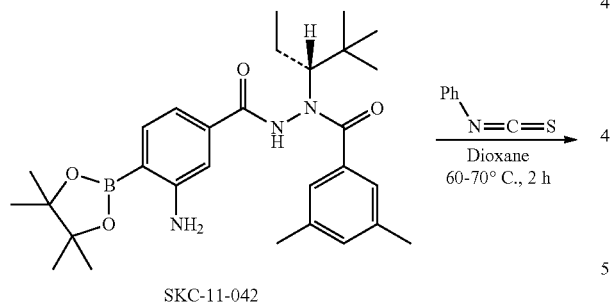

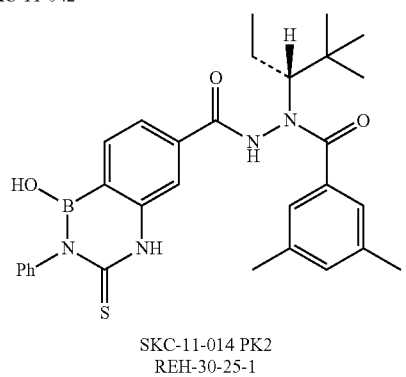

SKC-11-014 PK2
REH-30-25-1

The SKC-11-010 mixture (oxazaborole+ortho-amino B-pinacolate, 300 mg, 0.591 mmole) was heated with phenyl isothiocyanate (80 mg in 2 mL dioxane at 80 C for 30 min. Solvent was removed and the product mixture was purified by reverse phase flash chromatography. LC-MS: (M+1) 543 found.

Example 88

Synthesis of N'-(tert-butyl)-3-methoxy-2-methyl-N'-(3-nitro-4-(4,4,5,5-tetramethyl-1,3,2-dioxaborolan-2-yl)benzoyl)benzohydrazide

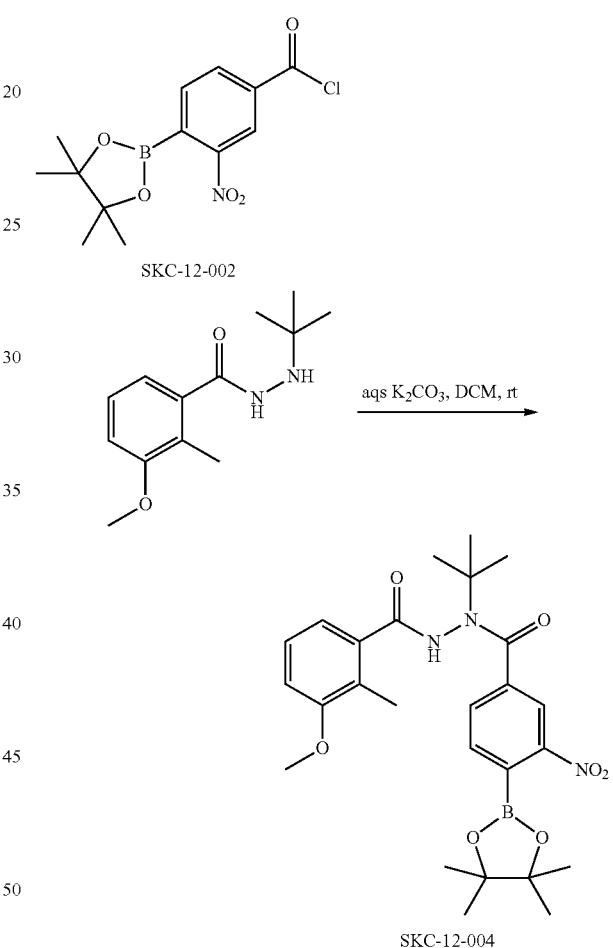

N'-(tert-butyl)-3methoxy-2-methylbenzohydrazide (4.02 g, 17.01 mmol) was taken in a 500 ml RB flask and added anhy K$_2$CO$_3$ (7.05 g, 51.0 mmol), 70 ml DCM and 18.67 ml water and stirred the mixture at room temperature for few minutes. To this mixture, freshly synthesized acid chloride (SKC-12-002, 5.3 g, 17.01 mmol) was added and stirred at room temperature for 10 minutes. LCMS showed formation of product, continued to stir overnight at room temperature. After aqueous work up and extraction in DCM, the crude mixture was triturated with ether/pentane mixture, collected the solid precipitate, dried under vacuum and used for the next step. $^1$H NMR showed it as the pure product (SKC-12-004, 8.3 g, 95% yield). LC-MS: (M+1)=512 found.

Example 89

Synthesis of N'-(3-amino-4-(4,4,5,5-tetramethyl-1,3,2-dioxaborolan-2-yl)benzoyl-N'-(tert-butyl)-3-methoxy-2-methylbenzohydrazide

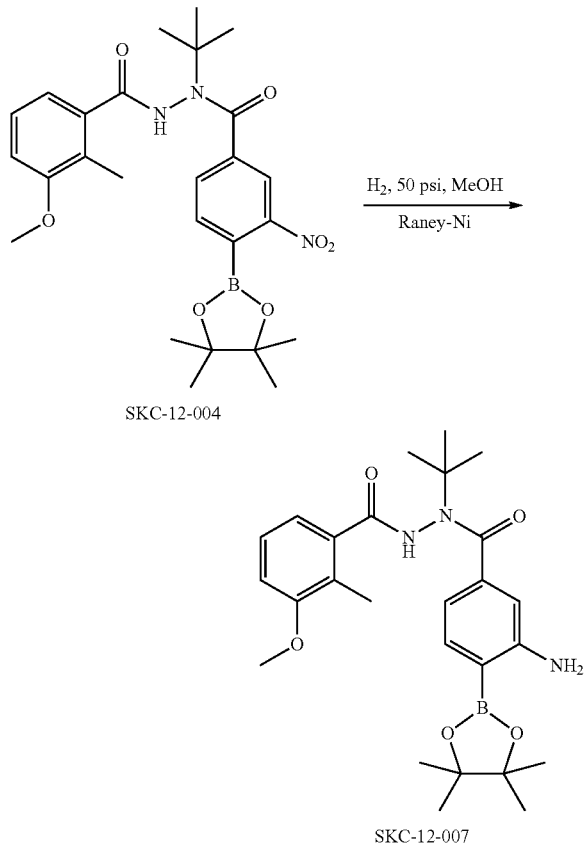

The reaction was done using a Paar shaker hydrogenation apparatus. To the Paar bottle was added a spec of Raney-Nickel (Neutral pH), the above synthesized DAH (SKC-12-004, 5.0 g, 9.78 mmol) and 100 ml of MeOH. The mixture was flushed with argon. The bottle was fixed tightly on the hydrogenation apparatus, evacuated under vacuum and filled with H₂ up to 50 Psi. The reaction mixture was let shake overnight at rt. LCMS showed complete conversion to product. Filtered the crude mixture through a short pad of celite and removed the solvent on a rotavapor under vacuum to get the crude product. The product is a light green solid. ¹H NMR was consistent with the assigned chemical structure. Kept the sample (SKC-12-004, 4.34 g, 92% yield) in the refrigerator and used as such (no column chromatography) for further condensation reactions. LC-MS: (M+1) =400 (loss of pinacol under LC-MS conditions).

General procedure for addition or condensation reactions: see Groziak, M P; Chapter 1, boron Heterocycles as platforms for building new bioactive agents and *JACS* 116: 7597-7605 (1994).

The reactions were done in scintillation vials in dioxane at 60° C., stirred for 30 min-2 h. LCMS checked to monitor the reaction. After the reaction, added 0.5 ml of water, continued to stir for another 10 min. Removed the solvent under vacuum on a rotavapor, dissolved the crude in DMSO and purified using reverse phase C18 column on ISCO. The major peak fractions with the expected product mass collected and removed the solvent, dried under vacuum.

In many cases, the ¹H NMR in DMSO is like that of equilibrium mixture may be of open and closed forms. The NMR after adding few drops of D₂O to the same tube gave a better clear spectrum, like that of a single compound.

Example 90

Synthesis of N-(tert-butyl)-1-hydroxy-N'-(3-methoxy-2-methylbenzoyl)-3-methyl-1H-benzo[c][1,5,2]oxazaborinine-6-carbohydrazide

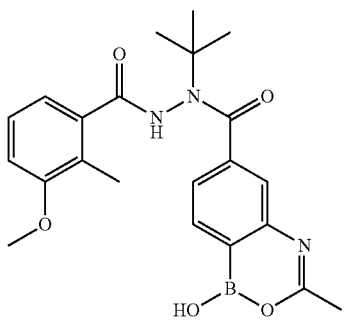 [SMILES: COc1cccc(C(=O)NN(C(=O)c2ccc3c(c2)N=C(C)OB3O)C(C)(C)C)c1C]

Following the general procedure and using N'-(3-amino-4-(4,4,5,5-tetramethyl-1,3,2-dioxaborolan-2-yl)benzoyl-N'-(tert-butyl)-3-methoxy-2-methylbenzohydrazide (SKC-12-007, 250 mg, 0.519 mmol), acetic anhydride (0.735 ml, 7.79 mmol) and 2 ml of dioxane at 60° C. for 2 h. After purification, the title compound SKC-12-009A was isolated as a solid product (185 mg, 84% yield). LC-MS (M+1): 424.

Example 91

Synthesis of N-(tert-butyl)-1-hydroxy-N'-(3-methoxy-2-methylbenzoyl)-1H-benzo[c][1,5,2]oxazaborinine-6-carbohydrazide

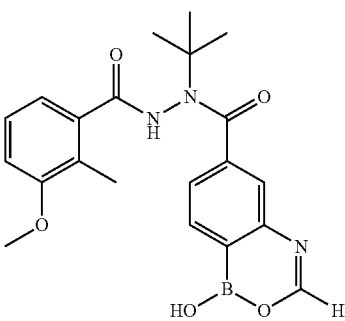 [SMILES: COc1cccc(C(=O)NN(C(=O)c2ccc3c(c2)N=COB3O)C(C)(C)C)c1C]

Following the general procedure and using N'-(3-amino-4-(4,4,5,5-tetramethyl-1,3,2-dioxaborolan-2-yl)benzoyl-N'-(tert-butyl)-3-methoxy-2-methylbenzohydrazide (SKC-12-007, 250 mg, 0.519 mmol), formic acid (0.398 ml, 10.39 mmol) and 2 ml of dioxane at 60° C. for 2 h. After purification, the title compound SKC-12-009B was isolated as a solid product (125 mg, 58.8% yield). LC-MS (M+1): 410.

Example 92

Synthesis of N-(tert-butyl)-1-hydroxy-N'-(3-methoxy-2-methylbenzoyl)-2-phenyl-3-thioxo-1,2,3,4-tetrahydrobenzo[c][1,5,2]diazaborinine-6-carbohydrazide

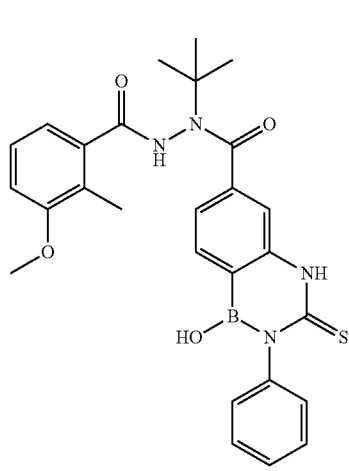 [SMILES: COc1cccc(C(=O)NN(C(=O)c2ccc3c(c2)NC(=S)N(c2ccccc2)B3O)C(C)(C)C)c1C]

Following the general procedure and using N'-(3-amino-4-(4,4,5,5-tetramethyl-1,3,2-dioxaborolan-2-yl)benzoyl-N'-(tert-butyl)-3-methoxy-2-methylbenzohydrazide (SKC-12-007, 250 mg, 0.519 mmol), isothiocyanatobenzene (0.062 ml, 0.519 mmol) and 2 ml of dioxane at 60° C. for 2 h. After purification, the title compound SKC-12-010A was isolated as a solid product (178 mg, 66.4% yield). LC-MS (M+1): 517.

Example 93

Synthesis of N-(tert-butyl)-1-hydroxy-N'-(3-methoxy-2-methylbenzoyl)-3-oxo-2-phenyl-1,2,3,4-tetrahydrobenzo[c][1,5,2]diazaborinine-6-carbohydrazide

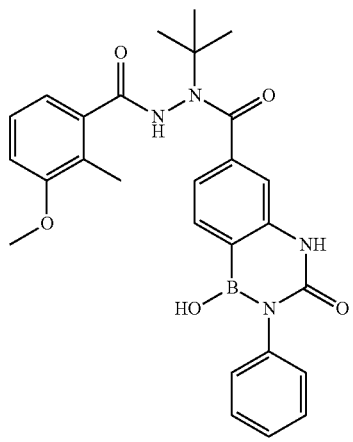 [SMILES: COc1cccc(C(=O)NN(C(=O)c2ccc3c(c2)NC(=O)N(c2ccccc2)B3O)C(C)(C)C)c1C]

Following the general procedure and using N'-(3-amino-4-(4,4,5,5-tetramethyl-1,3,2-dioxaborolan-2-yl)benzoyl-N'-(tert-butyl)-3-methoxy-2-methylbenzohydrazide (SKC-12-007, 250 mg, 0.519 mmol), isocyanatobenzene (0.056 ml, 0.519 mmol) and 2 ml of dioxane at 60° C. for 2 h. After purification, the title compound SKC-12-010B was isolated as a solid product (186 mg, 71.6% yield). LC-MS (M+1): 501.

Example 94

Synthesis of (4-(1-(tert-butyl)-2-(3-methoxy-2-methylbenzoyl)hydrazine-1-carbonyl)-2-(phenylsulfonamido)phenyl)boronic Acid

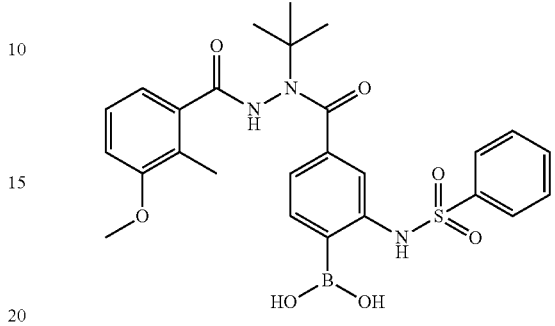

Following the general procedure and using N'-(3-amino-4-(4,4,5,5-tetramethyl-1,3,2-dioxaborolan-2-yl)benzoyl-N'-(tert-butyl)-3-methoxy-2-methylbenzohydrazide (SKC-12-007, 250 mg, 0.519 mmol), benzenesulfonyl chloride (0.067 ml, 0.519 mmol) and 2 ml of dioxane at 60° C. for overnight. After purification, the title compound SKC-12-012 was isolated as a solid product (51 mg, 18.2% yield). LC-MS (M+1): 540.

Example 95

Synthesis of N-(tert-butyl)-1-hydroxy-2-isopropyl-3-(isopropylamino)-N'(3-methoxy-2-methylbenzoyl)-1,2-dihydrobenzo[c][1,5,2]diazaborinine-6-carbohydrazide

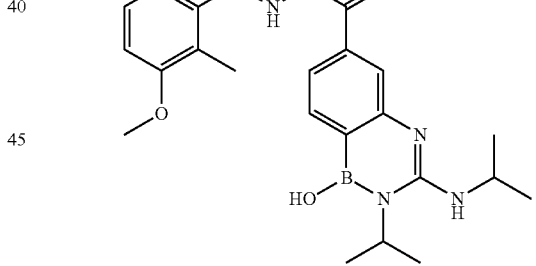

Following the general procedure and using N'-(3-amino-4-(4,4,5,5-tetramethyl-1,3,2-dioxaborolan-2-yl)benzoyl-N'-(tert-butyl)-3-methoxy-2-methylbenzohydrazide (SKC-12-007, 250 mg, 0.519 mmol), N,N'methanediylidenebis(propan-2-amine (0.081 ml, 0.519 mmol) and 2 ml of dioxane at 60° C. for overnight. After purification, the title compound SKC-12-013 was isolated as a solid product (14 mg, 5.13% yield). LC-MS (M+1): 508, 526.

The LC-MS and $^1$H NMR is consistent with the following interpretation. Two species are observed in DMSO-d6 (3:1) and DMSO-d6 spiked with $D_2O$ (1:1). The first (left-hand structure) shows aromatic signals more upfield, and is the more prominent species. The second species (right-hand structure, zwitterion), becomes more abundant when $D_2O$ is present. This zwitterionic species is also the most abundant under the aqueous and ionizing conditions of reverse-phase LC-MS.

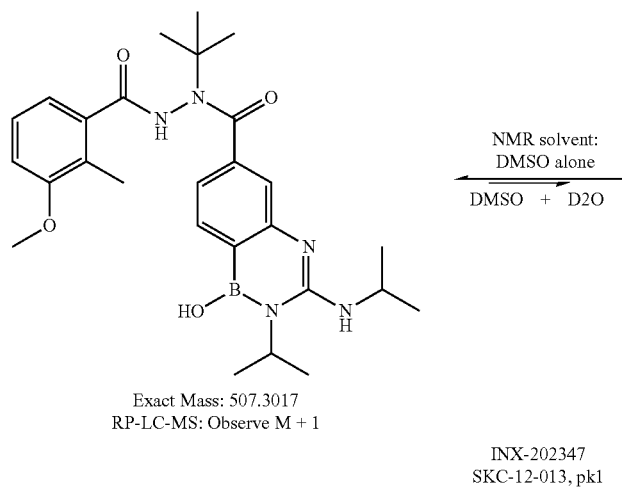

Exact Mass: 507.3017
RP-LC-MS: Observe M + 1

NMR solvent:
DMSO alone
⇌
DMSO + D2O

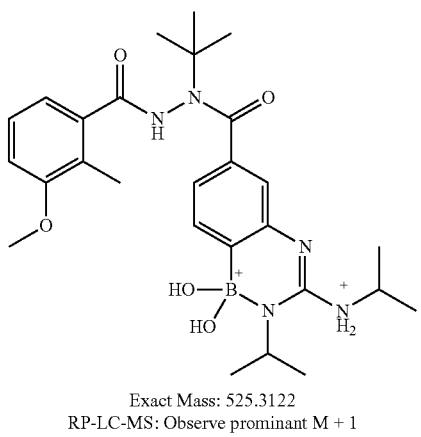

Exact Mass: 525.3122
RP-LC-MS: Observe prominant M + 1

INX-202347
SKC-12-013, pk1

The mass of the second species is also consistent with the chain tautomer:

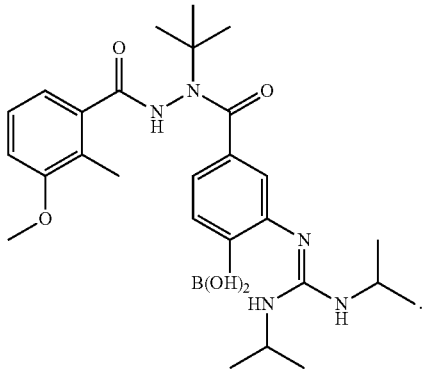 [SMILES: COc1cccc(C(=O)NN(C(=O)c2ccc(B(O)O)c(N=C(NC(C)C)NC(C)C)c2)C(C)(C)C)c1C]

The ring tautomer assignment is in agreement with literature precedent. See Progress in Heterocyclic Chemistry, Michael P. Groziak, Volume 12, 2000 pages 1-21, but the chain tautomer is also possible.

Example 96

Synthesis of N-(2-bromo-4-(2-(tert-butyl)hydrazine-1-carbonyl)phenyl)acetamide

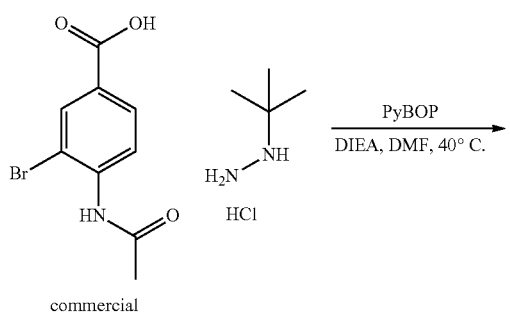

-continued

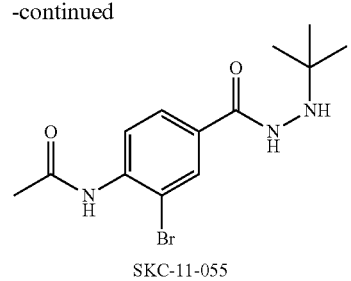

SKC-11-055

Mixed together 4-acetamido-3-bromobenzoic acid (600 mg, 2.33 mmol), PyBOP (1.21 g, 2.33 mmol) and Diisopropylethylamine (0.812 ml, 4.65 mmol) and DMF (4 ml) in a 100 ml RB flask under argon and stirred at 40° C. for 3 min. To the stirred mixture, tert-butylhydrazine hydrochloride (290 mg) was added and continued to stir at 40° C. for 1.5 h. LCMS showed a single peak with the expected product mass. Removed the solvent in a genevac, diluted with EtOAc and water and extracted; the organic fractions collected and removed the solvent under vacuum. Finally purified the crude mixture using C18 column on ISCO and the major fractions (fr-29-34) collected, removed the solvent and dried to get the target compound (SKC-11-055, 587 mg, 77% yield). LC-MS: (M+1 for $^{81}$Br)=330 found.

Example 97

Synthesis of N-(2-bromo-4-(2-(tert-butyl)-2-(3,5-dimethylbenzoyl)hydrazine-1-carbonyl)phenyl)acetamide

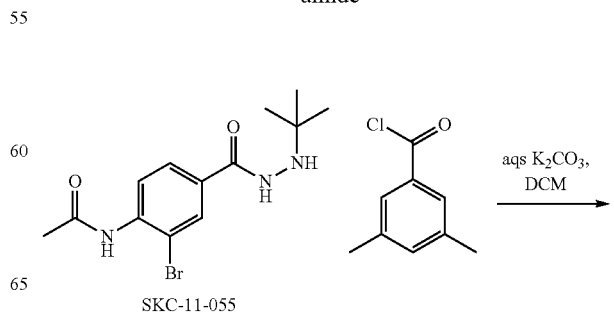

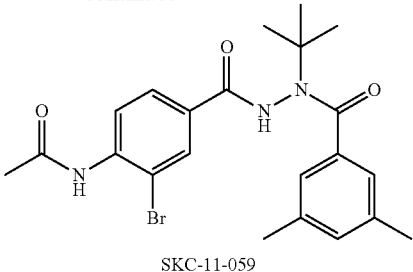

SKC-11-059

The above monoA (SKC-11-055, 577 mg, 1.75 mmol) was taken in a 100 ml RB flask and added anhy $K_2CO_3$ (729 mg, 5.27 mmol), 8 ml DCM and 2.7 ml water; stirred the mixture at 0° C. for few minutes. To this mixture, 3,5-dimethylbenzoylchloride (296 mg, 1.76 mmol) in 2 ml of DCM was added and stirred at room temperature for 2 hrs, allowing it to warm to room temperature. LCMS checked after 10 min showed formation of pdt. Diluted with water and extracted in DCM. LCMS of the aqs fraction showed that some impurity went in aqs phase. The organic fractions collected, dried and purified using C18 column on ISCO. ISCO fr 14-18 collected and removed the solvent to get a solid product (SKC-11-059) LC-MS: (M+1 for $^{81}Br$)=462 found.

Example 98

Synthesis of N'-(tert-butyl)-N'-(3,5-dimethylbenzoyl)-1-hydroxy-3-methyl-1H-benzo[c][1,5,2]oxazaborinine-7-carbohydrazide

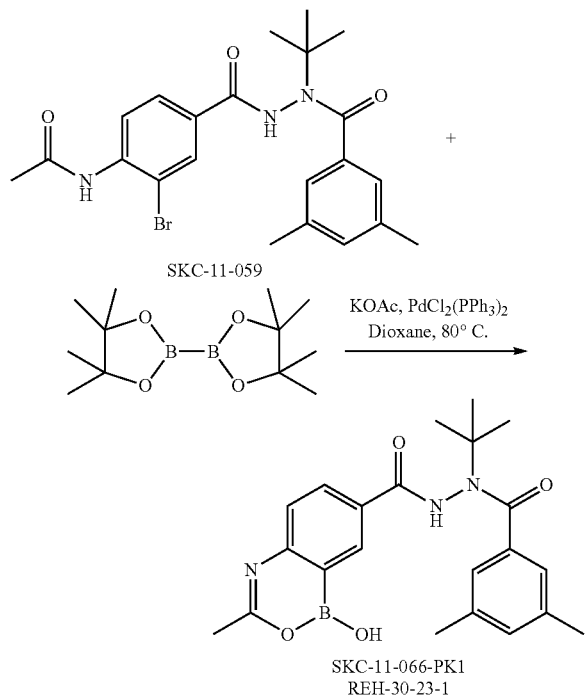

N-(2-bromo-4-(2-(tert-butyl)-2-(3,5-dimethylbenzoyl)hydrazine-1-carbonyl)phenyl)acetamide (150 mg), 4,4,4',4',5,5,5',5'-octamethyl-2,2'-bi(1,3,2-dioxaborolane) (99 mg), KOAc (96 mg), and $PdCl_2(PPh_3)_2$ (11.4 mg) were mixed and stirred in dry dioxane under argon overnight at 80° C. The mixture was allowed to cool and was filtered through a short pad of Celite. The solids were washed with methanol. Solvent was removed in vacuo, and the crude product was purified by reverse phase flash chromatography twice iteratively. $^1H$ NMR (400 MHz, DMSO-$d_6$+$D_2O$) δ 7.74 (d, J=2.2 Hz, 1H), 7.49 (dd, J=8.5, 2.6 Hz, 1H), 7.36 (dd, 1H), 7.04 (s, 2H), 6.89 (s, 1H), 2.17 (s, 6H), 2.09 (s, 3H), 1.44 (s, 9H ppm). Exchangeable signals at 11.9 and 10.5 appear in dry DMSO-$d_6$.

Example 99

Synthesis of (R)-(4-(2-(3,5-dimethylbenzoyl)-2-(2,2-dimethylpentan-3-yl)hydrazine-1-carbonyl)-2-formylphenyl)boronic Acid Step 1:

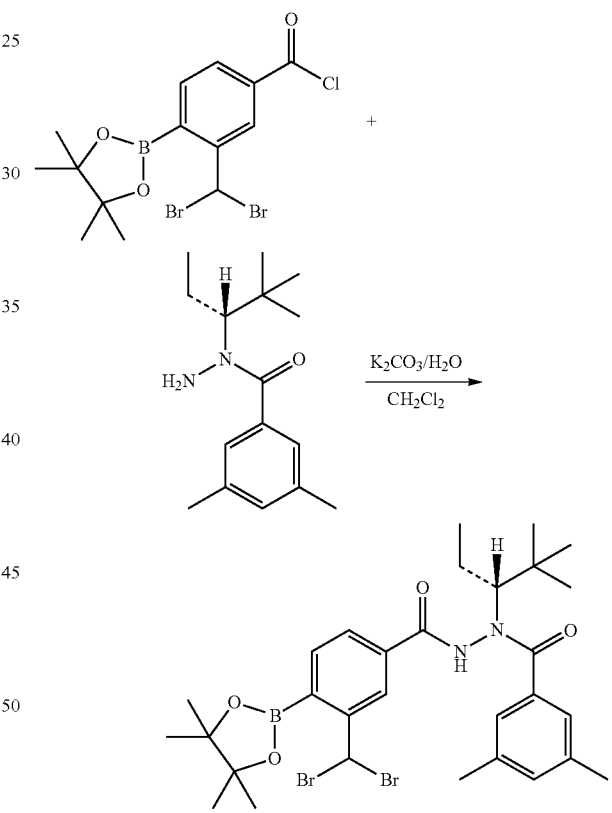

REH-30-28-1

By analogy to the synthesis procedure to prepare (R)—N'-(tert-butyl)-4-(dibromomethyl)-N'-(3,5-dimethylbenzoyl)-3-(4,4,5,5-tetramethyl-1,3,2-dioxaborolan-2-yl)benzohydrazide (Example 8), 3-(dibromomethyl)-4-(4,4,5,5-tetramethyl-1,3,2-dioxaborolan-2-yl)benzoyl chloride was coupled to (R)—N-(2,2-dimethylpentan-3-yl)-3,5-dimethylbenzohydrazide to provide (R)-3-(dibromomethyl)-N'-(3,5-dimethylbenzoyl)-N'-(2,2-dimethylpentan-3-yl)-4-(4,4,5,5-tetramethyl-1,3,2-dioxaborolan-2-yl)benzohydrazide.

Step 2:

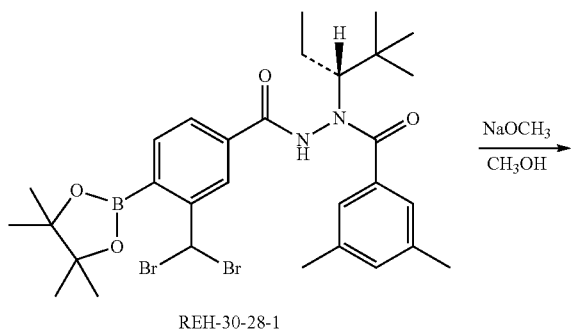

REH-30-28-1

REH-30-35-1

By analogy to the synthesis procedure to prepare (R)-4-(dimethoxymethyl)-N'-(3,5-dimethylbenzoyl)-N'-(2,2-dimethylpentan-3-yl)-3-(4,4,5,5-tetramethyl-1,3,2-dioxaborolan-2-yl)benzohydrazide (Example 8), (R)-3-(dibromomethyl)-N'-(3,5-dimethylbenzoyl)-N'-(2,2-dimethylpentan-3-yl)-4-(4,4,5,5-tetramethyl-1,3,2-dioxaborolan-2-yl)benzohydrazide was converted to (R)-3-(dimethoxymethyl)-N'-(3,5-dimethylbenzoyl)-N'-(2,2-dimethylpentan-3-yl)-4-(4,4,5,5-tetramethyl-1,3,2-dioxaborolan-2-yl)benzohydrazide.

Step 3:

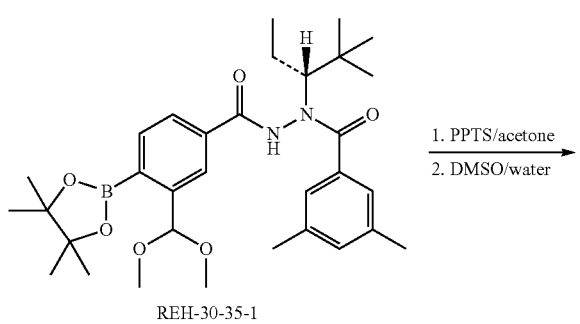

REH-30-35-1

1. PPTS/acetone
2. DMSO/water

REH-30-36-1

(R)-3-(dimethoxymethyl)-N'-(3,5-dimethylbenzoyl)-N'-(2,2-dimethylpentan-3-yl)-4-(4,4,5,5-tetramethyl-1,3,2-dioxaborolan-2-yl)benzohydrazide (ca. 890 mg, 1.57 mmol) and 54 mg pyridinium toluenesulfonate were dissolved in 15 mL acetone. The mixture was stirred at 60 C for 6.25 hours, then filtered to remove a small amount of precipitated solids. The solvent was removed in vacuo. DMSO (4.8 g) was added to the residual solid. The resultant solution was heated to 45 C, stirred rapidly, while 0.94 g water was added dropwise over a period of 15 min. An additional 0.5 mL DMSO was added to the off-white solution. The mixture was allowed to cool to room temperature and stirred for 18.5 hours. The solution, without further treatment, was applied to a reverse phase flash chromatography column and the product was eluted with a water-acetonitrile gradient containing 0.1% formic acid to provide 380 mg (R)-(4-(2-(3,5-dimethylbenzoyl)-2-(2,2-dimethylpentan-3-yl)hydrazine-1-carbonyl)-2-formylphenyl) boronic acid as a white electrostatic solid: $^1$H NMR (400 MHz, DMSO) δ 10.47+10 0.26 (2s, 1H, exchangeable), 10.1 (s, 1H), 8.34 (br s, 2H, exchangeable), 7.95+7.89 (2s, 1H), 7.63 (m, 2H), 7.16+7.2 (2s, 2H), 6.94 9s, 1H), 4.45+4.25 (2d, 1H), 2.2 (s, 6H), 1.8-1.4 (m, 2H), 1.1-0.93 (12H) ppm.

Example 100

In Vitro Activity

Representative Compounds of the Disclosure were tested for biological activity in an in vitro gene switch assay (Table 3). Gene switch assays are disclosed, e.g., in U.S. Pat. Nos. 8,076,517; 7,456,315; 7,304,161; and 6,258,603.

Stable Cell-Line Production

CHO-K1 cells were stably transfected with a plasmid (RS-1, FIG. 1) coding for firefly Luciferase (fLUC) under the control of the RheoSwitch® resulting in the stable cell line CHO-K1_RS-1. A master cell bank was created containing approximately 100 vials at $5\times10^6$ cells per vial. One vial of CHO-K1_RS-1 was thawed and cultured for two weeks prior to each in vitro potency screening. The nucleic acid sequence of RS-1 showing the location of the components is presented in FIGS. 2A-2E.

Potency Screen

Twenty-four (24) hours prior to treatment with the control and test compounds the CHO-K1_RS-1 cells were seeded into white-opaque 384-well cell culture plates at 3,600 cells per well in 30 µl of culture medium. The cells were incubated in a humidified $CO_2$ incubator at 37° C. until compound treatment.

Compounds were prepared at 25 mM in 100% dry DMSO and stored at room temperature in sealed 1 ml tubes prior to subsequent dilution and assay. On the day of cell treatment the tubes containing the control and test compounds were sorted and the ligands transferred to a 96-well polypropylene plate for subsequent dilution. The compounds were diluted in 100% dry DMSO in an 8-point, 10-fold dilution series ranging from 25 mM to 2.5 nM using the Biomek FX automated liquid handler.

The diluted compounds were then transferred to each well of 384-well polypropylene plate in quadruplicate resulting in a single 384-well plate with four replicates of each compound dilution in a different quadrant of the plate. Each well on the 384-well plate received 20 µl of diluted compound. The 384-well plates containing diluted compound and the plates containing cells in culture were loaded onto the Biomek FX and 30 nl of compound was delivered to each well containing cells using a 384-pin V&P Scientific Pin Tool. The resulting 1000-fold dilution (30 nl to 30 µl) generated a final dosing range of 25 µM to 2.5 pM in 0.1%

DMSO. Two replicate plates were produced to supply a dedicated plate for the Luciferase expression assay and the APH cell viability assay.

The cells were incubated with the compound for 24 hours in a humidified $CO_2$ incubator at 37° C. Following incubation, the cells were assayed for Luciferase expression (fLUC assay) using the Steady Glo assay from Promega. Cells were equilibrated to room temperature for 15 minutes prior to reagent addition. Thirty micro liters (30 μl) of assay reagent was added to each well of the 384-well plate using the Biomek FX. The reagent was incubated with the cells for 10-120 minutes prior to reading on a Molecular Devices Spectramax L luminometer. The assay reagents were prepared as per the manufacturer's instructions.

Data Analysis

The Luciferase expression data was normalized to the baseline signal from cells treated with DMSO alone. The ratio of signal from treated cells to vehicle-treated cells was plotted and non-linear regress was performed using Graph Pad Prism software. $EC_{50}$, (log)$EC_{50}$ and Hill slope data was generated. Reporter gene expression, e.g., luciferase expression, serves as a proxy for the expression of a gene of interest. See, e.g., US 2009/0123441 and WO 2011/119773.

TABLE 3

| Cpd. No. | $EC_{50}$ (μM) |
|---|---|
| 1 | >500 |
| 2 | >500 |
| 3 | >500 |
| 4 | >500 |
| 5 | ~62.20 |
| 6 | >500 |
| 7 | >500 |
| 8 | ~2.779 |
| 9 | >500 |
| 10 | >500 |
| 11 | >500 |
| 12 | >500 |
| 13 | >500 |
| 14 | >500 |
| 15 | >500 |
| 16 | >500 |
| 17 | >500 |
| 18 | >500 |
| 19 | ~27.07 |
| 20 | 255.5 |
| 21 | 3.314 |
| 22 | ~4.786 |
| 23 | ~108.4 |
| 24 | ~18.64 |
| 25 | ~13.72 |
| 26 | ~5.066 |
| 27 | 5.942 |
| 28 | 735.4 |
| 71 | ~175.3 |
| 29 | ~62.58 |
| 30 | ~8.032 |
| 31 | >500 |
| 32 | >500 |
| 33 | 2.643 |
| 34 | ~120.2 |
| 35 | >500 |
| 36 | ~225.1 |
| 37 | >500 |
| 38 | 4.827 |
| 39 | ~21.40 |
| 40 | >500 |
| 41 | ~5.572 |
| 42 | ~320.2 |
| 43 | ~251.4 |
| 44 | >500 |
| 45 | ~9.569 |
| 46 | >500 |
| 47 | >500 |

TABLE 3-continued

| Cpd. No. | $EC_{50}$ (μM) |
|---|---|
| 48 | >500 |
| 49 | ~28.16 |

Example 101

Solubility

Representative Compounds of the Disclosure were tested for solubity (Table 4) as follows:

Materials:
 0.1 M Phosphate Buffer Ionic Strength ~0.15M
 Simulated Intestinal Fluid pH 7.5 (USP)
 1 Dram Vials
 Microcentrifuge tubes Procedure
 Weigh ~2 mgs of compound into clean glass 1 dram vails.
 Add ~4 μl of appropriate media to vial to yield a target concentration of 5 mg/ml.
 Place vials on a rotating shaker and equilibrate for 24 hrs. at RT.
 Remove supernatant to microcentrifuge tubes and centrifuge at 1300 rpm for 30 minutes.
 Remove an aliquot of supernatant, dilute accordingly with acetonitrile.

Data Processing
 Assay Samples by HPLC-UV Against Standards.

TABLE 4

| Cpd. No. | Solubility pH 7.4 ug/ml | Solubility SIF ug/ml |
|---|---|---|
| 1 | >5000 | 4874.3 |
| 2 | 4313.9 | 4048.2 |
| 3 | 39.4 | 90.2 |
| 4 | 3562.1 | 2640.2 |
| 5 | 1.7 | 1.3 |
| 6 | 1.7 | 0.4 |
| 7 | 4.1 | 10.7 |
| 8 | 42.3 | 120.7 |
| 9 | 4921.0 | 4507.1 |
| 10 | 4871.5 | 4799.1 |
| 11 | 4702.3 | 4647.6 |
| 12 | 3757.1 | 3798.2 |
| 13 | 221.0 | 333.6 |
| 14 | 2271.1 | 1784.5 |
| 15 | 540.0 | 416.7 |
| 16 | 6.9 | 24.1 |
| 17 | 0.13 | 59.3 |
| 18 | 505.0 | 491.8 |
| 19 | 16.8 | 31.4 |
| 20 | 2680.1 | 3330.9 |

It is to be understood that the foregoing described embodiments and exemplifications are not intended to be limiting in any respect to the scope of the disclosure, and that the claims presented herein are intended to encompass all embodiments and exemplifications whether or not explicitly presented herein All patents and publications cited herein are fully incorporated by reference in their entirety.

What is claimed is:

1. A compound having Formula I:

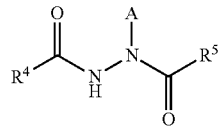

or a pharmaceutically acceptable salt, solvate, or boronic anhydride thereof, wherein:

A is selected from the group consisting of hydrogen and —C($R^1$)($R^2$)($R^3$);

$R^1$, $R^2$, and $R^3$ are each independently selected from the group consisting of hydrogen and optionally substituted alkyl;

$R^4$ is selected from the group consisting of:

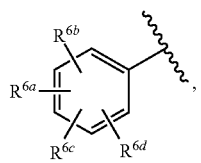 $R^4$-1

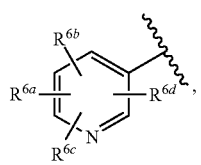 $R^4$-2

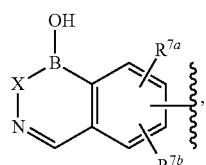 $R^4$-3

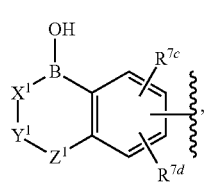 $R^4$-4

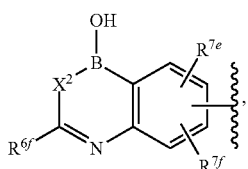 $R^4$-5

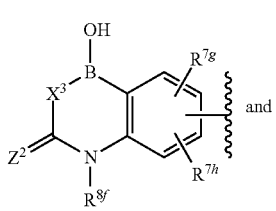 $R^4$-6
and

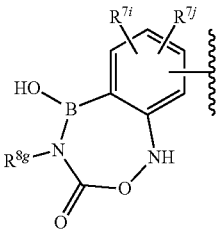 $R^4$-7

X is selected from the group consisting of —O— and —N($R^{8a}$)—;

$X^1$ is selected from the group consisting of —O— and —N($R^{8b}$)—;

$X^2$ is selected from the group consisting of —O— and —N($R^{8c}$)—;

$X^3$ is selected from the group consisting of —O— and —N($R^{8d}$)—;

$Y^1$ is —(C$R^{9a}R^{9b}$)$_m$—;

m is 0, 1, 2, or 3;

$Z^1$ is selected from the group consisting of —O— and —N($R^{8e}$)—, or $Z^1$ is absent;

$Z^2$ is selected from the group consisting of O, S, and NH;

$R^{6a}$ is selected from the group consisting of hydrogen, —B(OH)$_2$, and pinacolborane;

$R^{6b}$, $R^{6c}$, and $R^{6d}$ are each independently selected from the group consisting of hydrogen, halo, nitro, cyano, hydroxy, amino, —N(H)CHO, —N(H)CN, —N(H)(cyano)alkyl, —CHO, optionally substituted alkyl, haloalkyl, alkoxyalkyl, hydroxyalkyl, arylalkyl, (amino)alkyl, (alkylamino)alkyl, (dialkylamino)alkyl, (cyano)alkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{10}$, —SO$_2$R$^{11}$, —N(R$^{12}$)COR$^{13}$, —N(R$^{12}$)SO$_2$R$^{14}$ or N(R$^{12}$)C=N(R$^{15}$)-amino; or $R^{6b}$ is selected from the group consisting of hydrogen, halo, nitro, cyano, hydroxy, —N(H)CHO, —N(H)CN, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{10}$, —SO$_2$R$^{11}$, —N(R$^{12}$)COR$^{13}$, —N(R$^{12}$)SO$_2$R$^{14}$ or N(R$^{12}$)C=N(R$^{15}$)-amino; and/or $R^{6c}$ and $R^{6d}$ taken together with two adjacent carbon atoms form a fused optionally substituted cycloalkyl, optionally substituted heterocyclo, or optionally substituted heteroaryl group;

$R^{6f}$ is selected from the group consisting of hydrogen, alkyl, amino, alkylamino, dialkylamino, and hydroxy;

$R^{7a}$, $R^{7b}$, $R^{7c}$, $R^{7d}$, $R^{7e}$, $R^{7f}$, $R^{7g}$, $R^{7h}$, $R^{7i}$, and $R^{7j}$ are each independently selected from the group consisting of hydrogen, halo, nitro, cyano, hydroxy, amino, optionally substituted alkyl, haloalkyl, hydroxyalkyl, alkoxy, and alkylthio;

$R^{8a}$, $R^{8b}$, $R^{8c}$, $R^{8d}$, $R^{8e}$, $R^{8f}$, and $R^{8g}$ are each independently selected from the group consisting of hydrogen, alkyl, optionally substituted aryl, optionally substituted heteroaryl, alkylsulfonyl, arylsulfonyl, alkylcarbonyl, and arylcarbonyl;

$R^{9a}$ and $R^{9b}$ are each independently selected from the group consisting of hydrogen, alkyl, and cyano;

$R^5$ is selected from the group consisting of:

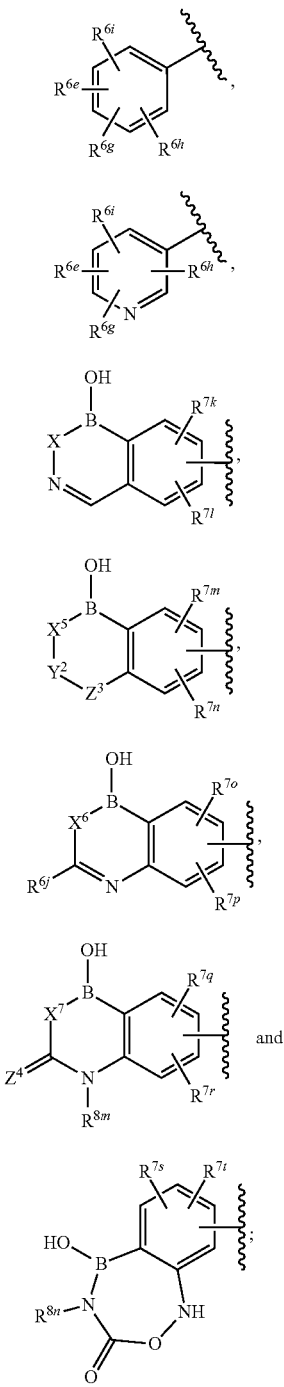

$X^4$ is selected from the group consisting of —O— and —N($R^{8h}$)—;
$X^5$ is selected from the group consisting of —O— and —N($R^{8i}$)—;
$X^6$ is selected from the group consisting of —O— and —N($R^{8j}$)—;
$X^7$ is selected from the group consisting of —O— and —N($R^{8k}$)—;
$Y^2$ is —(C$R^{9c}R^{9d}$)$_n$—;
n is 0, 1 2, or 3;
$Z^3$ is selected from the group consisting of —O— and —N($R^{8l}$)—, or $Z^3$ is absent;
$Z^4$ is selected from the group consisting of O, S, and NH;
$R^{6e}$ is selected from the group consisting of hydrogen, —B(OH)$_2$, and pinacolborane;
$R^{6g}$, $R^{6h}$, and $R^{6i}$ are each independently selected from the group consisting of hydrogen, halo, nitro, cyano, hydroxy, amino, —N(H)CHO, —N(H)CN, —N(H)(cyano)alkyl, —CHO, optionally substituted alkyl, haloalkyl, alkoxyalkyl, hydroxyalkyl, arylalkyl, (amino)alkyl, (alkylamino)alkyl, (dialkylamino)alkyl, (cyano)alkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{10}$, —SO$_2$R$^{11}$, —N(R$^{12}$)COR$^{13}$, —N(R$^{12}$)SO$_2$R$^{14}$ or N(R$^{12}$)C=N(R$^{15}$)-amino; or
$R^{6g}$ is selected from the group consisting of hydrogen, halo, nitro, cyano, hydroxy, —N(H)CHO, —N(H)CN, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, heteroalkyl, carboxamido, sulfonamido, —COR$^{10}$, —SO$_2$R$^{11}$, —N(R$^{12}$)COR$^{13}$, —N(R$^{12}$)SO$_2$R$^{14}$ or N(R$^{12}$)C=N(R$^{15}$)-amino; and/or
$R^{6h}$ and $R^{6i}$ taken together with two adjacent carbon atoms form a fused optionally substituted cycloalkyl, optionally substituted heterocyclo, or optionally substituted heteroaryl group;
$R^{6j}$ is selected from the group consisting of hydrogen, alkyl, amino, and hydroxy;
$R^{7k}$, $R^{7l}$, $R^{7m}$, $R^{7n}$, $R^{7o}$, $R^{7p}$, $R^{7q}$, $R^{7r}$, $R^{7s}$, and $R^{7t}$ are each independently selected from the group consisting of hydrogen, halo, nitro, cyano, hydroxy, amino, optionally substituted alkyl, haloalkyl, hydroxyalkyl, alkoxy, and alkylthio;
$R^{8h}$, $R^{8i}$, $R^{8j}$, $R^{8k}$, $R^{8l}$, $R^{8m}$, and $R^{8n}$ are each independently selected from the group consisting of hydrogen, alkyl, optionally substituted aryl, optionally substituted heteroaryl, alkylsulfonyl, arylsulfonyl, alkylcarbonyl, and arylcarbonyl;
$R^{9c}$ and $R^{9d}$ are each independently selected from the group consisting of hydrogen, alkyl, and cyano;
$R^{10}$ is selected from the group consisting of hydrogen, hydroxy, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy, and arylalkyloxy;
$R^{11}$ is selected from the group consisting of haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, and optionally substituted heteroaryl;

R¹² is selected from the group consisting of hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, and optionally substituted heteroaryl;

R¹³ is selected from the group consisting of hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy, arylalkyloxy, and amino;

R¹⁴ is selected from the group consisting of haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, and amino; and R¹⁵ is selected from the group consisting of hydrogen, alkyl, aryl, cyano, and nitro, with the provisos that:
1) when R⁴ is R⁴-1 or R⁴-2 and R⁵ is R⁵-1 or R⁵-2, then one of R⁶ᵃ or R⁶ᵉ is —B(OH)₂ or pinacolborane; and
2) said compound having Formula I is not:

(3-(2-(tert-butyl)-2-(3,5-dimethylbenzoyl)hydrazine-1-carbonyl)-2-methylphenyl)boronic acid;
(R)-(2-chloro-3-(2-(3,5-dimethylbenzoyl)-2-(2,2-dimethylhexan-3-yl)hydrazine-1-carbonyl)phenyl)boronic acid;
(4-(2-(tert-butyl)-2-(3,5-dimethylbenzoyl)hydrazine-1-carbonyl)phenyl)boronic acid;
(R)-(4-(2-(3,5-dimethylbenzoyl)-2-(2,2-dimethylhexan-3-yl)hydrazine-1-carbonyl)-3-isopropylphenyl)boronic acid;
(R)-(4-(2-(3,5-dimethylbenzoyl)-2-(2,2-dimethylhexan-3-yl)hydrazine-1-carbonyl)-3-fluorophenyl)boronic acid;
(R)-(4-(2-(2,6-dimethylisonicotinoyl)-2-(2,2-dimethylpentan-3-yl)hydrazine-1-carbonyl)-3-fluorophenyl)boronic acid;
(R)-(4-(2-(3,5-dimethylbenzoyl)-2-(2,2-dimethylhexan-3-yl)hydrazine-1-carbonyl)-2-fluorophenyl)boronic acid;
(4-(2-(tert-butyl)-2-(3,5-dimethylbenzoyl)hydrazine-1-carbonyl)-3,5-difluorophenyl)boronic acid;
(2-(1-(2,2-dimethylpentan-3-yl)-2-(3-methoxy-2-methylbenzoyl)hydrazine-1-carbonyl)phenyl)boronic acid;
(3-(1-(2,2-dimethylpentan-3-yl)-2-(3-methoxy-2-methylbenzoyl)hydrazine-1-carbonyl)-4-fluorophenyl)boronic acid;
(3-(1-(2,2-dimethylpentan-3-yl)-2-(3-methoxy-2-methylbenzoyl)hydrazine-1-carbonyl)-5-methoxyphenyl)boronic acid;
(4-(1-(tert-butyl)-2-(2-ethyl-3-methoxybenzoyl)hydrazine-1-carbonyl)phenyl)boronic acid;
N'-(tert-butyl)-N'-(3,5-dimethylbenzoyl)-2-methyl-3-(4,4,5,5-tetramethyl-1,3,2-dioxaborolan-2-yl)benzohydrazide;
N'-(3-chloro-5-methylbenzoyl)-N'-(2,2-dimethylhexan-3-yl)-2-methyl-3-(4,4,5,5-tetramethyl-1,3,2-dioxaborolan-2-yl)benzohydrazide;
N-(2,2-dimethylhexan-3-yl)-N'-(2-methyl-3-(4,4,5,5-tetramethyl-1,3,2-dioxaborolan-2-yl)benzoyl)-2-oxo-1,2-dihydropyridine-3-carbohydrazide;
(R)—N'-(3,5-dimethylbenzoyl)-N'-(2,2-dimethylpentan-3-yl)-1-hydroxy-1,3-dihydrobenzo[c][1,2]oxaborole-6-carbohydrazide;
N'-(tert-butyl)-N'-(3,5-dimethylbenzoyl)-7-fluoro-1-hydroxy-1,3-dihydrobenzo[c][1,2]oxaborole-6-carbohydrazide;
(S)—N'-(3,5-dimethylbenzoyl)-N'-(2,2-dimethylpentan-3-yl)-7-fluoro-1-hydroxy-1,3-dihydrobenzo[c][1,2]oxaborole-6-carbohydrazide;
(R)—N'-(3,5-dimethylbenzoyl)-N'-(2,2-dimethylpentan-3-yl)-4-fluoro-1-hydroxy-1,3-dihydrobenzo[c][1,2]oxaborole-5-carbohydrazide;
N'-(3,5-dimethylbenzoyl)-1-hydroxy-N'-isopropyl-6-methyl-3,4-dihydro-1H-benzo[c][1,5,2]dioxaborepine-7-carbohydrazide;
N'-(3,5-dimethylbenzoyl)-1-hydroxy-6-methyl-N'-(tert-pentyl)-3,4-dihydro-1H-benzo[c][1,5,2]dioxaborepine-7-carbohydrazide;
(R)—N'-(3,5-dimethylbenzoyl)-N'-(2,2-dimethylpentan-3-yl)-1-hydroxy-6-methyl-3,4-dihydro-1H-benzo[c][1,5,2]dioxaborepine-7-carbohydrazide;
N'-(3,5-dimethylbenzoyl)-N'-(1-fluorobutan-2-yl)-1-hydroxy-6-methyl-3,4-dihydro-1H-benzo[c][1,5,2]dioxaborepine-7-carbohydrazide;
N'-(tert-butyl)-N'-(3,5-dimethylbenzoyl)-2-methyl-3-(2-((tetrahydro-2H-pyran-2-yl)oxy)ethoxy)-4-(4,4,5,5-tetramethyl-1,3,2-dioxaborolan-2-yl)benzohydrazide;
(R)—N'-(3,5-dimethylbenzoyl)-N'-(2,2-dimethylpentan-3-yl)-3-(2-methoxyethoxy)-2-methyl-4-(4,4,5,5-tetramethyl-1,3,2-dioxaborolan-2-yl)benzohydrazide;
(R)—N'-(3,5-dimethylbenzoyl)-N'-(2,2-dimethylhexan-3-yl)-3-fluoro-4-(4,4,5,5-tetramethyl-1,3,2-dioxaborolan-2-yl)benzohydrazide;
N'-(tert-butyl)-N'-(3,5-dimethylbenzoyl)-2,6-difluoro-4-(4,4,5,5-tetramethyl-1,3,2-dioxaborolan-2-yl)benzohydrazide;
N'-(tert-butyl)-3-(cyanomethoxy)-N'-(3,5-dimethylbenzoyl)-2-methyl-4-(4,4,5,5-tetramethyl-1,3,2-dioxaborolan-2-yl)benzohydrazide;
(R)—N'-(3,5-dimethylbenzoyl)-N'-(2,2-dimethylpentan-3-yl)-2-fluoro-4-(4,4,5,5-tetramethyl-1,3,2-dioxaborolan-2-yl)benzohydrazide;
(R)-(4-(2-(3,5-dimethylbenzoyl)-2-(2,2-dimethylpentan-3-yl)hydrazine-1-carbonyl)-3-fluorophenyl)boronic acid;
(3-(2-(tert-butyl)-2-(3,5-dimethylbenzoyl)hydrazine-1-carbonyl)-2-fluoro-6-(methoxymethyl)phenyl)boronic acid;
N'-(tert-butyl)-N'-(3,5-dimethylbenzoyl)-1-hydroxy-6-methyl-1,2,3,4-tetrahydrobenzo[f][1,4,5]oxazaborepine-7-carbohydrazide;
N'-(tert-butyl)-N'-(3,5-dimethylbenzoyl)-2-fluoro-4-(methoxymethyl)-3-(4,4,5,5-tetramethyl-1,3,2-dioxaborolan-2-yl)benzohydrazide;
(R)-(3-(2-(3,5-dimethylbenzoyl)-2-(2,2-dimethylhexan-3-yl)hydrazine-1-carbonyl)-2-methylphenyl)boronic acid;
(3-(2-(tert-butyl)-2-(3,5-dimethylbenzoyl)hydrazine-1-carbonyl)-2-fluorophenyl)boronic acid;
(R)-(4-(2-(3,5-dimethylbenzoyl)-2-(2,2-dimethylhexan-3-yl)hydrazine-1-carbonyl)phenyl)boronic acid;
(4-(2-(tert-butyl)-2-(3,5-dimethylbenzoyl)hydrazine-1-carbonyl)-3-isopropylphenyl)boronic acid;
(R)-(4-(2-(3,5-dimethylbenzoyl)-2-(6-fluoro-2,2-dimethylhexan-3-yl)hydrazine-1-carbonyl)-3-fluorophenyl)boronic acid;
(R)-(4-(2-(2,2-dimethylpentan-3-yl)-2-(4,6-dimethylpyrimidine-2-carbonyl)hydrazine-1-carbonyl)-3-fluorophenyl)boronic acid;

(R)-(3-chloro-4-(2-(3,5-dimethylbenzoyl)-2-(2,2-dimethylhexan-3-yl)hydrazine-1-carbonyl)phenyl)boronic acid;

(4-(2-(tert-butyl)-2-(3,5-dimethylbenzoyl)hydrazine-1-carbonyl)-2-fluorophenyl)boronic acid;

(R)-(4-(2-(3,5-dimethylbenzoyl)-2-(2,2-dimethylpentan-3-yl)hydrazine-1-carbonyl)-2-(2-methoxyethoxy)-3-methylphenyl)boronic acid;

(R)—N'-(3,5-dimethylbenzoyl)-N'-(2,2-dimethylhexan-3-yl)-3-methoxy-2-methyl-4-(3-(4,4,5,5-tetramethyl-1,3,2-dioxaborolan-2-yl)propyl)benzohydrazide;

(3-(1-(2,2-dimethylpentan-3-yl)-2-(3-methoxy-2-methylbenzoyl)hydrazine-1-carbonyl)phenyl)boronic acid;

(3-(1-(2,2-dimethylpentan-3-yl)-2-(3-methoxy-2-methylbenzoyl)hydrazine-1-carbonyl)-5-fluorophenyl)boronic acid;

N'-(3,5-dimethylbenzoyl)-N'-(2,2-dimethylhexan-3-yl)-2-methyl-3-(4,4,5,5-tetramethyl-1,3,2-dioxaborolan-2-yl)benzohydrazide;

N-(2,2-dimethylpentan-3-yl)-3,5-dimethoxy-4-methyl-N'-(2-methyl-3-(4,4,5,5-tetramethyl-1,3,2-dioxaborolan-2-yl)benzoyl)benzohydrazide;

N'-(tert-butyl)-N'-(3,5-dimethylbenzoyl)-1-hydroxy-1,3-dihydrobenzo[c][1,2]oxaborole-6-carbohydrazide;

(S)—N'-(3,5-dimethylbenzoyl)-N'-(2,2-dimethylpentan-3-yl)-1-hydroxy-1,3-dihydrobenzo[c][1,2]oxaborole-6-carbohydrazide;

(R)—N-(2,2-dimethylpentan-3-yl)-N'-(1-hydroxy-1,3-dihydrobenzo[c][1,2]oxaborole-6-carbonyl)-4,6-dimethylpyrimidine-2-carbohydrazide;

(R)—N'-(3,5-dimethylbenzoyl)-N'-(2,2-dimethylpentan-3-yl)-7-fluoro-1-hydroxy-1,3-dihydrobenzo[c][1,2]oxaborole-6-carbohydrazide;

(S)—N'-(3,5-bis(methyl-d3)benzoyl)-N'-(2,2-dimethylpentan-3-yl)-7-fluoro-1-hydroxy-1,3-dihydrobenzo[c][1,2]oxaborole-6-carbohydrazide;

N'-(tert-butyl)-N'-(3,5-dimethylbenzoyl)-4-fluoro-1-hydroxy-1,3-dihydrobenzo[c][1,2]oxaborole-5-carbohydrazide;

N'-(3,5-dimethylbenzoyl)-1-hydroxy-6-methyl-N'-neopentyl-3,4-dihydro-1H-benzo[c][1,5,2]dioxaborepine-7-carbohydrazide;

N'-(3,5-bis(methyl-d3)benzoyl)-1-hydroxy-6-methyl-N'-(tert-pentyl)-3,4-dihydro-1H-benzo[c][1,5,2]dioxaborepine-7-carbohydrazide;

(S)—N'-(3,5-dimethylbenzoyl)-N'-(2,2-dimethylpentan-3-yl)-1-hydroxy-6-methyl-3,4-dihydro-1H-benzo[c][1,5,2]dioxaborepine-7-carbohydrazide;

N'-(3,5-dimethylbenzoyl)-N'—((R)-2,2-dimethylpentan-3-yl)-2-methyl-3-(2-((tetrahydro-2H-pyran-2-yl)oxy)ethoxy)-4-(4,4,5,5-tetramethyl-1,3,2-dioxaborolan-2-yl)benzohydrazide;

N'-(tert-butyl)-N'-(3,5-dimethylbenzoyl)-3-fluoro-4-(4,4,5,5-tetramethyl-1,3,2-dioxaborolan-2-yl)benzohydrazide;

(R)-3-(cyanomethoxy)-N'-(3,5-dimethylbenzoyl)-N'-(2,2-dimethylpentan-3-yl)-2-methyl-4-(4,4,5,5-tetramethyl-1,3,2-dioxaborolan-2-yl)benzohydrazide;

(R)-(3-(2-(3,5-dimethylbenzoyl)-2-(2,2-dimethylpentan-3-yl)hydrazine-1-carbonyl)-2-fluoro-6-(methoxymethyl)phenyl)boronic acid;

(R)—N'-(3,5-dimethylbenzoyl)-N'-(2,2-dimethylpentan-3-yl)-1-hydroxy-6-methyl-1,2,3,4-tetrahydrobenzo[f][1,4,5]oxazaborepine-7-carbohydrazide;

(3-(2-(tert-butyl)-2-(3,5-dimethylbenzoyl)hydrazine-1-carbonyl)-2-chlorophenyl)boronic acid;

(R)-(3-(2-(3,5-dimethylbenzoyl)-2-(2,2-dimethylhexan-3-yl)hydrazine-1-carbonyl)-2-fluorophenyl)boronic acid;

(4-(2-(tert-butyl)-2-(3,5-dimethylbenzoyl)hydrazine-1-carbonyl)-3-methylphenyl)boronic acid;

(4-(2-(tert-butyl)-2-(3,5-dimethylbenzoyl)hydrazine-1-carbonyl)-3-fluorophenyl)boronic acid;

(R)-(4-(2-(3,5-bis(methyl-d3)benzoyl)-2-(2,2-dimethylpentan-3-yl)hydrazine-1-carbonyl)-3-fluorophenyl)boronic acid;

(4-(2-(tert-butyl)-2-(3,5-dimethylbenzoyl)hydrazine-1-carbonyl)-3-chlorophenyl)boronic acid;

(R)-(4-(2-(3,5-dimethylbenzoyl)-2-(2,2-dimethylhexan-3-yl)hydrazine-1-carbonyl)-3,5-difluorophenyl)boronic acid;

(R)-(3-(4-(2-(3,5-dimethylbenzoyl)-2-(2,2-dimethylhexan-3-yl)hydrazine-1-carbonyl)-2-methoxy-3-methylphenyl)propyl)boronic acid;

(R)-3-(difluoromethoxy)-N'-(3,5-dimethylbenzoyl)-N'-(2,2-dimethylhexan-3-yl)-2-methyl-4-(3-(4,4,5,5-tetramethyl-1,3,2-dioxaborolan-2-yl)propyl)benzohydrazide;

(R)-(3-(1-(2,2-dimethylpentan-3-yl)-2-(3-methoxy-2-methylbenzoyl)hydrazine-1-carbonyl)-5-methylphenyl)boronic acid;

(3-(1-(2,2-dimethylpentan-3-yl)-2-(3-methoxy-2-methylbenzoyl)hydrazine-1-carbonyl)-5-nitrophenyl)boronic acid;

(R)—N'-(2,2-dimethylpentan-3-yl)-3-methoxy-2-methyl-N'-(3-methyl-5-(4,4,5,5-tetramethyl-1,3,2-dioxaborolan-2-yl)benzoyl)benzohydrazide;

(R)-(3-(2-(3-borono-5-methylbenzoyl)-1-(2,2-dimethylpentan-3-yl)hydrazine-1-carbonyl)-5-methylphenyl)boronic acid;

(R)—N'-(3,5-dimethylbenzoyl)-N'-(2,2-dimethylhexan-3-yl)-2-methyl-3-(4,4,5,5-tetramethyl-1,3,2-dioxaborolan-2-yl)benzohydrazide;

N'-(2,5-dimethoxybenzoyl)-N'-(2,2-dimethylhexan-3-yl)-2-methyl-3-(4,4,5,5-tetramethyl-1,3,2-dioxaborolan-2-yl)benzohydrazide;

N'-(3,5-dimethylbenzoyl)-N'-(2,2-dimethylpentan-3-yl)-1-hydroxy-1,3-dihydrobenzo[c][1,2]oxaborole-6-carbohydrazide;

(S)—N'-benzoyl-N'-(2,2-dimethylpentan-3-yl)-1-hydroxy-1,3-dihydrobenzo[c][1,2]oxaborole-6-carbohydrazide;

N-(tert-butyl)-N'-(1-hydroxy-1,3-dihydrobenzo[c][1,2]oxaborole-6-carbonyl)-2,6-dimethylisonicotinohydrazide;

(R)—N'-benzoyl-N'-(2,2-dimethylpentan-3-yl)-7-fluoro-1-hydroxy-1,3-dihydrobenzo[c][1,2]oxaborole-6-carbohydrazide;

N-(tert-butyl)-N'-(7-fluoro-1-hydroxy-1,3-dihydrobenzo[c][1,2]oxaborole-6-carbonyl)-2,6-dimethylisonicotinohydrazide;

N'-(3,5-bis(methyl-d3)benzoyl)-N'-(tert-butyl)-4-fluoro-1-hydroxy-1,3-dihydrobenzo[c][1,2]oxaborole-5-carbohydrazide;

N'-(tert-butyl)-N'-(3,5-dimethylbenzoyl)-2-hydroxy-9-methyl-2,3,4,5-tetrahydrobenzo[f][1,2]oxaborepine-8-carbohydrazide;

N'-(3-chloro-5-methylbenzoyl)-1-hydroxy-6-methyl-N'-neopentyl-3,4-dihydro-1H-benzo[c][1,5,2]dioxaborepine-7-carbohydrazide;

N'-(tert-butyl)-N'-(3,5-dimethylbenzoyl)-1-hydroxy-6-methyl-3,4-dihydro-1H-benzo[c][1,5,2]dioxaborepine-7-carbohydrazide;

N'-(3,5-dimethylbenzoyl)-N'-(2,3-dimethylbutan-2-yl)-1-hydroxy-6-methyl-3,4-dihydro-1H-benzo[c][1,5,2]dioxaborepine-7-carbohydrazide;

(S)—N'-(3,5-bis(methyl-d3)benzoyl)-N'-(2,2-dimethylpentan-3-yl)-1-hydroxy-6-methyl-3,4-dihydro-1H-benzo[c][1,5,2]dioxaborepine-7-carbohydrazide;

(R)—N'-(3,5-bis(methyl-d3)benzoyl)-N'-(2,2-dimethyl-pentan-3-yl)-4-fluoro-1-hydroxy-1,3-dihydrobenzo[c][1,2]oxaborole-5-carbohydrazide;

N'-(3,5-dimethylbenzoyl)-N'-(1-fluorobutan-2-yl)-2-methyl-3-(2-((tetrahydro-2H-pyran-2-yl)oxy)ethoxy)-4-(4,4,5,5-tetramethyl-1,3,2-dioxaborolan-2-yl)benzohydrazide;

(R)—N'-(3,5-dimethylbenzoyl)-N'-(2,2-dimethylhexan-3-yl)-2-fluoro-4-(4,4,5,5-tetramethyl-1,3,2-dioxaborolan-2-yl)benzohydrazide;

(R)—N'-(3,5-dimethylbenzoyl)-N'-(2,2-dimethylhexan-3-yl)-2,6-difluoro-4-(4,4,5,5-tetramethyl-1,3,2-dioxaborolan-2-yl)benzohydrazide;

(R)-(4-(2-(3,5-dimethylbenzoyl)-2-(2,2-dimethylpentan-3-yl)hydrazine-1-carbonyl)-2-hydroxy-3-methylphenyl)boronic acid;

(R)—N'-(3,5-dimethylbenzoyl)-N'-(2,2-dimethylpentan-3-yl)-2-fluoro-4-(methoxymethyl)-3-(4,4,5,5-tetramethyl-1,3,2-dioxaborolan-2-yl)benzohydrazide;

(R)-(3-(2-(3,5-dimethylbenzoyl)-2-(2,2-dimethylpentan-3-yl)hydrazine-1-carbonyl)-6-(ethoxymethyl)-2-fluorophenyl)boronic acid;

potassium (R)-(4-(2-(3,5-dimethylbenzoyl)-2-(2,2-dimethylhexan-3-yl)hydrazine-1-carbonyl)-3-fluorophenyl)trifluoroborate;

(R)—N'-(3,5-dimethylbenzoyl)-N'-(2,2-dimethylhexan-3-yl)-3-hydroxy-2-methyl-4-(3-(4,4,5,5-tetramethyl-1,3,2-dioxaborolan-2-yl)propyl)benzohydrazide;

N'-(tert-butyl)-N'-(3,5-dimethylbenzoyl)-3-hydroxy-2-methyl-4-(3-(4,4,5,5-tetramethyl-1,3,2-dioxaborolan-2-yl)propyl)benzohydrazide;

(R)-(3-(4-(2-(3,5-dimethylbenzoyl)-2-(2,2-dimethyl-hexan-3-yl)hydrazine-1-carbonyl)-2-hydroxy-3-methylphenyl)propyl)boronic acid;

(3-(4-(2-(tert-butyl)-2-(3,5-dimethylbenzoyl)hydrazine-1-carbonyl)-2-hydroxy-3-methylphenyl)propyl)boronic acid;

tert-butyl (2-(3-(2-(tert-butyl)-2-(3,5-dimethylbenzoyl)hydrazine-1-carbonyl)-2-methyl-6-(4,4,5,5-tetramethyl-1,3,2-dioxaborolan-2-yl)phenoxy)ethyl)carbamate;

N'-(tert-butyl)-N'-(3,5-dimethylbenzoyl)-3-hydroxy-2-methyl-4-(4,4,5,5-tetramethyl-1,3,2-dioxaborolan-2-yl)benzohydrazide; or

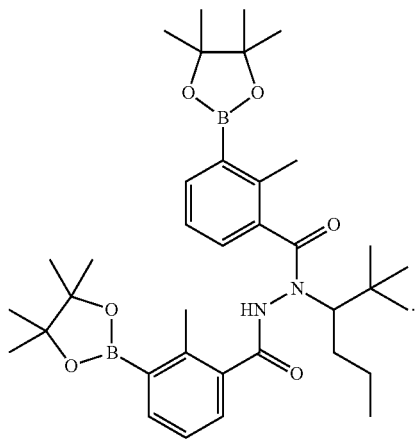 [SMILES: CCCC(N(NC(=O)c1cccc(B2OC(C)(C)C(C)(C)O2)c1C)C(=O)c1cccc(B2OC(C)(C)C(C)(C)O2)c1C)C(C)(C)C]

2. The compound claim 1 having Formula II:

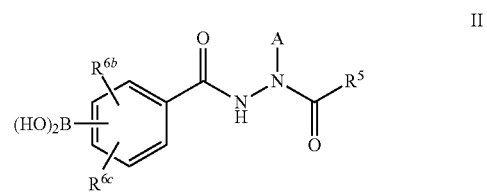

wherein $R^5$ is selected from the group consisting of $R^5$-1 and $R^5$-2; $R^{6e}$ is hydrogen; and $R^{6b}$ is selected from the group consisting of —CHO, —N(R$^{12}$)SO$_2$R$^{14}$, hydroxyalkyl, (amino)alkyl, (alkylamino)alkyl, (dialkylamino)alkyl, and —N(H)(cyano)alkyl, or a pharmaceutically acceptable salt or solvate thereof.

3. The compound of claim 1 having Formula IV:

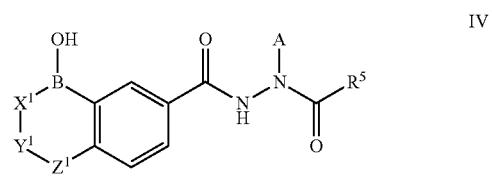

wherein $R^5$ is selected from the group consisting of $R^5$-1 and $R^5$-2; and $R^{6e}$ is hydrogen, or a pharmaceutically acceptable salt, solvate, or boronic anhydride thereof.

4. The compound of claim 1 having Formula V:

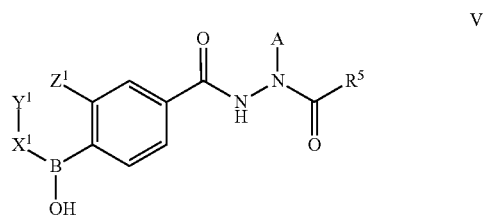

wherein $R^5$ is selected from the group consisting of $R^5$-1 and $R^5$-2; and $R^{6e}$ is hydrogen, or a pharmaceutically acceptable salt, solvate, or boronic anhydride thereof.

5. The compound of claim 3, or a pharmaceutically acceptable salt, solvate, or boronic anhydride thereof, wherein $Z^1$ is absent; $Y^1$ is selected from the group consisting of —CH$_2$— and —CH$_2$CH$_2$—; and $X^1$ is selected from the group consisting of —O— and —N(H)—.

6. The compound of claim 3, or a pharmaceutically acceptable salt, solvate, or boronic anhydride thereof, wherein $Z^1$ is —N(H)—; $Y^1$ is —CH$_2$CH$_2$—; and $X^1$ is —O—.

7. The compound of claim 1 having Formula VIII:

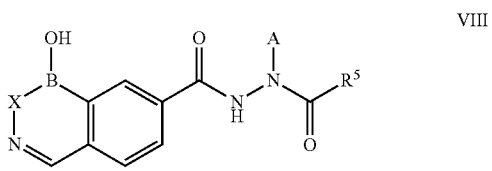

wherein $R^5$ is selected from the group consisting of $R^5$-1 and $R^5$-2; and $R^{6e}$ is hydrogen, or a pharmaceutically acceptable salt, solvate, or boronic anhydride thereof.

8. The compound of claim 1 having Formula IX:

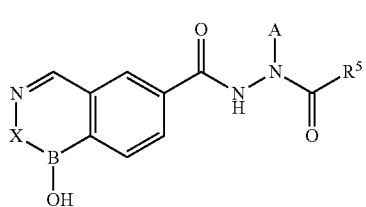

wherein $R^5$ is selected from the group consisting of $R^5$-1 and $R^5$-2; and $R^{6e}$ is hydrogen, or a pharmaceutically acceptable salt, solvate, or boronic anhydride thereof.

9. The compound of claim 7, or a pharmaceutically acceptable salt, solvate, or boronic anhydride thereof, wherein X is —O— or —N($R^{8a}$)—; and $R^{8a}$ is selected from the group consisting of hydrogen, alkyl, optionally substituted aryl, optionally substituted heteroaryl, alkylsulfonyl, arylsulfonyl, and alkylcarbonyl.

10. The compound of claim 1 having Formula XII:

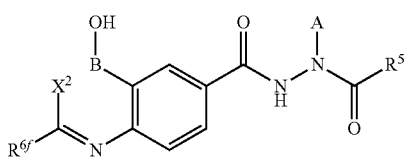

wherein $R^5$ is selected from the group consisting of $R^5$-1 and $R^5$-2; and $R^{6e}$ is hydrogen, or a pharmaceutically acceptable salt, solvate, or boronic anhydride thereof.

11. The compound of claim 10, or a pharmaceutically acceptable salt, solvate, or boronic anhydride thereof, wherein $X^2$ is —O— or N($R^{8b}$)—; and $R^{8b}$ is selected from the group consisting of hydrogen and alkyl.

12. The compound of claim 1 having Formula XVI:

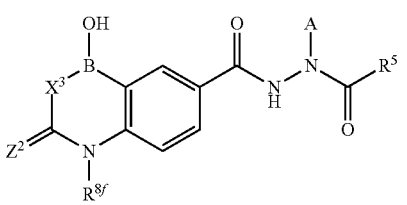

wherein $R^5$ is selected from the group consisting of $R^5$-1 and $R^5$-2; and $R^{6e}$ is hydrogen, or a pharmaceutically acceptable salt, solvate, or boronic anhydride thereof.

13. The compound of claim 12, or a pharmaceutically acceptable salt, solvate, or boronic anhydride thereof, wherein $Z^2$ is O; $X^3$ is —N($R^{8d}$)—; and $R^{8d}$ is selected from the group consisting of hydrogen, alkyl, and optionally substituted aryl.

14. The compound of claim 1, or a pharmaceutically acceptable salt, solvate, or boronic anhydride thereof, wherein A is —C($R^1$)($R^2$)($R^3$).

15. The compound of claim 1 having Formula XX

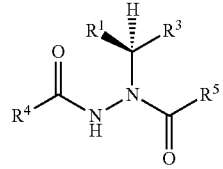

wherein $R^1$ does not equal $R^3$, or a pharmaceutically acceptable salt, solvate, or boronic anhydride thereof.

16. The compound of claim 1, or a pharmaceutically acceptable salt, solvate, or boronic anhydride thereof, selected from the group consisting of:
  N'-(tert-butyl)-N'-(3,5-dimethylbenzoyl)-1-hydroxy-2,3-dihydro-1H-benzo[c][1,2]azaborole-6-carbohydrazide;
  N'-(tert-butyl)-N'-(3,5-dimethylbenzoyl)-1-hydroxy-3-methyl-1H-benzo[c][1,5,2]oxazaborinine-6-carbohydrazide;
  N'-(tert-butyl)-N'-(3,5-dimethylbenzoyl)-1-hydroxy-1H-benzo[c][1,5,2]oxazaborinine-6-carbohydrazide;
  N'-(tert-butyl)-N'-(3,5-dimethylbenzoyl)-1-hydroxy-2-phenyl-3-thioxo-1,2,3,4-tetrahydrobenzo[c][1,5,2]diazaborinine-6-carbohydrazide;
  N'-(tert-butyl)-N'-(3,5-dimethylbenzoyl)-1-hydroxy-3-oxo-2-(p-tolyl)-1,2,3,4-tetrahydrobenzo[c][1,5,2]diazaborinine-6-carbohydrazide;
  N'-(3,5-dimethylbenzoyl)-1-hydroxy-3-(trifluoromethyl)-1H-benzo[c][1,5,2]oxazaborinine-6-carbohydrazide;
  (4-(2-(tert-butyl)-2-(3,5-dimethylbenzoyl)hydrazine-1-carbonyl)-2-(phenylsulfonamido)phenyl)boronic acid;
  N-(tert-butyl)-1-hydroxy-N'-(3-methoxy-2-methylbenzoyl)-1,3-dihydrobenzo[c][1,2]oxaborole-6-carbohydrazide;
  N-(tert-butyl)-1-hydroxy-N'-(3-methoxy-2-methylbenzoyl)-2,3-dihydro-1H-benzo[c][1,2]azaborole-6-carbohydrazide;
  (5-(2-(tert-butyl)-2-(3,5-dimethylbenzoyl)hydrazine-1-carbonyl)-2-((methylamino)methyl)phenyl)boronic acid;
  (5-(2-(tert-butyl)-2-(3,5-dimethylbenzoyl)hydrazine-1-carbonyl)-2-((dimethylamino)methyl)phenyl)boronic acid;
  N-(tert-butyl)-1-hydroxy-N'-(3-methoxy-2-methylbenzoyl)-3-methyl-1H-benzo[c][1,5,2]oxazaborinine-6-carbohydrazide;
  N-(tert-butyl)-1-hydroxy-N'-(3-methoxy-2-methylbenzoyl)-1H-benzo[c][1,5,2]oxazaborinine-6-carbohydrazide;
  N-(tert-butyl)-1-hydroxy-N'-(3-methoxy-2-methylbenzoyl)-2-phenyl-3-thioxo-1,2,3,4-tetrahydrobenzo[c][1,5,2]diazaborinine-6-carbohydrazide;
  N-(tert-butyl)-1-hydroxy-N'-(3-methoxy-2-methylbenzoyl)-3-oxo-2-phenyl-1,2,3,4-tetrahydrobenzo[c][1,5,2]diazaborinine-6-carbohydrazide;
  (4-(1-(tert-butyl)-2-(3-methoxy-2-methylbenzoyl)hydrazine-1-carbonyl)-2-(phenylsulfonamido)phenyl)boronic acid;
  (4-(2-(tert-butyl)-2-(3,5-dimethylbenzoyl)hydrazine-1-carbonyl)-2-((cyanomethyl)amino)phenyl)boronic acid;
  N'-(tert-butyl)-N'-(3,5-dimethylbenzoyl)-1-hydroxy-1,2,3,4-tetrahydrobenzo[c][1,2]azaborinine-7-carbohydrazide;
  (5-(2-(tert-butyl)-2-(3,5-dimethylbenzoyl)hydrazine-1-carbonyl)-2-(cyanomethyl)phenyl)boronic acid;

N'-(tert-butyl)-N'-(3,5-dimethylbenzoyl)-1-hydroxy-1H-benzo[d][1,2,6]oxazaborinine-7-carbohydrazide;

N'-(tert-butyl)-N'-(3,5-dimethylbenzoyl)-1-hydroxy-1,2-dihydrobenzo[d][1,2,3]diazaborinine-7-carbohydrazide;

(5-(2-(tert-butyl)-2-(3,5-dimethylbenzoyl)hydrazine-1-carbonyl)-2-formylphenyl)boronic acid;

N-(tert-butyl)-1-hydroxy-2-isopropyl-3-(isopropylamino)-N'-(3-methoxy-2-methylbenzoyl)-1,2-dihydrobenzo[c][1,5,2]diazaborinine-6-carbohydrazide;

N'-(3-amino-4-(4,4,5,5-tetramethyl-1,3,2-dioxaborolan-2-yl)benzoyl)-N'-(tert-butyl)-3-methoxy-2-methylbenzohydrazide;

N'-(tert-butyl)-N'-(3,5-dimethylbenzoyl)-1-hydroxy-2-isopropyl-1,2-dihydrobenzo[d][1,2,3]diazaborinine-7-carbohydrazide;

N'-(tert-butyl)-N'-(3,5-dimethylbenzoyl)-1-hydroxy-2-methyl-1,2-dihydrobenzo[d][1,2,3]diazaborinine-7-carbohydrazide;

1,1'-oxybis(N'-(tert-butyl)-N'-(3,5-dimethylbenzoyl)-2-(pyridin-2-yl)-1,2-dihydrobenzo[d][1,2,3]diazaborinine-7-carbohydrazide);

N'-(tert-butyl)-N'-(3,5-dimethylbenzoyl)-1-hydroxy-2-phenyl-1,2-dihydrobenzo[d][1,2,3]diazaborinine-7-carbohydrazide;

(R)—N'-(3,5-dimethylbenzoyl)-N'-(2,2-dimethylpentan-3-yl)-1-hydroxy-3-oxo-2-phenyl-1,2,3,4-tetrahydrobenzo[c][1,5,2]diazaborinine-6-carbohydrazide;

(R)—N'-(3,5-dimethylbenzoyl)-N'-(2,2-dimethylpentan-3-yl)-5-hydroxy-3-oxo-4-phenyl-1,3,4,5-tetrahydrobenzo[c][1,2,6,5]oxadiazaborepine-8-carbohydrazide;

(4-(2-(tert-butyl)-2-(3,5-dimethylbenzoyl)hydrazine-1-carbonyl)-2-formylphenyl)boronic acid;

N'-(tert-butyl)-N'-(3,5-dimethylbenzoyl)-1-hydroxy-1H-benzo[d][1,2,6]oxazaborinine-6-carbohydrazide;

N'-(tert-butyl)-N'-(3,5-dimethylbenzoyl)-1-hydroxy-1,2-dihydrobenzo[d][1,2,3]diazaborinine-6-carbohydrazide;

N-(tert-butyl)-1-hydroxy-N'-(3-methoxy-2-methylbenzoyl)-1,2-dihydrobenzo[d][1,2,3]diazaborinine-7-carbohydrazide;

N-(tert-butyl)-1-hydroxy-N'-(3-methoxy-2-methylbenzoyl)-2-methyl-1,2-dihydrobenzo[d][1,2,3]diazaborinine-7-carbohydrazide;

N-(tert-butyl)-1-hydroxy-2-isopropyl-N'-(3-methoxy-2-methylbenzoyl)-1,2-dihydrobenzo[d][1,2,3]diazaborinine-7-carbohydrazide;

(5-(1-(tert-butyl)-2-(3-methoxy-2-methylbenzoyl)hydrazine-1-carbonyl)-2-formylphenyl)boronic acid;

N'-(tert-butyl)-N'-(3,5-dimethylbenzoyl)-1-hydroxy-2-methyl-1,2-dihydrobenzo[d][1,2,3]diazaborinine-6-carbohydrazide;

(4-(1-(tert-butyl)-2-(3-methoxy-2-methylbenzoyl)hydrazine-1-carbonyl)-2-formylphenyl)boronic acid;

N-(tert-butyl)-1-hydroxy-N'-(3-methoxy-2-methylbenzoyl)-1H-benzo[d][1,2,6]oxazaborinine-6-carbohydrazide;

N-(tert-butyl)-1-hydroxy-N'-(3-methoxy-2-methylbenzoyl)-1,2-dihydrobenzo[d][1,2,3]diazaborinine-6-carbohydrazide;

N-(tert-butyl)-1-hydroxy-N'-(3-methoxy-2-methylbenzoyl)-2-methyl-1,2-dihydrobenzo[d][1,2,3]diazaborinine-6-carbohydrazide;

N'-(tert-butyl)-3-cyano-N'-(3,5-dimethylbenzoyl)-1-hydroxy-1,3-dihydrobenzo[c][1,2]oxaborole-6-carbohydrazide;

N'-(tert-butyl)-N'-(3,5-dimethylbenzoyl)-1-hydroxy-2-(methylsulfonyl)-1,2-dihydrobenzo[d][1,2,3]diazaborinine-7-carbohydrazide;

N'-(tert-butyl)-N'-(3,5-dimethylbenzoyl)-1-hydroxy-2-tosyl-1,2-dihydrobenzo[d][1,2,3]diazaborinine-7-carbohydrazide;

N'-(tert-butyl)-1-hydroxy-N'-(3-methoxy-2-methylbenzoyl)-2-(methylsulfonyl)-1,2-dihydrobenzo[d][1,2,3]diazaborinine-7-carbohydrazide;

N-(tert-butyl)-1-hydroxy-N'-(3-methoxy-2-methylbenzoyl)-2-tosyl-1,2-dihydrobenzo[d][1,2,3]diazaborinine-7-carbohydrazide;

N-(tert-butyl)-1-hydroxy-N'-(3-methoxy-2-methylbenzoyl)-2-phenyl-1,2-dihydrobenzo[d][1,2,3]diazaborinine-7-carbohydrazide;

N-(tert-butyl)-3-cyano-1-hydroxy-N'-(3-methoxy-2-methylbenzoyl)-1,3-dihydrobenzo[c][1,2]oxaborole-6-carbohydrazide;

(R)—N'-(3,5-dimethylbenzoyl)-N'-(2,2-dimethylpentan-3-yl)-1-hydroxy-1,2-dihydrobenzo[d][1,2,3]diazaborinine-7-carbohydrazide;

(R)—N'-(3,5-dimethylbenzoyl)-N'-(2,2-dimethylpentan-3-yl)-1-hydroxy-2-methyl-1,2-dihydrobenzo[d][1,2,3]diazaborinine-7-carbohydrazide;

(R)—N'-(3,5-dimethylbenzoyl)-N'-(2,2-dimethylpentan-3-yl)-1-hydroxy-2-(methylsulfonyl)-1,2-dihydrobenzo[d][1,2,3]diazaborinine-7-carbohydrazide;

(R)—N'-(3,5-dimethylbenzoyl)-N'-(2,2-dimethylpentan-3-yl)-1-hydroxy-2-tosyl-1,2-dihydrobenzo[d][1,2,3]diazaborinine-7-carbohydrazide;

(R)-(5-(2-(3,5-dimethylbenzoyl)-2-(2,2-dimethylpentan-3-yl)hydrazine-1-carbonyl)-2-formylphenyl)boronic acid;

(R)—N-(2,2-dimethylpentan-3-yl)-1-hydroxy-N'-(3-methoxy-2-methylbenzoyl)-1H-benzo[d][1,2,6]oxazaborinine-7-carbohydrazide;

(R)—N-(2,2-dimethylpentan-3-yl)-1-hydroxy-N'-(3-methoxy-2-methylbenzoyl)-1,2-dihydrobenzo[d][1,2,3]diazaborinine-7-carbohydrazide;

(R)—N-(2,2-dimethylpentan-3-yl)-1-hydroxy-N'-(3-methoxy-2-methylbenzoyl)-2-methyl-1,2-dihydrobenzo[d][1,2,3]diazaborinine-7-carbohydrazide;

(R)-(5-(1-(2,2-dimethylpentan-3-yl)-2-(3-methoxy-2-methylbenzoyl)hydrazine-1-carbonyl)-2-formylphenyl)boronic acid;

2-acetyl-N'-(tert-butyl)-N'-(3,5-dimethylbenzoyl)-1-hydroxy-1,2-dihydrobenzo[d][1,2,3]diazaborinine-6-carbohydrazide;

N'-(tert-butyl)-N'-(3,5-dimethylbenzoyl)-1-hydroxy-2-phenyl-1,2-dihydrobenzo[d][1,2,3]diazaborinine-6-carbohydrazide;

N'-(tert-butyl)-N'-(3,5-dimethylbenzoyl)-1-hydroxy-2-(methylsulfonyl)-1,2-dihydrobenzo[d][1,2,3]diazaborinine-6-carbohydrazide;

(R)—N'-(3,5-dimethylbenzoyl)-N'-(2,2-dimethylpentan-3-yl)-1-hydroxy-1,3,4,5-tetrahydrobenzo[c][1,5,2]oxazaborepine-7-carbohydrazide;

(R)—N'-(3,5-dimethylbenzoyl)-N'-(2,2-dimethylpentan-3-yl)-1-hydroxy-2-phenyl-3-thioxo-1,2,3,4-tetrahydrobenzo[c][1,5,2]diazaborinine-6-carbohydrazide;

(R)—N-(2,2-dimethylpentan-3-yl)-1-hydroxy-N'-(3-methoxy-2-methylbenzoyl)-2-(methylsulfonyl)-1,2-dihydrobenzo[d][1,2,3]diazaborinine-7-carbohydrazide;

(R)—N-(2,2-dimethylpentan-3-yl)-1-hydroxy-N'-(3-methoxy-2-methylbenzoyl)-1H-benzo[d][1,2,6]oxazaborinine-7-carbohydrazide;

(4-(1-(tert-butyl)-2-(5-methoxy-4-methylnicotinoyl)hydrazine-1-carbonyl)-3-fluorophenyl)boronic acid;

(R)-(4-(2-(3,5-dimethylbenzoyl)-2-(2,2-dimethylpentan-3-yl)hydrazine-1-carbonyl)-2-formylphenyl)boronic acid;

(R)—N'-(3,5-dimethylbenzoyl)-N'-(2,2-dimethylpentan-3-yl)-1-hydroxy-1H-benzo[d][1,2,6]oxazaborinine-6-carbohydrazide;

(R)—N'-(3,5-dimethylbenzoyl)-N'-(2,2-dimethylpentan-3-yl)-1-hydroxy-1,2-dihydrobenzo[d][1,2,3]diazaborinine-6-carbohydrazide;

(R)—N'-(3,5-dimethylbenzoyl)-N'-(2,2-dimethylpentan-3-yl)-1-hydroxy-1H-benzo[d][1,2,6]oxazaborinine-7-carbohydrazide;

N-(tert-butyl)-1-hydroxy-N'-(3-methoxy-2-methylbenzoyl)-1H-benzo[d][1,2,6]oxazaborinine-7-carbohydrazide; and R)—N'-(3,5-dimethylbenzoyl)-3-hydroxy-N'-(2,2,3-trimethylpentan-3-yl)-1,3-dihydrobenzo[c][1,2,5]oxazaborole-6-carbohydrazide.

17. A pharmaceutical composition comprising the compound of claim 1, or a pharmaceutically acceptable salt, solvate, or boronic anhydride thereof, and a pharmaceutically acceptable carrier.

18. A method of regulating gene expression of a gene of interest in an isolated host cell or a non-human organism, the method comprising contacting said host cell with the compound of claim 1, or a pharmaceutically acceptable salt, solvate, or boronic anhydride thereof, wherein said host cell or non-human organism comprises a polynucleotide encoding a gene switch that comprises a ligand binding domain that binds said compound.

19. A kit comprising the compound of claim 1, or a pharmaceutically acceptable salt, solvate, or boronic anhydride thereof.

* * * * *

UNITED STATES PATENT AND TRADEMARK OFFICE
CERTIFICATE OF CORRECTION

PATENT NO.       : 9,944,659 B2
APPLICATION NO.  : 14/855646
DATED            : April 17, 2018
INVENTOR(S)      : James et al.

Page 1 of 1

It is certified that error appears in the above-identified patent and that said Letters Patent is hereby corrected as shown below:

In the Claims

In Claim 4, at Column 260, Lines 33-43, change the structure:

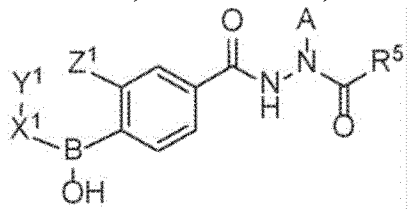

To:

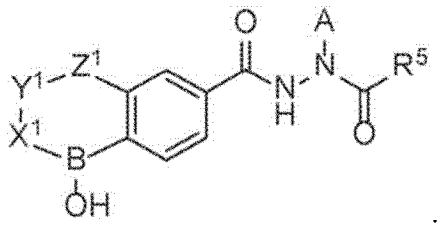

In Claim 10, at Column 261, Lines 25-34, change the structure:

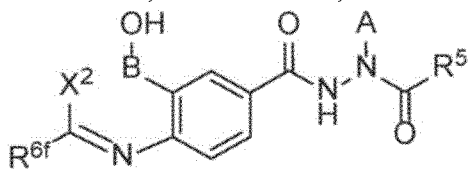

To:

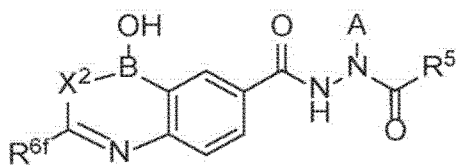

Signed and Sealed this
Seventh Day of August, 2018

Andrei Iancu
*Director of the United States Patent and Trademark Office*

SEQUENCE LISTING

<160> NUMBER OF SEQ ID NOS: 1

<210> SEQ ID NO 1
<211> LENGTH: 10975
<212> TYPE: DNA
<213> ORGANISM: Artificial sequence
<220> FEATURE:
<223> OTHER INFORMATION: RheoSwitch(R) Vector

<400> SEQUENCE: 1

| | | | | | |
|---|---|---|---|---|---|
| gctgagctat | gcctaatcaa | gtcacggtaa | ctatgactct | cttaaggtag | ccaaatggcg | 60 |
| ccacgaaagg | aggtcgtgaa | atggataaaa | aaatacagcg | ttttttcatgt | acaactatac | 120 |
| tagttgtagt | gcctaaataa | tgcttttaaa | acttaaaaat | atcagataac | agcttggtgg | 180 |
| cacccattgt | gttcacagga | gatacagctt | tatctgtact | gatattaatg | acatgctgca | 240 |
| ctcggtgtga | aagggcatct | agtaggctat | ggcagggcct | gccgccccga | cgttggctgc | 300 |
| gagccctggg | ccttcacccg | aacttggggg | gtggggtggg | gaaaaggaag | aaacgcgggc | 360 |
| gtattggccc | caatggggtc | tcggtggggt | atcgacagag | tgccagccct | gggaccgaac | 420 |
| cccgcgttta | tgaacaaacg | acccaacacc | gtgcgtttta | ttctgtcttt | ttattgccgt | 480 |
| catagcgcgg | gttccttccg | gtattgtctc | cttccgtgtt | tcatcagaaa | aactcgtcca | 540 |
| gcaggcggta | gaaagcgatg | cgctgagaat | ctggtgcagc | gatgccgtac | agaaccagga | 600 |
| agcggtcagc | ccattcgccg | cccagttctt | cagcgatgtc | gcgggtagcc | agagcgatgt | 660 |
| cctggtagcg | gtcagcaacg | cccagacgac | cacagtcgat | gaagcagag | aagcggccgt | 720 |
| tttcaaccat | gatgttcggc | aggcaagcgt | cgccgtgggt | aacaaccagg | tcttcgccgt | 780 |
| ctggcatacg | agctttcagg | cgagcgaaca | gttcagccgg | agccaggccc | tggtgttctt | 840 |
| cgtccaggtc | gtcctggtca | accaggccag | cttccatgcg | ggtgcgagcg | cgttcgatgc | 900 |
| ggtgtttagc | ctggtggtcg | aacgacaag | tagccgggtc | cagggtgtgc | aggcggcgca | 960 |
| tagcgtcagc | catgatagaa | acttttttcag | ccggagccag | gtgagaagac | agcagatcct | 1020 |
| ggcccggaac | ttcgcccagc | agcagccagt | cgcggccagc | ttcggtaaca | acgtccagaa | 1080 |
| cagcagcgca | cggaacgccg | gtggtagcca | gccaagacag | gcgagcagct | tcgtcttgca | 1140 |
| gttcgttcag | agcgccagac | aggtcggttt | taacgaacag | aaccgggcgg | ccctgagcag | 1200 |
| acaggcggaa | aacagcagcg | tcagagcagc | cgatggtttg | ttgtgcccag | tcgtaaccaa | 1260 |
| acagacgttc | aacccaagca | gccggagagc | cagcgtgcag | gccgtcctgt | tcgatcatgg | 1320 |
| tggccccccc | ccccccgga | atagctctga | ggccgaggca | gcttcggcct | ctgcataaat | 1380 |
| aaaaaaaatt | agtcagccat | ggggcggaga | atgggcggaa | ctgggcggag | ttaggggcgg | 1440 |
| gatgggcgga | gttaggggcg | ggactatggt | tgctgactaa | ttgagatgct | tgctttgcat | 1500 |
| acttctgcct | gctggggagc | ctggggactt | tccacacctg | gttgctgact | aattgagatg | 1560 |
| cttgctttgc | atacttctgc | ctgctgggga | gcctggggac | tttccacacc | ctaaccatgc | 1620 |
| attcaactat | cccaacgagg | gattcgaagg | acgataccta | cgttagactt | aactataacg | 1680 |
| gtcctaaggt | agcgaccact | tagacgtgtt | gaaaccctag | ggccgcacag | gcccgccgac | 1740 |
| gatccgagcg | tggccatcgt | ggcccaccta | agtggtccag | gaacggcgtg | ggctcgttta | 1800 |
| aaccgtacca | ttagggaaag | tacccactta | tgtgggcgat | cgcttaatta | aggcggccg | 1860 |
| ccgcaataaa | atatctttat | tttcattaca | tctgtgtgtt | ggttttttgt | gtgaatccat | 1920 |
| agtactaaca | tacgctctcc | atcaaaacaa | aacgaaacaa | aacaaactag | caaaataggc | 1980 |
| tgtccccagt | gcaagtccag | gtgccagaac | atttctctat | ccataatgca | ggggtaccgg | 2040 |

-continued

```
gtgatgacgg tgaaaacctc caattgcgga gtactgtcct ccgagcggag tactgtcctc    2100
cgagcggagt actgtcctcc gagcggagta ctgtcctccg agcggagtac tgtcctccga    2160
gcggagtact gtcctccgag cggagagtcc cggggaccct agagggtata taatgggtgc    2220
cttagctggt gtgtgacctc atcttcctgt acgcccctgc aggggcgcgc cacgcgtccg    2280
cgggctagcg ccaccatgga agatgccaaa aacattaaga agggcccagc gccattctac    2340
ccactcgaag acgggaccgc tggcgagcag ctgcacaaag ccatgaagcg ctacgccctg    2400
gtgcccggca ccatcgcctt taccgacgca catatcgagg tggacattac ctacgccgag    2460
tacttcgaga tgagcgttcg gctggcagaa gctatgaagc gctatgggct gaatacaaac    2520
catcggatcg tggtgtgcag cgagaatagc ttgcagttct tcatgcccgt gttgggtgcc    2580
ctgttcatcg gtgtggctgt ggccccagct aacgacatct acaacgagcg cgagctgctg    2640
aacagcatgg gcatcagcca gcccaccgtc gtattcgtga gcaagaaagg gctgcaaaag    2700
atcctcaacg tgcaaaagaa gctaccgatc atacaaaaga tcatcatcat ggatagcaag    2760
accgactacc agggcttcca aagcatgtac accttcgtga cttcccattt gccacccggc    2820
ttcaacgagt acgacttcgt gcccgagagc ttcgaccggg acaaaaccat cgccctgatc    2880
atgaacagta gtggcagtac cggattgccc aagggcgtag ccctaccgca ccgcaccgct    2940
tgtgtccgat tcagtcatgc ccgcgacccc atcttcggca accagatcat ccccgacacc    3000
gctattctca gcgtggtgcc atttcaccac ggcttcggca tgttcaccac gctgggctac    3060
ttgatctgcg gctttcgggt cgtgctcatg taccgcttcg aggaggagct attcttgcgc    3120
agcttgcaag actataagat tcaatctgcc ctgctggtgc ccacactatt tagcttcttc    3180
gctaagagca ctctcatcga caagtacgac ctaagcaact gcacgagat cgccagcggc    3240
ggagcgcctc tcagcaagga ggtaggtgag gccgtggcca aacgcttcca cctaccaggc    3300
atccgccagg gctacggcct gacagaaaca accagcgcca ttctgatcac ccccgaaggg    3360
gacgacaagc ctggcgcagt aggcaaggtg gtgcccttct cgaggctaa ggtggtggac    3420
ttggacacag gtaagaccct gggtgtgaac cagcgcggcg agctgtgcgt ccgtggcccc    3480
atgatcatga gcggctacgt gaacaacccc gaggctacaa acgctctcat cgacaaggac    3540
ggctggctgc acagcggcga catcgcctac tgggacgagg acgagcactt cttcatcgtg    3600
gaccggctca gagagcctga tcaaatacaag ggctaccagg tagccccagc cgaactggag    3660
agcatcctgc tgcaacaccc caacatcttc gacgccgggg tcgctggcct gcccgacgac    3720
gatgctggca gctgcccgc cgcagtcgtc gtgctggaac acggtaaaac catgaccgag    3780
aaggagatcg tggactatgt ggccagccag gttacaaccg ccaagaagct gcgcggtggt    3840
gttgtgttcg tggacgaggt gcctaaagga ctgaccggca agttggacgc ccgcaagatc    3900
cgcgagattc tcattaaggc caagaagggc ggcaagatcg ccgtgtaaat cgattgcgca    3960
aagctttcgc gataggcgag accaatgggt gtgtacgtag cggccgcgtc gactgatggg    4020
tggcatccct gtgacccctc cccagtgcct ctcctggccc tggaagttgc cactccagtg    4080
cccaccagcc ttgtcctaat aaaattaagt tgcatcattt tgtctgacta ggtgtccttc    4140
tataatatta tggggtggag gggggtggta tggagcaagg gcaagttgg gaagacaacc    4200
tgtagggcct gcggggtcta ttgggaacca agctggagtg cagtggcaca atcttggctc    4260
actgcaatct ccgcctcctg ggttcaagcg attctcctgc ctcagcctcc cgagttgttg    4320
ggattccagg catgcatgac caggctcagc taatttttgt ttttttggta gagacggggt    4380
```

```
ttcaccatat tggccaggct ggtctccaac tcctaatctc aggtgatcta cccaccttgg    4440
cctcccaaat tgctgggatt acaggcgtga accactgctc ccttccctgt ccttctgatt    4500
ttaaaataac tataccagca ggaggacgtc cagacacagc ataggctacc tggccatgcc    4560
caaccggtgg gacatttgag ttgcttgctt ggcactgtcc tctcatgcgt tgggtccact    4620
cagtagatgc ctgttgaatt atttaaatcg gtccgcgtac ggctcttctc cccctcgagg    4680
gcctccgcgc cgggttttgg cgcctcccgc gggcgcgccc ctcctcacgg cgagcgctgc    4740
cacgtcagac gaagggcgca gcgagcgtcc tgatccttcc gcccggacgc tcaggacagc    4800
ggcccgctgc tcataagact cggccttaga accccagtat cagcagaagg acattttagg    4860
acgggacttg ggtgactcta gggcactggt tttctttcca gagagcggaa caggcgagga    4920
aaagtagtcc cttctcggcg attctgcgga gggatctccg tggggcggtg aacgccgatg    4980
attatataag gacgcgccgg gtgtggcaca gctagttccg tcgcagccgg gatttgggtc    5040
gcggttcttg tttgtggatc gctgtgatct tcacttggtg agtagcgggc tgctgggctg    5100
ggtacgtgcg ctcggggttg gcgagtgtgt tttgtgaagt ttttaggca ccttttgaaa    5160
tgtaatcatt tgggtcaata tgtaattttc agtgttagac tagtaaattg tccgctaaat    5220
tctggccgtt tttggctttt ttgttagacg ccgcgggggg ggggggggg ctagcgccac    5280
catgggcccc aagaagaaaa ggaaggtggc cccccccacc gacgtgagcc tgggcgacga    5340
gctgcacctg gacggcgagg acgtggccat ggcccacgcc gacgccctgg acgacttcga    5400
cctggacatg ctgggcgacg gcgacagccc cggccccggc ttcacccccc acgacagcgc    5460
cccctacggc gccctggaca tggccgactt cgagttcgag cagatgttca ccgacgccct    5520
gggcatcgac gagtacggcg gcgaattcga gatgcccgtg gacaggattc tggaggccga    5580
actcgccgtg gagcagaaaa cgaccagggg cgtggagggc cccggcggaa ccggcggcag    5640
cggcagcagc cccaacgacc ccgtgaccaa catctgccag gccgccgaca agcagctgtt    5700
caccctggtg gagtgggcca agaggattcc ccacttcagc agcctgcccc tggacgacca    5760
ggtgatcctg ctgagggccg gatggaacga gctgctgatc gccagcttca gccacaggag    5820
catcgacgtg agggacggca tcctgctggc caccggcctg cacgtccata ggaacagcgc    5880
ccacagcgcc ggagtgggcg ccatcttcga cagggtgctg accgagctgg tgagcaagat    5940
gagggacatg aggatggaca agaccgagct gggctgcctg agggccatca tcctgttcaa    6000
ccccgaggtg aggggcctga aaagcgccca ggaggtggag ctgctgaggg agaaggtgta    6060
cgccgccctg gaggagtaca ccaggaccac ccaccccgac gagcccggca gattcgccaa    6120
gctgctgctg aggctgccca gcctgaggag catcggcctg aagtgcctgg agcacctgtt    6180
cttcttcagg ctgatcggcg acgtgcccat cgacaccttc ctgatggaga tgctggagag    6240
ccccagcgac agctgagcat gccccctct ccctcccccc ccctaacgt tactggccga    6300
agccgcttgg aataaggccg gtgtgcgttt gtctatatgt tatttccac catattgccg    6360
tcttttggca atgtgagggc ccggaaacct ggccctgtct tcttgacgag cattcctagg    6420
ggtctttccc ctctcgccaa aggaatgcaa ggtctgttga atgtcgtgaa ggaagcagtt    6480
cctctggaag cttcttgaag acaaacaacg tctgtagcga ccctttgcag gcagcggaac    6540
cccccacctg gcgacaggtg cctctgcggc caaaagccac gtgtataaga tacacctgca    6600
aaggcggcac aaccccagtg ccacgttgtg agttggatag ttgtggaaag agtcaaatgg    6660
ctctcctcaa gcgtattcaa caaggggctg aaggatgccc agaaggtacc ccattgtatg    6720
ggatctgatc tggggcctcg gtgcacatgc tttacatgtg tttagtcgag gttaaaaaac    6780
```

```
gtctaggccc cccgaaccac ggggacgtgg ttttcctttg aaaaacacga tccatatggc    6840
caccatgaag ctgctgagca gcatcgagca ggcttgcgac atctgcaggc tgaagaagct    6900
gaagtgcagc aaggagaagc ccaagtgcgc caagtgcctg aagaacaact gggagtgcag    6960
atacagcccc aagaccaaga ggagcccct gaccagggcc cacctgaccg aggtggagag     7020
caggctggag aggctggagc agctgttcct gctgatcttc cccagggagg acctggacat    7080
gatcctgaag atggacagcc tgcaagacat caaggccctg ctgaccggcc tgttcgtgca    7140
ggacaacgtg aacaaggacg ccgtgaccga caggctggcc agcgtggaga ccgacatgcc    7200
cctgaccctg aggcagcaca ggatcagcgc caccagcagc agcgaggaga gcagcaacaa    7260
gggccagagg cagctgaccg tgagcccga gtttcccggg atcaggcccg agtgcgtggt     7320
gcccgagacc cagtgcgcca tgaaaaggaa ggagaagaag gccagaaagg agaaggacaa    7380
gctgcccgtg agcaccacca ccgtcgatga ccacatgccc cccatcatgc agtgcgagcc    7440 ccccccccc gaggccgcca ggattcacga ggtcgtgccc aggttcctga gcgacaagct     7500
gctggtgacc aacaggcaga gaacatccc ccagctgacc gccaaccagc agttcctgat     7560
cgccaggctg atctggtatc aggacggcta cgagcagccc agcgacgagg acctgaaaag    7620
gatcacccag acctggcagc aggccgacga cgagaacgag gagagcgaca ccccctcag     7680 gcagatcacc gagatgacca tcctgaccgt gcagctgatc gtggagttcg ccaagggcct    7740
gcccggattc gccaagatca gccagcccga ccagatcacc ctgctgaagg cttgcagcag    7800
cgaggtgatg atgctgaggg tggccaggag gtacgacgcc gccagcgaca gcatcctgtt    7860
cgccaacaac caggcttaca ccagggacaa ctacaggaag ctggcatgg ccgaggtgat     7920 cgaggacctc ctgcacttct gcagatgtat gtacagcatg gccctggaca catccacta     7980 cgccctgctg accgccgtgg tgatcttcag cgacaggccc ggcctggagc agccccagct    8040
ggtggaggag atccagaggt actacctgaa caccctgagg atctacatcc tgaaccagct    8100
gagcggcagc gccaggagca gcgtgatcta cggcaagatc ctgagcatcc tgagcgagct    8160
gaggaccctg ggaatgcaga acagcaatat gtgtatcagc ctgaagctga agaacaggaa    8220 gctgccccc ttcctggagg agatttggga cgtggccgac atgagccaca cccagccccc     8280
ccccatcctg gagagcccca ccaacctgtg aatcgattag acatgataag atacattgat    8340
gagtttggac aaaccacaac tagaatgcag tgaaaaaaat gctttaattg tgaaatttgt    8400
gatgctattg cttaatttgt aaccattata agctgcaata acaagttaa taaaacattt     8460 gcattcattt tatgtttcag gttcaggggg agatgtggga ggttttttaa agcaagtaaa    8520
acctctacaa atgtggtatc tagagctctt ccaaaattaa tacgcattcg cgtgcgaaat    8580
cattaccctg ttatccctac gcctagcctt agggttcaca tctatgtcgg gtgcggagaa    8640
agaggtaatg aaatggcaat aacaggctag aaccagctaa cgttaggagc atagattggg    8700
gcattccgga actataaatt gcgttgcgct cactgcccgc tttccagtcg ggaaacctgt    8760
cgtgccagct gcataaatga atcggccaac gcgcggggag aggcggtttg cgtattgggc    8820
gcgcttccgc ttcctcgctc actgactcgc tgcgctcggt cgttcggctg cggcgagcgg    8880
```

```
tatcagctca ctcaaaggcg gtaatacggt tatccacaga atcaggggat aacgcaggaa    8940
agaacatgtg agcaaaaggc cagcaaaagg ccaggaaccg taaaaaggcc gcgttgctgg    9000
cgttttccca taggctccgc ccccctgacg agcatcacaa aaatcgacgc tcaagtcaga    9060
ggtggcgaaa cccgacagga ctataaagat accaggcgtt tccccctgga agctccctcg    9120
tgcgctctcc tgttccgacc ctgccgctta ccggatacct gtccgccttt ctcccttcgg    9180
gaagcgtggc gctttctcat agctcacgct gtaggtatct cagttcggtg taggtcgttc    9240
gctccaagct gggctgtgtg cacgaacccc ccgttcagcc cgaccgctgc gccttatccg    9300
gtaactatcg tcttgagtcc aacccggtaa gacacgactt atcgccactg gcagcagcca    9360
ctggtaacag gattagcaga gcgaggtatg taggcggtgc tacagagttc ttgaagtggt    9420
ggcctaacta cggctacact agaagaacag tatttggtat ctgcgctctg ctgaagccag    9480
ttaccttcgg aaaaagagtt ggtagctctt gatccggcaa acaaaccacc gctggtagcg    9540
gtggtttttt tgtttgcaag cagcagatta cgcgcagaaa aaaggatctc aagaagatc     9600 ctttgatctt ttctacgggg tctgacgctc agtggaacga aaactcacgt taagggattt    9660
tggtcatgag attatcaaaa aggatcttca cctagatcct tttaaattaa aaatgaagtt    9720
ttaaatcaat ctaaagtata tatgagtaaa cttggtctga catgcgcagt taccaatgct    9780
taatcagtga ggcacctatc tcagcgatct gtctatttcg ttcatccata gttgcctgac    9840
tccccgtcgt gtagataact acgatacggg agggcttacc atctggcccc agtgctgcaa    9900
tgataccgcg agacccacgc tcaccggctc cagatttatc agcaataaac cagccagccg    9960
gaagcgccga gcgcagaagt ggtcctgcaa ctttatccgc ctccatccag tctattaact   10020
gttgccggga agctagagta agtagttcgc cagttaatag tttgcggagc gttgttgcca   10080
ttgctacagg catcgtggtg tcacgctcgt cgtttggtat ggcttcattc agctccggtt   10140
cccaacgatc aaggcgagtt acatgatccc ccatgttgtg caaaaaagcg gttagctcct   10200
tcggtcctcc gatggttgtc agaagtaagt tggccgcagt gttatcactc atggttatgg   10260
cagcactgca taattctctt actgtcatgc catccgtaag atgcttttct gtgactggtg   10320
agtattcaac caagtcattc tgagaatagt gtatgcggcg accgagttgc tcttgcccgg   10380
cgtcaatacg ggataatacc gcgccacata gcagaacttt aaaagtgctc atcattggga   10440
agcgttcttc ggggcgaaaa ctctcaagga tcttaccgct gttgagatcc agttcgatgt   10500
aacccacacg agcacccaac tgatcttcag catcttttac tttcaccagc gtttctgggt   10560
gagcaaaaac aggaaggcaa aatgccgcaa aaagggaat aagggcgaca cggaaatgtt    10620
gaatactcat actcttcctt tttcaatatt attgaagcat ttatcagggt tattgtctca   10680
tgagcggata catatttgaa tgtatttaga aaaataaaca aataggggtt ccgcgcacat   10740
ttccccgaaa agtgccacct gaggtctaag aaaccattat tatcatgaca ttaacctata   10800
aaaataggcg tatcacgagg ccctttcttc tcgcgcgttt cggtgatgac ggtgaaaacc   10860
tctgacacat gcagctcccg gatacggtca cagcttgtct gtaagcggat gccgggagca   10920
gacaagcccg tcagggcgcg tcagcgggtg ttggcgggtg tcggggctgg cttaa         10975
```